US012577239B2

(12) United States Patent
Shanbhag et al.

(10) Patent No.: US 12,577,239 B2
(45) Date of Patent: Mar. 17, 2026

(54) SULFILIMINES OR SULFOXIMINES CONTAINING FUNGICIDAL HETEROCYCLIC COMPOUNDS

(71) Applicant: PI INDUSTRIES LTD., Udaipur-Rajasthan (IN)

(72) Inventors: Gajanan Shanbhag, Bangalore-Karnataka (IN); Singaraboena Prabhakar, Warangal-Telengana (IN); Aditya Sharma, Nagaur-Rajasthan (IN); Dipankar Roy, West Bengal (IN); Mohan Lal Mehta, Baran-Rajasthan (IN); Nitin Shivanna Kore, Solapur-Maharashtra (IN); Mohan Kumar Shivani Puttaswamy, Shivamogga-Karnataka (IN); Santosh Shridhar Autkar, Akola-Maharashtra (IN); Ruchi Garg, Varanasi-Up (IN); Vishwanath Gade, Thane West-Maharashtra (IN); Alexander G.M. Klausener, Pulheim (DE)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 960 days.

(21) Appl. No.: 17/775,979

(22) PCT Filed: Nov. 10, 2020

(86) PCT No.: PCT/IB2020/060550

§ 371 (c)(1),
(2) Date: May 11, 2022

(87) PCT Pub. No.: WO2021/094904

PCT Pub. Date: May 20, 2021

(65) Prior Publication Data

US 2023/0012782 A1 Jan. 19, 2023

(30) Foreign Application Priority Data

Nov. 11, 2019 (IN) ............................ 201911045760

(51) Int. Cl.

| | |
|---|---|
| ***C07D 417/14*** | (2006.01) |
| ***A01N 43/40*** | (2006.01) |
| ***A01N 43/56*** | (2006.01) |
| ***A01N 43/78*** | (2006.01) |
| ***A01N 43/80*** | (2006.01) |

(52) U.S. Cl.
CPC ........... *C07D 417/14* (2013.01); *A01N 43/80* (2013.01)

(58) Field of Classification Search
CPC ...... C07D 417/14; A01N 43/78; A01N 43/40; A01N 43/80; A01N 43/56
See application file for complete search history.

(56) References Cited

FOREIGN PATENT DOCUMENTS

| | | | |
|---|---|---|---|
| WO | 2019048988 | A1 | 3/2019 |
| WO | 2019048989 | A1 | 3/2019 |

OTHER PUBLICATIONS

PCT ISR dated May 12, 2021(5 pages.

*Primary Examiner* — Bruck Kifle
(74) *Attorney, Agent, or Firm* — Lippes Mathias LLP

(57) ABSTRACT

The present invention relates to a compound formula (I) and a process for preparing the same, Formula (I)

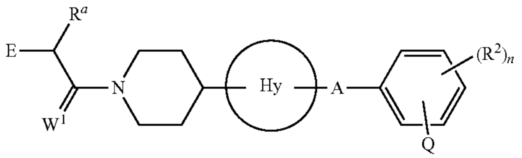

wherein, $R^2$, A, E, Hy, $R^a$, n, Q and $W^1$ are each as defined in the description.
The invention also relates to the combination and composition comprising the compound of formula (I).

16 Claims, No Drawings

SULFILIMINES OR SULFOXIMINES CONTAINING FUNGICIDAL HETEROCYCLIC COMPOUNDS

This application is a National Stage Entry of International Application No. PCT/IB2020/060550, filed Nov. 10, 2020, and entitled "NOVEL SULFILIMINES OR SULFOXIMINES CONTAINING FUNGICIDAL HETEROCYCLIC COMPOUNDS;" which claims priority to Indian Application No. 201911045760, filed Nov. 11, 2019, and entitled "NOVEL SULFILIMINES OR SULFOXIMINES CONTAINING FUNGICIDAL HETEROCYCLIC COMPOUNDS," the contents of which are incorporated by reference herein.

FIELD OF THE INVENTION

The present invention relates to novel sulfilimines or sulfoximines containing heterocyclic compounds and its agrochemically active salts, combinations, compositions and method of use of the compounds for controlling or preventing phytopathogenic fungi. The present invention also relates to the preparation and to intermediates useful in the preparation of the novel sulfilimines or sulfoximines containing heterocyclic compounds.

BACKGROUND

It is known from prior art, for example, WO2008013925, WO2012020060, WO2016024434, WO2019048988 and WO2019048989 that oxazole-thiazole piperdine heterocyclic compounds can be used as fungicidal crop protection agents.

The effectiveness of the oxazole-thiazole piperdine heterocyclic compounds described in the prior art is satisfactory, but leaves problems to be solved, for example, relating to biological and ecological characteristics, fungicidal activity, spectrum, toxicity, selectivity, application rate, residue formation and occurrences of resistance. There is always a high interest in agriculture to use novel fungicidal compounds which have advantages over the known fungicidal compounds at least in some of these problems.

Surprisingly, it has now been found that the sulfilimines or sulfoximines containing heterocyclic compounds and compositions thereof of the present invention have advantages over the prior art, for example, by improved fungicidal activity. Other advantages may include broader application methods, improved biological and ecological characteristics, enhanced compatibility with useful plants, may also have the potential to solve some of the above problems and are suitable for crop protection against phytopathogenic microorganisms, particularly fungi. The sulfilimines or sulfoximines containing heterocyclic compounds can be used in combination with other pesticidal agents to enhance the efficacy especially against difficult to control fungi.

SUMMARY OF THE INVENTION

The present invention relates to a compound formula (I),

Formula (I)

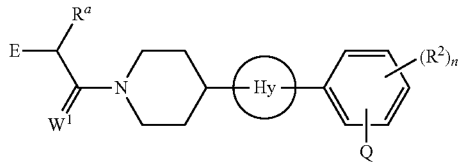

wherein, $R^2$, A, $R^a$, E, Hy, n, Q and $W^1$ are each as defined in the description.

The present invention will now be described in the detailed description.

DETAILED DESCRIPTION OF THE INVENTION

Definitions

The definitions provided herein for the terminologies used in the present disclosure are for illustrative purpose only and in no manner limit the scope of the present invention disclosed in the present disclosure. As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and *nematodes*, helminths of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous *nematodes* (Nematoda), flukes (Tematoda), *acanthocephala* and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food, feed and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the present invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

Compounds of the present disclosure may be present either in pure form or as mixtures of different possible isomeric forms such as stereoisomers or constitutional isomers. The various stereoisomers include enantiomers, diastereomers, chiral isomers, atropisomers, conformers, rotamers, tautomers, optical isomers, polymorphs, and geometric isomers. Any desired mixtures of these isomers fall within the scope of the claims of the present disclosure. One skilled in the art will appreciate that one stereoisomer may be more active and/or may exhibit beneficial effects when enriched relative to the other isomer(s) or when separated from the other isomer(s). Additionally, the person skilled in the art knows processes or methods or technology to separate, enrich, and/or to selectively prepare said isomers.

The meaning of various terms used in the description shall now be illustrated.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Non-limiting examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxy, halogen, carbonyl, carbonyloxy and the like, are at the end.

The term "alkenyl", used either alone or in compound words includes straight-chain or branched $C_2$ to $C_{24}$ alkenes, preferably $C_2$ to $C_{15}$ alkenes, more preferably $C_2$ to $C_{10}$ alkenes, most preferably $C_2$ to $C_6$ alkenes. Non-limiting examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. "Alkenyl" also includes polyenes such as 1,2-propadienyl and 2,4-hexadienyl. This definition also applies to alkenyl as a part of a composite substituent, for example haloalkenyl and the like, unless defined specifically elsewhere.

Non-limiting examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl and the different isomers. This definition also applies to alkynyl as a part of a composite substituent, for example haloalkynyl etc., unless specifically defined elsewhere. The term "alkynyl" can also include moieties comprised of multiple triple bonds such as 2,5-hexadiynyl.

The term "cycloalkyl" means alkyl closed to form a ring. Non-limiting examples include cyclopropyl, cyclopentyl and cyclohexyl. This definition also applies to cycloalkyl as a part of a composite substituent, for example cycloalkyl-alkyl etc., unless specifically defined elsewhere.

The term “cycloalkenyl” means alkenyl closed to form a ring including monocyclic, partially unsaturated hydrocarbyl groups. Non-limiting examples include cyclopropenyl, cyclopentenyl and cyclohexenyl. This definition also applies to cycloalkenyl as a part of a composite substituent, for example cycloalkenylalkyl etc., unless specifically defined elsewhere.

The term “cycloalkynyl” means alkynyl closed to form a ring including monocyclic, partially unsaturated groups. Non-limiting examples include cyclopropynyl, cyclopentynyl and cyclohexynyl. This definition also applies to cycloalkynyl as a part of a composite substituent, for example cycloalkynylalkyl etc., unless specifically defined elsewhere.

The term “cycloalkoxy”, “cycloalkenyloxy” and the like are defined analogously. Non limiting examples of cycloalkoxy include cyclopropyloxy, cyclopentyloxy and cyclohexyloxy. This definition also applies to cycloalkoxy as a part of a composite substituent, for example cycloalkoxy alkyl etc., unless specifically defined elsewhere.

The term “halogen”, either alone or in compound words such as “haloalkyl”, includes fluorine, chlorine, bromine or iodine. Further, when used in compound words such as “haloalkyl”, said alkyl may be partially or fully substituted with halogen atoms which may be the same or different. Non-limiting examples of “haloalkyl” include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms “haloalkenyl”, “haloalkynyl” are defined analogously except that, instead of alkyl groups, alkenyl and alkynyl groups are present as a part of the substituent.

The term “haloalkoxy” means straight-chain or branched alkoxy groups where some or all of the hydrogen atoms in these groups may be replaced by halogen atoms as specified above. Non-limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term “haloalkylthio” means straight-chain or branched alkylthio groups where some or all of the hydrogen atoms in these groups may be replaced by halogen atoms as specified above. Non-limiting examples of haloalkylthio include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as a part of a composite substituent, for example haloalkylthioalkyl etc., unless specifically defined elsewhere. Non-limiting examples of “haloalkylsulfinyl” include $CF_3S(O)$, $CCl_3S(O)$, $CF_3CH_2S(O)$ and $CF_3CF_2S(O)$. Non-limiting examples of “haloalkylsulfonyl” include $CF_3S(O)_2$, $CCl_3S(O)_2$, $CF_3CH_2S(O)_2$ and $CF_3CF_2S(O)_2$.

The term “hydroxy” means —OH, Amino means —NRR, wherein R can be H or any possible substituent such as alkyl. Carbonyl means —C(═O)—, carbonyloxy means —OC(═O)—, sulfinyl means SO, sulfonyl means S(O).

The term “alkoxy” used either alone or in compound words included $C_1$ to $C_{24}$ alkoxy, preferably $C_1$ to $C_{15}$ alkoxy, more preferably $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term “alkoxyalkyl” denotes alkoxy substitution on alkyl. Non-limiting examples of “alkoxyalkyl” include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

The term “alkoxyalkoxy” denotes alkoxy substitution on alkoxy.

The term “alkylthio” includes branched or straight-chain alkylthio moieties such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio and the different isomers.

Halocycloalkyl, halocycloalkenyl, alkylcycloalkyl, cycloalkylalkyl, cycloalkoxyalkyl, alkylsulfinylalkyl, alkylsulfonylalkyl, haloalkylcarbonyl, cycloalkylcarbonyl, haloalkoxylalkyl, and the like, are defined analogously to the above examples.

The term “alkylthioalkyl” denotes alkylthio substitution on alkyl. Non-limiting examples of “alkylthioalkyl” include $—CH_2SCH_2$, $—CH_2SCH_2CH_2$, $CH_3CH_2SCH_2$, $CH_3CH_2CH_2CH_2SCH_2$ and $CH_3CH_2SCH_2CH_2$. “Alkylthioalkoxy” denotes alkylthio substitution on alkoxy. The term “cycloalkylalkylamino” denotes cycloalkyl substitution on alkyl amino.

The terms “alkoxyalkoxyalkyl”, “alkylaminoalkyl”, “dialkylaminoalkyl”, “cycloalkylaminoalkyl”, “cycloalkylaminocarbonyl" and the like, are defined analogously to "alkylthioalkyl" or "cycloalkylalkylamino".

The term "alkoxycarbonyl" is an alkoxy group bonded to a skeleton via a carbonyl group (—CO—). This definition also applies to alkoxycarbonyl as a part of a composite substituent, for example cycloalkylalkoxycarbonyl and the like, unless specifically defined elsewhere.

The term "alkoxycarbonylalkylamino" denotes alkoxy carbonyl substitution on alkyl amino. "Alkylcarbonylalkylamino" denotes alkyl carbonyl substitution on alkyl amino. The terms alkylthioalkoxycarbonyl, cycloalkylalkylaminoalkyl and the like are defined analogously.

Non-limiting examples of "alkylsulfinyl" include methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl and the different isomers. The term "arylsulfinyl" includes Ar—S(O), wherein Ar can be any carbocyle or heterocylcle. This definition also applies to alkylsulphinyl as a part of a composite substituent, for example haloalkylsulphinyl etc., unless specifically defined elsewhere.

Non-limiting examples of "alkylsulfonyl" include methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl and the different isomers. The term "arylsulfonyl" includes Ar—$S(O)_2$, wherein Ar can be any carbocyle or heterocylcle. This definition also applies to alkylsulphonyl as a part of a composite substituent, for example alkylsulphonylalkyl etc., unless defined elsewhere. "Alkylamino", "dialkylamino", and the like, are defined analogously to the above examples.

The term "carbocycle or carbocyclic" includes "aromatic carbocyclic ring system" and "non-aromatic carbocylic ring system" or polycyclic or bicyclic (spiro, fused, bridged, nonfused) ring compounds in which ring may be aromatic or non-aromatic (where aromatic indicates that the Huckel rule is satisfied and non-aromatic indicates that the Huckel rule is not satisfied).

The term "heterocycle or heterocyclic" includes "aromatic heterocycle or heteroaryl ring system" and "non-aromatic heterocycle ring system" or polycyclic or bicyclic (spiro, fused, bridged, nonfused) ring compounds in which ring may be aromatic or non-aromatic, wherein the heterocycle ring contains at least one heteroatom selected from N, O, $S(O)_{0-2}$, and or C ring member of the heterocycle may be replaced by C(═O), C(═S), C(═CR*R*) and C═NR*, * indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; non-limiting examples oxetanyl, oxiranyl, aziridinyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-1-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, pyrrolinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidinyl, 2-piperidinyl, 3-piperidinyl, 4-piperidinyl, pyrazynyl, morpholinyl, thiomorphlinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, cycloserines, 2,3,4,5-tetrahydro[1H]azepin-1- or -2- or -3- or -4- or -5- or -6- or -7-yl, 3,4,5,6-tetra-hydro[2H]azepin-2- or -3- or -4- or -5- or -6- or -7-yl, 2,3,4,7-tetrahydro[1H]azepin-1- or -2- or -3- or -4- or -5- or -6- or -7-yl, 2,3,6,7-tetrahydro[1H]azepin-1- or -2- or -3- or -4- or -5- or -6- or -7-yl, hexahydroazepin-1- or -2- or -3- or -4-yl, tetra- and hexahydrooxepinyl such as 2,3,4,5-tetrahydro[1H]oxepin-2- or -3- or -4- or -5- or -6- or -7-yl, 2,3,4,7-tetrahydro[1H]oxepin-2- or -3- or -4- or -5- or -6-or -7-yl, 2,3,6,7-tetrahydro[1H]oxepin-2- or -3- or -4- or -5- or -6- or -7-yl, hexahydroazepin-1- or -2- or -3- or -4-yl, tetra- and hexahydro-1,3-diazepinyl, tetra- and hexahydro-1,4- diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl. This definition also applies to heterocyclyl as a part of a composite substituent, for example heterocyclylalkyl etc., unless specifically defined elsewhere.

The term "heteroaryl" or "aromatic heterocyclic" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom; 5-membered heteroaryl groups which, in addition to carbon atoms, may contain one to four nitrogen atoms or one to three nitrogen atoms and one sulphur or oxygen atom as ring members, non-limiting examples furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, non-limiting examples 1-pyrrolyl, 1-pyrazolyl, 1,2,4-triazol-1-yl, 1-imidazolyl, 1,2,3-triazol-1-yl and 1,3,4-triazol-1-yl.

6-membered heteroaryl which contains one to four nitrogen atoms: 6-membered heteroaryl groups which, in addition to carbon atoms, may contain, respectively, one to three and one to four nitrogen atoms as ring members, non-limiting examples 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl; benzofused 5-membered heteroaryl containing one to three nitrogen atoms or one nitrogen atom and one oxygen or sulphur atom: non-limiting examples indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl; benzofused 6-membered heteroaryl which contains one to three nitrogen atoms: non-limiting examples quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

The term "trialkylsilyl" includes 3 branched and/or straight-chain alkyl radicals attached to and linked through a silicon atom such as trimethylsilyl, triethylsilyl and t-butyl-dimethylsilyl. "Halotrialkylsilyl" denotes at least one of the three alkyl radicals is partially or fully substituted with halogen atoms which may be the same or different. The term"alkoxytrialkylsilyl" denotes at least one of the three alkyl radicals is substituted with one or more alkoxy radicals which may be the same or different. The term "trialkylsilyloxy" denotes a trialkylsilyl moiety attached through oxygen.

Non-limiting examples of "alkylcarbonyl" include $C(=O)CH_3$, $C(=O)CH_2CH_2CH_3$ and $C(=O)CH(CH_3)_2$. Non-limiting examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Non-limiting examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Non-limiting examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH_3)C(=O)$. Non-limiting examples of "alkoxyalkylcarbonyl" include $CH_3OCH_2C(=O)$, $CH_3OCH_2CH_2C(=O)$, $CH_3CH_2OCH_2C(=O)$, $CH_3CH_2CH_2CH_2OCH_2C(=O)$ and $CH_3CH_2OCH_2CH_2C(=O)$. Non-limiting examples of "alkylthioalkylcarbonyl" include $CH_3SCH_2C(=O)$, $CH_3SCH_2CH_2C(=O)$, $CH_3CH_2SCH_2C(=O)$, $CH_3CH_2CH_2CH_2SCH_2C(=O)$ and $CH_3CH_2SCH_2CH_2C(=O)$. The term haloalkylsufonylaminocarbonyl, alkylsulfonylaminocarbonyl, alkylthioalkoxycarbonyl, alkoxycarbonylalkyl amino and the like are defined analogously Non-limiting examples of "alkylaminoalkylcarbonyl" include $CH_3NHCH_2C(=O)$, $CH_3NHCH_2CH_2C(=O)$, $CH_3CH_2NHCH_2C(=O)$, $CH_3CH_2CH_2CH_2NHCH_2C(=O)$ and $CH_3CH_2NHCH_2CH_2C(=O)$.

The term "amide" means A-R'C=ONR"-B, wherein R' and R" indicates substituents and A and B indicate any group.

The term "thioamide" means A-R'C=SNR"-B, wherein R' and R" indicates substituents and A and B indicate any group.

The total number of carbon atoms in a substituent group is indicated by the "$C_i$-$C_j$" prefix where i and j are numbers from 1 to 21. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of formula (I) is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript m in $(R)_m$ indicates an integer ranging from for example 0 to 4 then the number of substituents may be selected from the integers between 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the description/claims though might form a critical part of the present invention of the present invention, any deviation from such numerical values shall still fall within the scope of the present invention if that deviation follows the same scientific principle as that of the present invention disclosed in the present invention.

The inventive compound of the present invention may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

The term "pest" for the purpose of the present disclosure includes but is not limited to fungi, stramenopiles (oomycetes), bacteria, *nematodes*, mites, ticks, insects and rodents.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis.

Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; cucurbitaceae; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention includes but is not limited to cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground. For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxillary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which includes but is not limited to spraying, coating, dipping, fumigating, impregnating, injecting and dusting.

The term "applied" means adhered to a plant or plant part either physically or chemically including impregnation.

The present invention relates to a compound of formula (I),

Formula (I)

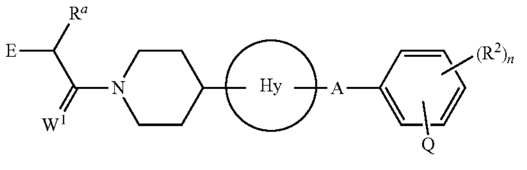

wherein,

E is selected from the group consisting of E-1 to E-3 and may be optionally substituted with one or more $R^1$;

E-1

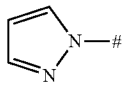

E-2

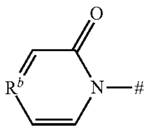

E-3

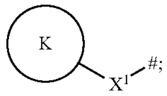

wherein, # indicates the point of attachment;

Hy is selected from the group consisting of Hy-1 and Hy-2;

Hy-1

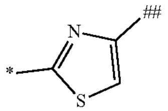

Hy-2

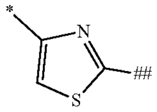

* indicates the point of attachment to piperidine;

indicates the point of attachment to A;

K represents a 5- or 6-membered heteroaryl ring;

$R^a$ is selected from the group consisting of hydrogen and $C_1$-$C_4$alkyl;

$R^b$ is selected from atoms selected from C or N;

$R^1$ is selected from the group consisting of hydrogen, halogen, cyano, hydroxy, $C_1$-$C_6$ alkyl, $C_1$-$C_6$ alkoxy, $C_1$-$C_6$ alkylthio, $C_1$-$C_6$ alkylsulfonyl, $C_1$-$C_6$ alkylsulfinyl, $C_2$-$C_6$ alkenyl, $C_2$-$C_6$ alkynyl, $C_1$-$C_6$ haloalkyl, $C_1$-$C_6$ haloalkoxy, $C_2$-$C_6$ haloalkenyl, $C_2$-$C_6$ haloalkynyl and $C_3$-$C_6$ cycloalkyl;

two $R^1$ together with the atom to which they are attached or together with further atoms selected from the group consisting of C, N, O, S and optionally including 1 to 3 ring members selected from the group consisting of C(═O), C(═S), S(O)m and $Si(R')_2$ may form a five to six membered ring, which for its part may be substituted by one or more groups selected from the group consisting of halogen, cyano, $C_1$-$C_4$ alkyl, $C_1$-$C_3$ haloalkyl, $C_1$-$C_4$ alkoxy, $C_1$-$C_4$ alkylthio;

$X^1$ is selected from the group consisting of —O—, —$S(O)_{0-2}$—, —$NR^3$;

$R^3$ is selected from the group consisting of halogen, cyano, hydroxy, $C_1$-$C_6$ alkyl, $C_1$-$C_6$ alkoxy, and $C_3$-$C_6$ cycloalkyl;

$W^1$ is O or S;

A is selected from the group consisting of $A^1$ and $A^2$;

$A^1$

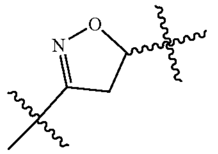

$A^2$

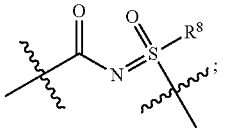

wherein, $R^1$ represents $C_1$-$C_6$ alkyl group; or

A and a contiguous phenyl ring together is a fragment $A^3$, $A^3$

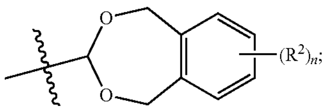

$R^2$ is selected from the group consisting of halogen, cyano, hydroxy, $C_1$-$C_6$ alkyl, $C_1$-$C_6$ alkoxy, $C_1$-$C_6$ alkylthio, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_1$-$C_6$ alkylsulfinyl, and $C_1$-$C_6$ alkylsulfonyl; n is an integer selected from 0 to 3;

Q is selected from —$S(=O)_{0-1}(R^5)(=NR^4)$ or —$N=S(=O)_{0-1}(R^6)(R^7)$ $R^4$ is selected from the group consisting of hydrogen, cyano, hydroxy, $C_1$-$C_4$ alkyl and $C_3$-$C_6$ cycloalkyl, $C_3$-$C_6$ cycloalkyl-$C_1$-$C_4$ alkyl, $C_1$-$C_4$ alkyl carbonyl and $C_1$-$C_4$ haloalkyl carbonyl;

$R^5$ and $R^6$ are independently selected from the group consisting of $C_1$-$C_4$ alkyl, $C_2$-$C_6$ alkenyl, $C_3$-$C_6$ cycloalkyl, $C_3$-$C_6$ cycloalkyl-$C_1$-$C_4$ alkyl, $C_1$-$C_4$ haloalkyl, and $C_3$-$C_6$ halocycloalkyl; or $R^7$ is independently selected from the group consisting of $C_1$-$C_4$ alkyl, $C_2$-$C_6$ alkenyl, $C_3$-$C_6$ cycloalkyl, $C_3$-$C_6$ cycloalkyl-$C_1$-$C_4$ alkyl, $C_1$-$C_4$ haloalkyl, $C_3$-$C_6$ halocycloalkyl and phenyl;

$R^4$ or $R^5$ with the C atom contiguous to the C atom substituted with Q may form a 4- to 6-membered heterocyclic ring, wherein the C atoms of the heterocyclic ring may be optionally replaced by C(═O) or C(═S);

$R^6$ and $R^7$ together with the S atom to which they are attached may form a 4- to 6-membered heterocyclic ring, wherein the C atoms of the heterocyclic ring may be optionally replaced by C(═O) or C(═S); or $R^5$ or $R^6$ or $R^7$ with the $R^2$ may form a 4- to 6-membered heterocyclic ring, wherein the C atoms of the heterocyclic ring may be optionally replaced by C(═O) or C(═S); or $R^6$ or $R^7$ with the C atom contiguous to the C atom substituted with Q may form a 4- to 6-membered heterocyclic ring, wherein the C atoms of the heterocyclic ring may be optionally replaced by C(═O) or C(═S); wherein, said heterocyclic rings may be optionally substituted with the group consisting of halogen, cyano, $C_1$-$C_4$ alkyl, $C_3$-$C_6$ cycloalkyl, $C_1$-$C_4$ haloalkyl and $C_3$-$C_6$ halocycloalkyl; or salts, metal complexes, N-oxides, isomers, and polymorphs thereof.

In one embodiment, K is selected from the group consisting of $K^1$ to $K^{19}$:

$K^1$

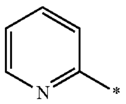

$K^2$

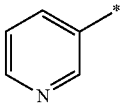

$K^3$

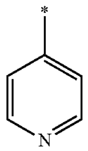

$K^4$

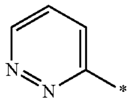

$K^5$

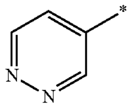

$K^6$

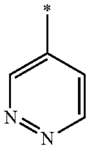

$K^7$

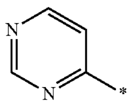

$K^8$

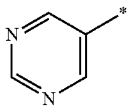

$K^9$

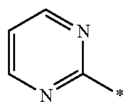

$K^{10}$

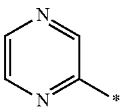

-continued $K^{11}$

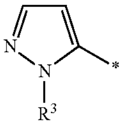

$K^{12}$

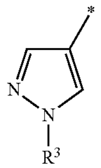

$K^{13}$

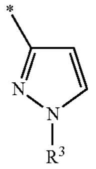

$K^{14}$

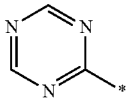

$K^{15}$

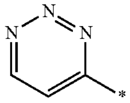

$K^{16}$

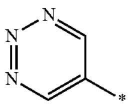

$K^{17}$

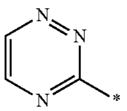

$K^{18}$

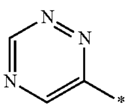

$K^{19}$

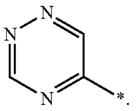

In one embodiment, the present invention provides a compound of formula (Ia) or salt thereof, Formula (Ia)

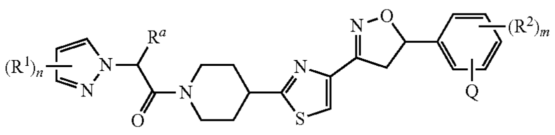

wherein, the substituent $R^1$, Q, $R^a$ and $R^2$ are as defined above.

In one embodiment, the present invention provides a compound of formula (Ia-1) or salt thereof, Formula (Ia-1)

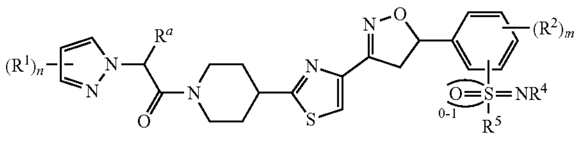

wherein, the substituent $R^1$, $R^2$, $R^a$, $R^4$ and $R^5$ are as defined above.

In one embodiment, the present invention provides a compound of formula (Ia-2) or salt thereof, Formula (Ia-2)

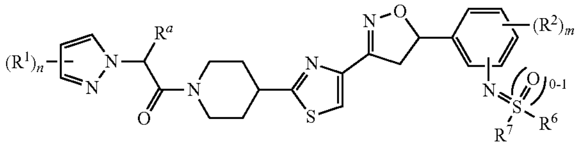

wherein, the substituent $R^1$, $R^2$, $R^a$, $R^6$ and $R^7$ are as defined above.

In one embodiment, the present invention provides a compound of formula (Ib) or salt thereof, Formula (Ib)

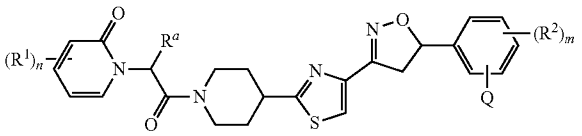

wherein, the substituent $R^1$, $R^2$, $R^a$ and Q are as defined above.

In one embodiment, the present invention provides a compound of formula (Ic) or salt thereof, Formula (Ic)

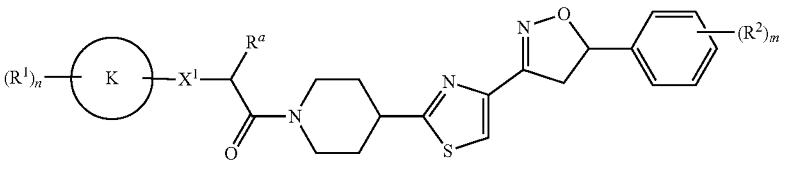

wherein, the substituent $R^1$, $R^2$, $R^a$ and K are as defined above.

In a preferred embodiment of the present invention,

K is selected from the group consisting of $K^1$ to $K^{14}$;

$K^1$

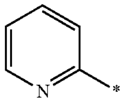

-continued $K^2$

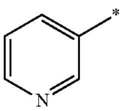

$K^3$

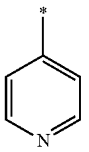

$K^4$

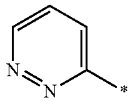

$K^5$

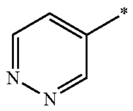

$K^6$

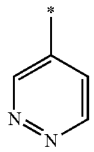

$K^7$

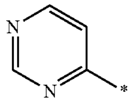

$K^8$

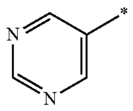

-continued $K^9$

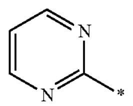

$K^{10}$

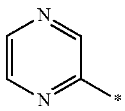

-continued

K11

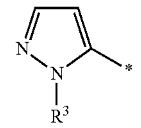

K12

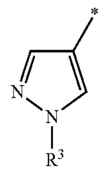

K13

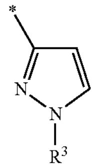

and

K14

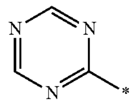

In one embodiment of the present invention, the compound of formula (I) selected from, 5-chloro-1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one; 3-chloro-1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one; (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(methyl)-l6-sulfanone; (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(methyl)-l6-sulfanone; (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone; ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)dimethyl-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)dimethyl-l6-sulfanone; ((3-fluoro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)dimethyl-l6-sulfanone; ((2-(3-(2-(1-(2-(4-chloro-1H-pyrazol-1-yl)acetyl)piperidin-4-yl)thiazol-4-yl)-4,5-dihydroisoxazol-5-yl)-3-fluorophenyl)imino)dimethyl-l6-sulfanone; ((2-(3-(2-(1-(2-(2H-indazol-2-yl)acetyl)piperidin-4-yl)thiazol-4-yl)-4,5-dihydroisoxazol-5-yl)-3-fluorophenyl)imino)dimethyl-l6-sulfanone; 3-chloro-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-5-(trifluoromethyl)pyridin-2(1H)-one; 1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one; ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)dimethyl-l6-sulfanone; ((3-fluoro-2-(3-(2-(1-(2-((6-methyl-3-(trifluoromethyl)pyridin-2-yl)oxy)acetyl)piperidin-4-yl)thiazol-4-yl)-4,5-dihydroisoxazol-5-yl)phenyl)imino)dimethyl-l6-sulfanone; 5-bromo-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-6-oxo-1,6-dihydropyridine-3-carbonitrile; ((3-(3-(2-(1-(2-(3,5-bis(difluoromethyl)-1H-pyrazol-1-yl)acetyl)piperidin-4-yl)thiazol-4-yl)-4,5-dihydroisoxazol-5-yl)phenyl)imino)dimethyl-l6-sulfanone; dimethyl((3-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)-l6-sulfanone; ((3-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)dimethyl-l6-sulfanone; 1-(4-(4-((5S)-5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-((5R)-5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-(5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 2-(3,5-dimethyl-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one; 2-(5-methyl-3-(trifluoromethyl)-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one; 2-(3,5-bis(difluoromethyl)-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one; ((2-(3-(2-(1-(2-(1H-pyrazol-1-yl)acetyl)piperidin-4-yl)thiazol-4-yl)-4,5-dihydroisoxazol-5-yl)-3-fluorophenyl)imino)dimethyl-l6-sulfanone; 2-(3,5-bis(difluoromethyl)-1H-pyrazol-1-yl)-1-(4-(4-(5-(2-fluoro-6-((1-oxidotetrahydro-1l6-thiophen-1-ylidene)amino)phenyl)-4,5-dihydroisoxazol-3-yl)thiazol-2-yl)piperidin-1-yl)ethan-1-one; 1-(4-(4-(5-(2-fluoro-6-((1-oxidotetrahydro-1l6-thiophen-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one; 3-bromo-5-chloro-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)pyridin-2(1H)-one; 1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-5-(trifluoromethyl)pyridin-2(1H)-one; (3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)(imino)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)dimethyl-l6-sulfanone; 2-(3,5-bis(difluoromethyl)-1H-pyrazol-1-yl)-1-(4-(4-((5S)-5-(6-fluoro-2-methyl-2-oxido-3H-2l4-benzo[c]isothiazol-7-yl)-4,5-dihydroisoxazol-3-yl)thiazol-2-yl)piperidin-1-yl)ethan-1-one; 2-(3,5-bis(difluoromethyl)-1H-pyrazol-1-yl)-1-(4-(4-((5R)-5-(6-fluoro-2-methyl-2-oxido-3H-2l4-benzo[c]isothiazol-7-yl)-4,5-dihydroisoxazol-3-yl)thiazol-2-yl)piperidin-1-yl)ethan-1-one; 2-(3,5-bis(difluoromethyl)-1H-pyrazol-1-yl)-1-(4-(4-((5S)-5-(2-methyl-2-oxido-3H-2l4-benzo[c]isothiazol-7-yl)-4,5-dihydroisoxazol-3-yl)thiazol- 2-yl)piperidin-1-yl)ethan-1-one; 2-(3,5-bis(difluoromethyl)-1H-pyrazol-1-yl)-1-(4-(4-((5R)-5-(2-methyl-2-oxido-3H-2l4-benzo[c]isothiazol-7-yl)-4,5-dihydroisoxazol-3-yl)thiazol-2-yl)piperidin-1-yl)ethan-1-one; 2-(3,5-bis(difluoromethyl)-1H-pyrazol-1-yl)-1-(4-(4-(5-(2-methyl-2-oxido-3H-2l4-benzo[c]isothiazol-7-yl)-4,5-dihydroisoxazol-3-yl)thiazol-2-yl)piperidin-1-yl)ethan-1-one; N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)(methyl)(oxo)-l6-sulfaneylidene)cyanamide; (Z)—N-((3-fluoro-2-(3-(2-(1-(2-(3-methyl-1H-pyrazol-1-yl)acetyl)piperidin-4-yl)thiazol-4-yl)-4,5-dihydroisoxazol-5-yl)phenyl)(methyl)-l4-sulfaneylidene)cyanamide; N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(oxo)-l6-sulfaneylidene)cyanamide; (E)-N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide; (Z)—N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide; (E)-N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)(methyl)-l4-sulfaneylidene)cyanamide; (3-chloro-2-((R)-3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(isopropyl)-l6-sulfanone; (3-chloro-2-((S)-3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(isopropyl)-l6-sulfanone; (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(isopropyl)-l6-sulfanone; 1-(4-(4-((5S)-5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-((5R)-5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-(5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one; 1-(2-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one; 1-(2-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one; 1-(2-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one; 2-(3,5-bis(difluoromethyl)-1H-pyrazol-1-yl)-1-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one; 2-(3,5-bis(difluoromethyl)-1H-pyrazol-1-yl)-1-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one; 2-(3,5-bis(difluoromethyl)-1H-pyrazol-1-yl)-1-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one; 1-(2-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one; 1-(2-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one; 1-(2-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one; (2-((R)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(isopropyl)-l6-sulfanone; (3-chloro-2-(3-(2-(1-(2-(4-chloro-1H-pyrazol-1-yl)acetyl)piperidin-4-yl)thiazol-4-yl)-4,5-dihydroisoxazol-5-yl)phenyl)(imino)(isopropyl)-l6-sulfanone; (3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)(imino)(isopropyl)-l6-sulfanone; 1-(2-(4-(4-(5-(2-chloro-6-(propan-2-ylsulfonimidoyl)phenyl)-4,5-dihydroisoxazol-3-yl)thiazol-2-yl)piperidin-1-yl)-2-oxoethyl)-3-(trifluoromethyl)pyrazin-2(1H)-one; (3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(isopropyl)-l6-sulfanone; rac-N—((Z)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide; rac-N-((E)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide; (2-((S)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(isopropyl)-l6-sulfanone; N-((E)-((6R)-6-((SR)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-5-chlorocyclohexa-2,4-dien-1-yl)(methyl)-l4-sulfaneylidene)cyanamide; (2-((5R)-3-(2-(1-(2-(3,5-bis(difluoromethyl)-1H-pyrazol-1-yl)propanoyl)piperidin-4-yl)thiazol-4-yl)-4,5-dihydroisoxazol-5-yl)-3-chlorophenyl)(methyl)(methylimino)-l6-sulfanone; (2-((5S)-3-(2-(1-(2-(3,5-bis(difluoromethyl)-1H-pyrazol-1-yl)propanoyl)piperidin-4-yl)thiazol-4-yl)-4,5-dihydroisoxazol-5-yl)-3-chlorophenyl)(methyl)(methylimino)-l6-sulfanone; (3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone; (3-chloro-2-((S)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone; ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)dimethyl-l6-sulfanone; (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(ethylimino)(methyl)-l6-sulfanone; (Z)—N-((3-chloro-2-(3-(2-(1-(2-(5- methyl-3-(trifluoromethyl)-1H-pyrazol-1-yl)acetyl)piperidin-4-yl)thiazol-4-yl)-4,5-dihydroisoxazol-5-yl)phenyl)(isopropyl)-l4-sulfaneylidene)cyanamide; imino(methyl)(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)-l6-sulfanone; (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(imino)(methyl)-l6-sulfanone; (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-$\lambda^3$-(trifluoromethyl)phenyl)(imino)(methyl)-l6-sulfanone; (Z)—N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-$\lambda^3$-chlorophenyl)(isopropyl)-l4-sulfaneylidene)cyanamide; 1-(4-(4-(5-(2-chloro-6-((1-oxido-1l6-thietan-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)dimethyl-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)dimethyl-l6-sulfanone; ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)dimethyl-l6-sulfanone; dimethyl((2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)imino)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)imino)dimethyl-l6-sulfanone; 1-(2-(4-(4-(5-(2-chloro-6-((dimethyl(oxo)-l6-sulfaneylidene)amino)phenyl)-4,5-dihydroisoxazol-3-yl)thiazol-2-yl)piperidin-1-yl)-2-oxoethyl)-6-methyl-3-(trifluoromethyl)pyridin-2(1H)-one; ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)dimethyl-l6-sulfanone; ethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone; ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone; ethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(methyl)-l6-sulfanone; ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(ethyl)(methyl)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(ethyl)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(ethyl)(methyl)-l6-sulfanone; ((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)(ethyl)(methyl)-l6-sulfanone; ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(ethyl)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)imino)dimethyl-l6-sulfanone; ((2-(3-(2-(1-(2-((3-methoxypyridin-2-yl)oxy)acetyl)piperidin-4-yl)thiazol-4-yl)-4,5-dihydroisoxazol-5-yl)-3-(trifluoromethyl)phenyl)imino)dimethyl-l6-sulfanone; (3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(methyl)-l6-sulfanone; (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(difluoromethyl)phenyl)(imino)(methyl)-l6-sulfanone; 1-(2-(4-(4-(5-(2-(difluoromethyl)-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one; 2-(3-(2-(1-(2-((3-methoxypyridin-2-yl)oxy)acetyl)piperidin-4-yl)thiazol-4-yl)-4,5-dihydroisoxazol-5-yl)-3-(S-methylsulfonimidoyl)benzonitrile; 2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile; 2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile; 1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one; 2-(3,5-bis(difluoromethyl)-1H-pyrazol-1-yl)-1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)ethan-1-one; 1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-((3-(trifluoromethyl)pyridin-2-yl)oxy)ethan-1-one; 1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-((3-methoxypyridin-2-yl)oxy)ethan-1-one; 2-(3,5-bis(trifluoromethyl)-1H-pyrazol-1-yl)-1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)ethan-1-one; methyl(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)(methylimino)-l6-sulfanone; (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(methyl)(methylimino)-l6-sulfanone; (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)(ethylimino)(methyl)-l6-sulfanone; (ethylimino)(methyl)(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)-l6-sulfanone; (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(ethylimino)(methyl)-l6-sulfanone; (2-(3-(2-(1-(2-((3-methoxypyridin-2-yl)oxy)acetyl)piperidin-4-yl)thiazol-4-yl)-4,5-dihydroisoxazol-5-yl)-3-(trifluoromethyl)phenyl)(methyl)(methylimino)-l6-sulfanone; ((3-chloro-2-(3-(2-(1-(2-(5-methyl-3-(trifluoromethyl)-1H-pyrazol-1-yl)acetyl)piperidin-4-yl)thiazol-4-yl)-4,5- dihydroisoxazol-5-yl)phenyl)imino)(isopropyl)(methyl)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(isopropyl)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(isopropyl)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(isopropyl)(methyl)-l6-sulfanone; ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)(methyl)-l6-sulfanone; ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)(methyl)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(isopropyl)(methyl)-l6-sulfanone; ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)(propyl)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(methyl)(propyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(methyl)(propyl)-l6-sulfanone; ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)(propyl)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(methyl)(propyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(methyl)(propyl)-l6-sulfanone; ((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(methyl)(propyl)-l6-sulfanone; ((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(methyl)(propyl)-l6-sulfanone; ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(methyl)(propyl)-l6-sulfanone; ((3-fluoro-2-(3-(2-(1-(2-((2-methoxypyridin-3-yl)oxy)acetyl)piperidin-4-yl)thiazol-4-yl)-4,5-dihydroisoxazol-5-yl)phenyl)imino)dimethyl-l6-sulfanone; ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diethyl-l6-sulfanone; ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diethyl-l6-sulfanone; ((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diethyl-l6-sulfanone; diethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diethyl-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diethyl-l6-sulfanone; diethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)-l6-sulfanone; diethyl((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)-l6-sulfanone; diethyl((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)-l6-sulfanone; (3-(difluoromethyl)-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(methyl)(methylimino)-l6-sulfanone; 1-(2-(4-(4-(5-(2-(difluoromethyl)-6-(N,S-dimethylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one; 3-chloro-1-(2-(4-(4-(5-(2-(difluoromethyl)-6-(N,S-dimethylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one; (3-(difluoromethyl)-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)(methyl)(methylimino)-l6-sulfanone; (3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone; (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(difluoromethyl)phenyl)(methyl)(methylimino)-l6-sulfanone; (Z)—N-((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)-l4-sulfaneylidene)cyanamide; (E)-N-((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)-l4-sulfaneylidene)cyanamide; (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(difluoromethyl)phenyl)(methyl)(methylimino)-l6-sulfanone; 1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one; (3-(difluoromethyl)-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)(methylimino)-l6-sulfanone; (3-(difluoromethyl)-2-(3-(2-(1-(2-((5-(trifluoromethyl)pyridin-2-yl)oxy)acetyl)piperidin-4-yl)thiazol-4-yl)-4,5-dihydroisoxazol-5-yl)phenyl)(methyl)(methylimino)-l6-sulfanone; (3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)(methylimino)-l6-sulfanone: (3-chloro-2-(3-(2-(1-(2-((3-methoxypyridin-2-yl)oxy)acetyl)piperidin-4-yl)thiazol-4-yl)-4.5-dihydroisoxazol-5-yl)phenyl)(ethylimino)(methyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)diethyl-l6-sulfanone; ((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diethyl-l6-sulfanone; 5-chloro-1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one; 1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-6-methyl-3-(trifluoromethyl)pyridin-2(1H)-one;

1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one; 2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile (3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(imino)(methyl)-l6-sulfanone; (3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(methyl)-l6-sulfanone; (3-chloro-2-(3-(2-(1-(2-((5-(trifluoromethyl)pyridin-2-yl)oxy)acetyl)piperidin-4-yl)thiazol-4-yl)-4,5-dihydroisoxazol-5-yl)phenyl)(imino)(methyl)-l6-sulfanone; 1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one; 1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one; (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)(imino)(methyl)-l6-sulfanone; (3-chloro-2-(3-(2-(1-(2-(3-methyl-1H-pyrazol-1-yl)acetyl)piperidin-4-yl)thiazol-4-yl)-4,5-dihydroisoxazol-5-yl)phenyl)(imino)(methyl)-l6-sulfanone; (3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(methyl)-l6-sulfanone; 1-(2-(4-(4-(5-(2-chloro-6-(N,S-dimethylsulfonimidoyl)phenyl)-4,5-dihydroisoxazol-3-yl)thiazol-2-yl)piperidin-1-yl)-2-oxoethyl)-6-methyl-3-(trifluoromethyl)pyridin-2(1H)-one; ((3-fluoro-2-(3-(4-(1-(2-(5-methyl-3-(trifluoromethyl)-1H-pyrazol-1-yl)acetyl)piperidin-4-yl)thiazol-2-yl)-4,5-dihydroisoxazol-5-yl)phenyl)imino)dimethyl-l6-sulfanone; ((2-(3-(4-(1-(2-(3,5-bis(difluoromethyl)-1H-pyrazol-1-yl)acetyl)piperidin-4-yl)thiazol-2-yl)-4,5-dihydroisoxazol-5-yl)-3-fluorophenyl)imino)dimethyl-l6-sulfanone; ((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)dimethyl-l6-sulfanone; ((2-(3-(4-(1-(2-(3,5-bis(trifluoromethyl)-1H-pyrazol-1-yl)acetyl)piperidin-4-yl)thiazol-2-yl)-4,5-dihydroisoxazol-5-yl)-3-fluorophenyl)imino)dimethyl-l6-sulfanone; ((3-fluoro-2-(3-(4-(1-(2-((3-methoxypyridin-2-yl)oxy)acetyl)piperidin-4-yl)thiazol-2-yl)-4,5-dihydroisoxazol-5-yl)phenyl)imino)dimethyl-l6-sulfanone; 1-(2-(4-(2-(5-(2-((dimethyl(oxo)-l6-sulfaneylidene)amino)-6-fluorophenyl)-4,5-dihydroisoxazol-3-yl)thiazol-4-yl)piperidin-1-yl)-2-oxoethyl)-3-(trifluoromethyl)pyridin-2(1H)-one; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(ethyl)(isopropyl)-l6-sulfanone; ethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(ethyl)(isopropyl)-l6-sulfanone; ethyl((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)-l6-sulfanone; 1-(2-(4-(4-(5-(2-((ethyl(isopropyl)(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one; ethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(isopropyl)-l6-sulfanone; (3-(difluoromethyl)-2-(3-(2-(1-(2-((3-methoxypyridin-2-yl)oxy)acetyl)piperidin-4-yl)thiazol-4-yl)-4,5-dihydroisoxazol-5-yl)phenyl)(imino)(isopropyl)-l6-sulfanone; (3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(isopropyl)-l6-sulfanone; (3-(difluoromethyl)-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(isopropyl)-l6-sulfanone; (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(difluoromethyl)phenyl)(imino)(isopropyl)-l6-sulfanone; (3-(difluoromethyl)-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)(imino)(isopropyl)-l6-sulfanone; (2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)-3-(difluoromethyl)phenyl)(imino)(isopropyl)-l6-sulfanone; (2-(3-(2-(1-(2-(4-chloro-1H-pyrazol-1-yl)acetyl)piperidin-4-yl)thiazol-4-yl)-4,5-dihydroisoxazol-5-yl)-3-(difluoromethyl)phenyl)(imino)(isopropyl)-l6-sulfanone; (2-(3-(2-(1-(2-(2H-indazol-2-yl)acetyl)piperidin-4-yl)thiazol-4-yl)-4,5-dihydroisoxazol-5-yl)-3-(difluoromethyl)phenyl)(imino)(isopropyl)-l6-sulfanone; ((3-fluoro-2-(3-(4-(1-(2-((3-(trifluoromethyl)pyrazin-2-yl)oxy)acetyl)piperidin-4-yl)thiazol-2-yl)-4,5-dihydroisoxazol-5-yl)phenyl)imino)dimethyl-l6-sulfanone; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(isopropyl)(propyl)-l6-sulfanone; ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)(propyl)-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(isopropyl)(propyl)-l6-sulfanone; ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(isopropyl)(propyl)-l6-sulfanone; ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)(propyl)-l6-sulfanone; ((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(isopropyl)(propyl)-l6-sulfanone; 1-(2-(4-(4-(5-(2-fluoro-6-((isopropyl(oxo)(propyl)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one; 1-(4-(4-(5-(2-fluoro-6-((1-oxido-1l6-thietan-1-ylidene)amino)phenyl)-4,5-dihydroisoxazol-3-yl)thiazol-2-yl)piperidin-1-yl)-2-((3-(trifluoromethyl)pyrazin-2-yl)oxy)ethan-1-one; ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diisopropyl-l6-sulfanone; ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diisopropyl-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diisopropyl-l6-sulfanone; ((2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)-3-fluorophenyl)imino)diisopropyl-l6-sulfanone; ((3-fluoro-2-(3-(2-(1-(2-((3-methoxypyrazin-2-yl)oxy)acetyl)piperidin- 4-yl)thiazol-4-yl)-4,5-dihydroisoxazol-5-yl)phenyl)imino) diisopropyl-l6-sulfanone; ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diisopropyl-l6-sulfanone; 1-(2-(4-(4-(5-(2-((diisopropyl(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one; ((3-fluoro-2-(3-(2-(1-(2-((3-methoxypyridin-2-yl)oxy)acetyl) piperidin-4-yl)thiazol-4-yl)-4,5-dihydroisoxazol-5-yl) phenyl)imino)diisopropyl-l6-sulfanone; ((3-fluoro-2-(3-(2-(1-(2-((3-(trifluoromethyl)pyrazin-2-yl)oxy)acetyl) piperidin-4-yl)thiazol-4-yl)-4,5-dihydroisoxazol-5-yl) phenyl)imino)diisopropyl-l6-sulfanone; ((2-(3-(2-(1-(2-(3,5-dimethyl-1H-pyrazol-1-yl)acetyl)piperidin-4-yl)thiazol-4-yl)-4,5-dihydroisoxazol-5-yl)-$\lambda^3$-fluorophenyl)imino) diisopropyl-l6-sulfanone; ((2-(3-(2-(1-(2-((3-chloropyrazin-2-yl)oxy)acetyl)piperidin-4-yl)thiazol-4-yl)-4,5-dihydroisoxazol-5-yl)-3-fluorophenyl)imino)dimethyl-l6-sulfanone; ((3-fluoro-2-(3-(2-(1-(2-((3-(methylthio)pyrazin-2-yl)oxy)acetyl)piperidin-4-yl)thiazol-4-yl)-4,5-dihydroisoxazol-5-yl)phenyl)imino)dimethyl-l6-sulfanone; ((3-fluoro-2-(3-(2-(1-(2-((3-(trifluoromethyl)pyrazin-2-yl) oxy)acetyl)piperidin-4-yl)thiazol-4-yl)-4,5-dihydroisoxazol-5-yl)phenyl)imino)(isopropyl)(phenyl)-l6-sulfanone; ((3-fluoro-2-(3-(2-(1-(2-((3-methoxypyridin-2-yl)oxy) acetyl)piperidin-4-yl)thiazol-4-yl)-4,5-dihydroisoxazol-5-yl)phenyl)imino)(isopropyl)(phenyl)-l6-sulfanone; 3-chloro-1-(2-(4-(4-(5-(2-fluoro-6-((isopropyl(oxo)(phenyl)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one; ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(isopropyl) (phenyl)-l6-sulfanone; 1-(2-(4-(4-(5-(2-fluoro-6-((isopropyl (oxo)(phenyl)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one; ((2-(3-(2-(1-(2-(3,5-bis(difluoromethyl)-1H-pyrazol-1-yl)acetyl) piperidin-4-yl)thiazol-4-yl)-4,5-dihydroisoxazol-5-yl)-3-fluorophenyl)imino)(isopropyl)(phenyl)-l6-sulfanone; 1-(2-(4-(4-(5-(2-fluoro-6-((isopropyl(oxo)(phenyl)-l6-sulfaneylidene)amino)phenyl)-4,5-dihydroisoxazol-3-yl) thiazol-2-yl)piperidin-1-yl)-2-oxoethyl)-3-(trifluoromethyl) pyridin-2(1H)-one; ((3-fluoro-2-(3-(2-(1-(2-((3-(trifluoromethyl)pyridin-2-yl)oxy)acetyl)piperidin-4-yl) thiazol-4-yl)-4,5-dihydroisoxazol-5-yl)phenyl)imino) (isopropyl)(phenyl)-l6-sulfanone; ((2-(3-(2-(1-(2-(3,5-bis (trifluoromethyl)-1H-pyrazol-1-yl)acetyl)piperidin-4-yl) thiazol-4-yl)-4,5-dihydroisoxazol-5-yl)-3-chlorophenyl) imino)diisopropyl-l6-sulfanone; ((3-chloro-2-(3-(2-(1-(2-(5-methyl-3-(trifluoromethyl)-1H-pyrazol-1-yl)acetyl) piperidin-4-yl)thiazol-4-yl)-4,5-dihydroisoxazol-5-yl) phenyl)imino)diisopropyl-l6-sulfanone; ((3-chloro-2-(3-(2-(1-(2-(5-cyclopropyl-3-(trifluoromethyl)-1H-pyrazol-1-yl) acetyl)piperidin-4-yl)thiazol-4-yl)-4,5-dihydroisoxazol-5-yl)phenyl)imino)diisopropyl-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)diisopropyl-l6-sulfanone; ((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino) diisopropyl-l6-sulfanone; ((3-chloro-2-(3-(2-(1-(2-((3-(trifluoromethyl)pyridin-2-yl)oxy)acetyl)piperidin-4-yl) thiazol-4-yl)-4,5-dihydroisoxazol-5-yl)phenyl)imino) diisopropyl-l6-sulfanone; ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diisopropyl-l6-sulfanone; 1-(2-(4-(4-(5-(2-chloro-6-((diisopropyl(oxo)-l6-sulfaneylidene)amino)phenyl)-4,5-dihydroisoxazol-3-yl) thiazol-2-yl)piperidin-1-yl)-2-oxoethyl)-3-(trifluoromethyl) pyridin-2(1H)-one; ((3-chloro-2-(3-(2-(1-(2-((3-(trifluoromethyl)pyrazin-2-yl)oxy)acetyl)piperidin-4-yl) thiazol-4-yl)-4,5-dihydroisoxazol-5-yl)phenyl)imino) diisopropyl-l6-sulfanone; ((2-(3-(2-(1-(2-(2H-indazol-2-yl) acetyl)piperidin-4-yl)thiazol-4-yl)-4,5-dihydroisoxazol-5-yl)-3-chlorophenyl)imino)diisopropyl-l6-sulfanone; ((2-(3-(2-(1-(2-(3,5-bis(trifluoromethyl)-1H-pyrazol-1-yl)acetyl) piperidin-4-yl)thiazol-4-yl)-4,5-dihydroisoxazol-5-yl)-3-fluorophenyl)imino)(isopropyl)(phenyl)-l6-sulfanone; ((3-fluoro-2-(3-(2-(1-(2-((3-(methylsulfonyl)pyrazin-2-yl)oxy) acetyl)piperidin-4-yl)thiazol-4-yl)-4,5-dihydroisoxazol-5-yl)phenyl)imino)dimethyl-l6-sulfanone; ((3-fluoro-2-(3-(2-(1-(2-((6-(trifluoromethyl)pyridazin-3-yl)thio)acetyl) piperidin-4-yl)thiazol-4-yl)-4,5-dihydroisoxazol-5-yl) phenyl)imino)dimethyl-l6-sulfanone; ((2-(3-(2-(1-(2-(3,5-bis(trifluoromethyl)-1H-pyrazol-1-yl)acetyl)piperidin-4-yl) thiazol-4-yl)-4,5-dihydroisoxazol-5-yl)-3-chlorophenyl) imino)(ethyl)(isopropyl)-l6-sulfanone; ((2-(3-(2-(1-(2-(3,5-bis(difluoromethyl)-1H-pyrazol-1-yl)acetyl)piperidin-4-yl) thiazol-4-yl)-4,5-dihydroisoxazol-5-yl)-3-chlorophenyl) imino)(ethyl)(isopropyl)-l6-sulfanone; ((3-chloro-2-(3-(2-(1-(2-(5-methyl-3-(trifluoromethyl)-1H-pyrazol-1-yl) acetyl)piperidin-4-yl)thiazol-4-yl)-4,5-dihydroisoxazol-5-yl)phenyl)imino)(ethyl)(isopropyl)-l6-sulfanone; ((3-chloro-2-(3-(2-(1-(2-(3,5-dimethyl-1H-pyrazol-1-yl)acetyl) piperidin-4-yl)thiazol-4-yl)-4,5-dihydroisoxazol-5-yl) phenyl)imino)(ethyl)(isopropyl)-l6-sulfanone; ((3-chloro-2-(3-(2-(1-(2-((3-(trifluoromethyl)pyrazin-2-yl)oxy)acetyl) piperidin-4-yl)thiazol-4-yl)-4,5-dihydroisoxazol-5-yl) phenyl)imino)(ethyl)(isopropyl)-l6-sulfanone; ((3-chloro-2-(3-(2-(1-(2-((3-(trifluoromethyl)pyridin-2-yl)oxy)acetyl) piperidin-4-yl)thiazol-4-yl)-4,5-dihydroisoxazol-5-yl) phenyl)imino)(ethyl)(isopropyl)-l6-sulfanone; ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino) (ethyl)(isopropyl)-l6-sulfanone; ((2-(3-(4-(1-(2-(3,5-bis (trifluoromethyl)-1H-pyrazol-1-yl)acetyl)piperidin-4-yl) thiazol-2-yl)-4,5-dihydroisoxazol-5-yl)-3-fluorophenyl) imino)diethyl-l6-sulfanone; ((2-(3-(4-(1-(2-(3,5-bis (difluoromethyl)-1H-pyrazol-1-yl)acetyl)piperidin-4-yl) thiazol-2-yl)-4,5-dihydroisoxazol-5-yl)-3-fluorophenyl) imino)diethyl-l6-sulfanone; diethyl((3-fluoro-2-(3-(4-(1-(2-(5-methyl-3-(trifluoromethyl)-1H-pyrazol-1-yl)acetyl) piperidin-4-yl)thiazol-2-yl)-4,5-dihydroisoxazol-5-yl) phenyl)imino)-l6-sulfanone; diethyl((3-fluoro-2-(3-(4-(1-(2-((3-methoxypyridin-2-yl)oxy)acetyl)piperidin-4-yl) thiazol-2-yl)-4,5-dihydroisoxazol-5-yl)phenyl)imino)-l6-sulfanone; diethyl((3-fluoro-2-(3-(4-(1-(2-((3-(trifluoromethyl)pyridin-2-yl)oxy)acetyl)piperidin-4-yl) thiazol-2-yl)-4,5-dihydroisoxazol-5-yl)phenyl)imino)-l6-sulfanone; diethyl((3-fluoro-2-(3-(4-(1-(2-((3-(trifluoromethyl)pyrazin-2-yl)oxy)acetyl)piperidin-4-yl) thiazol-2-yl)-4,5-dihydroisoxazol-5-yl)phenyl)imino)-l6-sulfanone; 1-(2-(4-(2-(5-(2-((diethyl(oxo)-l6-sulfaneylidene)amino)-6-fluorophenyl)-4,5-dihydroisoxazol-3-yl)thiazol-4-yl)piperidin-1-yl)-2-oxoethyl)-3-(trifluoromethyl)pyridin-2(1H)-one; ((3-fluoro-2-(3-(2-(1-(2-((6-methoxypyrimidin-4-yl)oxy)acetyl) piperidin-4-yl)thiazol-4-yl)-4,5-dihydroisoxazol-5-yl) phenyl)imino)dimethyl-l6-sulfanone; ((2-(3-(2-(1-(2-(3,5-bis(trifluoromethyl)-1H-pyrazol-1-yl)acetyl)piperidin-4-yl) thiazol-4-yl)-4,5-dihydroisoxazol-5-yl)-3-fluorophenyl) imino)diisobutyl-l6-sulfanone; ((3-fluoro-2-(3-(2-(1-(2-(5- methyl-3-(trifluoromethyl)-1H-pyrazol-1-yl)acetyl)piperidin-4-yl)thiazol-4-yl)-4,5-dihydroisoxazol-5-yl)phenyl)imino)diisobutyl-l6-sulfanone; ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)diisobutyl-l6-sulfanone; ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diisobutyl-l6-sulfanone; ((2-(3-(2-(1-(2-(4-chloro-1H-pyrazol-1-yl)acetyl)piperidin-4-yl)thiazol-4-yl)-4,5-dihydroisoxazol-5-yl)-3-fluorophenyl)imino)diisobutyl-l6-sulfanone; ((3-fluoro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)diisobutyl-l6-sulfanone; ((2-(3-(2-(1-(2-(2H-indazol-2-yl)acetyl)piperidin-4-yl)thiazol-4-yl)-4,5-dihydroisoxazol-5-yl)-3-fluorophenyl)imino)diisobutyl-l6-sulfanone; ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diisobutyl-l6-sulfanone; ((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diisobutyl-l6-sulfanone; ((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diisobutyl-l6-sulfanone; ((3-fluoro-2-(3-(2-(1-(2-((2-(trifluoromethyl)pyridin-3-yl)oxy)acetyl)piperidin-4-yl)thiazol-4-yl)-4,5-dihydroisoxazol-5-yl)phenyl)imino)dimethyl-l6-sulfanone; ((2-(3-(2-(1-(2-(1H-pyrazol-1-yl)acetyl)piperidin-4-yl)thiazol-4-yl)-4,5-dihydroisoxazol-5-yl)-3-chlorophenyl)imino)(ethyl)(isopropyl)-l6-sulfanone; ((3-chloro-2-(3-(2-(1-(2-(3-(trifluoromethyl)-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone; ((3-chloro-2-(3-(2-(1-(2-((6-methyl-3-(trifluoromethyl)pyridin-2-yl)oxy)acetyl)piperidin-4-yl)thiazol-4-yl)-4,5-dihydroisoxazol-5-yl)phenyl)imino)(ethyl)(isopropyl)-l6-sulfanone; ((3-chloro-2-(3-(2-(1-(2-(4-chloro-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone; ((3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone; 1-(2-(4-(4-(5-(2-chloro-6-((ethyl(isopropyl)(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one and ((3-chloro-2-(3-(2-(1-(2-(4-chloro-3,5-dimethyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone.

In one embodiment, the present invention provides a process for the preparation compounds of formula (I).

In another embodiment, the present invention provides a process for preparing compound of formula (I), wherein the process comprising following steps:

a) converting a compound of formula (IX) to a compound of formula (VIII) according to the reaction scheme as depicted below:

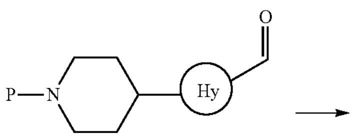

(IX)

-continued

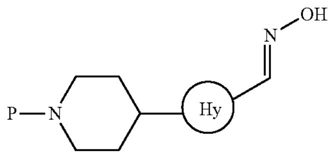

(VIII)

b) reacting compound of formula (VIII) with a compound of formula (VII) to obtain a compound of formula (VI) according to the reaction scheme as depicted below:

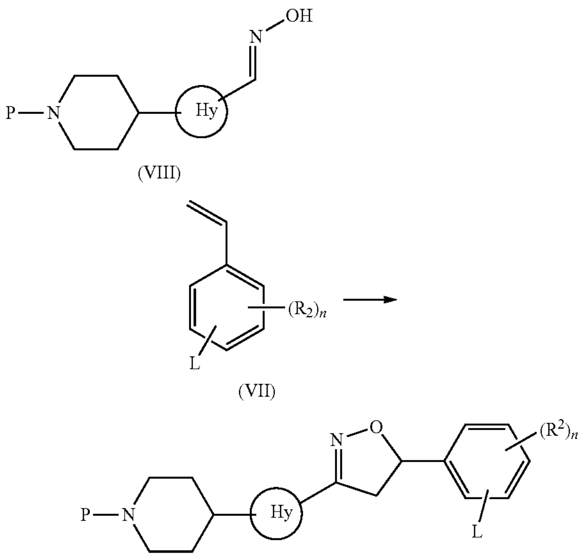

(VIII)

(VII)

(VI)

c) converting compound of formula (VI) to compound of formula (IV) according to the reaction scheme as depicted below:

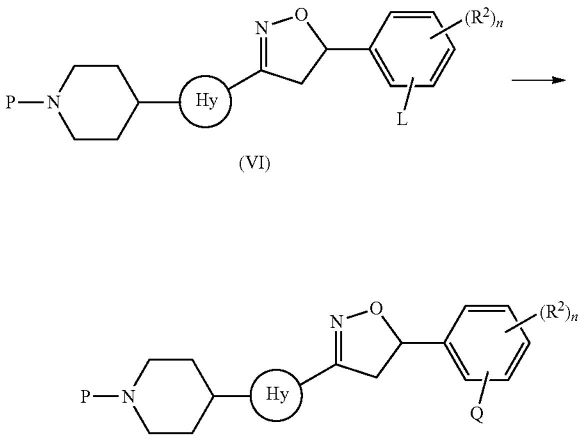

(VI)

(IV)

d) converting compound of formula (IV) to compound of formula (III) according to the reaction scheme as depicted below:

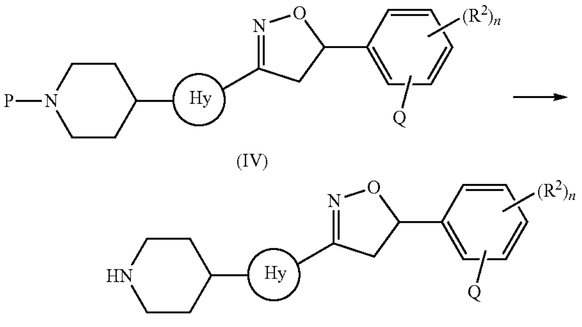

(IV)

(III)

e) reacting compound of formula (III) with compound of formula (II) to obtain a compound of formula (I) according to the reaction scheme as depicted below:

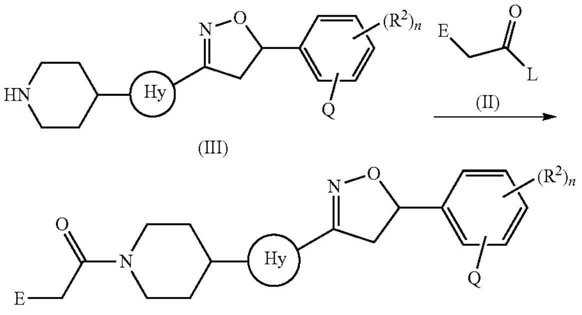

(III)

(II)

(I)

wherein in the above reaction schemes, P is protecting group, L is leaving group and Q, E, Hy $R^2$ and n are as defined above.

In an embodiment, compound of formula (VI) is reacted with compound of formula (V) to obtain compound of formula (IV) according to the reaction scheme as depicted below:

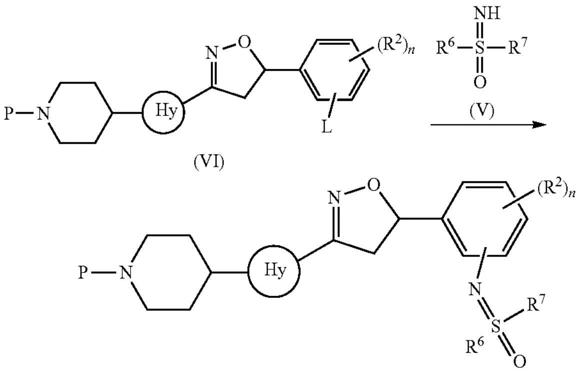

(VI)

(V)

(IV)

In another embodiment, compound of formula (VI) is reacted with compound of formula (V) to obtain compound of formula (IVa) followed by conversion of compound of formula (IVa) to (IV) according to the reaction scheme as depicted below:

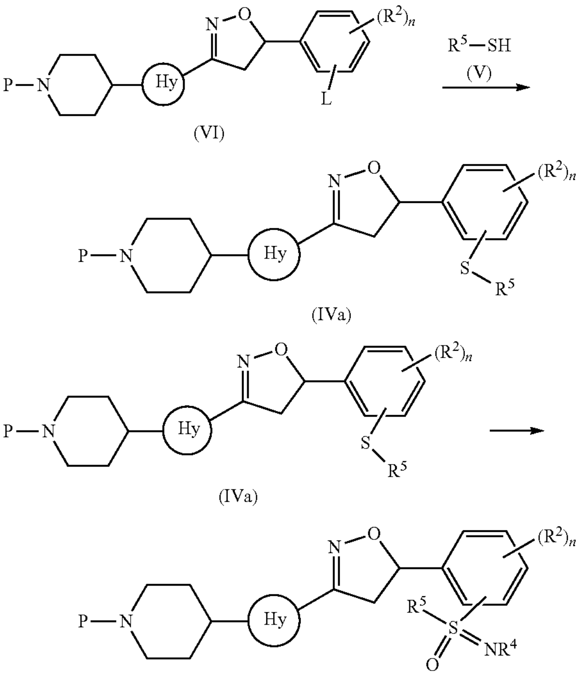

(VI)

(V)

(IVa)

(IVa)

(IV)

In an embodiment, compound of formula (IV) is converted to compound of formula (III) according to the reaction scheme as depicted below:

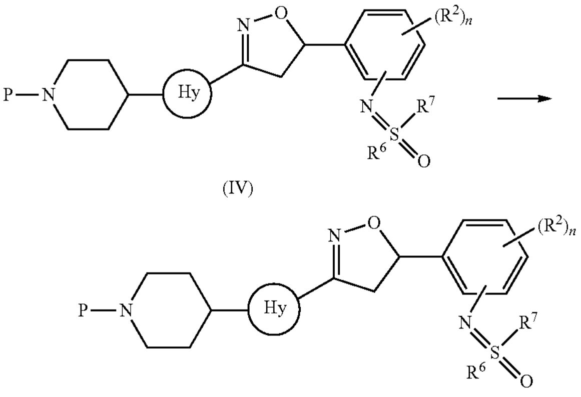

(IV)

(III)

In another embodiment, compound of formula (IV) is converted to compound of formula (III) according to the reaction scheme as depicted below:

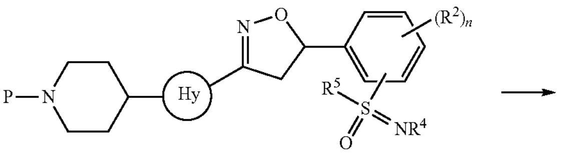

(IV)

-continued

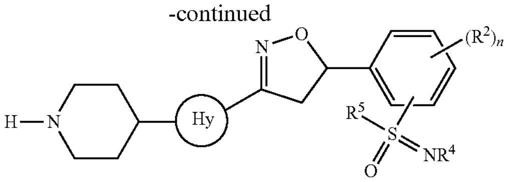

(III)

In an embodiment, compound of formula (III) is converted to compound of formula (I) by reacting compound of formula (III) with compound of formula (II) according to the reaction scheme as depicted below:

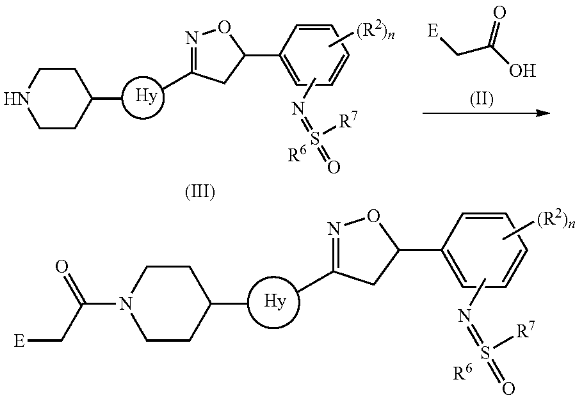

(I)

In another embodiment, compound of formula (III) is converted to compound of formula (I) by reacting compound of formula (III) with compound of formula (II) according to the reaction scheme as depicted below:

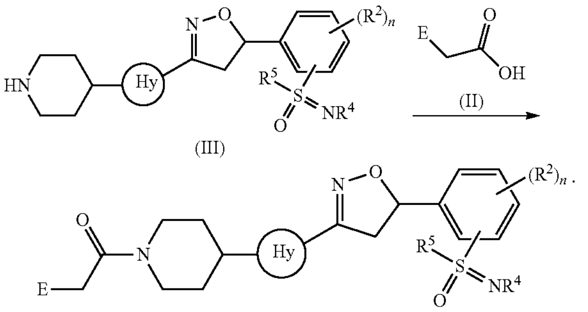

(I)

In one embodiment, a compound of formula (I)

Formula (T)

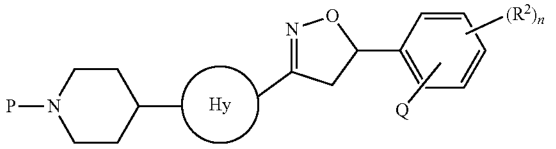

wherein,

P is selected from the group consisting of hydrogen and —C(O)OC$_1$-C$_6$ alkyl; Hy, Q, $R^2$ and n are as defined above.

The compounds of formula (I) can be prepared by one or more of the following methods and variations as described in schemes 1-17.

The definitions of $R^2$, A, E, Q, $W^1$ and n in the schemes below are as defined herein before in the description unless otherwise noted.

Scheme 1

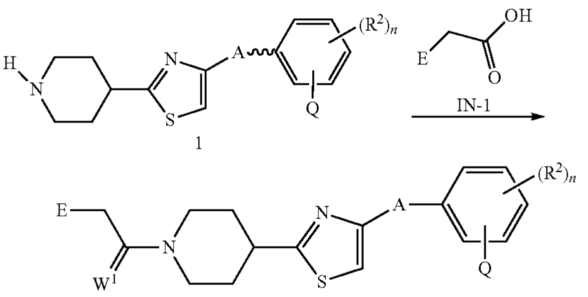

I

As shown in scheme 1, a compound of formula (I) involves coupling of an acid of formula IN-1 with an amine of Formula 1 (or its acid salt) in the presence of a dehydrative coupling reagent such as dicyclohexylcarbodiimide (DCC), 1-(3-dimethylaminopropyl)-3-ethylcarbodiimide hydrochloride (EDC) O-benzotriazol-1-yl-tetramethyluronium hexafluoro-phosphate (HBTU), or 1-[Bis(dimethylamino)methylene]-1H-1,2,3-triazolo[4,5-b]pyridinium 3-oxide hexafluorophosphate (HATU). Polymer-supported reagents useful for the purpose include polymer-bound cyclohexylcarbodiimide. These reactions can typically be carried out at 0-40° C. in a solvent such as dichloromethane, acetonitrile or dimethylformamide in the presence of a base such as triethylamine or diisopropylethylamine.

In the subsequent step, amides of formula (I) wherein $W^1$ is O can be converted to thioamides of formula (I) wherein $W^1$ is S using a variety of standard thiating reagents such as phosphorus pentasulfide or 2,4-bis(4-methoxyphenyl)-1,3-dithia-2, 4-diphosphetane-2,4-disulfide (Lawesson's reagent).

Scheme 2

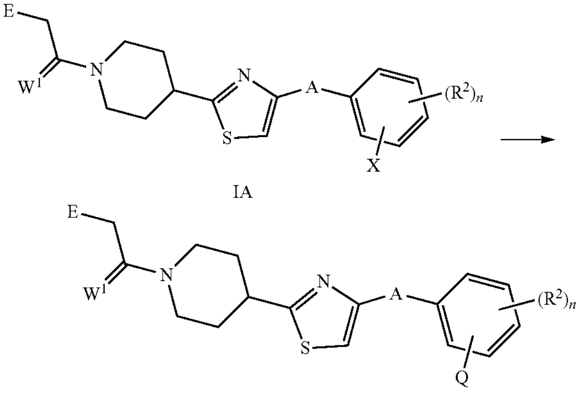

I

-continued

X = Cl, Br, F, 2-$R^5$

Alternatively, the compound of the formula (I) can be prepared by converting the "X" following the schemes 6, 7 and 8.

Scheme 3

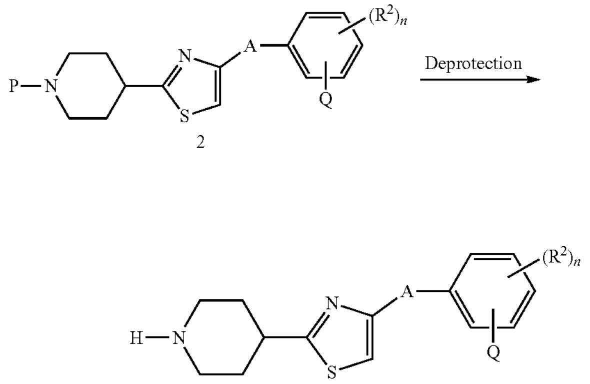

2

1

The compound of Formula 1 can be prepared from the protected amine compound of Formula 2 where P is an amine-protecting group as shown in Scheme 3.

The compound of the Formula 2 can be converted to the compound of the Formula 1 by suitable methods for removing protecting groups described in the literature (Protective Groups in Organic Synthesis; Theodora W. Greene, Peter G. M. Wuts; Wiley-Interscience; Third Edition; 1999; 494-653).

For example, tert-Butoxycarbonyl and benzyloxycarbonyl protecting groups can be removed in an acidic medium (for example with hydrochloric acid or trifluoroacetic acid). Acetyl protecting groups can be removed under basic conditions (for example with potassium carbonate or cesium carbonate). Benzylic protecting groups can be removed hydrogenolytically with hydrogen in the presence of a catalyst (for example palladium on activated carbon).

After completion of the reaction, the compound of Formula 1 can be separated from the reaction mixture by one of the customary separation techniques. If necessary, the compound can be purified by recrystallization or chromatography, or can, if desired, also be used in the next step without prior purification. It is also possible to isolate the compound of Formula 1 as a salt, for example as a salt of hydrochloric acid or of trifluoroacetic acid.

Scheme 4

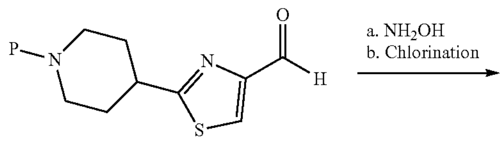

3

-continued

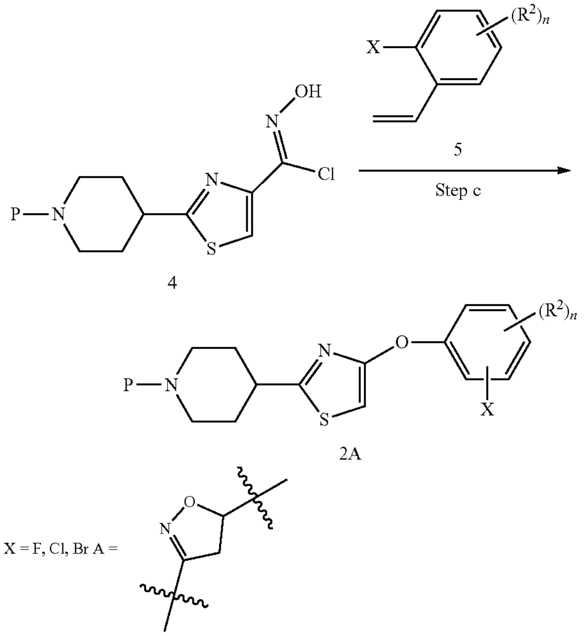

5

4

2A

X = F, Cl, Br A =

A compound of Formula 4 can be obtained by condensation of an aldehyde of Formula 3 with hydroxylamine and subsequent chlorination (see, for example, WO05/0040159, WO08/013622 and Synthesis, 1987, 11, 998-1001).

In the process, the aldehyde of Formula 3 and hydroxylamine are first reacted. The corresponding oxime is subsequently chlorinated in the presence of a suitable chlorinating agent. Preferred chlorinating reagents are N-chlorosuccinimide, NaOCl, HClO and chlorine. After step (a), the reaction mixture can be worked up by customary methods or converted further directly in step (b).

The step (a) can be performed using one or more diluents preferably with protic solvents, for example ethanol, as the solvent are used preferentially. After the formation of the corresponding oxime, the reaction mixture is diluted in step (b) with a further solvent, for example tetrahydrofuran, and then aqueous sodium hypochlorite is added. The chlorination can likewise be effected with the aid of N-chlorosuccinimide in N,N-dimethyl formamide or ethyl acetate. The workup can be carried out by customary methods. The compounds can be used in the next step without prior purification.

The alkene of Formula 5 are commercially available or can be prepared from commercially available precursors by methods described in the literature, for example, from ketones or aldehydes by a Wittig or Horner-Wadsworth-Emmons olefination: Chem. Rev. 1989, 89, 863-927 and *Julia* olefination: Tetrahedron Lett., 1973, 14, 4833-4836; Peterson olefination: J. Org. Chem. 1968, 33, 780.

The compound of Formula 2A (wherein A is isoxazoline) can be obtained from an alkene of the Formula 5 and the compound of Formula 4 by a cycloaddition reaction (see, for example, WO08/013622 and Synthesis, 1987, 11, 998-1001).

The step (c) can be performed in the presence of a suitable base. Preferred bases are tertiary amines (e.g. triethylamine), and alkali metal or alkaline earth metal carbonates (for example potassium or sodium carbonate), hydrogen carbonates and phosphates.

The step (c) can be preferably performed using one or more diluents. In the performance of the process, inert organic solvents are preferred options, for example, toluene and ethyl acetate. Water is likewise a suitable solvent.

The workup can be carried out by customary methods. If necessary, the compounds are purified by recrystallization or chromatography.

Scheme 5

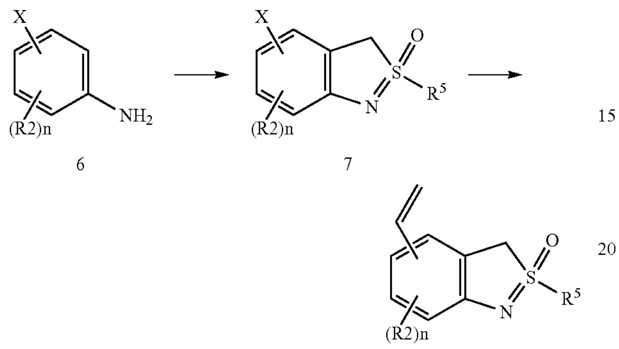

6 7

5A

X = F, Cl, Br

Certain styrenes of the Formula 5A can be prepared by following the procedure described in Adv. Synth. Catal. 2016, 358, 1-6 (Bolm et al) (scheme 5). Typical procedure involves in-situ formation of dimethylsulfilimines by reacting aniline of Formula 6 with a mixture of dimethyl sulfoxide (DMSO) and phosphorus pentoxide. The subsequent addition of sodium hydroxide afforded benzyl methyl sulfide, which in an intramolecular oxidative sulfur imidations with N-chlorosuccinimide led to benzo[c]isothiazoles, which were subsequently oxidized with potassium permanganate (KMnO4) to give the compound benzo[c]isothiazole 2-oxide of Formula 7.

Further, the compound of Formula 7 can be converted into styrene of Formula 5A by treating with pinacol vinylboronate or vinylboronate. A range of bases, common palladium sources and ligands can be used for the conversion and to obtain the selectivity.

Scheme 6

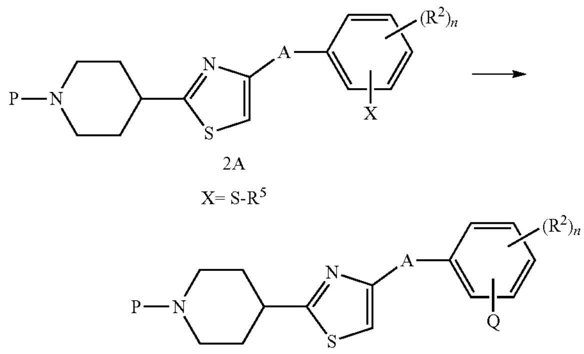

2A

X= S-$R^5$

2

General process for the preparation of compound of Formula 2 involves oxidation of sulfide Formula 2A into sulfoxide and subsequent transformation into sulfoximine.

For the conversion of a thioether into a sulfoxide, many methods are available (see e.g.: a) M. H. Ali, W. C. Stevens, *Synthesis* 1997, 764; b) I. Fernandez, N. Khiar, *Chem. Rev.* 2003, 103, 3651). Particularly suitable for the preparation of sulfoxide compounds, is the use of periodic acid/iron (III) chloride. For the transformation of sulfoxide into sulfoximine various conditions are known to the person skilled in the art.

These procedures provides the synthesis of either free ($R^5$=H) or substituted ($R^5$≠H) sulfoximine. Free sulfoximines ($R^2$=H) can be further functionalized by various general methods, including the following specific transformations:

a) Alkylation (see e.g.: C. R. Johnson, *J. Org. Chem.* 1993, 58, 1922-1923);

b) Acylation (see e.g.: a) C. P. R. Hackenberger, G. Raabe, C. Bolm, *Chem Europ. J.* 2004, 10, 2942-2952; b) C. Bolm, C. P. R. Hackenberger, O. Simic, M. Verrucci, D. Müller, F. Bienewald, *Synthesis* 2002, 7, 879-887; c) C. Bolm, G. Moll, J. D. Kahmann, *Chem. Europ. J.* 2001, 7, 1118-1128);

c) Arylation (see e.g.: a) C. Bolm, J. P. Hildebrand, *Tetrahedron Lett.* 1998, 39, 5731-5734; b) C. Bolm, J. P. Hildebrand, *J. Org. Chem.* 2000, 65, 169-175; c) C. Bolm, J. P. Hildebrand, J. Rudolph, *Synthesis* 2000, 7, 911-913; d) Y. C. Gae, H. Okamura, C. Bolm, *J. Org. Chem.* 2005, 70, 2346-2349);

d) Reaction with isocyanates/isothiocyanates (see e.g.: a) V. J. Bauer, W. J. Fanshawe, S. R. Safir, *J. Org. Chem.* 1966, 31, 3440-3441; b) C. R. Johnson, M. Haake, C. W. Schroeck, *J. Am. Chem. Soc.* 1970, 92, 6594-6598; e) Reaction with sulphonyl chlorides (see e.g.: a) D. J. Cram, J. Day, D. R. Rayner, D. MvonSchriltz, D. J. Duchamp, D. C. Garwood. *J. Am. Chem. Soc.* 1970, 92, 7369-7384), b) C. R. Johnson, H. G. Corkins, *J. Org. Chem.* 1978, 43, 4136-4140; c) D. Craig, N. J. Geach, C. J. Pearson, A. M. Z. Slawin, A. J. P. White, D. J. Williams, *Tetrahedron* 1995, 51, 6071-6098);

f) Reaction with chloroformates or anhydrides (see e.g.: a) D. J. Cram, J. Day, D. R. Rayner, D. M von Schriltz, D. J. Duchamp, D. C Garwood. *J. Am. Chem. Soc.* 1970, 92, 7369-7384); b) S. G. Pyne, Z. Dong, B. W. Skelton, A. H. Allan, *J. Chem. Soc. Chem. Commun.* 1994, 6, 751-752; c) C. R. Johnson, H. G. Corkins, *J. Org. Chem.* 1978, 43, 4136-4140; d) Y. C. Gae, H. Okamura, C. Bolm, *J. Org. Chem.* 2005, 2346-2349); and g) Silylation: (see e.g.: A. J. Pearson, S. L. Blystone, H. Nar, A. A. Pinkerton, B. A. Roden, J. Yoon, *J. Am. Chem. Soc.* 1989, 111, 134-144).

The compound of formula (I), wherein

Q= 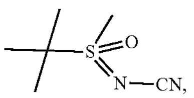

can be prepared as described in Bolm et al. (Org. Lett. 2007, 9, 3809-3811) via direct imination of a thioether (intermediate 2A) with cyanamide by reaction with an halogenating agent, for example N-bromo- or N-chlorosuccinimide, tert-butyl hypochlorite or iodine in the presence of cyanamide and a base, for example potassium or sodium tert-butoxide, in an organic solvent, for example, methanol, tetrahydrofuran (THF) or acetonitrile. The reaction usually takes place within 1 to 72 hours. Preferred reaction temperatures are between 0° C. and 50° C.

Alternatively, the imination can be achieved as described in Bolm et al. (*Org. Lett.* 2007, 9, 2951-2954), by using phenyliodo diacetate [$PhI(OAc)_2$] and cyanamide in an organic solvent, for example acetonitrile or tetrahydrofuran (THF). The reaction usually takes place within 1 to 72 hours. Further, oxidation can be achieved using a peroxycarboxylic acid as oxidizing agent, for example, meta-chloroperoxy-benzoic acid (mCPBA), optionally in the presence of a base, for example, potassium carbonate, in an organic solvent, for example, ethanol, methanol, dichloromethane or chloroform. The reaction usually takes place within 1 to 72 hours. Alternatively, other common oxidizing agents may be used to achieve this transformation, for example, hydrogen peroxide, tert-butyl hydroperoxide, sodium hypochlorite, sodium iodate, sodium periodate, potassium permanganate, ruthenium tetroxide, potassium peroxymonosulfate (oxone) or dimethyldioxirane.

The compound of formula (I), wherein

Q= 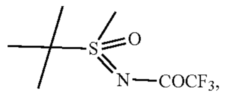

can be obtained by imination of intermediates as described in Bolm. et al. (*Org. Lett.* 2004, 6, 1305-1307), by reacting a thioether (intermediates 2A) with trifluoroacetamide, phenyliodo diacetate [$PhI(OAc)_2$], rhodium acetate dimer [$Rh_2(OAc)_4$] and MgO in an organic solvent, for example, dichloromethane. The reaction usually takes place within 1 to 72 hours.

The cleavage of the trifluoroacetamide to form the compound of formula (I), wherein $R^5$=H, can be achieved as described in Bolm. et al. (*Org. Lett.* 2004, 6, 1305-1307), using a suitable base, for example, potassium carbonate, in an organic solvent, for example, methanol. The reaction usually takes place within 1 to 72 hours. Preferred reaction temperatures are between 0° C. and 50° C.

Alternatively, the compound of formula (I), wherein

Q= 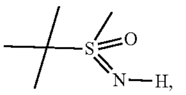

can be prepared by the imination of intermediates 2A using other electrophilic nitrogen sources, for example, tert-butyl 3-(4-cyano-phenyl)-oxaziridine-2-carboxylate (followed by cleavage of the boc-protecting group), O-mesityl sulfonyl hydroxylamine (MSH), or hydrazoic azid.

The compound of formula (I), wherein

Q= 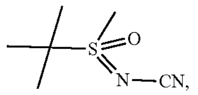

the cyanation of sulfinimides or sulfonimides can be achieved as described in Bolm et al. (*Org. Lett.* 2007, 9, 2951-2954), by reacting the starting material with cyanogen bromide, optionally in the presence of 4-dimethylaminopyridine (DMAP) and optionally a base, for example, triethylamine, in an organic solvent, for example, dichloromethane.

The reaction usually takes place within 1 to 72 hours. Preferred reaction temperatures are between 0° C. and 50° C.

Scheme 7

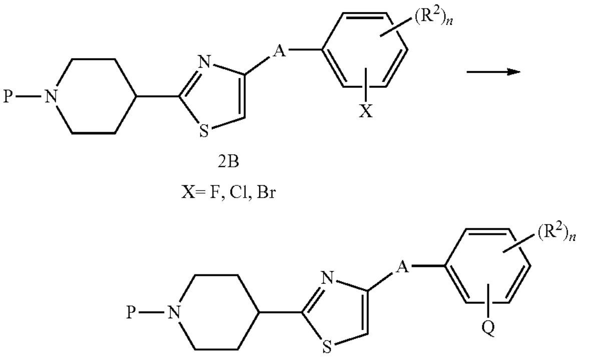

2B

X= F, Cl, Br

2

The coupling reactions of halogen compound of Formula 2B, with N-linked sulfoximine can be conducted as mentioned in Scheme 7. The reaction can be preferably carried out with a palladium or palladium derived catalyst and a suitable ligand, for example, tris(dibenzylideneacetone)dipalladium(0) and 2-dicyclohexylphosphino-2',4',6'-triisopropylbiphenyl (X-phos) or dichlorobis(tri-o-tolylphosphine)-palladium(II) and 2,2'-bis(diphenylphosphino)-1,1'-binaphthyl (BINAP), in the presence of a base, for example, cesium carbonate, in 1,4-dioxane or toluene at 40 to 150° C. Refer WO2015007669.

Scheme 8

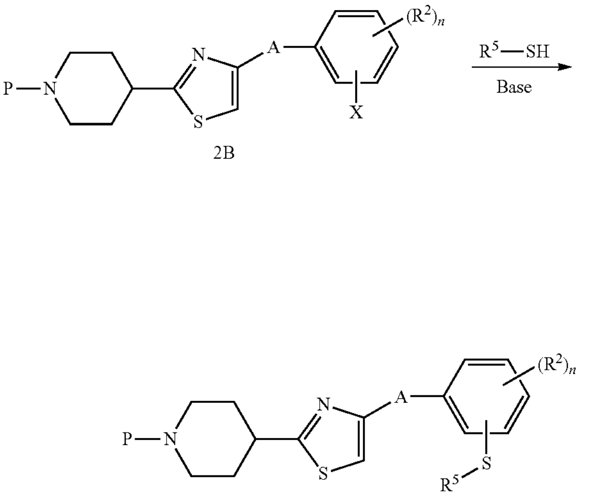

2B

2A

X = F, Cl, Br

The compound of Formula 2A can be prepared by the reaction of a halogen compound of Formula 2B with a thiol of Formula $R^5$-SH, optionally in the presence of a base, such as cesium carbonate, potassium carbonate or sodium carbonate, at an elevated temperature.

Scheme 9

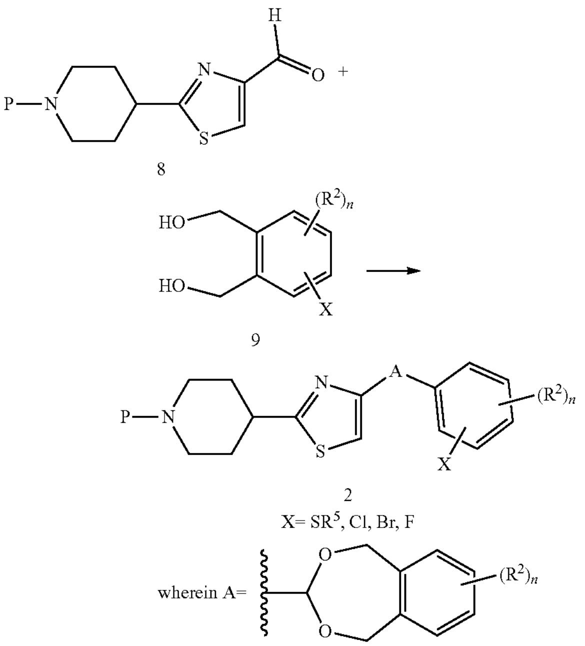

8

9

2

X= $SR^5$, Cl, Br, F wherein A=

As shown in the Scheme 9, the compound of Formula 2 can be prepared by treating the compound of Formula 8 with a compound of the formula 9 in the presence of an acid or a Lewis acid, preferably in the presence of an acid.

Examples of the acid which can be used in this step include inorganic acids such as hydrochloric acid, hydrobromic acid, sulfuric acid and the like, organic acids such as acetic acid, trifluoroacetic acid, p-toluene sulfonic acid, trifluoromethanesulfonic acid and the like. Examples of the Lewis acid which can be used in this step include zinc chloride, aluminum chloride, tin chloride, boron trichloride, boron trifluoride, trimethylsilyltrifluoromethane sulfonate and the like.

The solvent which can be used in this step may be any solvent which does not inhibit the progress of this reaction and examples thereof include nitriles such as acetonitrile; ethers such as diethyl ether, diisopropyl ether, tetrahydrofuran, dioxane, monoglyme, diglyme; dichloromethane, dichloroethane, halogenated hydrocarbons such as chloroform, carbon tetrachloride and tetrachloroethane; aromatic hydrocarbons such as benzene, chlorobenzene, nitrobenzene and toluene; amides such as N,N-dimethylformamide and N,N-dimethylacetamide; imidazolinones such as 1,3-dimethyl-2-imidazolinone; sulfur compounds such as dimethylsulfoxide and the like can be used, and mixed solvents thereof can also be used.

The reaction temperature may be selected from the range of −20° C. to the boiling point of the inert solvent to be used, preferably in the range of 0° C. to 150° C.

The reaction time varies depending on the reaction temperature, the reaction substrate, the reaction amount and the like, but is usually from 10 minutes to 48 hours.

Scheme 10

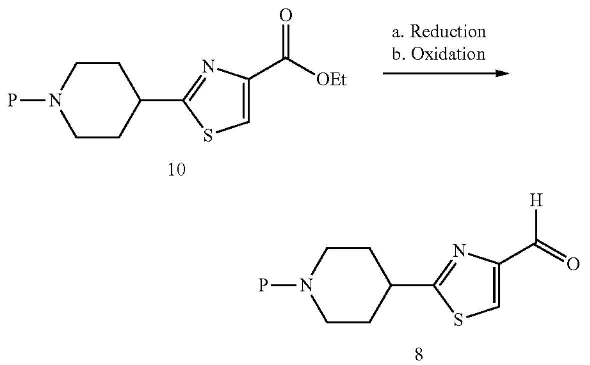

10

8

As shown in Scheme 10, synthesis of the compound of Formula 8 involves (step a) a simple one-pot aromatic ethyl ester reduction into the corresponding alcohol using $NaBH_4$-MeOH system or any other appropriate reduction system, basically known from literature. The reduction is achieved by the method explained for instance in the *ARKIVOC* 2006, 128-133, involving the reduction of aromatic ethyl esters within 15-60 minutes after refluxing in tetrahydrofuran (THF).

The corresponding alcohol was oxidized subsequently to an aldehyde of Formula 8 (Scheme 10, Step b) using oxidizing agents like $MnO_2$, Dess-Martin periodinane, IBX, TEMPO. Preferred solvents for the conversion can be acetonitrile or dichloromethane. For references, see Dess, D. B.; Martin, J. C. *J. Am. Chem. Soc.* 1991, 113, 7277 Quesada, E.; Taylor, R. J. K., *Tetrahedron Lett.* 2005, 46, 6473-6476. Naik, N.; Braslau, R. *Tetrahedron* 1998, 54, 667).

Scheme 11

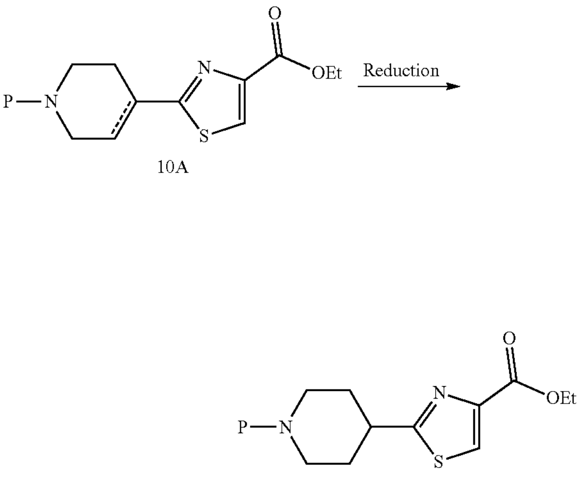

10A

10

The reduction of the endocyclic double bond can be carried out using catalytic hydrogenation to give a compound of Formula 10. Pd/C can be the preferred catalyst. For references, see Sarah Sulzer-Mosse et al *Bioorganic & Medicinal Chemistry* 2015, 23, 2129-2138.

Scheme 12

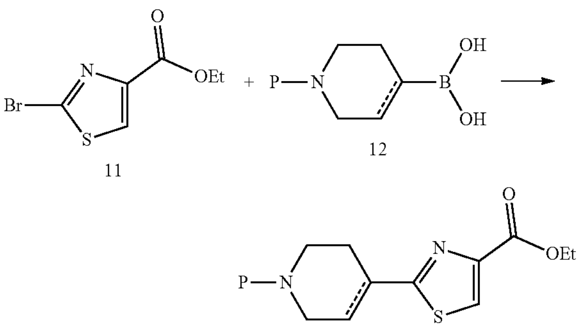

11 12 10A

Syntheses of a compound of Formula 10A can be carried out using the Suzuki reaction involving Pd-catalyzed cross-coupling of an iodide or bromide of Formula 11 with a boronic acid or ester of Formula 12, as shown in Scheme 12. Many catalysts are useful for this type of transformation. A typical catalyst is tetrakis (triphenylphosphine) palladium, or bis (triphenylphosphine) palladium chloride. Solvents such as tetrahydrofuran, acetonitrile, diethyl ether and dioxane or dioxane:water mixtures are suitable. The Suzuki reaction and related coupling procedures offer many alternatives for creation of the C-G bond. For references, see C. A. Zificsak and D. J. Hlasta, *Tetrahedron* 2004, 60, 8991-9016. For a thorough review of palladium chemistry applicable to the synthesis of C-G bonds see J. J. Li and G. W. Gribble, editors, Palladium in Heterocyclic Chemistry: A Guide for the Synthetic Chemist, Elsevier: Oxford, U K, 2000. Many variations of catalyst type, base and reaction conditions are known in the art for this reaction.

Outline for preparation of acid of formula (I)N-1 is described in Scheme 13. Suitably substituted compound of Formula 13 can be obtained commercially or can be prepared from the corresponding chloro derivatives using known methods in the literature. The reagents useful for these conversions can be sulfuric acid, hydrochloric acid, sodium hydroxide. Please refer WO2007/39563 WO2014/71044, Lavecchia; Berteina-Raboin; Guillaumet, *Tetrahedron Letters,* 2004, 45, 6633-6636.

The substituted compound of Formula 13 can be further functionalized using known methods in the literature like chlorination, bromination, trifluromethylation to obtain appropriately substituted Formula 14. References for the said transformations are Zhang, Pei-Zhi et al *Tetrahedron,* 2016, 72, 3250-3255; Canibano; Rodriguez; Santos; Sanz-Tejedor; Carreno; Gonzalez; Garcia-Ruano *Synthesis,* 2001, 14, 2175-2179, WO2004/50637.

A substituted functionalized heterocyclic ring containing a pyridone-like moiety can be alkylated by reaction with an alkyl ester containing a suitable leaving group such as halogen, mesylate or tosylate, in the presence of a base such as silver carbonate ($Ag_2CO_3$) or cesium carbonate ($Cs_2CO_3$), in a polar solvent such as N,N-dimethyl formamide (DMF) or N-methyl pyrolidone (NMP), or non polar solvent such as toluene, xylene with or without heating to obtain the compound of Formula 15. Typically, mixtures of O- and N-alkylated products are obtained, and the two regio-isomeric products can be separated by means of silica gel or reverse phase chromatography. The addition of lithium salts, for example, lithium chloride (LiCl), to the reaction mixture can be employed to favor N- over O-alkylation. The obtained alkyl ester can be further hydrolyzed to the corresponding acids by heating or stirring at room temperature in the presence of a suitable base such as lithium hydroxide or sodium hydroxide in solvents like ethanol, water to obtain the novel compound of formula (I)N-1.

Scheme 13

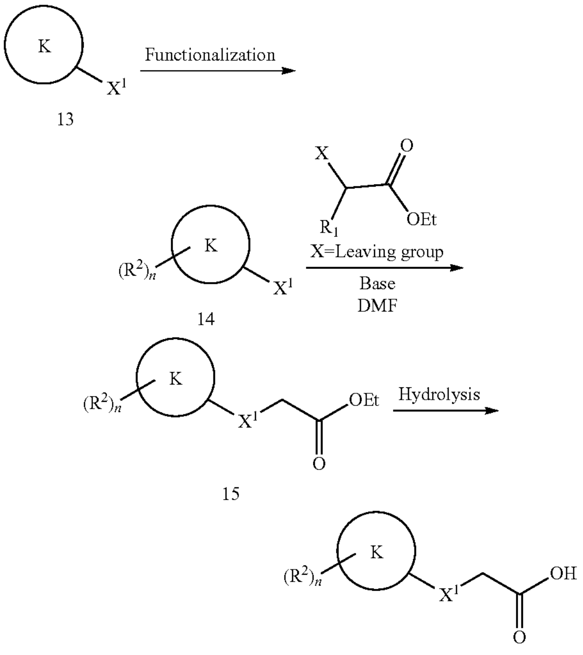

13 14 15 IN-1

Scheme 14

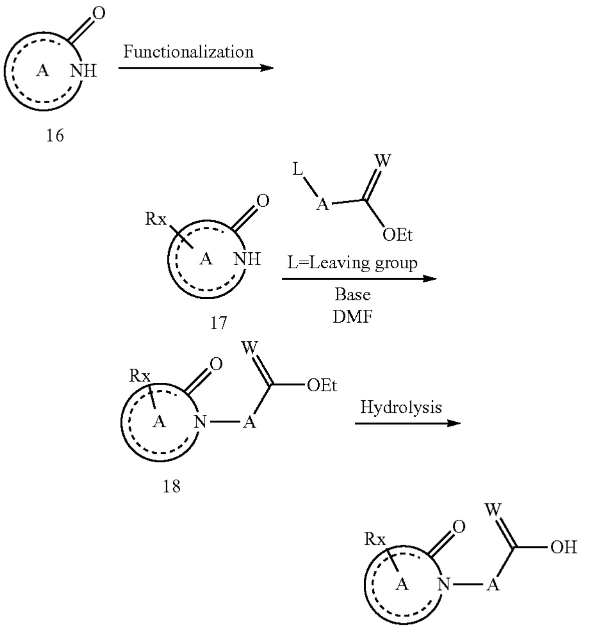

16 17 18 IN-1

Outline for the preparation of acids of formula (I)N-1 is described in Scheme 14. Suitably substituted compound of Formula 16 were sourced commercially or can be prepared from the corresponding chloro derivatives using known methods in the literature. Preferred reagents for these conversions are sulfuric acid, hydrochloric acid and sodium hydroxide. Please refer WO2007/39563 WO2014/71044 Lavecchia; Berteina-Raboin; Guillaumet, Tetrahedron Letters, 2004, vol. 45, 35, 6633-6636.

The compound of Formula 16 can be further functionalized using known methods in the literature like chlorionation, bromination, trifluromethylation to obtain appropriately substituted heterocyclic ring like pyridone (Formula 17). References for the said transformations are Zhang, Pei-Zhi et al Tetrahedron, 72(23), 3250-3255; 2016 Canibano; Rodriguez; Santos; Sanz-Tejedor; Carreno; Gonzalez; Garcia-Ruano Synthesis, 2001, 14, 2175-2179, WO2004/50637.

The substituted functionalized heterocyclic ring containing a pyridone-like moiety can be acylated by reaction with an alkyl ester containing a suitable leaving group such as halogen, mesylate or tosylate, in the presence of a base such as potassium carbonate ($K_2CO_3$) or cesium carbonate ($Cs_2CO_3$), in a polar solvent such as N,N-dimethyl formamide (DMF) or N-methyl pyrolidone (NMP), with or without heating to obtain the compound of Formula 18. Typically, mixtures of O- and N-alkylated products are obtained, and the two regio-isomeric products can be separated by means of silica gel or reverse phase chromatography. The addition of lithium salts, for example, lithium chloride (LiCl), to the reaction mixture can be employed to favor N- vs O-alkylation. The obtained alkyl ester can be further hydrolyzed to the corresponding acids by heating or stirring at room temperature in the presence of lithium hydroxide or sodium hydroxide in solvents like ethanol, water to obtain the compound of formula (I)N-1.

Scheme 15

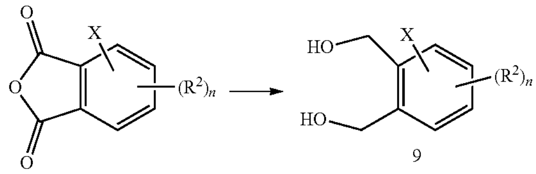

19 9

A compound of Formula 9 can be prepared by reducing the compound of Formula 19 with a reducing agent in a solvent as shown in the scheme 10. The reducing agent suitable in this step, are lithium aluminum hydride, diisobutylaluminum hydride, borane and the like. Preferred solvent that can be used in this step is tetrahydrofuran, dioxane or the like.

The reaction temperature can be selected from the range of from −20° C. to the boiling point range of the inert solvent to be used, preferably in the range of 0° C. to 100° C.

Scheme 16

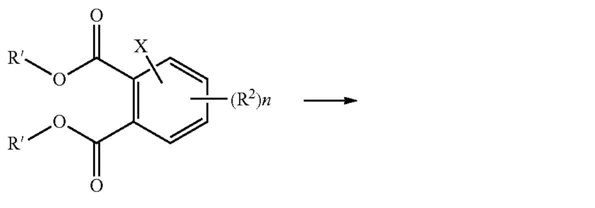

20

9

The compound of Formula 9 can also be prepared by reducing the compound of Formula 20 with a reducing agent in a solvent as shown in the scheme 16. The reducing agent suitable in this step, are lithium aluminum hydride, diisobutylaluminum hydride, borane and the like. Preferred solvent that can be used in this step is tetrahydrofuran, dioxane or the like.

The reaction temperature may be selected from the range of from −20° C. to the boiling point range of the inert solvent to be used, preferably in the range of 0° C. to 100° C.

Scheme 17

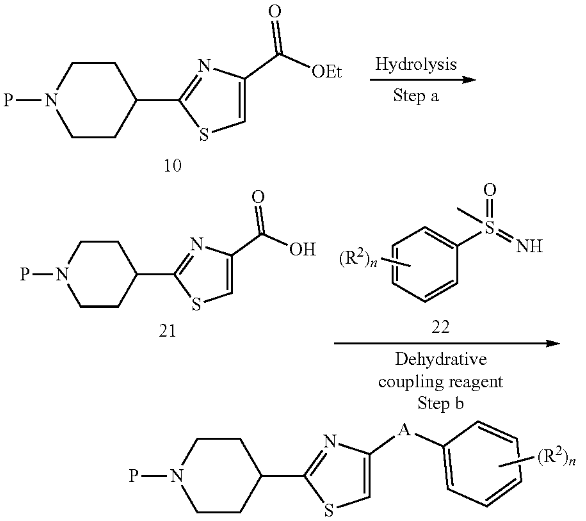

10

21 22

2C wherein A=

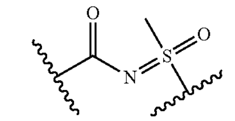

As shown in Scheme 17, a compound of the Formula 21 can be prepared by hydrolyzing the compound of Formula 10 using a suitable base. Preferred bases for the conversion are sodium hydroxide (NaOH), lithium hydroxide (LiOH). Preferred solvents for the hydrolysis conditions are water, ethanol, or tetrahydrofuran.

The compound of Formula 2C wherein (A is acyl sulfoximine moiety), involves coupling of an acid of Formula 21 with an amine of Formula 22 (or its acid salt) in the presence of a dehydrative coupling reagent such as dicyclohexylcarbodiimide (DCC), 1-(3-dimethylaminopropyl)-3-ethylcarbodiimide hydrochloride (EDC), O-benzotriazol-1-yl-tetramethyluronium hexafluoro-phosphate (HBTU), or 1-[Bis (dimethylamino)methylene]-1H-1,2,3-triazolo[4,5-b] pyridinium 3-oxid hexafluorophosphate (HATU). Polymer-supported reagents useful here include polymer-bound cyclohexylcarbodiimide. These reactions are typically carried out at 0-40° C. in a solvent such as dichloromethane, acetonitrile or dimethylformamide in the presence of a base such as triethylamine or diisopropylethylamine.

The novel and inventive compounds of the present invention, the salts, isomers, metal complexes, N-oxides and polymorphs thereof are effective in preventing against and controlling phytopathogenic micro-organisms.

An anion part of the salt in case the compound of formula (I) is cationic or capable of forming a cation can be inorganic or organic.

Alternatively, a cation part of the salt in case the compound of formula (I) is anionic or capable of forming an anion can be inorganic or organic.

Examples of inorganic anion part of the salt include but are not limited to chloride, bromide, iodide, fluoride, sulphate, phosphate, nitrate, nitrite, hydrogen carbonates and hydrogen sulphate.

Examples of organic anion part of the salt include but are not limited to formate, alkanoates, carbonates, acetates, trifluoroacetate, trichloroacetate, propionate, glycolate, thiocyanate, lactate, succinate, malate, citrates, benzoates, cinnamates, oxalates, alkylsulphates, alkylsulphonates, arylsulphonates aryldisulphonates, alkylphosphonates, arylphosphonates, aryldiphosphonates, p-toluenesulphonate, and salicylate.

Examples of inorganic cation part of the salt include but are not limited to alkali and alkaline earth metals.

Examples of organic cation part of the salt include but are not limited to pyridine, methyl amine, imidazole, benzimidazole, histidine, phosphazene, tetramethyl ammonium, tetrabutyl ammonium, choline and trimethyl amine.

Metal ions in metal complexes of the compound of formula (I) formula (I) are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period and the first to eighth transition groups. Here, the metals can be present in the various valencies that they can assume.

Compounds of the present invention may exist in more than one form, and thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term “polymorph” refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of the present invention can exhibit beneficial effects (e.g., suitability for preparation of useful formulations, improved biological performance) relative to another polymorph or a mixture of polymorphs of the same compound of the present invention. Preparation and isolation of a particular polymorph of a compound of the present invention can be achieved by methods known to those skilled in the art including, for example, crystallization using selected solvents and temperatures.

The present invention also relates to a process for preparing the compound of formula (I). The process can be as described in general schemes or example section.

The present invention also relates to a compound of formula (I) in a composition for controlling or preventing phytopathogenic micro-organisms comprising one or more agrochemicaly acceptable excipients.

The compound of formula (I) of the present invention in the composition can be an agriculturally acceptable salt, metal complex, constitutional isomer, stereo-isomer, diastereoisomer, enantiomer, chiral isomer, atropisomer, conformer, rotamer, tautomer, optical isomer, geometric isomer, polymorph, or N-oxide thereof.

The excipient may be an inert carrier or any other essential ingredient such as surfactants, additives, solid diluents and liquid diluents.

The composition of the present invention may additionally comprise at least one active compatible compound selected from fungicides, insecticides, nematicides, acaricides, biopesticides, herbicides, plant growth regulators, antibiotics, fertilisers and nutrients. The compounds used in the composition and in the combination with the compound of formula (I) are also termed as active compatible compounds.

In one embodiment biologically effective amount of compound of formula (I) ranges from 0.1% to 99% by weight with respect to the total weight of the composition, preferably ranges from 1 to 50% by weight with respect to the total weight of the composition.

The known and reported active compounds such as fungicides, insecticides, nematicides, acaricides, biopesticides, herbicides, plant growth regulators, antibiotics and nutrients can be combined with at least one compound of formula (I) of the present invention. The present invention also relates to such combinations comprising the compound of the present invention and active compatible compounds, particularly, for example, reported in WO2019155066 pages 35 to 50.

The active compatible compounds reported in WO2019155066 pages 35 to 50, are not reproduced herein for the sake of brevity and are incorporated herein by way of reference as non-limiting examples to be combined with at least one compound of formula (I) of the present invention.

The present invention relates to a combination comprising a biologically effective amount of the compound of formula (I) and at least one additional biological active compatible compound selected from fungicides, insecticides, nematicides, acaricides, biopesticides, herbicides, plant growth regulators, antibiotics, fertilizers and nutrients.

The present invention also relates to a use of the compound of formula (I) or the combination comprising the compound of formula (I) or the composition comprising the compound of formula (I) for controlling or preventing phytopathogenic micro-organisms such as fungi, stramenopiles, bacteria, insects, *nematodes*, trematodes, and mites in agricultural crops and or horticultural crops.

Particularly, the present invention also relates to a use of the compound of formula (I) or the combination or the composition for controlling or preventing phytopathogenic micro-organisms in agricultural crops and or horticulture crops.

The compound of formula (I) or the combination or the composition of the present invention may be used to treat several fungal pathogens. Non-limiting examples of pathogens of fungal diseases which can be treated in accordance with the invention include: Diseases caused by pathogens from the group of the Stramenopiles, particularly by Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;*

Diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator; Erysiphe* species, for example *Erysiphe* cichoracearu;

Diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* oder *Puccinia striiformis; Uromyces* species, for example *Uromyces appendiculatus;*

Leaf blotch diseases and leaf wilt diseases caused, for example, by *Alternaria* species, for example *Alternaria solani; Cercospora* species, for example *Cercospora beticola*; Cladiosporium species, for example Cladiosporium *cucumerinum; Cochliobolus* species, for example *Cochliobolus sativus* (conidial form: *Drechslera*, syn: *Helminthosporium*) or *Cochliobolus miyabeanus; Colletotrichum* species, for example *Colletotrichum* lindemuthanium; *Cycloconium* species, for example *Cycloconium* oleaginum; *Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii* or *Septoria lycopersici; Stagonospora* species, for example *Stagonospora nodorum; Typhula* species, for example *Typhula incarnata; Venturia* species, for example *Venturia inaequalis*; Root and stem diseases caused, for example, by *Corticium* species, for example *Corticium graminearum; Fusarium* species, for example *Fusarium oxysporum; Gaeumannomyces* species, for example *Gaeumannomyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium oryzae; Tapesia* species, for example *Tapesia acuformis; Thielaviopsis* species, for example *Thielaviopsis basicola; Ganoderma* species, for example *Ganoderma lucidum;*

Ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis*; Stagnospora species, for example Stagnospora *nodorum;*

Diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda;*

Fruit rot caused, for example, by *Aspergillus* species, for example *Aspergillus flavus; Botrytis* species, for example *Botrytis cinerea; Penicillium* species, for example *Penicillium expansum* or *Penicillium purpurogenum; Rhizopus* species, for example *Rhizopus stolonifer; Sclerotinia* species, for example *Sclerotinia sclerotiorum*; Verticilium species, for example Verticilium *alboatrum;*

Seed- and soil-borne rot and wilt diseases, and also diseases of seedlings, caused, for example, by *Alternaria* species, for example *Alternaria brassicicola; Aphanomyces* species, for example *Aphanomyces euteiches; Ascochyta* species, for example *Ascochyta lentis; Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum coccodes; Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma lingam; Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum; Typhula* species, for example *Typhula incarnata; Verticillium* species, for example *Verticillium dahliae;*

Cancers, galls and witches' broom caused, for example, by *Nectria* species, for example *Nectria galligena;*

Wilt diseases caused, for example, by *Monilinia* species, for example *Monilinia laxa;*

Deformations of leaves, flowers and fruits caused, for example, by *Exobasidium* species, for example *Exobasidium vexans; Taphrina* species, for example *Taphrina deformans;*

Degenerative diseases in woody plants, caused, for example, by Esca species, for example *Phaeomoniella chla-*

*mydospora, Phaeoacremonium aleophilum* or *Fomitiporia mediterranea; Ganoderma* species, for example *Ganoderma boninense;*

Diseases of flowers and seeds caused, for example, by *Botrytis* species, for example *Botrytis cinerea;*

Diseases of plant tubers caused, for example, by *Rhizoctonia* species, for example *Rhizoctonia solani; Helminthosporium* species, for example *Helminthosporium solani;*

Diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Ralstonia* species, for example *Ralstonia solanacearum;*

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. caulivora), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* southern blight (*Sclerotinia rolfsii*), *thielaviopsis* root rot (*Thielaviopsis basicola*).

In a preferred embodiment, the compound of formula (I) of the present invention can be used to control crop diseases which includes grape downy mildew (*Plasmopara viticola*), late Blight on potato & tomato (*Phytophthora infestans*), durian/citrus stem canker (*Phytophthora palmivora*), tobacco black shank (*Phytophthora nicotianae*), peppers foot rot (*Phytophthora capsici*), cucurbits downy mildew (*Pseudoperonospora cubensis*), hops downy mildew (*Pseudoperonospora humuli*), onion/Leek/shallots (*peronospora* destructor) cabbage downy mildew (*Peronospora parasitica*), poppy downy mildew (*Peronospora arborescens*) lettuce downy mildew (*Bremia lactucae*).

Plants which can be treated in accordance with the invention include the following: Rosaceae sp (for example pome fruits such as apples, pears, apricots, cherries, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Vitaceae sp. (for example grapes); Solanaceae sp. (for example tomatoes, peppers), Liliaceae sp., Asteraceae sp. (for example lettuce), *Umbelliferae* sp., *Cruciferae* sp., Chenopodiaceae sp., Cucurbitaceae sp. (for example cucumber), Alliaceae sp. (for example leek, onion), Papilionaceae sp. (for example peas); major crop plants, such as Poaceae/Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), Fabacae sp. (for example bean, peanuts), Papilionaceae sp. (for example soya bean), Solanaceae sp. (for example potatoes), Chenopodiaceae sp. (for example sugar beet, fodder beet, swiss chard, beetroot); Malvaceae (for example cotton); useful plants and ornamental plants for gardens and wooded areas; and genetically modified varieties of each of these plants.

The agricultural or horticulture crops are wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Particularly, the agriculture or horticulture crops are cereals, corn, rice, soybean and other leguminous plants, fruits and fruit trees, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers, other vegetables and ornamentals.

The present invention further relates to the use of the compound of formula (I) or the combination comprising the compound of formula (I) or the composition comprising the compound of formula (I) for treating seeds with the purpose of protecting the seeds, the germinating plants and emerged seedlings against phytopathogenic micro-organisms.

The present invention further relates to seeds which have been treated with the compound of formula (I) or the combination comprising the compound of formula (I) or the composition comprising the compound of formula (I) for protection from phytopathogenic micro-organisms.

The present invention also relates to a method of controlling or preventing infestation of useful plants by phytopathogenic micro-organisms in agricultural crops and or horticultural crops wherein the compound of formula (I) or the combination comprising the compound of formula (I) or the composition comprising the compound of formula (I), is applied to the plants, to parts thereof or the locus thereof. The effective amount of compound of formula (I) ranges from 1 to 500 gai per hectare.

Also, the present invention relates to the compound of formula (I) or the combination comprising the compound of formula (I) or the composition comprising the compound of formula (I) applied to a plant, plant parts or locus thereof.

The present invention furthermore includes a method for treating seed, particularly seeds (dormant, primed, pregerminated or even with emerged roots and leaves) treated with the compound of formula (I) or the combination comprising the compound of formula (I) or the composition comprising the compound of formula (I). In these methods, the compound of formula (I) or the combination comprising the compound of formula (I) or the composition comprising the compound of formula (I) is applied to the seeds of plants for controlling or preventing infestation of useful plants by phytopathogenic micro-organisms in agricultural and or horticultural corps.

It is also desirable to optimize the amount of the active ingredient used so as to provide the best possible protection for the plants, the plant parts, or the seeds, the germinating plants and emerged seedlings from attack by phytopathogenic micro-organisms, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

One of the advantages of the present invention is that the treatment of the seeds with the compound of formula (I) or the combination comprising the compound of formula (I) or the composition comprising the compound of formula (I) not only protects the seed itself, but also the resulting plants after emergence, from animal pests and/or phytopathogenic harmful micro-organisms. In this way, the immediate treatment of the crop at the time of sowing or shortly thereafter protect plants as well as seeds prior to sowing. It is likewise considered to be advantageous that the compound of formula (I) or the combination comprising the compound of formula (I) or the composition comprising the compound of formula (I) can be used especially also for transgenic seed, in which case the plant which grows from this seed is capable of expressing a protein which acts against pests, herbicidal damage or abiotic stress. The treatment of such seeds with the compound of formula (I) or the combination comprising the compound of formula (I) or the composition comprising the compound of formula (I), for example an insecticidal protein, can result in control of certain pests. Surprisingly, a further enhanced effect can be observed in this case, which additionally increases the effectiveness for protection against attack by pests, micro-organisms, weeds or abiotic stress.

The compound of formula (I) or the combination comprising the compound of formula (I) or the composition comprising the compound of formula (I) is suitable for the protection of seeds of any plant variety which is used in agriculture, in the greenhouse, in forests or in horticulture. More particularly, the seed is that of cereals (such as wheat, barley, rye, millet and oats), oilseed rape, maize, cotton, soybeen, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the compound of formula (I) or the combination comprising the compound of formula (I) or the composition comprising the compound of formula (I), is of particular significance. This refers to the seed of plants containing at least one heterologous gene which allows the expression of a polypeptide or protein, e.g. having insecticidal properties. These heterologous genes in transgenic seeds may originate, for example, from micro-organisms of the species of *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm.

Particularly preferably, the heterologous genes originate from *Bacillus thuringiensis.*

In the context of the present invention, the compound of formula (I) or the combination comprising the compound of formula (I) or the composition comprising the compound of formula (I) is applied to seeds. Particularly, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the compound of formula (I) or the combination comprising the compound of formula (I) or the composition comprising the compound of formula (I) is applied to the seed and/or the amount of further additives is selected such that the germination of the seed is not impaired, or that the resulting plant is not damaged.

The compound of formula (I) or the combination comprising the compound of formula (I) or the composition comprising the compound of formula (I) can be applied directly, i.e. without containing any other components and without having been diluted. In general, it is preferable to apply the compositions comprising compounds of formula (I) to the seed in the form of a suitable formulation. Suitable formulations and methods for seed treatment are known to those skilled in the art. The compound of formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV Formulations.

In the treatment of seeds to facilitate plantability, seeds can be coated with polymer. The polymer coating is comprised of a binder, a wax and a pigment, and one or more stabilizers in an amount effective to stabilize the suspension. The binder can be a polymer selected from the group comprising of vinyl acetate-ethylene copolymer, vinyl acetate homopolymer, vinyl acetate-acrylic copolymer, vinylacrylic, acrylic, ethylene-vinyl chloride, vinyl ether maleic anhydride, or butadiene styrene. Other similar polymers can be used.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing Formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seeds either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the diluted preparations thereof, can also be used for seeds of transgenic plants. In this case, enhanced effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient are generally between 0.001 and 15 gai per kilogram of seed, preferably between 0.01 and 5 gai per kilogram of seed.

When using the compound of formula (I) as fungicides, the application rates can be varied within a relatively wide range, depending on the kind of application. The application rate of the compound of formula (I) or the combination comprising the compound of formula (I) or the composition comprising the compound of formula (I), is:

in the case of treatment of plant parts, for example leaves: from 0.1 to 10000 gai/ha, preferably from 5 to 1000 gai/ha, more preferably from 5 to 100 gai/ha (in the case of application by watering or dripping, it is even possible to reduce the application rate, especially when inert substrates such as rockwool or perlite are used);

in the case of seed treatment: from 0.1 to 200 gai per 100 kg of seed, preferably from 1 to 150 gai per 100 kg of seed, more preferably from 2.5 to 25 gai per 100 kg of seed.

in the case of soil treatment: from 0.1 to 10000 gai/ha, preferably from 1 to 1000 gai/ha.

These application rates are merely by way of example and are not limiting for the purposes of the invention.

In some cases, the compound of formula (I) may, at particular concentrations or application rates, also be used as safeners, growth regulators or agents to improve plant properties, or as microbicides, for example as fungicides, antimycotics, bactericides, viricides (including compositions against viroids) or as compositions against phytoplasmas MLO (*Mycoplasma*-like organisms) and RLO (*Rickettsia*-like organisms).

The compound of formula (I) may intervene in the physiological processes of plants and can therefore also be used as plant growth regulators. Plant growth regulators may exert various effects on plants. The effect of the substances depends essentially on the time of application in relation to the developmental stage of the plant, the plant variety and also on the amounts of active ingredient applied to the plants or their environment and on the type of application. In each case, growth regulators should have a particular desired effect on the crop plants.

Growth regulating effects, comprise earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/$m^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising: improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.; and further comprising decreased undesired ingredients such as e.g. less mycotoxines, less aflatoxines, geosmin level, phenolic aromas, lacchase, polyphenol oxidases and peroxidases, nitrate content etc.

Furthermore, beneficial effects on growth or yield can be achieved through improved nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"). In addition, it is possible to use growth regulators at the time of harvest to reduce the forces required to detach the fruits, in order to allow mechanical harvesting or to facilitate manual harvesting.

In addition, growth regulators can also be used to synchronize maturation within a certain period of time. This establishes the prerequisites for complete mechanical or manual harvesting in a single operation, for example in the case of tobacco, tomatoes or coffee.

Finally, growth regulators can induce resistance of the plants to frost, drought or high salinity of the soil. This allows the cultivation of plants in regions which are normally unsuitable for this purpose.

The compound of formula (I) or the combination comprising the compound of formula (I) or the composition comprising the compound of formula (I) also exhibit potent strengthening effect in plants.

Accordingly, they can be used for mobilizing the defences of the plant against attack by undesirable micro-organisms.

Plant-strengthening (resistance-inducing) substances in the present context are substances capable of stimulating the defence system of plants in such a way that the treated plants, when subsequently inoculated with undesirable micro-organisms, develop a high degree of resistance to these micro-organisms.

Further, in context with the present invention plant physiology effects comprise the following: Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance comprising increased fungal resistance and increased resistance against *nematodes*, viruses and bacteria. In context with the present invention, biotic stress tolerance preferably comprises increased fungal resistance and increased resistance against *nematodes.*

Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency.

In addition, the compound of formula (I) or the combination comprising the compound of formula (I) or the composition comprising the compound of formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti*, F. fujikoroi, *F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum*, F. verticilihoides etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana*, Stachybotrys spec. and others.

The compound of formula (I) or the combination comprising the compound of formula (I) or the composition comprising the compound of formula (I) can also be used in the protection of materials, for protection of industrial materials against attack and destruction by phytopathogenic micro-organisms.

In addition, the compound of formula (I) or the combination comprising the compound of formula (I) or the composition comprising the compound of formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by micro-organisms. Parts of production plants and buildings, for example cooling-water circuits, cooling and heating systems and ventilation and air-conditioning units, which may be impaired by the proliferation of micro-organisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compound of formula (I) or the combination comprising the compound of formula (I) or the composition comprising the compound of formula (I) may prevent adverse effects, such as rotting, decay, discoloration, decoloration or formation of mould.

In the case of treatment of wood the compound of formula (I) or the compound of formula (I) in the composition optionally comprising at least one active compatible compound may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

The compound of formula (I) or the combination comprising the compound of formula (I) or the composition comprising the compound of formula (I) can also be employed for protecting storage goods.

Storage goods are understood to mean natural substances of vegetable or animal origin or processed products thereof which are of natural origin, and for which long-term protection is desired.

Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compound of formula (I) or the combination comprising the compound of formula (I) or the composition comprising the compound of formula (I) may prevent adverse effects, such as rotting, decay, discoloration, decoloration or formation of mould.

Micro-organisms capable of degrading or altering the industrial materials include, for example, bacteria, fungi, yeasts, algae and slime organisms. The compound of formula (I) or the combination comprising the compound of formula (I) or the composition comprising the compound of formula (I) preferably act against fungi, especially moulds, wood-discoloring and wood-destroying fungi (Ascomycetes, Basidiomycetes, Deuteromycetes and Zygomycetes), and against slime organisms and algae. Examples include micro-organisms of the following genera: *Alternaria*, such as *Alternaria tenuis; Aspergillus*, such as *Aspergillus niger; Chaetomium*, such as *Chaetomium globosum; Coniophora*, such as *Coniophora* puetana; *Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae.*

In addition, the compound of formula (I) or the combination comprising the compound of formula (I) or the composition comprising the compound of formula (I) also has very good antimycotic effects. They have a very broad antimycotic activity spectrum, especially against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes*, Microsporon species such as Microsporon *canis* and *audouinii*. The enumeration of these fungi by no means constitutes a restriction of the mycotic spectrum covered, and is merely of illustrative character.

The compound of formula (I) or the combination comprising the compound of formula (I) or the composition comprising the compound of formula (I) can be used also to control important fungal pathogens in fish and *crustacea* farming, e.g. *saprolegnia diclina* in trouts, *saprolegnia parasitica* in crayfish.

The compound of formula (I) or the combination comprising the compound of formula (I) or the composition comprising the compound of formula (I) can therefore be used both in medical and in non-medical applications.

The compound of formula (I) or the combination comprising the compound of formula (I) or the composition comprising the compound of formula (I) can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

It is possible to treat all plants and their parts in accordance with the invention, preferably with wild plant species and plant cultivars, or those obtained by conventional biological breeding methods, such as crossing or protoplast fusion, and also parts thereof. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against *nematodes*, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as tobacco plants, with altered post-translational protein modification patterns.

The present invention shall now be described with non-limiting specific examples.

CHEMISTRY EXAMPLES

Example 1: Preparation of ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)dimethyl-$\lambda^6$-sulfanone (Compound 6)

Step A: Preparation of ethyl 2-bromo-1,3-thiazole-4-carboxylate

To a solution of ethyl 2-aminothiazole-4-carboxylate (100 g, 581 mmol) and copper (II) bromide (195 g, 871 mmol) in acetonitrile (1 L), tert-butylnitrite (104 mL, 871 mmol) was added dropwise at 0° C. The resulting reaction mixture was warmed to 25° C. and stirred for 12 h. The reaction mixture was diluted with ethyl acetate (1 L) and water (3 L) and acidified to pH 2 using 1N hydrochloric acid. Layers were separated, the aqueous layer was extracted thrice with ethyl acetate (500 mL) and dried over anhydrous sodium sulphate, concentrated and purified by recrystallization with hexane to obtain ethyl 2-bromo-1,3-thiazole-4-carboxylate (115 g, 84% yield).

$^1$H-NMR (400 MHz, DMSO-$d_6$) δ 8.52 (s, 1H), 4.29 (q, J=7.1 Hz, 2H), 1.29 (t, J=7.1 Hz, 3H) MS: m/z=235.90. [M+1].

Step B: Preparation of ethyl 2-(1-(tert-butoxycarbonyl)-1,2,3,6-tetrahydropyridin-4-yl)thiazole-4-carboxylate Bis(triphenylphosphine)palladium(II)chloride (9.46 g, 13.5 mmol), tert-butyl 4-(4,4,5,5-tetramethyl-1,3,2-dioxaborolan-2-yl)-3,6-dihydropyridine-1(2H)-carboxylate (100 g, 323 mmol) and a solution of sodium carbonate (86 g, 809 mmol) in water (100 mL) were consecutively added to a solution of ethyl 2-bromothiazole-4-carboxylate (63.6 g, 270 mmol) in dioxane (200 mL). The resulting reaction mixture was heated to 85° C. for 12 h. The reaction mixture was cooled to 25° C., filtered through celite bed and washed with methanol. The filtrate was concentrated and purified by column chromatography using 25% ethyl acetate and hexane as an eluent to give ethyl 2-(1-(tert-butoxycarbonyl)-1,2,3,6-tetrahydropyridin-4-yl) thiazole-4-carboxylate (50 g, 55% yield).

$^1$H-NMR (400 MHz, DMSO-$d_6$) δ 8.40 (s, 1H), 6.63 (s, 1H), 4.26 (q, J=7.0 Hz, 2H), 4.01 (s, 2H), 3.49 (t, J=5.7 Hz, 2H), 2.54 (d, J=1.7 Hz, 2H), 1.39 (d, J=6.4 Hz, 9H), 1.24-1.28 (m, 3H). MS: m/z=339 [M+1].

Step C: Preparation of ethyl 2-(1-(tert-butoxycarbonyl)piperidin-4-yl)thiazole-4-carboxylate To a solution of ethyl 2-(1-(tert-butoxycarbonyl)-1,2,3,6-tetrahydropyridin-4-yl)thiazole-4-carboxylate (12.8 g, 37.8 mmol) in ethanol (200 mL) was added a suspension of 10% Palladium on charcoal (16.1 g, 15.1 mmol) in ethanol (100 mL). The reaction mixture was maintained under hydrogen pressure of 70 bar at 65° C. for 12 h. The reaction mixture was cooled to 25° C. and filtered. The filtrate was concentrated to obtain ethyl 2-(1-(tert-butoxycarbonyl)piperidin-4-yl)thiazole-4-carboxylate (9.3 g, 72% yield).

$^1$H-NMR (400 MHz, DMSO-$d_6$) δ 8.41 (s, 1H), 4.28 (q, J=7.1 Hz, 2H), 4.00 (d, J=12.5 Hz, 2H), 3.20-3.27 (m, 1H), 2.87 (s, 2H), 2.00-2.03 (m, 2H), 1.53 (ddd, J=24.7, 12.2, 4.1 Hz, 2H), 1.37-1.43 (m, 9H), 1.28 (t, J=7.1 Hz, 3H). MS: m/z=341.10 [M+1].

Step D: Preparation of tert-butyl 4-(4-(hydroxymethyl)thiazol-2-yl)piperidine-1-carboxylate To a stirred solution of ethyl 2-(1-(tert-butoxycarbonyl) piperidin-4-yl)thiazole-4-carboxylate (30 g, 88 mmol) in tetrahydrofuran (500 mL), sodium borohydride (16.6 g, 441 mmol) was added and heated to 60° C. Methanol (40 mL) was added slowly into the reaction mixture, quenched with ammonium chloride solution (200 mL) and extracted twice with dichloromethane (200 mL). The combined dichloromethane layer was dried over anhydrous sodium sulphate and concentrated to obtain 4-(4-(hydroxymethyl)thiazol-2-yl)piperidine-1-carboxylate (21 g, 80% yield).

MS: m/z=299.401 [M+1].

Step E: Preparation of tert-butyl 4-(4-formylthiazol-2-yl)piperidine-1-carboxylate To a solution of tert-butyl 4-(4-(hydroxymethyl)thiazol-2-yl)piperidine-1-carboxylate (8.4 g, 28.2 mmol) in dichloromethane (350 mL), Dess-Martin periodinane (23.8 g, 56.3 mmol) was added. The resulting reaction mixture was allowed to stir for 12 h at 25° C. and quenched with aqueous sodium bicarbonate solution. The aqueous layer was extracted thrice with dichloromethane (200 mL), the combined dichloromethane layer was dried over sodium sulphate, concentrated and purified by column chromatography using 30% of ethyl acetate in hexane as eluent to obtain tert-butyl 4-(4-formylthiazol-2-yl)piperidine-1-carboxylate (5.3 g, 52% yield).

$^1$H-NMR (400 MHz, DMSO-$d_6$) δ 9.87 (s, 1H), 8.63 (s, 1H), 4.00 (d, J=13.0 Hz, 2H), 3.24-3.29 (m, 1H), 2.89 (s, 2H), 2.04 (dd, J=12.7, 1.8 Hz, 2H), 1.56 (ddd, J=24.6, 12.1, 4.1 Hz, 2H), 1.38-1.43 (m, 9H).

MS: m/z=297.385 [M+1].

Step F: Preparation of tert-butyl (E/Z)-4-(4-((hydroxyimino)methyl)thiazol-2-yl)piperidine-1-carboxylate To a stirred solution of hydroxylamine hydrochloride (0.56 g, 8.1 mmol) in ethanol (15 mL), pyridine (1.3 mL, 16.2 mmol) was added. After 10 min, tert-butyl 4-(4-formylthiazol-2-yl)piperidine-1-carboxylate (2 g, 6.7 mmol) was added and stirred for 1 h at 25° C. The reaction mixture was concentrated, quenched with aqueous ammonium chloride solution (20 mL) and extracted twice with ethyl acetate (50 mL). The combined ethyl acetate layer was dried over anhydrous sodium sulphate and concentrated to obtain tert-butyl (E/Z)-4-(4-((hydroxyimino)methyl)thiazol-2-yl)piperidine-1-carboxylate (2 g, 95% yield).

$^1$H-NMR (400 MHz, DMSO-$d_6$) δ 12.05-11.09 (1H), 8.49-7.96 (1H), 7.87-7.54 (1H), 3.99 (d, J=14.1 Hz, 2H), 3.25-3.13 (m, 1H), 2.88 (s, 2H), 2.01 (dd, J=12.8, 2.1 Hz, 2H), 1.61-1.45 (m, 2H), 1.39 (s, 9H).

MS: m/z=312.400 [M+1].

Step G: Preparation of tert-butyl 4-(4-(5-(2-bromo-6-fluorophenyl)-4,5-dihydroisoxazol-3-yl) thiazol-2-yl)piperidine-1-carboxylate To a stirred solution of tert-butyl (E)-4-(4-((hydroxyimino)methyl)thiazol-2-yl)piperidine-1-carboxylate (16 g, 51.4 mmol) in ethyl acetate (300 mL), N-chlorosuccinimide (10.29 g, 77 mmol) was added followed by addition of sodium bicarbonate (30.2 g, 360 mmol). To the reaction mixture, 1-bromo-3-fluoro-2-vinylbenzene (10.33 g, 51.4 mmol) and water (50 mL) were added. The reaction mixture was heated to 65° C. for 3 h, cooled to 15° C. and quenched with water. The aqueous layer was extracted thrice with ethyl acetate (100 mL). The combined ethyl acetate layer was dried over anhydrous sodium sulphate, concentrated and purified by column chromatography using 30% ethyl acetate in hexane as eluent to obtain the tert-butyl 4-(4-(5-(2-bromo-6-fluorophenyl)-4,5-dihydroisoxazol-3-yl)thiazol-2-yl)piperidine-1-carboxylate (20 g, 6.01 mmol, 76% yield). MS: m/z=511.80 [M+1].

Step H: Preparation of tert-butyl 4-(4-(5-(2-((dimethyl(oxo)-$\lambda^6$-sulfaneylidene)amino)-6-fluorophenyl)-4,5-dihydroisoxazol-3-yl)thiazol-2-yl)piperidine-1-carboxylate To a stirred solution of tert-butyl 4-(4-(5-(2-bromo-6-fluorophenyl)-4,5-dihydroisoxazol-3-yl)thiazol-2-yl)piperidine-1-carboxylate (12 g, 23.51 mmol) in toluene (150 mL) was added iminodimethyl-$\lambda^6$-sulfanone (2.19 g, 23.51 mmol) followed by sodium tert-butoxide (2.71 g, 28.2 mmol) at 25° C. The reaction mixture was degassed with nitrogen gas for 10 min then tris(dibenzylideneacetone) dipalladium (0) (1.08 g, 1.18 mmol) and 4,5-bis(diphenylphosphino)-9,9-dimethylxanthene (1.36 g, 2.35 mmol) were added to it and heated to 120° C. for 1 h. After completion of the reaction, the reaction mixture was evaporated and purified by column chromatography by using 60% ethyl acetate in n-hexane as eluent to obtain tert-butyl 4-(4-(5-(2-((dimethyl(oxo)-$\lambda^6$-sulfanylidene)amino)-6-fluorophenyl)-4,5-dihydroisoxazol-3-yl)thiazol-2-yl)piperidine-1-carboxylate (10.2 g, 19.52 mmol, 83% yield).

$^1$H-NMR (400 MHz, DMSO-$d_6$) δ 7.96 (s, 1H), 7.12-7.24 (m, 1H), 6.96 (d, J=7.8 Hz, 1H), 6.76 (ddd, J=10.7, 8.3, 0.9 Hz, 1H), 6.14 (dd, J=12.3, 9.2 Hz, 1H), 4.04 (q, J=7.2 Hz, 2H), 3.66-3.74 (m, 1H), 3.43-3.52 (m, 1H), 3.17-3.30 (m, 1H), 3.13 (d, J=5.4 Hz, 6H), 2.91-2.96 (m, 2H), 2.03-2.08 (m, 2H), 1.57 (qd, J=12.1, 4.2 Hz, 2H), 1.42 (s, 9H). MS: m/z=523.70 [M+1].

Step I: Preparation of ((3-fluoro-2-(3-(2-(piperidin-4-yl)thiazol-4-yl)-4,5-dihydroisoxazol-5-yl) phenyl) imino)dimethyl-$\lambda^6$-sulfanone To a solution of tert-butyl 4-(4-(5-(2-((dimethyl(oxo)-$\lambda^6$-sulfaneylidene)amino)-6-fluorophenyl)-4,5-dihydroisoxazol-3-yl)thiazol-2-yl)piperidine-1-carboxylate (10.2 g, 20 mmol) in dichloromethane (200 mL), trifluoroacetic acid (50 mL, 145 mmol) was added. The reaction mixture was stirred at 25° C. for 1 h, concentrated and quenched with aqueous sodium bicarbonate solution. Aqueous layer was extracted twice with ethyl acetate (100 mL) and the combined ethyl acetate layer was dried over anhydrous sodium sulphate and concentrated to obtain ((3-fluoro-2-(3-(2-(piperidin-4-yl) thiazol-4-yl)-4,5-dihydroisoxazol-5-yl)phenyl)imino)dimethyl-$\lambda^6$-sulfanone (3 g). MS: m/z=423.30 [M+1].

Step J: Preparation of ((3-fluoro-2-(3-(2-(1-(2-(5-methyl-3-(trifluoromethyl)-1H-pyrazol-1-yl) acetyl) piperidin-4-yl)thiazol-4-yl)-4,5-dihydroisoxazol-5-yl)phenyl)imino)dimethyl-$\lambda^6$-sulfanone To a solution ((3-fluoro-2-(3-(2-(piperidin-4-yl)thiazol-4-yl)-4,5-dihydroisoxazol-5-yl)phenyl) imino)dimethyl-$\lambda^6$-sulfanone (3 g, 7.10 mmol) and 2-(5-methyl-3-(trifluoromethyl)-1H-pyrazol-1-yl)acetic acid (1.48 g, 7.10 mmol) in N,N-dimethylformamide (40 mL), (1-[bis(dimethylamino) methylene]-1H-1,2,3-triazolo[4,5-b]pyridinium 3-oxide (HATU) (2.97 g, 7.81 mmol) and N,N-diisopropylethylamine (6.2 ml, 35.50 mmol) were added and stirred for 1 h at 25° C. The reaction mixture was diluted with water (100 mL), solid was filtered and dried. The obtained crude product was purified by column chromatography by using 70% ethyl acetate in n-hexane to obtain ((3-fluoro-2-(3-(2-(1-(2-(5-methyl-3-(trifluoromethyl)-1H-pyrazol-1-yl) acetyl)piperidin-4-yl)thiazol-4-yl)-4,5-dihydroisoxazol-5-yl)phenyl)imino)dimethyl-$\lambda^6$-sulfanone (3.7 g, 6.04 mmol, 81% yield).

$^1$H-NMR (400 MHz, DMSO-$d_6$) δ 7.97 (s, 1H), 7.19 (td, J=8.2, 6.8 Hz, 1H), 6.94 (d, J=7.8 Hz, 1H), 6.75 (dd, J=9.7, 8.4 Hz, 1H), 6.49 (s, 1H), 6.13 (dd, J=12.3, 9.2 Hz, 1H), 5.20-5.34 (m, 2H), 4.36 (d, J=12.7 Hz, 1H), 3.96 (d, J=13.7 Hz, 1H), 3.69 (dd, J=16.5, 13.1 Hz, 1H), 3.48 (dd, J=17.0, 9.2 Hz, 1H), 3.34-3.40 (m, 2H), 3.11 (d, J=5.4 Hz, 6H), 2.81-2.86 (m, 1H), 2.18-2.20 (m, 3H), 2.10 (t, J=12.5 Hz, 2H), 1.78-1.84 (m, 1H), 1.51-1.60 (m, 1H). MS: m/z=613.30 [M+1].

Example 2: Preparation of 1-bromo-3-fluoro-2-vinylbenzene

To a stirred solution of 2-bromo-6-fluorobenzaldehyde (20.0 g, 99 mmol) in ethyl acetate (500 mL), was added methyltriphenylphosphonium bromide (42.2 g, 118 mmol) at 0° C. followed by portion wise addition of sodium hydride (5.91 g, 148 mmol) under nitrogen atmosphere. The resulting reaction mixture was warmed to 25° C. and stirred for 2 h. The reaction was quenched with ice and extracted with ethyl acetate (500 mL). The ethyl acetate layer was washed with brine solution, dried and carried forward without distillation. GC-MS: m/z=200 [M+].

Example 3: Preparation of (2-(3-(2-(1-(2-(3,5-bis (difluoromethyl)-1H-pyrazol-1-yl) acetyl) piperidin-4-yl) thiazol-4-yl)-4,5-dihydroisoxazol-5-yl)-3-chlorophenyl) (imino) (methyl)-$\lambda^6$-sulfanone (Compound 3)

Step A: tert-butyl 4-(4-(5-(2-chloro-6-(methylthio) phenyl)-4,5-dihydroisoxazol-3-yl)thiazol-2-yl) piperidine-1-carboxylate To a solution of tert-butyl (E)-4-(4-((hydroxyimino) methyl)thiazol-2-yl)piperidine-1-carboxylate (3.04 g, 9.75 mmol) in ethyl acetate (100 mL), (3-chloro-2-vinylphenyl) (methyl)sulfane (1.5 g, 8.12 mmol) N-chlorosuccinimide (1.63 g, 12.18 mmol), sodium bicarbonate (4.78 g, 56.9 mmol), water (25 mL) were added. The resulting mixture was stirred at 60° C. for 2 h. The reaction mixture was diluted with water (100 mL) and extracted twice with ethyl acetate (200 mL). Ethyl acetate was evaporated and crude was purified by combiflash chromatography to obtain tert-butyl 4-(4-(5-(2-chloro-6-(methylthio)phenyl)-4,5-dihydroisoxazol-3-yl)thiazol-2-yl)piperidine-1-carboxylate (1.806 g, 3.65 mmol, 45% yield). MS: m/z=494.20 [M+1].

Step B: 5-(2-chloro-6-(methylthio) phenyl)-3-(2-(piperidin-4-yl) thiazol-4-yl)-4,5-dihydroisoxazole To a solution of tert-butyl 4-(4-(5-(2-chloro-6-(methylthio) phenyl)-4,5-dihydroisoxazol-3-yl) thiazol-2-yl) piperidine-1-carboxylate (0.58 g, 1.174 mmol) in DCM (25 mL), trifluoro acetic acid (0.452 mL, 5.87 mmol) was added at cooling. The resulting mixture was stirred at 25° C. for 3 h. The reaction mass was evaporated to obtain 5-(2-chloro-6-(methylthio) phenyl)-3-(2-(piperidin-4-yl) thiazol-4-yl)-4,5-dihydroisoxazole (0.46 g, 1.17 mmol, 100% yield).

Step C: 2-(3,5-bis(difluoromethyl)-1H-pyrazol-1-yl)-1-(4-(4-(5-(2-chloro-6-(methylthio)phenyl)-4,5-dihydroisoxazol-3-yl)thiazol-2-yl)piperidin-1-yl) ethan-1-one To a solution of 5-(2-chloro-6-(methylthio)phenyl)-3-(2-(piperidin-4-yl)thiazol-4-yl)-4,5-dihydroisoxazole (0.21 g, 0.53 mmol) in N,N-dimethyl formamide (5 mL), N,N-diisopropylethylamine (0.09 mL, 0.53 mmol) was added. 2-(3,5-bis(difluoromethyl)-1H-pyrazol-1-yl)acetic acid (0.12 g, 0.53 mmol) and (1-[bis(dimethylamino)methylene]-1H-1,2,3-triazolo[4,5-b]pyridinium-3-oxide hexafluorophosphate, (hexafluorophosphate azabenzotriazole tetramethyl uronium) (0.30 g, 0.80 mmol) were added sequentially to the reaction mass. The resulting mixture was stirred at 25° C. over 2 h. The reaction mixture was diluted with water (15 mL) and extracted twice with ethyl acetate (20 mL). Ethyl acetate layer was concentrated and crude was purified by combiflash chromatography to obtain 2-(3,5-bis(difluoromethyl)-1H-pyrazol-1-yl)-1-(4-(4-(5-(2-chloro-6-(methylthio)phenyl)-4,5-dihydroisoxazol-3-yl)thiazol-2-yl)piperidin-1-yl)ethan-1-one (0.13 g, 0.21 mmol, 39% yield).

MS: m/z=[M+1].

Step D: Preparation of (2-(3-(2-(1-(2-(3,5-bis(difluoromethyl)-1H-pyrazol-1-yl)acetyl)piperidin-4-yl) thiazol-4-yl)-4,5-dihydroisoxazol-5-yl)-3-chlorophenyl)(imino)(methyl)-$\lambda^6$-sulfanone To a solution of 2-(3,5-bis(difluoromethyl)-1H-pyrazol-1-yl)-1-(4-(4-(5-(2-chloro-6-(methylthio)phenyl)-4,5-dihydroisoxazol-3-yl)thiazol-2-yl)piperidin-1-yl)ethan-1-one (0.12 g, 0.2 mmol) in N,N-dimethyl formamide (5 mL), diacetoxyiodo benzene (0.13 g, 0.4 mmol) and ammonium carbamate (0.03 g, 0.4 mmol) were added. The resulting mixture was stirred at 25° C. over 2 h. The reaction mixture was diluted with water (15 mL) and extracted twice with ethyl acetate (20 mL). Ethyl acetate was evaporated and crude was purified by combiflash chromatography to obtain (2-(3-(2-(1-(2-(3,5-bis(difluoromethyl)-1H-pyrazol-1-yl)

acetyl)piperidin-4-yl)thiazol-4-yl)-4,5-dihydroisoxazol-5-yl)-3-chlorophenyl)(imino)(methyl)-$\lambda^6$-sulfanone (0.05 g, 0.08 mmol, 41% yield).

MS: m/z=633.15 [M+1].

Example 4: Preparation of (3-chloro-2-vinylphenyl)(methyl)sulfane

Step A: Preparation of 2-chloro-6-(methylthio) benzaldehyde

To a solution of 2-chloro-6-fluorobenzaldehyde (0.5 g, 3.15 mmol) in N,N-dimehtyl formamide (8 mL), sodium methanethiolate (0.22 g, 3.15 mmol) was added at 0° C. The reaction mixture was warmed to 25° C. and stirred over 5 h. The reaction mixture was diluted with water (10 mL) then extracted twice with ethyl acetate (35 mL). The combined ethyl acetate layer was washed with brine and evaporated under reduced pressure. The obtained crude was purified by combiflash chromatography to obtain 2-chloro-6-(methylthio)benzaldehyde (0.33 g, 1.77 mmol, 56% yield). MS: m/z=[M+1].

Step B: Preparation of (3-chloro-2-vinylphenyl)(methyl)sulfane

To a solution of 2-chloro-6-(methylthio)benzaldehyde (8 g, 42.9 mmol) in tetrahydrofuran (180 mL), sodium hydride (4.63 g, 193 mmol), methyltriphenylphosphonium bromide (22.97 g, 64.3 mmol) were added. The resulting mixture was stirred at 25° C. for 4 h. The reaction mixture was diluted with water (50 mL) and extracted twice with ethyl acetate (50 mL). Ethyl acetate was evaporated and the obtained crude material was purified by combiflash chromatography to obtain (3-chloro-2-vinylphenyl)(methyl) sulfane (5.54 g, 30.0 mmol, 70% yield).

MS: m/z=[M+1].

Example 5: Preparation of N-((E)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-$\lambda^4$-sulfaneylidene) cyanamide (Compound 69)

Step A: Preparation of tert-butyl 4-(4-(5-(2-bromo-6-fluorophenyl)-4,5-dihydroisoxazol-3-yl) thiazol-2-yl)piperidine-1-carboxylate To a stirred solution of tert-butyl (E/Z)-4-(4-((hydroxyimino)methyl)thiazol-2-yl)piperidine-1-carboxylate (3.04 g, 9.75 mmol), in ethyl acetate (145 mL) was added N-chlorosuccinimide (NCS) (1.627 g, 12.18 mmol) followed by sodium bicarbonate (4.78 g, 56.9 mmol). To the reaction mixture, (3-chloro-2-vinylphenyl)(methyl)sulfane and water (25 mL) were added. The reaction mixture was heated to 65° C. for 3 h, cooled to 15° C. and quenched with water. The aqueous layer was extracted thrice with ethyl acetate (100 mL). The combined ethyl acetate layer was dried over anhydrous sodium sulphate, concentrated and purified by column chromatography using 30% ethyl acetate in hexane as eluent to obtain the tert-butyl 4-(4-(5-(2-chloro-6-(methylthio)phenyl)-4,5-dihydroisoxazol-3-yl)thiazol-2-yl)piperidine-1-carboxylate (1.81 g, 3.65 mmol, 45% yield) MS: m/z=494.00 [M+1].

Step B: Preparation of ((3-fluoro-2-(3-(2-(piperidin-4-yl)thiazol-4-yl)-4,5-dihydroisoxazol-5-yl) phenyl) imino)dimethyl-$\lambda^6$-sulfanone To a solution of tert-butyl 4-(4-(5-(2-chloro-6-(methylthio)phenyl)-4,5-dihydroisoxazol-3-yl)thiazol-2-yl) piperidine-1-carboxylate (0.58 g, 1.17 mmol) in dichloromethane (25 mL), trifluoroacetic acid (0.94 mL, 11.74 mmol) was added. The reaction mixture was stirred at 25° C. for 1 h, concentrated and quenched by addition of an aqueous sodium bicarbonate solution. The aqueous layer was extracted twice with ethyl acetate (40 mL) and the combined ethyl acetate layer was dried over anhydrous sodium sulphate and concentrated to obtain 5-(2-chloro-6-(methylthio) phenyl)-3-(2-(piperidin-4-yl)thiazol-4-yl)-4,5-dihydroisoxazole (0.46 g, 1.17 mmol, 90% yield). MS: m/z=394 [M+1].

Step C: Preparation of 1-(4-(4-(5-(2-chloro-6-(methylthio)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one To a solution 5-(2-chloro-6-(methylthio)phenyl)-3-(2-(piperidin-4-yl)thiazol-4-yl)-4,5-dihydroisoxazole (0.21 g, 0.53 mmol) and 2-(5-methyl-3-(trifluoromethyl)-1H-pyrazol-1-yl)acetic acid (0.11 g, 0.53 mmol) in N,N-dimethylformamide (5 mL), (1-[bis(dimethylamino)methylene]-1H-1,2,3-triazolo[4,5-b]pyridinium 3-oxide hexafluorophosphate, (Hexafluorophosphate Azabenzotriazole Tetramethyl Uronium) (HATU) (0.30 g, 0.80 mmol), N,N-diisopropylethylamine (0.46 ml, 2.67 mmol) were added and the resulting mixture was stirred for 1 h at 25° C. The reaction mixture was then diluted with water (40 mL), solid was filtered and dried. The solid was purified by column chromatography by using 70% ethyl acetate in n-hexane to obtain 1-(4-(4-(5-(2-chloro-6-(methylthio)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one (0.13 g, 0.21 mmol, 40% yield).

Step D: Preparation of N-((E)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-$\lambda^4$-sulfaneylidene) cyanamide To a solution of 1-(4-(4-(5-(2-chloro-6-(methylthio)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one (0.5 g, 0.86 mmol) in methanol (10 mL), cyanimide (0.08 g, 1.88 mmol) and diacetoxyiodo benzene (0.61 g, 1.88 mmol) were added. The resulting mixture was stirred at 25° C. for 12 h. The reaction was quenched by addition of an aqueous sodium bicarbonate solution (20 mL) and extracted twice with ethyl acetate (30 mL). Ethyl acetate was evaporated and the obtained crude material was purified by column chromatography using 75% of ethyl acetate in hexane as eluent to obtain N—((Z)-(3-chloro-2-((S)-3-(2-(1-(2-(5-methyl-3-(trifluoromethyl)-1H-pyrazol-1-yl) acetyl)piperidin-4-yl)thiazol-4-yl)-4,5-dihydroisoxazol-5-yl)phenyl)(methyl)-$\lambda^4$-sulfanylidene)cyanamide (44 mg, 0.07 mmol, 9% yield).

$^1$H-NMR (400 MHz, DMSO-$d_6$) δ 8.15 (d, J=8.1 Hz, 1H), 8.10 (d, J=1.5 Hz, 1H), 7.85-7.88 (m, 1H), 7.74-7.78 (m, 1H), 6.49 (d, J=3.2 Hz, 1H), 6.24 (t, J=11.5 Hz, 1H), 5.28 (dd, J=36.8, 17.0 Hz, 2H), 4.37 (d, J=14.2 Hz, 1H), 4.08 (dd,

J=17.5, 11.6 Hz, 1H), 3.97 (d, J=14.4 Hz, 1H), 3.62 (dd, J=17.6, 11.5 Hz, 1H), 3.40 (d, J=11.5 Hz, 1H), 3.26 (s, 1H), 3.05 (s, 3H), 2.85 (d, J=12.5 Hz, 1H), 2.20 (s, 3H), 2.13 (d, J=11.7 Hz, 2H), 1.90-1.71 (1H), 1.56 (d, J=12.2 Hz, 1H). MS: m/z=394 [M+1]. 624.098.

Example 6: Preparation of (3-chloro-2-vinylphenyl)(methyl)sulfane

Step A: 2-chloro-6-(methylthio)benzaldehyde

To a solution of 2-chloro-6-fluorobenzaldehyde (4.0 g, 25.2 mmol) in N,N-dimethylformamide (32 ml), sodium methanethiolate (17.68 g, 37.8 mmol) was added. The resulting mixture was stirred at 25° C. for 4 h. The reaction was quenched by addition of saturated sodium thiosulfate ($Na_2S_2O_3$) solution and extracted twice with ethyl acetate (80 mL). Ethyl acetate was evaporated and the obtained crude material was purified by column chromatography using 35% of ethyl acetate and n-hexane as eluent to obtain 2-chloro-6-(methylthio) benzaldehyde (2.64 g, 14.13 mmol, 56% yield).

Step B: Preparation of (3-chloro-2-vinylphenyl)(methyl)sulfane

To a stirred solution of 2-chloro-6-(methylthio) benzaldehyde (8 g, 42.9 mmol) in tetrahydrofuran (180 ml), methyltriphenylphosphonium bromide (22.97 g, 64.3 mmol) was added to the reaction mass. To this sodium hydride (4.63 g, 193 mmol), was added portion wise under nitrogen atmosphere at 0° C. The reaction mixture was warmed to 25° C. and stirred for 2 h. The reaction mass was quenched by addition of ice and extracted with ethyl acetate (500 mL). The ethyl acetate layer was washed with brine solution, dried and the obtained material was carried further without distillation. GC-MS: m/z=184.

Example 7: Preparation of 1-(4-(4-(5-(6-fluoro-2-methyl-2-oxido-3H-2$\lambda^4$-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl) ethan-1-one (Compound 32)

Step A: Preparation of tert-butyl 4-(4-(5-(6-fluoro-2-methyl-2-oxido-3H-2$\lambda^4$-benzo[c]isothiazol-7-yl)-4,5-dihydroisoxazol-3-yl) thiazol-2-yl)piperidine-1-carboxylate To a stirred solution of tert-butyl (E)-4-(4-((hydroxyimino)methyl)thiazol-2-yl)piperidine-1-carboxylate (0.37 g, 1.18 mmol) in ethyl acetate (300 mL) N-chlorosuccinimide (0.17 g, 1.30 mmol) was added, followed by the addition of sodium bicarbonate (6.96 g, 8.28 mmol). To the reaction mixture, 6-fluoro-2-methyl-7-vinyl-3H-2$\lambda^4$-benzo[c]isothiazole-2-oxide (0.25 g, 1.18 mmol) and water (5 mL) were added. The reaction mixture was heated to 65° C. for 3 h, cooled to 15° C. and quenched by addition of water. The aqueous layer was extracted thrice with ethyl acetate (100 mL). The combined ethyl acetate layer was dried over anhydrous sodium sulphate, concentrated and the obtained residue was purified by column chromatography using 30% ethyl acetate in hexane as eluent to obtain tert-butyl 4-(4-(5-(6-fluoro-2-methyl-2-oxido-3H-2$\lambda^4$-benzo[c]isothiazol-7-yl)-4,5-dihydroisoxazol-3-yl)thiazol-2-yl)piperidine-1-carboxylate (140 mg, 23% yield). MS: m/z=521.10 [M+1].

Step B: Preparation of 6-fluoro-2-methyl-7-(3-(2-(piperidin-4-yl)thiazol-4-yl)-4,5-dihydroisoxazol-5-yl)-3H-2$\lambda^4$-benzo[c]isothiazole-2-oxide To a solution of tert-butyl 4-(4-(5-(6-fluoro-2-methyl-2-oxido-3H-2$\lambda^4$-benzo[c]isothiazol-7-yl)-4,5-dihydroisoxazol-3-yl)thiazol-2-yl)piperidine-1-carboxylate (140 mg, 0.27 mmol) in dichloromethane (5 mL), trifluoroacetic acid (0.52 mL, 6.72 mmol) was added. The reaction mixture was stirred at 25° C. for 1 h, concentrated and quenched by addition of aqueous sodium bicarbonate solution. The aqueous layer was extracted twice with ethyl acetate (100 mL) and the combined ethyl acetate layer was dried over anhydrous sodium sulphate and concentrated to obtain 6-fluoro-2-methyl-7-(3-(2-(piperidin-4-yl)thiazol-4-yl)-4,5-dihydroisoxazol-5-yl)-3H-2$\lambda^4$-benzo[c]isothiazole-2-oxide (110 mg, 97% yield). MS: m/z=413.00 [M+1].

Step C: Preparation of 1-(4-(4-(5-(6-fluoro-2-methyl-2-oxido-3H-2$\lambda^4$-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl) ethan-1-one To a solution 6-fluoro-2-methyl-7-(3-(2-(piperidin-4-yl) thiazol-4-yl)-4,5-dihydroisoxazol-5-yl)-3H-2$\lambda^4$-benzo[c] isothiazole-2-oxide (110 mg, 0.26 mmol) and 2-(5-methyl-3-(trifluoromethyl)-1H-pyrazol-1-yl)acetic acid (55 mg, 0.26 mmol) in N,N-dimethylformamide (4 mL), (1-[bis (dimethylamino)methylene]-1H-1,2,3-triazolo[4,5-b]pyridinium-3-oxide hexafluorophosphate, (HATU) (120 mg, 0.313 mmol), N,N-diisopropylethylamine (0.2 ml, 0.7 mmol) were added and the resulting mixture was stirred for 1 h at 25° C. The reaction mixture was diluted with water (10 mL), the solid was filtered off and dried. The obtained crude product was purified by column chromatography by using 10% methanol in ethyl acetate as eluents to obtain 1-(4-(4-(5-(6-fluoro-2-methyl-2-oxido-3H-2$\lambda^4$-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one.

$^1$H-NMR (400 MHz, DMSO-$d_6$) δ 7.97 (s, 1H), 7.02-7.30 (m, 3H), 6.89 (d, J=3.9 Hz, 1H), 6.50 (dd, J=11.4, 8.2 Hz, 1H), 6.03 (dd, J=11.6, 9.7 Hz, 1H), 5.39 (q, J=17.2 Hz, 2H), 4.96 (d, J=17.4 Hz, 1H), 4.55 (d, J=17.4 Hz, 1H), 4.34 (d, J=13.0 Hz, 1H), 3.91-4.03 (m, 1H), 3.69-3.77 (m, 1H), 3.54-3.60 (m, 4H), 3.23-3.43 (m, 2H), 2.81-2.86 (m, 1H), 2.07-2.19 (m, 2H), 1.79-1.85 (m, 1H), 1.53-1.62 (m, 1H) MS: m/z=628.95 [M+1].

Example 8: Preparation of 6-fluoro-2-methyl-7-vinyl-3H-2$\lambda^4$-benzo[c]isothiazole-2-oxide

Step A: Preparation of 2-bromo-3-fluoro-6-((methylthio)methyl)aniline

To a solution of 2-bromo-3-fluoroaniline (7 g, 36.8 mmol) in dichloromethane (140 mL), N-chlorosuccinimide (4.92 g, 36.8 mmol) was added at −78° C. over 10 min followed by the addition of dimethylsulfane (8.08 ml, 111 mmol) at the same temperature for 4 h. Trimethylamine (10.27 ml, 73.7 mmol) was added to the reaction mixture, which was then allowed to warm to 25° C. The reaction mixture was dissolved in acetonitrile (140 ml) and triethylamine (10.27 ml, 73.7 mmol) was added. The resulting mixture was then heated at 100° C. for 16 h. The reaction mixture was diluted with water (500 mL) and extracted twice with ethyl acetate (500 mL), the combined extract was dried over anhydrous sodium sulphate and concentrated to obtain 2-bromo-3-fluoro-6-((methylthio)methyl)aniline (5 g, 54% yield).

Step B: Preparation of 7-bromo-6-fluoro-2-methyl-3H-2$\lambda^4$-benzo[c]isothiazole-2-oxide To a stirred solution of 2-bromo-3-fluoro-6-((methylthio) methyl)aniline (5 g, 19.99 mmol) in dichloromethane (120 mL), N-chlorosuccinimide (2.67 g, 19.99 mmol) was added at −40° C. The reaction mixture was stirred for 1 h. 10% sodium hydroxide (40 mL) was added to it and the resulting mixture was warmed to 25° C. Water (150 mL) was added and the organic layer was separated. The organic layer was again cooled down to −40° C. and meta-chloroperoxybenzoic acid (4.93 g, 19.99 mmol) was added. The reaction mixture was allowed to warm up to 25° C. and stirred for 1 h. The reaction mass was washed with sodium thiosulfate and sodium bicarbonate solution. The organic layer was concentrated and the obtained residue was purified by crystallization from dichloromethane-hexane to obtain 7-bromo-6-fluoro-2-methyl-3H-2$\lambda^4$-benzo[c]isothiazole 2-oxide (1.7 g, 6.44 mmol, 32% yield)

$^1$H-NMR (400 MHz, DMSO-$d_6$) δ 7.19-7.23 (m, 1H), 6.60-6.64 (m, 1H), 5.09 (d, J=17.4 Hz, 1H), 4.71 (d, J=17.4 Hz, 1H), 3.59 (d, J=4.9 Hz, 3H) MS: m/z=265.85[M+1].

Step C: Preparation of 6-fluoro-2-methyl-7-vinyl-3H-2$\lambda^4$-benzo[c]isothiazole-2-oxide To a solution of 7-bromo-6-fluoro-2-methyl-3H-2$\lambda^4$-benzo[c]isothiazole-2-oxide (1.2 g, 4.54 mmol) in dioxane (16 ml) and water (4.00 ml), potassium vinyltrifluoroborate (1.22 g, 9.09 mmol) and cesium carbonate (3.70 g, 11.36 mmol) were added. The reaction mass was purged with nitrogen for 10 min after which (1,1'-bis(diphenylphosphino)ferrocene)-dichloropalladium (11) (0.33 g, 0.45 mmol) was added. The resulting mixture was purged with nitrogen for 5 min, and then it was stirred at 150° C. for 1.5 h in microwave. After completion of the reaction, the reaction mixture was diluted with ethyl acetate and filtered through celite. The filtrate was concentrated and the obtained residue was purified by column chromatography using ethyl acetate in hexane as eluent to obtain 6-fluoro-2-methyl-7-vinyl-3H-2$\lambda^4$-benzo[c]isothiazole-2-oxide (250 mg, 26% yield). MS: m/z=211.85 [M+1].

TABLE NO 1

The following compounds were prepared analogue to the procedure described in schemes 1-17 or Examples 1 to 8.

| Compd. No. | Compound Name | Analytical data |
|---|---|---|
| 1 | 5-chloro-1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.26 (d, J = 2.7 Hz, 1H), 8.04-8.10 (m, 3H), 7.81 (dd, J = 8.1, 3.4 Hz, 1H), 7.60-7.70 (m, 1H), 6.93 (td, J = 11.9, 5.5 Hz, 1H), 4.78-4.98 (m, 3H), 4.36 (d, J = 12.2 Hz, 1H), 3.79-4.00 (m, 2H), 3.60 (dd, J = 17.4, 11.7 Hz, 1H), 3.38-3.44 (m, −1H), 3.28 (s, 1H), 3.22 (s, 3H), 2.82-2.88 (m, 1H), 2.07-2.17 (m, 2H), 1.80 (d, J = 10.0 Hz, 1H), 1.56-1.60 (m, 1H); LCMS (M + 1): 662.1 |
| 2 | 3-chloro-1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one | $^1$H-NMR (400 MHz, DMSO-$d_6$) δ 8.26 (d, J = 2.7 Hz, 1H), 8.04-8.10 (m, 3H), 7.81 (dd, J = 8.1, 3.4 Hz, 1H), 7.60-7.70 (m, 1H), 6.93 (td, J = 11.9, 5.5 Hz, 1H), 4.78-4.98 (m, 3H), 4.36 (d, J = 12.2 Hz, 1H), 3.79-4.00 (m, 2H), 3.60 (dd, J = 17.4, 11.7 Hz, 1H), 3.38-3.44 (m, −1H), 3.28 (s, 1H), 3.22 (s, 3H), 2.82-2.88 (m, 1H), 2.07-2.17 (m, 2H), 1.80 (d, J = 10.0 Hz, 1H), 1.56-1.60 (m, 1H); LCMS (M + 1): 662 |
| 3 | (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(methyl)-l6-sulfanone | $^1$H-NMR (400 MHz, DMSO-$d_6$) δ 8.04-8.08 (m, 2H), 7.80-7.83 (m, 1H), 7.62 (td, J = 7.9, 2.0 Hz, 1H), 6.89-7.30 (m, 4H), 5.39 (dd, J = 32.9, 17.2 Hz, 2H), 4.84 (d, J = 40.1 Hz, 1H), 4.34 (d, J = 13.2 Hz, 1H), 3.79-3.98 (m, 2H), 3.60 (dd, J = 17.2, 11.9 Hz, 1H), 3.36-3.42 (m, 1H), 3.22-3.28 (m, 4H), 2.80-2.86 (m, 1H), 2.07-2.14 (m, 2H), 1.80 (d, J = 11.2 Hz, 1H), 1.57 (d, J = 14.9 Hz, 1H); LCMS (M + 1): 633.15 |
| 4 | (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(methyl)-l6-sulfanone | $^1$H-NMR (400 MHz, DMSO-$d_6$) δ 8.04-8.08 (m, 2H), 7.80-7.83 (m, 1H), 7.62 (td, J = 7.9, 2.0 Hz, 1H), 6.93 (td, J = 11.9, 5.7 Hz, 1H), 6.49 (s, 1H), 5.28 (dd, J = 36.2, 17.1 Hz, 2H), 4.84 (d, J = 39.1 Hz, 1H), 4.37 (d, J = 13.7 Hz, 1H), 3.79-3.98 (m, 2H), 3.60 (dd, J = 17.5, 11.9 Hz, 1H), 3.35-3.42 (m, 1H), 3.28 (d, J = 14.2 Hz, 1H), 3.22-3.23 (m, 3H), 2.65-2.88 (m, 1H), 2.26 (d, J = 48.2 Hz, 3H), 2.08-2.14 (m, 2H), 1.81 (d, J = 12.0 Hz, 1H), 1.57 (d, J = 9.3 Hz, 1H); LCMS (M + 1): 615.15 |
| 5 | (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone | $^1$H-NMR (400 MHz, DMSO-$d_6$) δ 7.98-8.09 (m, 2H), 7.84-7.86 (m, 1H), 7.64-7.71 (m, 1H), 6.86 (dt, J = 34.1, 11.9 Hz, 1H), 6.49 (s, 1H), 5.28 (dd, J = 36.8, 17.0 Hz, 2H), 4.37 (d, J = 13.7 Hz, 1H), 3.89-4.05 (m, 2H), 3.36-3.80 (m, 3H), 3.29 (d, J = 1.5 Hz, 2H), 3.23-3.32 (m, 3H), 2.80-2.86 (m, 1H), 2.55 (s, 1H), 2.17 (d, J = 22.3 Hz, 3H), 2.11 (t, J = 13.0 Hz, 2H), 1.81 (d, J = 12.0 Hz, 1H), 1.55 (t, J = 12.7 Hz, 1H); LCMS (M + 1): 629.2 |
| 6 | ((3-fluoro-2-(3-(2-(1-(2-(5-methyl-3-(trifluoromethyl)-1H-pyrazol-1-yl)acetyl)piperidin-4- | $^1$H-NMR (400 MHz, DMSO-$d_6$) δ 7.97 (s, 1H), 7.19 (td, J = 8.2, 6.8 Hz, 1H), 6.94 (d, J = 7.8 Hz, 1H), 6.75 (dd, J = 9.7, 8.4 Hz, 1H), 6.49 (s, 1H), 6.13 (dd, J = 12.3, 9.2 Hz, 1H), 5.20-5.34 (m, 2H), 4.36 (d, J = 12.7 Hz, 1H), 3.96 (d, J = 13.7 Hz, 1H), 3.69 (dd, J = |

TABLE NO 1-continued

The following compounds were prepared analogue to the procedure described in schemes 1-17 or Examples 1 to 8.

| Compd. No. | Compound Name | Analytical data |
|---|---|---|
| | yl)thiazol-4-yl)-4,5-dihydroisoxazol-5-yl)phenyl)imino)dimethyl-l6-sulfanone | 16.5, 13.1 Hz, 1H), 3.48 (dd, J = 17.0, 9.2 Hz, 1H), 3.34-3.40 (m, 2H), 3.11 (d, J = 5.4 Hz, 6H), 2.81-2.86 (m, 1H), 2.18-2.20 (m, 3H), 2.10 (t, J = 12.5 Hz, 2H), 1.78-1.84 (m, 1H), 1.51-1.60 (m, 1H); LCMS (M + 1): 613.2 |
| 7 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)dimethyl-l6-sulfanone | $^{1}$H-NMR (400 MHz, DMSO-$d_6$) δ 7.97 (d, J = 1.2 Hz, 1H), 7.59 (d, J = 2.9 Hz, 1H), 7.20 (dd, J = 14.9, 8.1 Hz, 1H), 6.93-6.96 (m, 1H), 6.72-6.77 (m, 1H), 6.13 (dd, J = 12.3, 9.2 Hz, 1H), 5.55 (dd, J = 43.5, 17.1 Hz, 2H), 4.33 (d, J = 13.0 Hz, 1H), 3.95 (d, J = 13.7 Hz, 1H), 3.69 (dd, J = 16.9, 12.5 Hz, 1H), 3.38-3.51 (m, 3H), 3.12 (d, J = 5.1 Hz, 6H), 2.86 (s, 1H), 2.06-2.13 (m, 2H), 1.78 (d, J = 12.2 Hz, 1H), 1.53 (d, J = 12.2 Hz, 1H); LCMS (M + 1): 667.05 |
| 8 | ((3-fluoro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)dimethyl-l6-sulfanone | $^{1}$H-NMR (400 MHz, DMSO-$d_6$) δ 7.96 (d, J = 0.7 Hz, 1H), 7.39 (d, J = 2.2 Hz, 1H), 7.16-7.23 (m, 2H), 6.94 (dd, J = 8.1, 2.4 Hz, 1H), 6.75 (dd, J = 12.7, 8.3 Hz, 1H), 6.13 (dd, J = 14.5, 9.4 Hz, 1H), 5.03-5.10 (m, 2H), 4.37 (d, J = 13.9 Hz, 1H), 3.99 (d, J = 13.9 Hz, 1H), 3.69 (dd, J = 16.9, 12.7 Hz, 1H), 3.35-3.51 (m, 2H), 3.24 (d, J = 28.4 Hz, 1H), 3.10-3.21 (m, 6H), 2.79 (s, 1H), 2.06 (d, J = 12.2 Hz, 2H), 2.00 (s, 3H), 1.80-1.60 (1H), 1.54 (s, 1H); LCMS (M + 1): 545.1 |
| 9 | ((2-(3-(2-(1-(2-(4-chloro-1H-pyrazol-1-yl)acetyl)piperidin-4-yl)thiazol-4-yl)-4,5-dihydroisoxazol-5-yl)-3-fluorophenyl)imino)dimethyl-l6-sulfanone | $^{1}$H-NMR (400 MHz, DMSO-$d_6$) δ 7.95 (d, J = 11.0 Hz, 1H), 7.87 (d, J = 0.7 Hz, 1H), 7.50-7.51 (m, 1H), 7.19 (td, J = 8.2, 6.8 Hz, 1H), 6.94 (d, J = 7.8 Hz, 1H), 6.72-6.77 (m, 1H), 6.13 (dd, J = 12.3, 9.2 Hz, 1H), 5.03-5.23 (m, 2H), 4.36 (d, J = 13.2 Hz, 1H), 3.94-4.03 (m, 1H), 3.68-3.73 (m, 1H), 3.47-3.51 (m, 1H), 3.37 (tt, J = 11.5, 3.8 Hz, 1H), 3.24 (dd, J = 23.2, 11.0 Hz, 1H), 3.11 (d, J = 5.9 Hz, 6H), 2.81 (t, J = 11.6 Hz, 1H), 2.07 (d, J = 8.8 Hz, 2H), 1.70-1.80 (m, 1H), 1.55 (qd, J = 12.3, 3.7 Hz, 1H); LCMS (M + 1): 565.05 |
| 10 | ((2-(3-(2-(1-(2-(2H-indazol-2-yl)acetyl)piperidin-4-yl)thiazol-4-yl)-4,5-dihydroisoxazol-5-yl)-3-fluorophenyl)imino)dimethyl-l6-sulfanone | $^{1}$H-NMR (400 MHz, DMSO-$d_6$) δ 8.29 (d, J = 2.0 Hz, 1H), 7.97 (d, J = 1.2 Hz, 1H), 7.69-7.73 (m, 1H), 7.54-7.57 (m, 1H), 7.18-7.23 (m, 2H), 6.93-7.03 (m, 2H), 6.73-6.78 (m, 1H), 6.13 (dd, J = 12.3, 9.2 Hz, 1H), 5.51 (d, J = 6.6 Hz, 2H), 4.40 (s, 1H), 4.19-3.98 (1H), 3.70 (dd, J = 16.9, 12.5 Hz, 1H), 3.39-3.52 (m, 3H), 3.12 (d, J = 5.6 Hz, 6H), 2.84 (s, 1H), 2.11 (s, 2H), 1.87-1.68 (1H), 1.68-1.47 (1H); LCMS (M + 1): 581 |
| 11 | 3-chloro-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-5-(trifluoromethyl)pyridin-2(1H)-one | $^{1}$H-NMR (400 MHz, DMSO-$d_6$) δ 8.36 (d, J = 5.6 Hz, 1H), 8.15-8.16 (m, 1H), 7.97 (d, J = 1.0 Hz, 1H), 7.16-7.23 (m, 1H), 6.94 (dd, J = 8.1, 2.4 Hz, 1H), 6.72-6.77 (m, 1H), 6.13 (dd, J = 12.3, 9.2 Hz, 1H), 5.03 (d, J = 16.1 Hz, 2H), 4.35 (d, J = 13.0 Hz, 1H), 3.96-4.01 (m, 1H), 3.69 (dd, J = 16.7, 12.6 Hz, 1H), 3.37-3.51 (m, 3H), 3.12 (d, J = 5.4 Hz, 6H), 2.82-2.88 (m, 1H), 2.07-2.16 (m, 2H), 1.78-1.81 (m, 1H), 1.57 (dd, J = 12.5, 3.4 Hz, 1H); LCMS (M + 1): 659.9 |
| 12 | 1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one | $^{1}$H-NMR (400 MHz, DMSO-$d_6$) δ 7.95 (td, J = 12.3, 7.3 Hz, 3H), 7.17-7.28 (m, 1H), 6.94-7.00 (m, 1H), 6.72-6.77 (m, 1H), 6.36-6.44 (m, 1H), 6.13 (dd, J = 12.2, 9.3 Hz, 1H), 4.83-4.99 (m, 2H), 4.36 (d, J = 13.0 Hz, 1H), 4.01 (d, J = 13.0 Hz, 1H), 3.69 (dd, J = 16.7, 12.3 Hz, 1H), 3.36-3.52 (m, 2H), 3.27 (d, J = 13.0 Hz, 1H), 3.12 (d, J = 4.9 Hz, 6H), 2.81-2.87 (m, 1H), 2.11 (dd, J = 23.7, 12.2 Hz, 2H), 1.79 (q, J = 10.8 Hz, 1H), 1.51-1.61 (m, 1H); LCMS (M + 1): 626.95 |
| 13 | ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)dimethyl-l6-sulfanone | $^{1}$H-NMR (400 MHz, DMSO-$d_6$) δ 7.96 (s, 1H), 7.19 (td, J = 8.2, 6.8 Hz, 1H), 6.94 (d, J = 8.1 Hz, 1H), 6.72-6.77 (m, 1H), 6.13 (dd, J = 12.3, 9.2 Hz, 1H), 5.76 (d, J = 13.7 Hz, 1H), 4.97 (q, J = 17.0 Hz, 2H), 4.36 (d, J = 13.0 Hz, 1H), 3.98-4.08 (m, 1H), 3.65-3.73 (m, 1H), 3.34-3.51 (m, 2H), 3.11-3.25 (m, 7H), 2.80 (t, J = 11.6 Hz, 1H),2.05-2.09 (m, 8H), 1.49-1.77 (m, 2H); LCMS (M + 1): 559.15 |
| 14 | ((3-fluoro-2-(3-(2-(1-(2-((6-methyl-3-(trifluoromethyl)pyridin-2-yl)oxy)acetyl)piperidin-4-yl)thiazol-4-yl)-4,5-dihydroisoxazol-5-yl)phenyl)imino)dimethyl-l6-sulfanone | $^{1}$H-NMR (400 MHz, DMSO-$d_6$) δ 7.95 (d, J = 7.1 Hz, 2H), 7.17-7.25 (m, 1H), 6.99-7.05 (m, 1H), 6.85-6.96 (m, 1H), 6.73-6.77 (m, 1H), 6.13 (dd, J = 12.3, 9.2 Hz, 1H), 5.12-5.26 (m, 2H), 4.34 (d, J = 12.2 Hz, 1H), 3.92-4.03 (m, 1H), 3.69 (dd, J = 16.6, 13.0 Hz, 1H), 3.37-3.51 (m, 1H), 3.39 (tt, J = 11.4, 3.7 Hz, 1H), 3.22-3.29 (m, 1H), 3.11 (d, J = 6.4 Hz, 6H), 2.66-2.93 (m, 1H), 2.31-2.43 (m, 3H), 1.98-2.19 (m, 2H), 1.80-1.93 (m, 1H), 1.46-1.58 (m, 1H); LCMS (M + 1): 640.15 |
| 15 | 5-bromo-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1- | $^{1}$H-NMR (400 MHz, DMSO-$d_6$) δ 8.55-8.56 (m, 1H), 8.33-8.34 (m, 1H), 7.97 (d, J = 1.2 Hz, 1H), 7.20 (dd, J = 14.9, 8.3 Hz, 1H), 6.93-6.96 (m, 1H), 6.72-6.77 (m, 1H), 6.13 (dd, J = 12.2, 9.3 Hz, 1H), 4.97 (s, 2H), 4.34 (d, J = 13.0 Hz, 1H), 3.97 (d, J = 14.2 Hz, 1H), 3.69 (dd, J = 17.0, 12.6 Hz, 1H), 3.40-3.51 (m, 2H), 3.30-3.30 (1H), 3.12 (d, J = 5.4 Hz, 6H), 2.87 (d, J = 11.2 Hz, 1H), 2.06 (s, 2H), |

TABLE NO 1-continued

| Compd. No. | Compound Name | Analytical data |
|---|---|---|
| | The following compounds were prepared analogue to the procedure described in schemes 1-17 or Examples 1 to 8. | |
| | yl)-2-oxoethyl)-6-oxo-1,6-dihydropyridine-3-carbonitrile | 1.78 (d, J = 12.0 Hz, 1H), 1.56 (d, J = 15.9 Hz, 1H); LCMS (M + 1): 663 |
| 16 | ((3-(3-(2-(1-(2-(3,5-bis(difluoromethyl)-1H-pyrazol-1-yl)acetyl)piperidin-4-yl)thiazol-4-yl)-4,5-dihydroisoxazol-5-yl)phenyl)imino)dimethyl-l6-sulfanone | $^1$H-NMR (400 MHz, DMSO-d$_6$) δ 8.02 (s, 1H), 6.86-7.30 (m, 7H), 5.61-5.74 (m, 1H), 5.38 (q, J = 16.7 Hz, 2H), 4.34 (d, J = 13.7 Hz, 1H), 3.80-3.97 (m, 2H), 3.31-3.41 (m, 3H), 3.14-3.23 (m, 6H), 2.80-2.86 (m, 1H), 2.09 (t, J = 13.7 Hz, 2H), 1.74-1.84 (m, 1H), 1.50-1.61 (m, 1H); LCMS (M + 1): 613.05 |
| 17 | dimethyl((3-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)-l6-sulfanone | $^1$H-NMR (400 MHz, DMSO-d$_6$) δ 8.01 (d, J = 1.5 Hz, 1H), 7.18 (t, J = 7.6 Hz, 1H), 6.85-6.89 (m, 4H), 6.49 (s, 1H), 5.64 (dd, J = 10.8, 8.1 Hz, 1H), 5.27 (dd, J = 36.7, 17.1 Hz, 2H), 4.36 (d, J = 13.4 Hz, 1H), 3.80-4.03 (m, 2H), 3.31-3.34 (m, 3H), 3.18 (d, J = 10.8 Hz, 6H), 2.72-2.88 (m, 1H), 2.20 (s, 3H), 2.06-2.12 (m, 2H), 1.80 (dd, J = 12.2, 3.2 Hz, 1H), 1.55 (dd, J = 12.2, 3.7 Hz, 1H); LCMS (M + 1): 595 |
| 18 | ((3-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)dimethyl-l6-sulfanone | $^1$H-NMR (400 MHz, DMSO-d$_6$) δ 8.01 (s, 1H), 7.18 (m, J = 7.6, 0.8 Hz, 1H), 6.86-6.89 (m, 3H), 5.78 (s, 1H), 5.63 (dd, J = 10.8, 8.1 Hz, 1H), 4.96 (dd, J = 34.4, 16.7 Hz, 2H), 4.36 (d, J = 13.2 Hz, 1H), 4.00 (d, J = 13.4 Hz, 1H), 3.83 (dd, J = 17.1, 11.0 Hz, 1H), 3.30-3.34 (m, 3H), 3.16-3.22 (m, 6H), 2.76-2.82 (m, 1H), 2.01-2.09 (m, 8H), 1.66-1.76 (m, 1H), 1.52 (ddd, J = 24.6, 12.0, 3.8 Hz, 1H); LCMS (M + 1): 541.05 |
| 19 | 1-(4-(4-((5S)-5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-d$_6$) δ 7.97 (s, 1H), 7.22 (dd, J = 7.9, 5.8 Hz, 1H), 6.48-6.53 (m, 2H), 6.02 (dd, J = 11.8, 9.6 Hz, 1H), 5.33 (d, J = 17.1 Hz, 1H), 5.23 (d, J = 16.8 Hz, 1H), 4.96 (d, J = 17.7 Hz, 1H), 4.55 (d, J = 17.4 Hz, 1H), 4.37 (d, J = 13.1 Hz, 1H), 3.97 (d, J = 14.4 Hz, 1H), 3.73 (dd, J = 16.4, 12.7 Hz, 1H), 3.54-3.60 (m, 4H), 3.37-3.41 (m, 1H), 3.25 (d, J = 11.6 Hz, 1H), 2.83 (t, J = 11.6 Hz, 1H), 2.20 (s, 3H), 2.11 (t, J = 12.1 Hz, 2H), 1.80 (dd, J = 20.8, 11.9 Hz, 1H), 1.56 (qd, J = 12.1, 3.6 Hz, 1H); LCMS (M + 1): 610.95 |
| 20 | 1-(4-(4-((5R)-5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-d$_6$) δ 7.97 (d, J = 2.8 Hz, 1H), 7.23 (dd, J = 8.1, 5.7 Hz, 1H), 6.49-6.54 (m, 2H), 6.01 (dd, J = 11.6, 10.1 Hz, 1H), 5.33 (d, J = 16.8 Hz, 1H), 5.23 (d, J = 17.1 Hz, 1H), 4.94 (d, J = 17.1 Hz, 1H), 4.56 (d, J = 17.4 Hz, 1H), 4.37 (d, J = 13.1 Hz, 1H), 3.97 (d, J = 14.2 Hz, 1H), 3.67-3.74 (m, 1H), 3.54-3.62 (m, 4H), 3.38 (tt, J = 11.4, 3.7 Hz, 1H), 3.25 (d, J = 11.3 Hz, 1H), 2.83 (t, J = 11.6 Hz, 1H), 2.17-2.20 (m, 3H), 2.08-2.15 (m, 2H), 1.80 (qd, J = 12.2, 3.5 Hz, 1H), 1.56 (qd, J = 12.1, 3.9 Hz, 1H); LCMS (M + 1): 610.95 |
| 21 | 1-(4-(4-(5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-d$_6$) δ 7.97 (s, 1H), 7.22 (dd, J = 7.9, 5.8 Hz, 1H), 6.48-6.53 (m, 2H), 6.02 (dd, J = 11.8, 9.6 Hz, 1H), 5.33 (d, J = 17.1 Hz, 1H), 5.23 (d, J = 16.8 Hz, 1H), 4.96 (d, J = 17.7 Hz, 1H), 4.55 (d, J = 17.4 Hz, 1H), 4.37 (d, J = 13.1 Hz, 1H), 3.97 (d, J = 14.4 Hz, 1H), 3.73 (dd, J = 16.4, 12.7 Hz, 1H), 3.54-3.60 (m, 4H), 3.37-3.41 (m, 1H), 3.25 (d, J = 11.6 Hz, 1H), 2.83 (t, J = 11.6 Hz, 1H), 2.20 (s, 3H), 2.11 (t, J = 12.1 Hz, 2H), 1.80 (dd, J = 20.8, 11.9 Hz, 1H), 1.56 (qd, J = 12.1, 3.6 Hz, 1H); LCMS (M + 1): 610.95 |
| 22 | 2-(3,5-dimethyl-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one | $^1$H-NMR (400 MHz, CHLOROFORM-D) δ 7.59 (s, 1H), 7.22 (d, J = 7.6 Hz, 1H), 6.99-7.06 (m, 3H), 5.86 (s, 1H), 5.67 (dd, J = 11.0, 8.6 Hz, 1H), 4.85-4.94 (m, 2H), 4.58 (d, J = 13.4 Hz, 1H), 4.06 (d, J = 12.8 Hz, 1H), 3.80 (dd, J = 17.1, 11.0 Hz, 1H), 3.36-3.46 (m, 3H), 3.13-3.33 (m, 4H), 2.85 (t, J = 11.5 Hz, 1H), 2.14-2.34 (m, 8H), 1.70-1.80 (m, 3H), 1.22-1.33 (m, 2H), 0.83-0.89 (m, 1H); LCMS (M + 1): 567.05 |
| 23 | 2-(5-methyl-3-(trifluoromethyl)-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one | $^1$H-NMR (400 MHz, CHLOROFORM-D) δ 7.60 (s, 1H), 7.23 (d, J = 7.6 Hz, 1H), 7.00-7.08 (m, 3H), 6.33 (s, 1H), 5.68 (dd, J = 11.0, 8.6 Hz, 1H), 4.99 (dd, J = 21.5, 16.0 Hz, 2H), 4.56 (d, J = 13.4 Hz, 1H), 4.04 (d, J = 13.8 Hz, 1H), 3.81 (dd, J = 17.1, 11.0 Hz, 1H), 3.40-3.49 (m, 3H), 3.27-3.35 (m, 2H), 3.14-3.22 (m, 2H), 2.86-2.92 (m, 1H), 2.16-2.32 (m, 6H), 1.76-1.84 (m, 3H), 1.25-1.29 (m, 2H); LCMS (M + 1): 621.1 |
| 24 | 2-(3,5-bis(difluoromethyl)-1H-pyrazol-1-yl)-1-(4-(4-(5-(3-((1-oxidotetrahydro-1l6-thiophen-1- | $^1$H-NMR (400 MHz, CHLOROFORM-D) δ 7.61 (s, 1H), 7.23 (d, J = 7.9 Hz, 1H), 6.53-7.07 (m, 6H), 5.68 (dd, J = 11.0, 8.6 Hz, 1H), 5.15 (t, J = 16.8 Hz, 2H), 4.55 (d, J = 13.8 Hz, 1H), 3.91 (d, J = 13.8 Hz, 1H), 3.81 (dd, J = 17.1, 11.0 Hz, 1H), 3.40-3.46 (m, 3H), 3.29- |

TABLE NO 1-continued

The following compounds were prepared analogue to the procedure described in schemes 1-17 or Examples 1 to 8.

| Compd. No. | Compound Name | Analytical data |
|---|---|---|
| | ylidene)amino)phenyl)-4,5-dihydroisoxazol-3-yl)thiazol-2-yl)piperidin-1-yl)ethan-1-one | 3.37 (m, 2H), 3.17 (td, J = 12.3, 6.7 Hz, 2H), 2.89-2.96 (m, 1H), 2.17-2.32 (m, 6H), 1.75-1.91 (m, 2H); LCMS (M + 1): 639.1 |
| 25 | ((2-(3-(2-(1-(2-(1H-pyrazol-1-yl)acetyl)piperidin-4-yl)thiazol-4-yl)-4,5-dihydroisoxazol-5-yl)-3-fluorophenyl)imino)dimethyl-l6-sulfanone | $^1$H-NMR (400 MHz, CHLOROFORM-D) δ 7.54 (d, J = 15.6 Hz, 2H), 7.46 (s, 1H), 7.13-7.19 (m, 1H), 7.08 (d, J = 7.9 Hz, 1H), 6.71-6.75 (m, 1H), 6.35 (s, 1H), 6.17 (dd, J = 12.5, 9.2 Hz, 1H), 5.02-5.11 (m, 2H), 4.63 (d, J = 13.8 Hz, 1H), 4.07 (d, J = 13.1 Hz, 1H), 3.79 (dd, J = 16.5, 9.2 Hz, 1H), 3.57 (dd, J = 16.5, 12.5 Hz, 1H), 3.22-3.34 (m, 2H), 3.09 (d, J = 15.6 Hz, 3H), 2.94 (d, J = 14.7 Hz, 3H), 2.85 (t, J = 12.4 Hz, 1H), 2.13-2.18 (m, 2H), 1.69-1.79 (m, 2H); LCMS (M + 1): 530.95 |
| 26 | 2-(3,5-bis(difluoromethyl)-1H-pyrazol-1-yl)-1-(4-(4-(5-(2-fluoro-6-((1-oxidotetrahydro-1l6-thiophen-1-ylidene)amino)phenyl)-4,5-dihydroisoxazol-3-yl)thiazol-2-yl)piperidin-1-yl)ethan-1-one | $^1$H-NMR (400 MHz, CHLOROFORM-D) δ 7.52 (s, 1H), 7.16 (td, J = 8.2, 6.5 Hz, 1H), 6.53-7.05 (m, 5H), 6.23 (dd, J = 12.4, 9.3 Hz, 1H), 5.14-5.16 (m, 2H), 4.59 (d, J = 13.1 Hz, 1H), 3.93 (d, J = 13.4 Hz, 1H), 3.82 (dd, J = 16.5, 9.2 Hz, 1H), 3.59 (dd, J = 16.7, 12.4 Hz, 1H), 3.30-3.43 (m, 3H), 3.11 (ddd, J = 26.6, 12.7, 6.9 Hz, 2H), 2.89-3.01 (m, 2H), 2.19-2.33 (m, 6H), 1.79-1.92 (m, 2H); LCMS (M + 1): 657 |
| 27 | 1-(4-(4-(5-(2-fluoro-6-((1-oxidotetrahydro-1l6-thiophen-1-ylidene)anlino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, CHLOROFORM-D) δ 7.51 (d, J = 4.3 Hz, 1H), 7.15 (m, J = 8.1, 6.5 Hz, 1H), 7.04 (d, J = 7.9 Hz, 1H), 6.67-6.72 (m, 1H), 6.34 (s, 1H), 6.23 (dd, J = 12.5, 9.5 Hz, 1H), 4.99 (dd, J = 26.6, 15.9 Hz, 2H), 4.57-4.61 (m, 1H), 4.07 (d, J = 13.4 Hz, 1H), 3.82 (dd, J = 16.7, 9.3 Hz, 1H), 3.58 (dd, J = 16.5, 12.5 Hz, 1H), 3.27-3.42 (m, 3H), 3.04-3.15 (m, 2H), 2.85-3.00 (m, 2H), 2.33 (s, 3H), 2.17-2.31 (m, 7H), 1.75-1.82 (m, 2H); LCMS (M + 1): 639 |
| 28 | 3-bromo-5-chloro-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)pyridin-2(1H)-one | $^1$H-NMR (400 MHz, CHLOROFORM-D) δ 7.76 (d, J = 2.8 Hz. 1H), 7.47 (s, 1H), 7.40 (d, J = 2.4 Hz, 1H), 7.16 (td, J = 8.1, 6.4 Hz, 1H), 7.09 (d, J = 7.6 Hz, 1H), 6.71-6.76 (m, 1H), 6.18 (dd, J = 12.5, 9.2 Hz, 1H), 4.79-4.85 (m, 1H), 4.74 (d, J = 14.7 Hz, 1H), 4.60 (d, J = 13.4 Hz, 1H), 4.08 (d, J = 13.8 Hz, 1H), 3.80 (dd, J = 16.5, 9.2 Hz, 1H), 3.58 (dd, J = 16.5, 12.5 Hz, 1H), 3.32-3.38 (m, 2H), 3.08 (s, 3H), 2.87-2.94 (m, 4H), 2.17-2.30 (m, 2H), 1.91-1.94 (m, 1H), 1.81 (d, J = 11.6 Hz, 1H); LCMS (M + 1): 671.8 |
| 29 | 1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-5-(trifluoromethyl)pyridin-2(1H)-one | $^1$H-NMR (400 MHz, CHLOROFORM-D) δ 7.71 (s, 1H), 7.48-7.52 (m, 2H), 7.17 (td, J = 8.1, 6.4 Hz, 1H), 7.09 (d, J = 7.6 Hz, 1H), 6.71-6.76 (m, 1H), 6.64 (d, J = 9.5 Hz, 1H), 6.18 (dd, J = 12.4, 9.0 Hz, 1H), 4.80-4.83 (m, 2H), 4.62 (d, J = 13.4 Hz, 1H), 4.07 (d, J = 14.4 Hz, 1H), 3.80 (dd, J = 16.5, 9.2 Hz, 1H), 3.58 (dd, J = 16.5, 12.5 Hz, 1H), 3.33-3.39 (m, 2H), 3.08 (s, 3H), 2.92 (d, J = 15.0 Hz, 4H), 2.23 (d, J = 44.3 Hz, 2H), 2.06-1.87 (1H), 1.83 (d, J = 3.7 Hz, 1H); LCMS (M + 1): 625.95 |
| 30 | (3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)(imino)(methyl)-l6-sulfanone | $^1$H-NMR (400 MHz, CHLOROFORM-D) δ 8.17 (ddd, J = 26.1, 8.0, 1.3 Hz, 1H), 7.62-7.70 (m, 2H), 7.48 (m, J = 8.0, 1.6 Hz, 1H), 7.35 (s, 1H), 7.31 (s, 1H), 6.82-6.92 (m, 1H), 4.94-4.99 (m, 2H), 4.60 (d, J = 13.4 Hz, 1H), 4.05 (d, J = 14.4 Hz, 1H), 3.78-3.83 (m, 2H), 3.37 (d, J = 3.9 Hz, 2H), 3.21-3.33 (m, 3H), 2.83-2.89 (m, 1H), 2.16-2.19 (m, 2H), 2.04-2.10 (m, 3H), 1.69-1.81 (m, 3H); LCMS (M + 1): 547.05 |
| 31 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)dimethyl-l6-sulfanone | $^1$H-NMR (400 MHz, CHLOROFORM-D) δ 7.48 (s, 1H), 7.16 (td, J = 8.2, 6.5 Hz, 1H), 7.08 (d, J = 7.6 Hz, 1H), 6.53-7.02 (m, 4H), 6.18 (dd, J = 12.5, 9.2 Hz, 1H), 5.13-5.16 (m, 2H), 4.60 (d, J = 13.4 Hz, 1H), 3.93 (d, J = 13.8 Hz, 1H), 3.80 (dd, J = 16.7, 9.0 Hz, 1H), 3.58 (dd, J = 16.5, 12.5 Hz, 1H), 3.30-3.39 (m, 2H), 3.08 (s, 3H), 2.87-2.94 (m, 4H), 2.24 (dd, J = 32.1, 13.4 Hz, 2H), 1.75-1.88 (m, 2H); LCMS (M + 1): 631.1 |
| 32 | 2-(3,5-bis(difluoromethyl)-1H-pyrazol-1-yl)-1-(4-(4-((5S)-5-(6-fluoro-2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 7.97 (s, 1H), 7.02-7.30 (m, 3H), 6.89 (d, J = 3.9 Hz, 1H), 6.50 (dd, J = 11.4, 8.2 Hz, 1H), 6.03 (dd, J = 11.6, 9.7 Hz, 1H), 5.39 (q, J = 17.2 Hz, 2H), 4.96 (d, J = 17.4 Hz, 1H), 4.55 (d, J = 17.4 Hz, 1H), 4.34 (d, J = 13.0 Hz, 1H), 3.91-4.03 (m, 1H), 3.69-3.77 (m, 1H), 3.54-3.60 (m, 4H), 3.23-3.43 (m, 2H), 2.81-2.86 (m, 1H), 2.07-2.19 (m, 2H), 1.79-1.85 (m, 1H), 1.53-1.62 (m, 1H); LCMS (M + 1): 628.95 |
| 33 | 2-(3,5-bis(difluoromethyl)-1H-pyrazol-1-yl)-1-(4-(4-((5R)-5-(6-fluoro-2-methyl-2-oxido-3H-2l4- | $^1$H-NMR (400 MHz, CHLOROFORM-D) δ 7.62 (s, 1H), 7.15 (dd, J = 7.9, 5.3 Hz, 1H), 6.69-6.91 (m, 3H), 6.53 (dd, J = 10.1, 7.9 Hz, 1H), 6.15-6.21 (m, 1H), 5.17 (s, 2H), 4.67-4.52 (1H), 4.45 (d, J = 9.8 Hz, 2H), 3.93 (dd, J = 16.6, 10.0 Hz, 2H), 3.64 (dd, J = 16.6, |

TABLE NO 1-continued

The following compounds were prepared analogue to the procedure described in schemes 1-17 or Examples 1 to 8.

| Compd. No. | Compound Name | Analytical data |
| --- | --- | --- |
| | benzo[c]isothiazol-7-yl)-4,5-dihydroisoxazol-3-yl)thiazol-2-yl)piperidin-1-yl)ethan-1-one | 12.0 Hz, 1H), 3.38 (s, 5H), 2.96 (s, 1H), 2.21 (s, 2H), 1.99-1.78 (2H); LCMS (M + 1): 629.1 |
| 34 | 2-(3,5-bis(difluoromethyl)-1H-pyrazol-1-yl)-1-(4-(4-((5S)-5-(2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 8.03 (d, J = 1.2 Hz, 1H), 6.90-7.32 (m, 5H), 6.72 (t, J = 7.6 Hz, 1H), 5.85 (dd, J = 10.9, 7.7 Hz, 1H), 5.40 (dd, J = 35.8, 17.0 Hz, 2H), 5.00 (d, J = 17.4 Hz, 1H), 4.56 (d, J = 17.6 Hz, 1H), 4.36 (d, J = 13.4 Hz, 1H), 3.81-4.06 (m, 2H), 3.54 (s, 3H), 3.23-3.40 (m, 3H), 2.83 (s, 1H), 2.08 (d, J = 14.4 Hz, 2H), 1.81 (d, J = 12.7 Hz, 1H), 1.56 (d, J = 12.7 Hz, 1H); LCMS (M + 1): 610.9 |
| 35 | 2-(3,5-bis(difluoromethyl)-1H-pyrazol-1-yl)-1-(4-(4-((5R)-5-(2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 8.03 (d. J = 6.6 Hz, 1H), 7.04-7.34 (m, 4H), 6.91 (d, J = 4.4 Hz, 1H), 6.73 (t, J = 7.6 Hz, 1H), 5.85 (dd, J = 10.8, 7.8 Hz, 1H), 5.40 (q, J = 17.0 Hz, 2H), 4.96-5.02 (m, 1H), 4.57 (d, J = 17.6 Hz, 1H), 4.36 (d, J = 13.2 Hz, 1H), 3.96-4.05 (m, 1H), 3.81 (dd, J = 17.1, 11.0 Hz, 1H), 3.55 (d, J = 3.7 Hz, 3H), 3.24-3.41 (m, 3H), 2.81-2.87 (m, 1H), 2.05-2.22 (m, 2H), 1.79-1.82 (m, 1H), 1.56 (dd, J = 12.1, 4.3 Hz, 1H); LCMS (M + 1): 611.15 |
| 36 | 2-(3,5-bis(difluoromethyl)-1H-pyrazol-1-yl)-1-(4-(4-(5-(2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 8.03 (d, J = 6.6 Hz, 1H), 6.90-7.32 (m, 6H), 6.73 (td, J = 7.6, 2.4 Hz, 1H), 5.85 (dd, J = 10.1, 8.2 Hz, 1H), 5.40 (q, J = 17.4 Hz, 2H), 4.99 (dd, J = 17.6, 4.4 Hz, 1H), 4.57 (d, J = 16.9 Hz, 1H), 4.36 (d, J = 13.0 Hz, 1H), 3.77-4.05 (m, 2H), 3.54-3.58 (m, 3H), 3.24-3.42 (m, 3H), 2.68-2.87 (m, 1H), 2.05-2.14 (m, 2H), 1.81 (d, J = 11.2 Hz, 1H), 1.51-1.61 (m, 1H); LCMS (M + 1): 610.85 |
| 37 | N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)(methyl)(oxo)-l6-sulfaneylidene)cyanamide | $^1$H-NMR (400 MHz, DMSO-$d_6$) δ 8.02 (d, J = 10.4 Hz, 1H), 7.85 (dd, J = 7.5, 4.7 Hz, 1H), 7.59-7.75 (m, 2H), 6.89-7.30 (m, 3H), 6.62-6.73 (m, 1H), 6.48 (d, J = 7.3 Hz, 1H), 6.15 (s, 1H), 5.43 (d, J = 16.8 Hz, 1H), 5.30-5.37 (m, 1H), 4.34 (d, J = 13.1 Hz, 1H), 3.92-4.07 (m, 2H), 3.36-3.52 (m, 2H), 3.23-3.29 (m, 1H), 2.80-2.86 (m, 1H), 2.06-2.14 (m, 3H), 1.75-1.84 (m, 1H), 1.52-1.62 (m, 1H); LCMS (M + 1): 643 |
| 38 | (Z)-N-((3-fluoro-2-(3-(2-(1-(2-(3-methyl-1H-pyrazol-1-yl)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-$d_6$) δ 8.12-8.00 (1H), 7.98-7.86 (1H), 7.83-7.72 (1H), 7.65-7.43 (1H), 7.40-7.30 (1H), 7.20-7.09 (1H), 6.21-6.09 (1H), 5.11-4.95 (2H), 4.42-4.30 (1H), 4.09-3.87 (2H), 3.70-3.39 (1H), 3.27-3.12 (2H), 3.12-2.94 (3H), 2.86-2.68 (1H), 2.17-2.01 (2H), 2.00-1.82 (3H), 1.77-1.61 (1H), 1.60-1.44 (1H); LCMS (M + 1): 540.1 |
| 39 | N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(oxo)-l6-sulfaneylidene)cyanamide | $^1$H-NMR (400 MHz, DMSO-$d_6$) δ 8.02 (d, J = 10.4 Hz, 1H), 7.85 (q, J = 3.8 Hz, 1H), 7.59-7.75 (m, 2H), 6.62-6.73 (m, 1H), 6.16 (s, 1H), 5.32 (d, J = 17.1 Hz, 1H), 5.23 (d, J = 17.1 Hz, 1H), 4.36 (d, J = 12.8 Hz, 1H), 3.84-4.07 (m, 2H), 3.36-3.59 (m, 4H), 3.23-3.29 (m, 1H), 2.80-2.88 (m, 1H), 2.21 (d, J = 13.8 Hz, 3H), 2.03-2.14 (m, 3H), 1.77-1.90 (m, 1H), 1.57 (qd, J = 12.2, 3.7 Hz, 1H); LCMS (M + 1): 625.1 |
| 40 | (E)-N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-$d_6$) δ 8.08 (s, 1H), 7.97 (d, J = 7.9 Hz, 1H), 7.80 (m, J = 8.1, 5.3 Hz, 1H), 7.62 (dd, J = 10.2, 8.1 Hz, 1H), 6.49 (s, 1H), 6.16-6.21 (m, 1H), 5.33 (d, J = 17.1 Hz, 1H), 5.23 (d, J = 16.8 Hz, 1H), 4.37 (d, J = 12.5 Hz, 1H), 3.95-4.04 (m, 2H), 3.62 (q, J = 9.3 Hz, 1H), 3.38-3.42 (m, 1H), 3.23-3.28 (m, 1H), 3.12 (d, J = 4.0 Hz, 2H), 2.80-2.86 (m, 1H), 2.53 (s, 1H), 2.22 (d, J = 14.4 Hz, 3H), 2.06-2.14 (m, 2H), 1.79-1.90 (m, 1H), 1.55-1.58 (m, 1H); LCMS (M + 1): 608.15 |
| 41 | (Z)-N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-$d_6$) δ 8.08 (s, 1H), 7.97 (d, J = 7.9 Hz, 1H), 7.80 (m, J = 8.1, 5.3 Hz, 1H), 7.62 (dd, J = 10.2, 8.1 Hz, 1H), 6.49 (s, 1H), 6.16-6.21 (m, 1H), 5.33 (d, J = 17.1 Hz, 1H), 5.23 (d, J = 16.8 Hz, 1H), 4.37 (d, J = 12.5 Hz, 1H), 3.95-4.04 (m, 2H), 3.62 (q, J = 9.3 Hz, 1H), 3.38-3.42 (m, 1H), 3.23-3.28 (m, 1H), 3.12 (d, J = 4.0 Hz, 2H), 2.80-2.86 (m, 1H), 2.53 (s, 1H), 2.22 (d, J = 14.4 Hz, 3H), 2.06-2.14 (m, 2H), 1.79-1.90 (m, 1H), 1.55-1.58 (m, 1H); LCMS (M + 1): 608.05 |
| 42 | (E)-N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3- | $^1$H-NMR (400 MHz, DMSO-$d_6$) δ 8.10 (d, J = 11.3 Hz, 1H), 7.97 (d, J = 7.9 Hz, 1H), 7.80 (td, J = 8.2, 5.3 Hz, 1H), 7.60-7.65 (m, 1H), 6.89-7.30 (m, 3H), 6.18 (dd, J = 11.5, 9.9 Hz, 1H), 5.43 (d, J = 17.1 Hz, 1H), 5.35 (d, J = 16.8 Hz, 1H), 4.34 (d, J = 12.5 Hz, 1H), 3.95-4.08 (m, 1H), 3.62 (dd, J = 17.9, 9.3 Hz, 1H), 3.37-3.43 (m, 1H), 3.25 (d, J = 11.9 Hz, 1H), 3.14 (dd, J = 13.6, 4.7 Hz, 1H), |

TABLE NO 1-continued

The following compounds were prepared analogue to the procedure described in schemes 1-17 or Examples 1 to 8.

| Compd. No. | Compound Name | Analytical data |
|---|---|---|
| | fluorophenyl)(methyl)-l4-sulfaneylidene)cyanamide | 2.80-2.87 (m, 1H), 2.06-2.15 (m, 5H), 1.79-1.85 (m, 1H), 1.57 (d, J = 11.6 Hz, 1H); LCMS (M + 1): 626.05 |
| 43 | (3-chloro-2-((R)-3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(isopropyl)-l6-sulfanone | $^1$H-NMR (400 MHz, DMSO-$d_6$) δ 8.00-8.06 (m, 2H), 7.83 (dd, J = 7.9, 1.2 Hz, 1H), 7.63 (t, J = 7.9 Hz, 1H), 6.94-7.04 (m, 1H), 5.76 (d, J = 11.6 Hz, 1H), 5.01 (d, J = 16.8 Hz, 1H), 4.93 (d, J = 15.3 Hz, 2H), 4.37 (d, J = 13.1 Hz, 1H), 4.00 (d, J = 12.5 Hz, 1H), 3.75-3.84 (m, 1H), 3.59 (dd, J = 17.3, 11.8 Hz, 1H), 3.36-3.40 (m, 1H), 3.22 (t, J = 11.9 Hz, 1H), 3.05-3.12 (m, 2H), 2.79 (t, J = 11.8 Hz, 1H), 2.05-2.09 (m, 11H), 1.72-1.77 (m, 1H), 1.53 (d, J = 12.5 Hz, 1H), 1.11-1.28 (m, 3H); LCMS (M + 1): 589.05 |
| 44 | (3-chloro-2-((S)-3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(isopropyl)-l6-sulfanone | $^1$H-NMR (400 MHz, DMSO-$d_6$) δ 8.00-8.06 (m, 2H), 7.83 (dd, J = 7.9, 1.2 Hz, 1H), 7.63 (t, J = 7.9 Hz, 1H), 6.94-7.04 (m, 1H), 5.76 (d, J = 11.6 Hz, 1H), 5.01 (d, J = 16.8 Hz, 1H), 4.93 (d, J = 15.3 Hz, 2H), 4.37 (d, J = 13.1 Hz, 1H), 4.00 (d, J = 12.5 Hz, 1H), 3.75-3.84 (m, 1H), 3.59 (dd, J = 17.3, 11.8 Hz, 1H), 3.36-3.40 (m, 1H), 3.22 (t, J = 11.9 Hz, 1H), 3.05-3.12 (m, 2H), 2.79 (t, J = 11.8 Hz, 1H), 2.05-2.09 (m, 10H), 1.72-1.77 (m, 1H), 1.53 (d, J = 12.5 Hz, 1H), 1.11-1.28 (m, 3H); LCMS (M + 1): 589.05 |
| 45 | (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(isopropyl)-l6-sulfanone | $^1$H-NMR (400 MHz, DMSO-$d_6$) δ 8.03 (t, J = 7.6 Hz, 1H), 7.95 (d, J = 2.8 Hz, 1H), 7.77 (dd, J = 8.1, 1.1 Hz, 1H), 7.58 (t, J = 7.9 Hz, 1H), 6.96-7.07 (m, 1H), 6.41 (s, 1H), 5.18 (s, 2H), 4.58 (s, 1H), 3.76 (dd, J = 17.3, 12.1 Hz, 1H), 3.55-3.64 (m, 1H), 3.31-3.40 (m, 2H), 3.16-3.29 (m, 1H), 2.19 (d, J = 12.5 Hz, 3H), 2.11 (d, J = 11.0 Hz, 2H), 1.72 (d, J = 15.3 Hz, 2H), 1.26 (t, J = 7.0 Hz, 3H), 1.15 (d, J = 6.7 Hz, 6H); LCMS (M + 1): 643 |
| 46 | 1-(4-(4-((5S)-5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-$d_6$) δ 8.01 (d, J = 7.3 Hz, 1H), 7.20 (dd, J = 7.2, 1.1 Hz, 1H),7.11 (d, J = 7.6 Hz, 1H), 6.70 (t, J = 7.6 Hz, 1H), 6.48 (s, 1H), 5.83 (dd, J = 11.0, 7.6 Hz, 1H), 5.32 (d, J = 17.1 Hz, 1H), 5.22 (d, J = 16.8 Hz, 1H), 4.98 (d, J = 17.4 Hz, 1H), 4.54 (d, J = 17.7 Hz, 1H), 4.36 (d, J = 12.8 Hz, 1H), 3.91-4.03 (m, 1H), 3.83 (dd, J = 17.1, 11.0 Hz, 1H), 3.52-3.57 (m, 3H), 3.38 (td, J = 7.6, 3.9 Hz, 1H), 3.22-3.29 (m, 2H), 2.82 (t, J = 11.5 Hz, 1H), 2.19 (t, J = 14.8 Hz, 3H), 2.03-2.12 (m, 2H), 1.79 (qd, J = 12.2, 3.6 Hz, 1H), 1.54 (qd, J = 12.2, 3.8 Hz, 1H); LCMS (M + 1): 593.15 |
| 47 | 1-(4-(4-((5R)-5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-$d_6$) δ 8.01 (d, J = 6.1 Hz, 1H), 7.21 (dd, J = 7.3, 0.9 Hz, 1H), 7.11 (d, J = 7.3 Hz, 1H), 6.70 (q, J = 7.3 Hz, 1H), 6.49 (s, 1H), 5.83 (dd, J = 10.7, 7.9 Hz, 1H), 5.32 (d, J = 16.8 Hz, 1H), 5.23 (d, J = 17.1 Hz, 1H), 4.97 (d, J = 17.4 Hz, 1H), 4.55 (d, J = 17.4 Hz, 1H), 4.36 (d, J = 13.1 Hz, 1H), 3.91-4.04 (m, 1H), 3.79 (dd, J = 17.0, 10.9 Hz, 1H), 3.48-3.57 (m, 3H), 3.34-3.40 (m, 2H), 3.22-3.29 (m, 1H), 2.82 (t, J = 11.5 Hz, 1H), 2.17-2.23 (m, 3H), 2.06-2.15 (m, 2H), 1.79 (qd, J = 12.1, 3.4 Hz, 1H), 1.54 (qd, J = 12.3, 3.9 Hz, 1H); LCMS (M + 1): 593.15 |
| 48 | 1-(4-(4-(5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-$d_6$) δ 8.01 (d, J = 6.4 Hz, 1H), 7.19-7.22 (m, 1H), 7.11 (d, J = 7.6 Hz, 1H), 6.71 (td, J = 7.6, 2.4 Hz, 1H), 6.49 (s, 1H), 5.83 (dd, J = 10.7, 7.9 Hz, 1H), 5.32 (d, J = 17.1 Hz, 1H), 5.23 (d, J = 16.8 Hz, 1H), 4.97 (dd, J = 17.4, 4.3 Hz, 1H), 4.55 (dd, J = 17.7, 1.8 Hz, 1H), 4.36 (d, J = 13.1 Hz, 1H), 3.91-4.03 (m, 1H), 3.75-3.86 (m, 1H), 3.49-3.57 (m, 3H), 3.33-3.40 (m, 2H), 3.22-3.31 (m, 1H), 2.82 (t, J = 11.8 Hz, 1H), 2.18 (d, J = 10.7 Hz, 3H), 2.03-2.15 (m, 2H), 1.79 (q, J = 11.5 Hz, 1H), 1.54 (qd, J = 12.2, 3.7 Hz, 1H); LCMS (M + 1): 593.15 |
| 49 | 1-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-$d_6$) δ 8.04 (s, 1H), 7.27 (s, 1H), 7.08 (d, J = 2.2 Hz, 1H), 6.48 (s, 1H), 5.79 (dd, J = 10.9, 7.2 Hz, 1H), 5.27 (dd, J = 39.6, 17.1 Hz, 2H), 5.00 (d, J = 17.6 Hz, 1H), 4.58 (d, J = 17.9 Hz, 1H), 4.36 (d, J = 13.2 Hz, 1H), 3.94-4.03 (m, 1H), 3.86 (dd, J = 17.4, 11.0 Hz, 1H), 3.55 (s, 3H), 3.21-3.37 (m, 3H), 2.78-2.84 (m, 1H), 2.19 (s, 3H), 2.03-2.12 (m, 2H), 1.78-1.81 (m, 1H), 1.52-1.56 (m, 1H); LCMS (M + 1): 626.8 |
| 50 | 1-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-$d_6$) δ 8.02 (d, J = 7.6 Hz, 1H), 7.27 (t, J = 1.1 Hz, 1H), 7.08 (d, J = 2.2 Hz, 1H), 6.48 (s, 1H), 5.74-5.81 (m, 1H), 5.26 (dd, J = 36.7, 16.9 Hz, 2H), 4.98 (d, J = 17.6 Hz, 1H), 4.57 (d, J = 17.9 Hz, 1H), 4.35 (d, J = 13.4 Hz, 1H), 3.93-4.00 (m, 1H), 3.81 (dd, J = 17.1, 11.0 Hz, 1H), 3.55 (d, J = 4.4 Hz, 3H), 3.21-3.39 (m, 3H), 2.78-2.87 (m, 1H), 2.19 (s, 3H), 2.02-2.16 (m, 2H), 1.74-1.84 (m, 1H), 1.49-1.59 (m, 1H); LCMS (M + 1): 626.8 |
| 51 | 1-(4-(4-(5-(5-chloro-2-methyl-2-oxido-3H-2l4-benzo[c]isothiazol-7-yl)-4,5-dihydroisoxazol-3-yl)thiazol-2-yl)piperidin-1- | $^1$H-NMR (400 MHz, DMSO-$d_6$) δ 8.02 (d, J = 7.6 Hz, 1H), 7.28 (s, 1H), 7.08 (d, J = 2.7 Hz, 1H), 7.08 (d, J = 2.7 Hz, 1H), 6.48 (s, 1H), 5.74-5.81 (m, 1H), 5.27 (dd, J = 38.6, 17.1 Hz, 2H), 4.99 (dd, J = 17.7, 4.5 Hz, 1H), 4.58 (d, J = 17.6 Hz, 1H), 4.35 (d, J = 13.2 Hz, 1H), 3.95 (d, J = 13.9 Hz, 1H), 3.78-3.89 (m, 1H), 3.55 (d, J = 4.6 |

TABLE NO 1-continued

The following compounds were prepared analogue to the procedure described in schemes 1-17 or Examples 1 to 8.

| Compd. No. | Compound Name | Analytical data |
|---|---|---|
| | yl)-2-(5-methyl-3-(trifluoromethyl)-1H-pyrazol-1-yl)ethan-1-one | Hz, 3H), 3.21-3.39 (m, 3H), 2.78-2.87 (m, 1H), 2.19 (s, 3H), 2.03-2.20 (m, 2H), 1.77-1.87 (m, 1H), 1.54 (dd, J = 12.5, 3.7 Hz, 1H); LCMS (M + 1): 626.8 |
| 52 | 1-(2-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.06 (s, 1H), 7.95 (dd, J = 12.5, 6.8 Hz, 2H), 7.30 (d, J = 2.2 Hz, 1H), 7.10 (d, J = 2.0 Hz, 1H), 6.40 (t, J = 7.0 Hz, 1H), 5.81 (dd, J = 10.9, 7.2 Hz, 1H), 4.95-5.05 (m, 3H), 4.60 (d, J = 17.9 Hz, 1H), 4.38 (d, J = 13.4 Hz, 1H), 3.84-4.05 (m, 2H), 3.57 (s, 3H), 3.35-3.42 (m, 2H), 3.30 (d, J = 2.2 Hz, 1H), 2.84-2.87 (m, 1H), 2.08-2.17 (m, 3H), 1.55 (d, J = 4.2 Hz, 1H); LCMS (M + 1): 640.15 |
| 53 | 1-(2-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ , 8.05 (d, J = 7.3 Hz, 1H), 7.95 (q, J = 6.8 Hz, 2H), 7.30 (d, J = 2.4 Hz, 1H), 7.11 (d, J = 2.4 Hz, 1H), 6.40 (t, J = 7.2 Hz, 1H), 5.82 (dd, J = 10.8, 7.3 Hz, 1H), 4.95-5.03 (m, 3H), 4.60 (d, J = 18.1 Hz, 1H), 4.38 (d, J = 12.5 Hz, 1H), 4.03 (d, J = 15.6 Hz, 1H), 3.84 (dd, J = 17.0, 10.9 Hz, 1H), 3.58 (d, J = 4.6 Hz, 3H), 3.36-3.43 (m, 2H), 3.30 (s, 1H), 2.86 (d, J = 11.5 Hz, 1H), 2.03-2.17 (m, 2H), 1.59 (s, 1H), 1.23-1.35 (m, 1H); LCMS (M + 1): 640.15 |
| 54 | 1-(2-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.13-8.05 (1H), 8.05-8.01 (1H), 8.01-7.95 (2H), 7.95-7.85 (1H), 7.38-7.23 (2H), 7.18-7.03 (2H), 6.48-6.31 (2H), 5.91-5.73 (2H), 5.11-4.85 (5H), 4.69-4.51 (2H), 4.47-4.29 (2H), 4.12-3.74 (3H), 3.66-3.50 (5H), 3.51-3.35 (3H), 3.31-3.19 (1H), 2.95-2.75 (1H), 2.24-1.99 (3H), 1.98-1.71 (1H), 1.66-1.48 (1H); LCMS (M + 1): 640.15 |
| 55 | 2-(3,5-bis(difluoromethyl)-1H-pyrazol-1-yl)-1-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 8.01 (s, 1H), 6.86-7.28 (m, 5H), 5.72-5.79 (m, 1H), 5.40 (d, J = 17.1 Hz, 1H), 5.31 (d, J = 17.1 Hz, 1H), 4.98 (d, J = 17.7 Hz, 1H), 4.55 (d, J = 17.7 Hz, 1H), 4.31 (d, J = 12.5 Hz, 1H), 3.91-3.97 (m, 1H), 3.83 (dd, J = 17.1, 11.0 Hz, 1H), 3.53(s, 3H), 3.19-3.38 (m, 3H), 2.79 (t, J = 11.8 Hz, 1H), 2.06 (t, J = 13.9 Hz, 2H), 1.77 (qd, J = 12.1, 3.4 Hz, 1H), 1.52 (qd, J = 12.3, 3.9 Hz, 1H); LCMS (M + 1): 644.8 |
| 56 | 2-(3,5-bis(difluoromethyl)-1H-pyrazol-1-yl)-1-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 8.03 (d, J = 7.6 Hz, 1H), 6.88-7.30 (m, 5H), 5.74-5.82 (m, 1H), 5.38 (q, J = 16.8 Hz, 2H), 4.99 (d, J = 17.9 Hz, 1H), 4.58 (d, J = 17.9 Hz, 1H), 4.34 (d, J = 13.4 Hz, 1H), 3.95 (d, J = 13.4 Hz, 1H), 3.82 (dd, J = 17.1, 11.0 Hz, 1H), 3.56 (d, J = 4.4 Hz, 3H), 3.22-3.41 (m, 3H), 2.79-2.85 (m, 1H), 2.03-2.12 (m, 2H), 1.77-1.90 (m, 1H), 1.51-1.60 (m, 1H); LCMS (M + 1): 645 |
| 57 | 2-(3,5-bis(difluoromethyl)-1H-pyrazol-1-yl)-1-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one | $^1$H-NMR (400 MHz, DMSO-$d_6$) δ 8.02 (d. J = 7.8 Hz, 1H). 6.88-7.29 (m, 5H), 5.74-5.81 (m, 1H), 5.38 (q, J = 17.1 Hz, 2H), 4.99 (dd, J = 17.7, 4.5 Hz, 1H), 4.58 (d, J = 17.6 Hz, 1H), 4.33 (d, J = 13.2 Hz, 1H), 3.78-4.04 (m, 2H), 3.55 (d, J = 4.4 Hz, 3H), 3.21-3.40 (m, 3H), 2.81 (t, J = 11.6 Hz, 1H), 2.08 (t, J = 14.1 Hz, 2H), 1.77-1.83 (m, 1H), 1.49-1.59 (m, 1H); LCMS (M + 1): 645 |
| 58 | 1-(2-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one | $^1$H-NMR (400 MHz, DMSO-$d_6$) δ 8.14-8.00 (1H), 7.93-7.77 (1H), 7.37-7.23 (1H), 7.17-7.03 (1H), 6.40-6.24 (1H), 5.90-5.70 (1H), 5.14-4.93 (3H), 4.69-4.51 (1H), 4.46-4.29 (1H), 4.15-3.97 (1H), 3.98-3.78 (1H), 3.65-3.50 (3H), 3.50-3.38 (1H), 3.38-3.35 (1H), 3.32-3.26 (1H), 2.96-2.62 (1H), 2.41-2.25 (3H), 2.27-1.99 (2H), 1.98-1.72 (1H), 1.65-1.48 (1H); LCMS(M + 1): 654.15 |
| 59 | 1-(2-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-l-yl)-2-oxoethyl)-6-methyl-3-(trifluoromethyl)pyridin-2(1H)-one | $^1$H-NMR (400 MHz, DMSO-$d_6$) δ 8.13-7.98 (1H), 7.93-7.77 (1H), 7.38-7.23 (1H), 7.18-7.04 (1H), 6.40-6.24 (1H), 5.91-5.73 (1H), 5.18-4.92 (3H), 4.70-4.51 (1H), 4.47-4.28 (1H), 4.15-3.96 (1H), 3.95-3.74 (1H), 3.67-3.50 (3H), 3.42-3.34 (2H), 3.31-3.27 (1H), 3.31-3.14 (−1H), 2.97-2.76 (1H), 2.39-2.25 (3H), 2.21-2.07 (2H), 1.85-1.76 (1H), 1.65-1.48 (1H); LCMS(M + 1): 654.1 |
| 60 | 1-(2-(4-(4-(5-(5-chloro-2-methyl-2-oxido-3H-2l4-benzo[c]isothiazol-7-yl)-4,5-dihydroisoxazol-3- | $^1$H-NMR (400 MHz, DMSO-$d_6$) δ 8.14-7.98 (1H), 7.93-7.77 (1H), 7.38-7.23 (1H), 7.18-7.03 (1H), 6.40-6.24 (1H), 5.91-5.73 (1H), 5.14-4.92 (3H), 4.69-4.51 (1H), 4.47-4.28 (1H), 4.15-3.96 (1H), 3.98-3.74 (1H), 3.67-3.50 (3H), 3.51-3.35 (2H), 3.31-3.24 (1H), |

TABLE NO 1-continued

The following compounds were prepared analogue to the procedure described in schemes 1-17 or Examples 1 to 8.

| Compd. No. | Compound Name | Analytical data |
|---|---|---|
| | yl)thiazol-2-yl)piperidin-1-yl)-2-oxoethyl)-6-methyl-3-(trifluoromethyl)pyridin-2(1H)-one | 2.97-2.76 (1H), 2.74-2.62 (0H), 2.41-2.25 (3H), 2.27-2.07 (2H), 1.85-1.71 (1H), 1.66-1.48 (1H); LCMS(M + 1): 654.15 |
| 61 | (2-((R)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(iso-propyl)-l6-sulfanone | $^1$H-NMR (400 MHz, DMSO-$d_6$) δ 8.00-8.04 (m, 2H), 7.83 (d, J = 7.9 Hz, 1H), 7.63 (t, J = 8.1 Hz, 1H), 6.88-7.30 (m, 4H), 5.43 (d, J = 16.8 Hz, 1H), 5.35 (d, J = 17.1 Hz, 1H), 4.84 (d, J = 51.4 Hz, 1H), 4.35 (d, J = 12.8 Hz, 1H), 3.95-4.01 (m, 1H), 3.75-3.84 (m, 1H), 3.59 (dd, J = 17.4, 11.9 Hz, 1H), 3.35-3.42 (m, 2H), 3.23-3.27 (m, 1H), 2.83 (t, J = 11.8 Hz, 1H), 2.07-2.14 (m, 2H), 1.75-1.85 (m, 1H), 1.52-1.61 (m, 1H), 1.14-1.25 (m, 6H); LCMS(M + 1): 661.1 |
| 62 | (3-chloro-2-(3-(2-(1-(2-(4-chloro-1H-pyrazol-1-yl)acetyl)piperidin-4-yl)thiazol-4-yl)-4,5-dihydroisoxazol-5-yl)phenyl)(imino)(iso-propyl)-l6-sulfanone | $^1$H-NMR (400 MHz, DMSO-$d_6$) δ 8.02 (qd. J = 4.1, 1.3 Hz. 2H), 7.87 (s, 1H), 7.83 (dd, J = 8.1, 1.2 Hz. 1H), 7.63 (t, J = 7.9 Hz, 1H), 7.51 (d, J = 0.7 Hz, 1H), 6.97-7.04 (m, 1H), 5.16 (dd, J = 26.9, 16.6 Hz, 2H), 4.83 (d, J = 51.4 Hz, 1H), 4.37 (d, J = 13.4 Hz, 1H), 3.96 (d, J = 12.7 Hz, 1H), 3.75-3.82 (m, 1H), 3.56-3.63 (m, 1H), 3.35-3.40 (m, 2H), 3.21 (d, J = 12.0 Hz, 1H), 2.80 (t, J = 11.1 Hz, 1H), 2.09-2.12 (m, 2H), 1.74-1.77 (m, 1H), 1.56 (d, J = 11.0 Hz, 1H), 1.14-1.25 (m, 6H); LCMS (M + 1): 594.95 |
| 63 | (3-chloro-2-(3-(2-(1-(2-(4-methyl-1H-pyrazol-1-yl)acetyl)piperidin-4-yl)thiazoL4-yl)-4,5-dihydroisoxazol-5-yl)phenyl)(imino)(iso-propyl)-l6-sulfanone | $^1$H-NMR (400 MHz, DMSO-$d_6$) δ 8.02 (qd, J = 3.8, 1.3 Hz, 2H), 7.83 (dd, J = 7.9, 1.3 Hz, 1H), 7.63 (t, J = 8.1 Hz, 1H), 7.39 (s, 1H) 7.20 (s, 1H), 7.01 (t, J = 12.0 Hz, 1H), 5.05 (dd, J = 26.7, 16.9 Hz, 2H), 4.83 (d, J = 51.6 Hz, 1H), 4.37 (d, J = 12.5 Hz, 1H), 3.99 (d, J = 15.6 Hz, 1H), 3.79 (dd, J = 17.4, 12.2 Hz, 1H), 3.59 (dd, J = 17.1, 11.7 Hz, 1H), 3.33-3.37 (m, 2H), 3.20 (t, J = 12.1 Hz, 1H), 2.78 (t, J = 11.2 Hz, 1H), 2.06-2.09 (m, 2H), 1.99 (d, J = 7.6 Hz, 3H), 1.72 (s, 1H), 1.54 (d, J = 10.5 Hz, 1H), 1.14-1.25 (m, 6H); LCMS (M + 1): 576.8 |
| 64 | 1-(2-(4-(4(5-(2-chloro-6-(propan-2-ylsulfonimidoyl)phenyl)-4,5-dihydroisoxazol-3-yl)thiazol-2-yl)piperidin-1-yl)-2-oxoethyl)-3-(trifluoromethyl)pyrazin-2(1H)-one | $^1$H-NMR (400 MHz, DMSO-$d_6$) δ 8.00-8.04 (m, 3H), 7.82 (dt, J = 8.1, 1.6 Hz, 1H), 7.63 (t, J = 7.9 Hz, 1H), 7.56 (d, J = 4.2 Hz, 1H), 6.98-7.04 (m, 1H), 5.02 (s, 2H), 4.83 (d, J = 52.3 Hz, 1H), 4.36 (d, J = 13.2 Hz, 1H), 3.98 (d, J = 13.7 Hz, 1H,3.76-3.83 (m, 1H), 3.60 (dd, J = 17.2, 11.9 Hz, 1H), 3.31-3-44 (m, 2H), 3.29 (d, J = 17.1 Hz, 1H), 2.83-2.88 (m, 1H), 2.08-2.17 (m, 2H),1.79-1.82 (m. 1H), 1.58 (dd, J = 12.2, 3.9 Hz, 1H), 1.14-1.27 (m, 6H); LCMS(M + 1): 656.85 |
| 65 | (3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(iso-propyl)-l6-sulfanone | $^1$H-NMR (400 MHz, DMSO-$d_6$) δ 8.00-8.06 (m, 2H), 7.94-7.96 (m, 1H), 7.83 (dd, J = 8.1, 1.2 Hz, 1H), 7.63 (t, J = 7.9 Hz, 1H), 6.99-7.04 (m, 2H), 5.19 (dd, J = 43.9, 14.3 Hz, 2H), 4.83 (d, J = 51.6 Hz, 1H), 4.35 (d, J = 13.4 Hz, 1H), 3.94 (d, J = 13.2 Hz, 1H), 3.75-3.84 (m, 1H), 3.59 (dd, J = 17.2, 11.9 Hz, 1H), 3.33-3.44 (m, 2H), 3.21-3.28 (m, 2H), 2.79 (t, J = 12.2 Hz, 1H), 2.05-2.13 (m, 2H), 1.83 (s, 1H), 1.56 (s, 1H), 1.14-1.25 (m, 6H); LCMS(M + 1): 654.9 |
| 66 | rac-N-((Z)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-$d_6$) δ 8.09-8.25 (m, 2H), 7.72-7.87 (m, 2H), 6.50 (d, J = 2.9 Hz, 1H), 6.23 (t, J = 11.1 Hz, 1H), 5.30 (dd, J = 35.8, 17.0 Hz, 2H), 4.40 (s, 1H), 4.18 (dd, J = 17.5, 11.6 Hz, 1H), 3.99 (d, J = 15.6 Hz, 1H), 3.61 (dd, J = 17.5, 10.9 Hz, 1H), 3.40 (d, J = 11.2 Hz, 1H), 3.26 (d, J = 13.9 Hz, 1H), 3.13 (s, 3H), 2.83 (d, J = 18.6 Hz, 1H), 2.22 (d, J = 4.6 Hz, 3H), 2.10 (d, J = 18.6 Hz, 2H), 1.90-1.78 (1H), 1.57 (s, 1H); LCMS(M + 1): 624.1 |
| 67 | rac-N-((E)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-$d_6$) δ 8.15 (d, J = 8.1 Hz. 1H), 8.10 (d. J = 1.5 Hz, 1H), 7.85-7.88 (m, 1H), 7.74-7.78 (m, 1H), 6.49 (d, J = 3.2 Hz, 1H), 6.24 (t, J = 11.5 Hz, 1H), 5.28 (dd, J = 36.8, 17.0 Hz, 2H), 4.37 (d, J = 14.2 Hz, 1H), 4.08 (dd, J = 17.5, 11.6 Hz, 1H), 3.97 (d, J = 14.4 Hz, 1H), 3.62 (dd, J = 17.6, 11.5 Hz, 1H), 3.40 (d, J = 11.5 Hz, 1H), 3.26 (s, 1H), 3.05 (s, 3H), 2.85 (d, J = 12.5 Hz, 1H), 2.20 (s, 3H), 2.13 (d, J = 11.7 Hz, 2H), 1.90-1.71 (1H), 1.56 (d, J = 12.2 Hz, 1H); LCMS(M + 1): 624.098 |
| 68 | (2-((S)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(iso-propyl)-l6-sulfanone | $^1$H-NMR (400 MHz, DMSO-$d_6$) δ 8.00-8.04 (m, 2H), 7.83 (d, J = 7.9 Hz, 1H), 7.63 (t, J = 8.1 Hz, 1H), 6.88-7.30 (m, 4H), 5.43 (d, J = 16.8 Hz, 1H), 5.35 (d, J = 17.1 Hz, 1H), 4.84 (d, J = 51.4 Hz, 1H), 4.35 (d, J = 12.8 Hz, 1H), 3.95-4.01 (m, 1H), 3.75-3.84 (m, 1H), 3.59 (dd, J = 17.4, 11.9 Hz, 1H), 3.35-3.42 (m, 2H), 3.23-3.27 (m, 1H), 2.83 (t, J = 11.8 Hz, 1H), 2.07-2.14 (m, 2H), 1.75-1.85 (m, 1H), 1.52-1.61 (m, 1H), 1.14-1.25 (m, 6H); LCMS(M + 1): 661.15 |
| 69 | N-((E)-((6R)-6-((SR)-3-(2-(1-(2-(3,5-bis(difluoromethyl)-1H-pyrazol-1- | $^1$H-NMR (400 MHz, DMSO-$d_6$) δ 8.14-8.16 (m, 1H), 8.11 (s, 1H), 7.87 (dd, J = 7.9, 0.9 Hz, 1H), 7.76 (t, J = 7.9 Hz, 1H), 6.89-7.30 (m, 3H), 6.24 (t, J = 11.5 Hz, 1H), 5.43 (d, J = 17.1 Hz, 1H), 5.35 (d, J = 17.1 Hz, 1H), 4.35 (d, J = 13.4 Hz, 1H), 4.08 (dd, J = 17.4, |

TABLE NO 1-continued

The following compounds were prepared analogue to the procedure described in schemes 1-17 or Examples 1 to 8.

| Compd. No. | Compound Name | Analytical data |
|---|---|---|
| | yl)acetyl)piperidin-4-yl)thiazol-4-yl)-4,5-dihydroisoxazol-5-yl)-5-chlorocyclohexa-2,4-dien-1-yl)(methyl)-l4-sulfaneylidene)cyanamide | 11.6 Hz, 1H), 3.96 (d, J = 13.8 Hz, 1H), 3.62 (dd, J = 17.6, 11.5 Hz, 1H), 3.39 (qd, J = 7.6, 4.0 Hz, 1H), 3.26 (t, J = 12.2 Hz, 1H), 3.05-3.11 (m, 3H), 2.80-2.86 (m, 1H), 2.10 (t, J = 14.1 Hz, 2H), 1.76-1.85 (m, 1H), 1.56 (qd, J = 12.3, 3.8 Hz, 1H); LCMS(M + 1): 642 |
| 70 | (2-((5R)-3-(2-(1-(2-(3,5-bis(difluoromethyl)-1H-pyrazol-1-yl)propanoyl)piperidin-4-yl)thiazol-4-yl)-4,5-dihydroisoxazol-5-yl)-3-chlorophenyl)(methyl)(methylimino)-l6-sulfanone | $^{1}$H-NMR (400 MHz, DMSO-$d_6$) δ 7.98-8.06 (m, 2H), 7.83-7.86 (m, 1H), 7.63-7.70 (m, 1H), 6.79-7.46 (m, 4H), 5.79 (q, J = 6.7 Hz, 1H), 4.37 (dd, J = 36.1, 11.6 Hz, 1H), 4.02 (q, J = 7.1 Hz, 1H), 3.93 (d, J = 13.1 Hz, 1H), 3.56-3.79 (m, 2H), 3.38 (t, J = 11.5 Hz, 2H), 3.22-3.29 (m, 4H), 2.76-2.88 (m, 1H), 2.55 (s, 2H), 2.52 (s, 1H), 1.98-2.08 (m, 2H), 1.62 (d, J = 6.1 Hz, 2H), 1.45 (d, J = 11.6 Hz, 1H); LCMS (M + 1): 660.85 |
| 71 | (2-((5S)-3-(2-(1-(2-(3,5-bis(difluoromethyl)-1H-pyrazol-1-yl)propanoyl)piperidin-4-yl)thiazol-4-yl)-4,5-dihydroisoxazol-5-yl)-3-chlorophenyl)(methyl)(methylimino)-l6-sulfanone | $^{1}$H-NMR (400 MHz, DMSO-$d_6$) δ 7.98-8.06 (m, 2H), 7.83-7.86 (m, 1H), 7.63-7.70 (m, 1H), 6.79-7.46 (m, 4H), 5.79 (q, J = 6.7 Hz, 1H), 4.37 (dd, J = 36.1, 11.6 Hz, 1H), 4.02 (q, J = 7.1 Hz, 1H), 3.93 (d, J = 13.1 Hz, 1H), 3.56-3.79 (m, 2H), 3.38 (t, J = 11.5 Hz, 1H), 3.22-3.29 (m, 5H), 2.76-2.88 (m, 1H), 2.55 (s, 2H), 2.52 (s, 1H), 1.98-2.08 (m, 2H), 1.62 (d, J = 6.1 Hz, 2H), 1.45 (d, J = 11.6 Hz, 1H); LCMS (M + 1): 661.05 |
| 72 | (3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone | $^{1}$H-NMR (400 MHz, DMSO-$d_6$) δ 7.98-8.09 (m, 2H), 7.85 (d, J = 7.8 Hz, 1H), 7.64-7.68 (m, 1H), 6.79-6.91 (m, 1H), 6.51 (d, J = 15.6 Hz, 1H), 5.28 (dd, J = 37.0, 17.0 Hz, 2H), 4.37 (d, J = 13.0 Hz, 1H), 3.97 (d, J = 13.2 Hz, 1H), 3.53-3.80 (m, 2H), 3.39 (t, J = 11.5 Hz, 1H), 3.29 (s, 1H), 3.09 (s, 1H), 2.84 (d, J = 11.5 Hz, 1H), 2.66 (d, J = 2.9 Hz, 1H), 2.55 (s, 3H), 2.32 (s, 1H), 2.20 (s, 3H), 2.13 (d, J = 12.0 Hz, 1H), 1.82 (s, 1H), 1.58 (s, 1H), 1.18-1.25 (m, 3H); LCMS (M + 1): 629.15 |
| 73 | (3-chloro-2-((S)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone | $^{1}$H-NMR (400 MHz, DMSO-$d_6$) δ 7.98-8.06 (m, 2H), 7.85 (d, J = 7.8 Hz, 1H), 7.64-7.68 (m, 1H), 6.82 (t, J = 11.7 Hz, 1H), 6.49 (s, 1H)5.40-5.17 (2H), 4.45-4.24 (1H), 4.18-3.84 (2H), 3.90-3.48 (1H), 3.48-3.34 (3H), 3.32-3.29 (1H), 2.95-2.76 (1H), 2.74-2.65 (1H), 2.59-2.53 (3H), 2.25-2.19 (3H), 2.19-2.06 (2H)1.87-1.72 (1H), 1.68-1.49 (1H); LCMS (M + 1): 629.1 |
| 74 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)dimethyl-l6-sulfanone | $^{1}$H-NMR (400 MHz, DMSO-$d_6$) δ 7.97 (s, 1H), 7.19 (t, J = 7.9 Hz, 1H), 7.10 (dd, J = 8.1, 1.2 Hz, 1H), 7.02 (dd, J = 7.8, 1.2 Hz, 1H), 6.49 (s, 1H), 6.28 (dd, J = 12.3, 10.1 Hz, 1H), 5.28 (dd, J = 36.1, 17.0 Hz, 2H), 4.36 (d, J = 13.7 Hz, 1H), 3.95-4.03 (m, 1H), 3.49-3.70 (m, 2H), 3.35-3.40 (m, 1H), 3.24-3.27 (m, 1H), 3.06 (s, 3H), 3.03 (s, 3H), 2.81-2.86 (m, 1H), 2.19 (d, J = 6.6 Hz, 3H), 2.07-2.14 (m, 2H), 1.80 (d, J = 11.7 Hz, 1H), 1.56 (dd, J = 12.1, 4.0 Hz, 1H); LCMS (M + 1): 629 |
| 75 | (3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(ethylimino)(methyl)-l6-sulfanone | $^{1}$H-NMR (400 MHz, DMSO-$d_6$) δ 8.02-8.08 (m, 2H), 7.86 (t, J = 7.7 Hz, 1H), 7.65-7.70 (m, 1H), 6.94 (d, J = 43.8 Hz, 1H), 6.51 (d, J = 2.9 Hz, 1H), 5.30 (dd, J = 37.5, 17.2 Hz, 2H), 4.41 (s, 1H), 3.99 (d, J = 12.2 Hz, 1H), 3.72 (dd, J = 11.9, 8.7 Hz, 2H), 3.36-3.41 (m, 1H), 3.29 (d, J = 10.3 Hz, 4H), 2.71-2.98 (m, 2H), 2.22 (s, 3H), 2.13 (s, 1H), 1.88-1.77 (1H), 1.65-1.52 (1H), 1.24-1.27 (m, 2H), 1.07-1.13 (m, 3H); LCMS (M + 1): 643.1 |
| 76 | (Z)-N-((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(isopropyl)-l4-sulfaneylidene)cyanamide | $^{1}$H-NMR (400 MHz, DMSO-$d_6$) δ 8.11 (d, J = 5.8 Hz, 1H), 8.03 (dd, J = 8.3, 1.1 Hz, 1H), 7.87 (dd, J = 7.9, 1.2 Hz, 1H), 7.76 (t, J = 7.9 Hz, 1H), 6.49 (s, 1H), 6.22 (t, J = 11.3 Hz, 1H), 5.32 (d, J = 17.1 Hz, 1H), 5.23 (d, J = 16.8 Hz, 1H), 4.37 (d, J = 12.8 Hz, 1H), 4.10 (dd, J = 17.7, 11.9 Hz, 1H), 3.97 (d, J = 13.4 Hz, 1H), 3.62 (dd, J = 17.6, 10.9 Hz, 1H), 3.36-3.42 (m, 2H), 3.23-3.28 (m, 1H), 2.80-2.86 (m, 1H), 2.20 (s, 3H), 2.07-2.14 (m, 2H), 1.76-1.81 (m, 1H), 1.56 (dd, J = 11.9, 3.7 Hz, 1H), 1.27 (d, J = 7.0 Hz, 4H), 1.21-1.25 (m, 3H); LCMS (M + 1): 652.2 |
| 77 | imino(methyl)(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)-l6-sulfanone | $^{1}$H-NMR (400 MHz, DMSO-$d_6$) δ 8.43-8.48 (m, 1H), 8.14 (d, J = 8.3 Hz, 1H), 8.05-8.07 (m, 1H), 7.82-7.89 (m, 1H), 6.42-6.49 (m, 2H), 5.32 (d, J = 17.1 Hz, 1H), 5.23 (d, J = 17.1 Hz, 1H), 4.37 (d, J = 13.4 Hz, 1H), 3.95-4.04 (m, 1H), 3.81-3.88 (m, 1H), 3.47-3.60 (m, 1H), 3.35-3.41 (m, 2H), 3.23-3.30 (m, 3H), 2.84 (q, J = 11.3 Hz, 1H), 2.17-2.24 (m, 3H), 2.07-2.14 (m, 2H), 1.55-1.61 (m, 1H), 1.32-1.38 (m, 1H); LCMS (M + 1): 649.3 |

TABLE NO 1-continued

The following compounds were prepared analogue to the procedure described in schemes 1-17 or Examples 1 to 8.

| Compd. No. | Compound Name | Analytical data |
|---|---|---|
| 78 | (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(imino)(methyl)-l6-sulfanone | $^1$H-NMR (400 MHz, DMSO-d$_6$) δ 8.45-8.48 (m, 1H), 8.13 (d, J = 8.1 Hz, 1H), 8.03-8.07 (m, 1H), 7.84 (t, J = 8.1 Hz, 1H), 6.88-7.30 (m, 3H), 6.46 (t, J = 12.1 Hz, 1H), 5.32-5.45 (m, 2H), 4.73 (d, J = 10.3 Hz, 1H), 4.35 (d, J = 12.7 Hz, 1H), 3.81-4.03 (m, 2H), 3.49-3.60 (m, 1H), 3.38-3.42 (m, 1H), 3.33-3.31 (m,3H), 3.24 (d, J = 11.5 Hz, 1H), 2.80-2.86 (m, 1H), 2.06-2.14 (m, 2H), 1.82 (t, J = 12.1 Hz, 1H), 1.57 (d, J = 6.1 Hz, 1H); LCMS (M + 1): 667.1 |
| 79 | (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)(imino)(methyl)-l6-sulfanone | $^1$H-NMR (400 MHz, DMSO-d$_6$) δ 8.46-8.48 (m, 1H), 8.11-8.14 (m, 1H), 8.05 (d, J = 2.8 Hz, 1H), 7.81-7.86 (m, 1H), 7.59 (s, 1H), 6.45 (t, J = 12.2 Hz, 1H), 5.60 (dd, J = 17.3, 6.3 Hz, 1H), 5.47-5.52 (m, 1H), 4.74 (d, J = 9.8 Hz, 1H), 4.34 (d, J = 12.5 Hz, 1H), 3.95 (d, J = 13.8 Hz, 1H), 3.81-3.88 (m, 1H), 3.52-3.60 (m, 1H), 3.35-3.44 (m, 2H), 3.23-3.30 (m, 3H), 2.81-2.87 (m, 1H), 2.07-2.13 (m, 2H), 1.76-1.82 (m, 1H), 1.49-1.58 (m, 1H); LCMS (M + 1): 703.1 |
| 80 | (Z)-N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(isopropyl)-l4-sulfaneylidene)cyanamide | $^1$H-NMR (400 MHz, DMSO-d$_6$) δ 8.11 (d, J = 3.7 Hz, 1H), 8.03 (dd, J = 8.3, 1.2 Hz, 1H), 7.84-7.88 (m, 1H), 7.71-7.78 (m, 1H), 6.89-7.30 (m, 3H), 6.19-6.25 (m, 1H), 5.43 (d, J = 17.1 Hz, 1H), 5.35 (d, J = 16.8 Hz, 1H), 4.35 (d, J = 12.8 Hz, 1H), 4.06-4.17 (m, 1H), 3.96 (d, J = 14.1 Hz, 1H), 3.55-3.68 (m, 1H), 3.35-3.43 (m, 1H), 3.23-3.29 (m, 2H), 2.80-2.86 (m, 1H), 2.10 (t, J = 13.9 Hz, 2H), 1.76-1.82 (m, 1H), 1.52-1.61 (m, 1H), 1.24-1.32 (m, 3H), 1.08 (t, J = 7.2 Hz, 3H); LCMS (M + 1): 670.05 |
| 81 | 1-(4-(4-(5-(2-chloro-6-((1-oxido-1l6-thietan-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, DMSO-d$_6$) δ 8.09-7.91 (1H), 7.31-7.14 (1H), 7.14-7.02 (1H), 7.02-6.91 (1H), 6.59-6.44 (1H), 6.42-6.23 (1H), 5.43-5.16 (2H), 4.47-4.30 (1H), 4.30-4.10 (2H), 4.09-3.82 (3H), 3.80-3.54 (2H), 3.50-3.35 (1H), 3.30-3.11 (1H), 2.96-2.76 (1H), 2.40-2.04 (7H), 1.87-1.70 (1H), 1.69-1.42 (1H); LCMS (M + 1): 642.05 |
| 82 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)dimethyl-l6-sulfanone | $^1$H-NMR (400 MHz, DMSO-d$_6$) δ 7.97 (s, 1H), 6.89-7.30 (m, 6H), 6.28 (dd, J = 12.2, 10.1 Hz, 1H), 5.43 (d, J = 16.8 Hz, 1H), 5.35 (d, J = 16.8 Hz, 1H), 4.34 (d, J = 13.4 Hz, 1H), 3.94-4.03 (m, 1H), 3.53-3.70 (m, 2H), 3.35-3.41 (m, 1H), 3.25 (d, J = 11.9 Hz, 1H), 3.05 (d, J = 10.4 Hz, 6H), 2.81-2.88 (m, 1H), 2.08 (dd, J = 26.7, 13.0 Hz, 2H), 1.79 (dd, J = 21.2, 12.1 Hz, 1H), 1.50-1.60 (m, 1H); LCMS (M + 1): 647.1 |
| 83 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)dimethyl-l6-sulfanone | $^1$H-NMR (400 MHz, DMSO-d$_6$) δ 8.06-7.90 (1H), 7.68-7.54 (1H), 7.29-7.15 (1H), 7.15-7.08 (1H), 7.08-6.96 (1H), 6.40-6.21 (1H), 5.71-5.56 (1H), 5.56-5.42 (1H), 4.44-4.25 (1H), 4.13-3.87 (1H), 3.78-3.49 (2H), 3.49-3.35 (1H), 3.32-3.23 (1H), 3.10-3.06 (3H), 3.07-3.04 (3H), 2.98-2.62 (1H), 2.21-2.00 (2H), 1.89-1.66 (1H), 1.65-1.46 (1H); LCMS (M + 1): 684.05 |
| 84 | ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, DMSO-d$_6$) δ 8.39 (d, J = 4.0 Hz, 1H), 8.10 (d, J = 7.6 Hz, 1H), 7.96 (s, 1H), 7.14-7.23 (m, 2H), 6.95 (d, J = 7.9 Hz, 1H), 6.72-6.77 (m, 1H), 6.13 (dd, J = 12.4, 9.3 Hz, 1H), 5.28 (d, J = 15.3 Hz, 2H), 4.32 (d, J = 12.8 Hz, 1H), 3.85-3.92 (m, 1H), 3.69 (dd, J = 16.8, 12.8 Hz, 1H), 3.48 (dd, J = 17.1, 9.2 Hz, 1H), 3.37 (td, J = 7.7, 4.0 Hz, 1H), 3.24 (t, J = 12.7 Hz, 1H), 3.11 (d, J = 5.8 Hz, 6H), 2.76-2.82 (m, 1H), 2.03-2.11 (m, 2H), 1.83 (t, J = 12.5 Hz, 1H), 1.56 (dd, J = 11.2, 9.3 Hz, 1H); LCMS (M + 1): 626.3 |
| 85 | dimethyl((2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)imino)-l6-sulfanone | $^1$H-NMR (400 MHz, CHLOROFORM-D) δ 7.56 (dd, J = 7.3, 5.6 Hz, 1H), 7.47 (s, 1H), 7.30-7.36 (m, 2H), 6.36 (s, 1H), 6.06-6.11 (m, 1H), 5.02 (q, J = 15.9 Hz, 2H), 4.62-4.65 (m, 1H), 4.11 (d, J = 13.2 Hz, 1H), 3.87 (dd, J = 16.4, 9.8 Hz, 1H), 3.57-3.62 (m, 1H), 3.29-3.39 (m, 2H), 3.09 (s, 3H), 2.96 (s, 3H), 2.86-2.92 (m, 1H), 2.36 (s, 3H), 2.03-2.28 (m, 2H), 1.76-1.86 (m, 2H); LCMS (M + 1): 663.4 |
| 86 | ((2-(3-(2-(1-(2-(3,5-bis(trifluoromethyl)-1H-pyrazol-1-yl)acetyl)piperidin-4- | $^1$H-NMR (400 MHz, CHLOROFORM-D) δ 7.52-7.56 (m, 1H), 7.47 (s, 1H), 7.28-7.34 (m, 2H), 6.96 (s, 1H), 6.03-6.09 (m, 1H), 5.19 (dd, J = 18.5, 16.4 Hz, 2H), 4.60 (d, J = 13.4 Hz, 1H), 3.86 (dd, J = 16.5, 9.8 Hz, 2H), 3.52-3.60 (m, 1H), 3.35 (q, J = 12.2 Hz, 2H), |

TABLE NO 1-continued

The following compounds were prepared analogue to the procedure described in schemes 1-17 or Examples 1 to 8.

| Compd. No. | Compound Name | Analytical data |
|---|---|---|
| | yl)thiazol-4-yl)-4,5-dihydroisoxazol-5-yl)-3-(trifluoromethyl)phenyl)imino)dimethyl-l6-sulfanone | 3.09 (d, J = 16.5 Hz, 3H), 2.87-2.96 (m, 4H), 2.13-2.28 (m, 2H), 1.75-1.93 (m, 2H); LCMS (M + 1): 717.65 |
| 87 | 1-(2-(4-(4-(5-(2-chloro-6-((dimethyl(oxo)-l6-sulfaneylidene)amino)phenyl)-4,5-dihydroisoxazol-3-yl)thiazol-2-yl)piperidin-1-yl)-2-oxoethyl)-6-methyl-3-(trifluoromethyl)pyridin-2(1H)-one | $^1$H-NMR (400 MHz, CHLOROFORM-D) δ 7.67 (d, J = 7.3 Hz, 1H), 7.45 (s, 1H), 7.24 (dd, J = 7.9, 0.9 Hz, 1H), 7.12 (t, J = 7.9 Hz, 1H), 7.04 (dd, J = 7.9, 1.2 Hz, 1H), 6.39 (dd, J = 12.5, 9.5 Hz, 1H), 6.16 (d, J = 7.3 Hz, 1H), 5.00 (d, J = 15.6 Hz, 1H), 4.85 (d, J = 15.3 Hz, 1H), 4.60 (d, J = 12.5 Hz, 1H), 4.08 (d, J = 12.5 Hz, 1H), 3.81 (dd, J = 16.4, 9.6 Hz, 1H), 3.57 (dd, J = 16.4, 12.7 Hz, 1H), 3.34-3.40 (m, 2H), 3.06-3.10 (m, 3H), 2.90 (t, J = 11.9 Hz, 4H), 2.40 (s, 3H), 2.30 (d, J = 12.8 Hz, 1H), 2.19 (d, J = 13.1 Hz, 1H), 1.95-2.04 (m, 1H), 1.83 (t, J = 12.1 Hz, 1H); LCMS (M + 1): 656.05 |
| 88 | ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, DMSO-$d_6$) δ 8.03 (s, 1H), 7.77 (s, 2H). 7.73 (d, J = 2.2 Hz, 1H), 7.51 (d, J = 2.2 Hz, 1H), 6.26-6.32 (m, 1H), 5.07 (d, J = 2.2 Hz, 2H), 4.36-4.25 (1H), 3.81-3.90 (m, 5H), 3.55 (dd, J = 17.2, 10.9 Hz, 2H), 3.22-3.20 (m, 1H), 2.77-275 (m, 1H), 2.05 (t, 2H), 1.90-1.65 (m, 1H), 1.58-1.39 (m, 1H); LCMS (M + 1): 660.75 |
| 89 | ethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)-l6-sulfanone | $^1$H-NMR (400 MHz, DMSO-$d_6$) δ 7.97 (s, 1H), 7.18 (ddd, J = 14.9, 8.2, 3.1 Hz, 1H), 6.96 (d, J = 7.9 Hz, 1H), 6.69-6.76 (m, 1H), 6.49 (s, 1H), 6.10-6.18 (m, 1H), 5.33 (d, J = 17.4 Hz, 1H), 5.23 (d, J = 17.1 Hz, 1H), 4.37 (d, J = 13.1 Hz, 1H), 3.97 (d, J = 13.4 Hz, 1H), 3.64-3.73 (m, 1H), 3.46-3.54 (m, 1H), 3.34-3.41 (m, 1H), 3.17-3.29 (m, 3H), 3.03 (d, J = 4.6 Hz, 3H), 2.83 (t, J = 11.5 Hz, 1H), 2.20 (s, 3H), 2.07-2.13 (m, 2H), 1.76-1.85 (m, 1H), 1.51-1.61 (m, 1H), 1.17 (dt, J = 37.9, 7.3 Hz, 4H); LCMS (M + 1): 627.4 |
| 90 | ((2-(3-(2-(1-(2-(3,5-bis(trifluoromethyl)1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone | $^1$H-NMR (400 MHz, CHLOROFORM-D) δ 7.49-7.52 (m, 1H), 7.06-7.19 (m, 2H), 6.98 (d, J = 15.9 Hz, 1H), 6.68-6.74 (m, 1H), 6.16-6.24 (m, 1H), 5.24 (d, J = 44.3 Hz, 2H), 4.62 (s, 1H), 3.77-3.88 (m, 2H), 3.54-3.63 (m, 1H), 3.23-3.39 (m, 3H), 3.08 (q, J = 7.4 Hz, 1H), 2.83-2.98 (m, 4H), 2.22-2.32 (m, 2H), 1.79-2.01 (m, 2H), 1.15-1.41 (m, 3H); LCMS (M + 1): 681.25 |
| 91 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone | $^1$H-NMR (400 MHz, CHLOROFORM-D) δ 7.48-7.52 (m, 1H), 7.08-7.17 (m, 2H), 6.67-6.88 (m, 4H), 6.16-6.24 (ηι, 1H), 5.15 (d, J = 3.4 Hz, 2H), 4.62 (s, 1H), 3.76-3.95 (m, 2H), 3.54-3.63 (m, 1H), 3.25-3.40 (m, 3H), 3.08 (q, J = 7.3 Hz, 1H), 2.83-2.98 (m, 4H), 2.22-2.30 (m, 2H), 1.79-2.04 (m, 2H), 1.14-1.41 (m, 3H); LCMS (M + 1): 645.35 |
| 92 | ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone | $^1$H-NMR (400 MHz, DMSO-$d_6$) δ 7.98 (d, J = 1.0 Hz, 1H), 7.17-7.23 (m, 1H), 6.98 (dd, J = 8.1, 1.5 Hz, 1H), 6.71-6.77 (m, 1H), 6.12-6.19 (m, 1H), 5.78 (d, J = 13.4 Hz, 1H), 4.99 (dd, J = 35.5, 16.9 Hz, 2H), 4.38 (d, J = 13.2 Hz, 1H), 4.02 (d, J = 14.7 Hz, 1H), 3.66-3.75 (m, 1H), 3.48-3.56 (m, 1H), 3.34-3.41 (m, 1H), 3.19-3.31 (m, 3H), 3.05-3.08 (m, 3H), 2.79-2.85 (m, 1H), 2.09 (d, J = 17.4 Hz, 8H), 1.53-1.75 (m, 2H), 1.19 (dt, J = 38.4, 7.3 Hz, 3H); LCMS (M + 1): 573.35 |
| 93 | ethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(methyl)-l6-sulfanone | $^1$H-NMR (400 MHz, DMSO-$d_6$) δ 7.98 (d, J = 1.0 Hz, 1H), 7.64 (dd, J = 5.1, 1.5 Hz, 1H), 7.17-7.31 (m, 2H), 6.91-6.99 (m, 2H), 6.71-6.78 (m, 1H), 6.12-6.20 (m, 1H), 5.09 (s, 2H), 4.36 (d, J = 14.7 Hz, 1H), 3.94-3.99 (m, 1H), 3.81 (s, 3H), 3.67-3.75 (m, 1H), 3.52 (ddd, J = 16.9, 9.2, 5.2 Hz, 1H), 3.36-3.42 (m, 1H), 3.18-3.30 (m, 3H), 3.05-3.07 (m, 3H), 2.67-2.90 (m, 1H), 2.09 (s, 2H), 1.83 (d, J = 11.0 Hz, 1H), 1.55 (d, J = 10.0 Hz, 1H), 1.19 (dt, J = 39.2, 7.5 Hz, 3H);LCMS (M + 1): 602.15 |
| 94 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(ethyl)(methyl)-l6-sulfanone | $^1$H-NMR (400 MHz, DMSO-$d_6$) δ 7.97 (s, 1H), 7.10-7.20 (m, 2H), 6.97-7.02 (m, 1H), 6.49 (s, 1H), 6.25-6.33 (m, 1H), 5.28 (dd, J = 38.3, 17.0 Hz, 2H), 4.36 (d, J = 13.4 Hz, 1H), 3.97 (d, J = 12.7 Hz, 1H), 3.55-3.70 (m, 2H), 3.37-3.42 (m, 1H), 3.08-3.27 (m, 3H), 2.97 (d, J = 12.2 Hz, 3H), 2.84 (t, J = 12.0 Hz, 1H), 2.18-2.32 (m, 3H), 2.10 (t, J = 12.5 Hz, 2H), 1.79 (d, J = 11.5 Hz, 1H), 1.55 (dd, J = 12.3, 3.8 Hz, 1H), 1.10 (dt, J = 62.4, 7.3 Hz, 3H); LCMS (M + 1): 643.05 |
| 95 | ((2-(3-(2-(1-(2-(3,5-bis(trifluoromethyl)-1H-pyrazol-1-yl)acetyl)piperidin-4- | $^1$H-NMR (400 MHz, DMSO-$d_6$) δ 7.99 (s, 1H), 7.61 (s, 1H), 6.99-7.22 (m, 3H), 6.31 (td, J = 12.2, 10.3 Hz, 1H), 5.49-5.76 (m, 2H), 4.35 (d, J = 13.0 Hz, 1H), 3.97 (d, J = 13.9 Hz, 1H), 3.57-3.72 (m, 2H), 3.38-3.44 (m, 1H), 3.10-3.31 (m, 3H), 2.99 (d, J = 12.2 Hz, |

TABLE NO 1-continued

The following compounds were prepared analogue to the procedure described in schemes 1-17 or Examples 1 to 8.

| Compd. No. | Compound Name | Analytical data |
|---|---|---|
| | yl)thiazol-4-yl)-4,5-dihydroisoxazol-5-yl)-3-chlorophenyl)imino)(ethyl)(methyl)-l6-sulfanone | 3H), 2.85-2.91 (m, 1H), 2.09-2.15 (m, 2H), 1.51-1.85 (m, 2H), 1.12 (dt, J = 62.1, 7.3 Hz, 3H); LCMS (M + 1): 697 |
| 96 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(ethyl)(methyl)-l6-sulfanone | $^{1}$H-NMR (400 MHz, DMSO-$d_6$) δ 7.99 (s, 1H), 6.91-7.32 (m, 6H), 6.27-6.36 (m, 1H), 5.41 (dd, J = 35.5, 17.1 Hz, 2H), 4.36 (d, J = 12.7 Hz, 1H), 3.98 (d, J = 13.7 Hz, 1H), 3.57-3.72 (m, 2H), 3.37-3.44 (m, 1H), 3.10-3.29 (m, 3H), 2.99 (d, J = 12.5 Hz, 3H), 2.86 (t, J = 11.5 Hz, 1H), 2.08-2.15 (m, 2H), 1.80-1.86 (m, 1H), 1.56-1.62 (m, 1H), 1.12 (dt, J = 62.0, 7.3 Hz, 3H); LCMS (M + 1): 661.15 |
| 97 | ((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)(ethyl)(methyl)-l6-sulfanone | $^{1}$H-NMR (400 MHz, DMSO-$d_6$) δ 7.96 (s, 1H), 7.10-7.20 (m, 2H), 6.97-7.02 (m, 1H), 6.29 (td, J = 12.2, 10.3 Hz, 1H), 5.78 (s, 1H), 5.01 (d, J = 17.7 Hz, 1H), 4.92 (d, J = 16.8 Hz, 1H), 4.36 (d, J = 14.1 Hz, 1H), 4.00 (d, J = 13.8 Hz, 1H), 3.55-3.70 (m, 2H), 3.36-3.39 (m, 1H), 3.07-3.27 (m, 3H), 2.99 (s, 2H), 2.96 (s, 2H), 2.80 (t, J = 11.6 Hz, 1H), 2.07 (d, J = 17.1 Hz, 8H), 1.67-1.76 (m, 1H), 1.47-1.58 (m, 1H), 1.18 (t, J = 7.5 Hz, 2H), 1.02 (t, J = 7.3 Hz, 2H); LCMS (M + 1): 589.1 |
| 98 | ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(ethyl)(methyl)-l6-sulfanone | $^{1}$H-NMR (400 MHz, DMSO-$d_6$) δ 7.96 (d, J = 1.0 Hz, 1H), 7.62 (dd, J = 5.1, 1.5 Hz, 1H), 7.27-7.31 (m, 1H), 7.10-7.20 (m, 2H), 6.97-7.02 (m, 1H), 6.91 (dd, J = 7.7, 5.0 Hz, 1H), 6.29 (td, J = 12.2, 10.4 Hz, 1H), 5.07 (s, 2H), 4.34 (d, J = 13.0 Hz, 1H), 3.91-3.97 (m, 1H), 3.79 (s, 3H), 3.56-3.70 (m, 2H), 3.34-3.40 (m, 1H), 3.07-3.27 (m, 3H), 2.97 (d, J = 13.0 Hz, 3H), 2.66-2.82 (m, 1H), 2.03-2.09 (m, 2H), 1.80-1.85 (m, 1H), 1.54 (t, J = 12.1 Hz, 1H), 1.10 (dt, J = 63.7, 7.4 Hz, 3H); LCMS (M + 1): 618.15 |
| 99 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)imino)dimethyl-l6-sulfanone | $^{1}$H-NMR (400 MHz, DMSO-$d_6$) δ 7.98 (s, 1H), 7.45 (d, J = 7.6 Hz, 1H), 7.39 (t, J = 7.8 Hz, 1H), 7.29 (d, J = 7.9 Hz, 1H), 7.16 (d, J = 5.8 Hz, 1H), 7.03 (d, J = 6.7 Hz, 1H), 6.89 (d, J = 5.2 Hz, 1H), 5.88 (t, J = 10.9 Hz, 1H), 5.43 (d, J = 17.1 Hz, 1H), 5.35 (d, J = 17.1 Hz, 1H), 4.33 (d, J = 13.1 Hz, 1H), 3.95 (d, J = 13.8 Hz, 1H), 3.62-3.71 (m, 2H), 3.37-3.41 (m, 1H), 3.24-3.28 (m, 1H), 3.01 (s, 3H), 2.95 (s, 3H), 2.84 (t, J = 11.6 Hz, 1H), 2.07 (t, J = 7.0 Hz, 2H), 1.79 (q, J = 12.2 Hz, 1H), 1.55 (dd, J = 22.8, 10.9 Hz, 1H); LCMS (M + 1): 681.2 |
| 100 | ((2-(3-(2-(1-(2-((3-methoxypyridin-2-yl)oxy)acetyl)piperidin-4-yl)thiazol-4-yl)-4,5-dihydroisoxazol-5-yl)-3-(trifluoromethyl)phenyl)imino)dimethyl-l6-sulfanone | $^{1}$H-NMR (400 MHz, DMSO-$d_6$) δ 7.97 (s. 1H), 7.62 (dd, J = 5.0, 1.4 Hz, 1H), 7.46 (d, J = 7.3 Hz, 1H), 7.39 (t, J = 7.9 Hz, 1H), 7.29 (dq, J = 7.7, 1.5 Hz, 2H), 6.91 (dd, J = 7.8, 5.0 Hz, 1H), 5.88 (t, J = 10.9 Hz, 1H), 5.07 (s, 2H), 4.33 (d, J = 12.2 Hz, 1H), 3.91-3.97 (m, 1H), 3.79 (s, 3H), 3.59-3.71 (m, 2H), 3.38 (td, J = 7.6, 3.9 Hz, 1H), 3.20-3.28 (m, 1H), 3.01 (s, 3H), 2.95 (s, 3H), 2.76-2.82 (m, 1H), 2.02-2.06 (m, 2H), 1.82 (t, J = 11.8 Hz, 1H), 1.51 (t, J = 12.2 Hz, 1H); LCMS (M + 1): 638.1 |
| 101 | (3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(methyl)-l6-sulfanone | $^{1}$H-NMR (400 MHz, CHLOROFORM-D) δ 7.48 (s, 1H). 7.19 (dd, J = 8.1, 1.1 Hz, 1H), 7.11 (t, J = 7.9 Hz, 1H), 7.01 (dd, J = 7.9, 1.2 Hz, 1H), 6.43 (dd, J = 12.7, 9.9 Hz, 1H), 6.34 (s, 1H), 4.99 (dd, J = 27.4, 16.0 Hz, 2H), 4.60 (d, J = 10.4 Hz, 1H), 4.08 (d, J = 14.1 Hz, 1H), 3.86 (dd, J = 16.5, 9.8 Hz, 1H), 3.56 (dd, J = 16.5, 12.5 Hz, 1H), 3.27-3.39 (m, 3H), 3.00-3.10 (m, 2H), 2.85-2.97 (m, 2H), 2.11-2.33 (m, 9H), 1.73-1.82 (m, 2H); LCMS (M + 1): 631.15 |
| 102 | (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(difluoromethyl)phenyl)(imino)(methyl)-l6-sulfanone | $^{1}$H-NMR (400 MHz, CHLOROFORM-D) δ 7.49 (s, 1H), 7.18-7.20 (m, 1H), 7.11 (t, J = 7.9 Hz, 1H), 6.53-7.02 (m, 4H), 6.43 (dd, J = 12.7, 9.9 Hz, 1H), 5.15 (dd, J = 19.2, 16.3 Hz, 2H), 4.59 (d, J = 13.4 Hz, 1H), 3.83-3.94 (m, 2H), 3.53-3.62 (m, 1H), 3.30-3.40 (m, 3H), 3.01-3.12 (m, 2H), 2.88-2.97 (m, 2H), 2.12-2.37 (m, 7H), 1.74-1.91 (m, 2H), 1.27 (d, J = 14.1 Hz, 2H); LCMS (M + 1): 685.1 |
| 103 | 1-(2-(4-(4-(5-(2-(difluoromethyl)-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one | $^{1}$H-NMR (400 MHz, CHLOROFORM-D) δ 8.30 (d, J = 3.7 Hz, 1H), 7.90 (d, J = 7.0 Hz, 1H), 7.47 (s, 1H), 7.20 (d, J = 7.9 Hz, 1H), 7.11 (t, J = 7.9 Hz, 1H), 7.00-7.03 (m, 2H), 6.42 (dd, J = 12.7, 9.9 Hz, 1H), 5.16 (s, 2H), 4.63 (d, J = 13.8 Hz, 1H), 4.01 (d, J = 13.1 Hz, 1H), 3.86 (dd, J = 16.5, 9.8 Hz, 1H), 3.56 (dd, J = 16.5, 12.5 Hz, 1H), 3.25-3.40 (m, 3H), 3.00-3.11 (m, 2H), 2.83-2.96 (m, 2H), 2.12-2.34 (m, 6H), 1.81-1.88 (m, 2H); LCMS (M + 1): 644.05 |
| 104 | 2-(3-(2-(1-(2-((3-methoxypyridin-2-yl)oxy)acetyl)piperidin-4- | $^{1}$H-NMR (400 MHz, CHLOROFORM-D) δ 7.68 (dd, J = 4.9, 0.9 Hz, 1H), 7.47 (s, 1H), 7.20 (d, J = 7.6 Hz, 1H), 7.08-7.13 (m, 2H), 7.01 (dd, J = 7.9, 0.9 Hz, 1H), 6.87 (dd, J = 7.8, 5.0 Hz, 1H), 6.42 |

TABLE NO 1-continued

The following compounds were prepared analogue to the procedure described in schemes 1-17 or Examples 1 to 8.

| Compd. No. | Compound Name | Analytical data |
|---|---|---|
| | yl)thiazol-4-yl)-4,5-dihydroisoxazol-5-yl)-3-(S-methylsulfonimidoyl)benzonitrile | (dd, J = 12.8, 9.8 Hz, 1H), 5.12 (d, J = 8.6 Hz, 2H), 4.65 (d, J = 13.1 Hz, 1H), 3.99-4.07 (m, 1H), 3.83-3.89 (m, 4H), 3.49-3.60 (m, 1H), 3.24-3.39 (m, 3H), 3.00-3.11 (m, 2H), 2.81-2.96 (m, 2H), 2.09-2.35 (m, 7H), 1.91 (s, 1H), 1.77 (s, 1H), 1.21-1.33 (m, 1H); LCMS (M + 1): 581.1 |
| 105 | 2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile | $^1$H-NMR (400 MHz, DMSO-$d_6$) δ 8.31-8.34 (m, 1H), 8.21 (d, J = 7.6 Hz, 1H), 8.06-8.08 (m, 1H), 7.80 (q, J = 7.7 Hz, 1H), 7.60 (d, J = 5.5 Hz, 1H), 6.77 (td, J = 12.0, 4.9 Hz, 1H), 5.61 (d, J = 17.4 Hz, 1H), 5.47-5.54 (m, 1H), 4.83-4.91 (m, 1H), 4.33 (d, J = 14.4 Hz, 1H), 3.94-4.04 (m, 3H), 3.49-3.57 (m, 1H), 3.35 (d, J = 7.9 Hz, 1H), 3.26 (d, J = 8.3 Hz, 3H), 2.82-2.89 (m, 1H), 2.08-2.19 (m, 2H), 1.84 (d, J = 12.8 Hz, 1H), 1.53-1.59 (m, 1H); LCMS (M + 1): 659.95 |
| 106 | 2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile | $^1$H-NMR (400 MHz, DMSO-$d_6$) δ 8.30-8.34 (m, 1H), 8.20-8.22 (m, 1H), 8.05-8.08 (m, 1H), 7.79 (t, J = 7.8 Hz, 1H), 6.75-6.78 (m, 1H), 6.48 (s, 1H), 5.27 (dd, J = 36.1, 17.0 Hz, 2H), 4.84-4.97 (m, 1H), 4.36 (d, J = 13.4 Hz, 1H), 3.96-4.04 (m, 3H), 3.26 (d, J = 8.1 Hz, 3H), 2.77-2.86 (m, 1H), 2.20 (d, J = 4.9 Hz, 5H), 2.06-2.11 (m, 2H), 2.00-1.76 (1H), 1.72-1.46 (1H); LCMS (M + 1): 605.95 |
| 107 | 1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one | $^1$H-NMR (400 MHz, CHLOROFORM-D) δ 7.48 (s, 1H), 7.19 (dd, J = 8.1, 1.1 Hz, 1H), 7.11 (t, J = 7.9 Hz, 1H), 7.01 (dd, J = 7.9, 1.2 Hz, 1H), 6.43 (dd, J = 12.7, 9.9 Hz, 1H), 6.34 (s, 1H), 4.99 (dd, J = 27.4, 16.0 Hz, 2H), 4.60 (d, J = 10.4 Hz, 1H), 4.08 (d, J = 14.1 Hz, 1H), 3.86 (dd, J = 16.5, 9.8 Hz, 1H), 3.56 (dd, J = 16.5, 12.5 Hz, 1H), 3.27-3.39 (m, 3H), 3.00-3.10 (m, 2H), 2.85-2.97 (m, 2H), 2.11-2.33 (m, 9H), 1.73-1.82 (m, 2H); LCMS (M + 1): 655.05 |
| 108 | 2-(3,5-bis(difluoromethyl)-1H-pyrazol-1-yl)-1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)ethan-1-one | $^1$H-NMR (400 MHz, CHLOROFORM-D) δ 7.49 (s, 1H), 7.18-7.20 (m, 1H), 7.11 (t, J = 7.9 Hz, 1H), 6.53-7.02 (m, 4H), 6.43 (dd, J = 12.7, 9.9 Hz, 1H), 5.15 (dd, J = 19.2, 16.3 Hz, 2H), 4.59 (d, J = 13.4 Hz, 1H), 3.83-3.94 (m, 2H), 3.53-3.62 (m, 1H), 3.30-3.40 (m, 3H), 3.01-3.12 (m, 2H), 2.88-2.97 (m, 2H), 2.12-2.37 (m, 7H), 1.74-1.91 (m, 2H), 1.27 (d, J = 14.1 Hz, 2H); LCMS (M + 1): 674.9 |
| 109 | l-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-((3-(trifluoromethyl)pyridin-2-yl)oxy)ethan-1-one | $^1$H-NMR (400 MHz, CHLOROFORM-D) δ 8.30 (d, J = 3.7 Hz, 1H), 7.90 (d, J = 7.0 Hz, 1H), 7.47 (s, 1H), 7.20 (d, J = 7.9 Hz, 1H), 7.11 (t, J = 7.9 Hz, 1H), 7.00-7.03 (m, 2H), 6.42 (dd, J = 12.7, 9.9 Hz, 1H), 5.16 (s,2H), 4.63 (d, J = 13.8 Hz, 1H), 4.01 (d, J = 13.1 Hz, 1H), 3.86 (dd, J = 16.5, 9.8 Hz, 1H), 3.56 (dd, J = 16.5, 12.5 Hz, 1H), 3.25-3.40 (m, 3H), 3.00-3.11 (m, 2H), 2.83-2.96 (m, 2H), 2.12-2.34 (m, 6H), 1.81-1.88 (m, 2H); LCMS (M + 1): 668 |
| 110 | 1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-((3-methoxypyridin-2-yl)oxy)ethan-1-one | $^1$H-NMR (400 MHz, CHLOROFORM-D) δ 7.68 (dd, J = 4.9, 0.9 Hz, 1H), 7.47 (s, 1H), 7.20 (d, J = 7.6 Hz, 1H), 7.08-7.13 (m, 2H), 7.01 (dd, J = 7.9, 0.9 Hz, 1H), 6.87 (dd, J = 7.8, 5.0 Hz, 1H), 6.42 (dd, J = 12.8, 9.8 Hz, 1H), 5.12 (d, J = 8.6 Hz, 2H), 4.65 (d, J = 13.1 Hz, 1H), 3.99-4.07 (m, 1H), 3.83-3.89 (m, 4H), 3.49-3.60 (m, 1H), 3.24-3.39 (m, 3H), 3.00-3.11 (m, 2H), 2.81-2.96 (m, 2H), 2.09-2.35 (m, 7H), 1.91 (s, 1H), 1.77 (s, 1H), 1.21-1.33 (m, 1H); LCMS (M + 1): 630.1 |
| 111 | 2-(3,5-bis(trifluoromethyl)-1H-pyrazol-1-yl)-1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)ethan-1-one | $^1$H-NMR (400 MHz, CHLOROFORM-D) δ 7.50 (t, J = 9.6 Hz, 1H), 7.19 (dd, J = 7.9, 0.9 Hz, 1H), 7.11 (t, J = 7.9 Hz, 1H), 7.01 (dd, J = 7.9, 1.2 Hz, 1H), 6.96 (s, 1H), 6.43 (dd, J = 12.5, 9.8 Hz, 1H), 5.16-5.25 (m, 2H), 4.58 (d, J = 13.1 Hz, 1H), 3.87 (dd, J = 16.5, 10.1 Hz, 2H), 3.57 (dd, J = 16.5, 12.8 Hz, 1H), 3.31-3.40 (m, 3H), 3.01-3.12 (m, 2H), 2.90-2.98 (m, 2H), 2.11-2.36 (m, 6H), 1.75-1.96 (m, 2H); LCMS (M + 1): 709.05 |
| 112 | methyl(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)(methylimino)-l6-sulfanone | $^1$H-NMR (400 MHz, DMSO-$d_6$) δ 8.28-8.30 (m, 1H), 8.13-8.17 (m, 1H), 8.07 (d, J = 1.0 Hz, 1H), 7.83-7.89 (m, 1H), 6.49 (d, J = 2.7 Hz, 1H), 6.26 (s, 1H), 5.21-5.31 (m, 2H), 4.35 (s, 1H), 3.97 (d, J = 14.2 Hz, 1H), 3.64-3.72 (m, 3H), 3.35 (d, J = 4.9 Hz, 4H), 3.26 (s, 2H), 2.80-2.86 (m, 1H), 2.52 (d, J = 4.2 Hz, 1H), 2.19 (d, J = 6.4 Hz, 3H), 2.13 (d, J = 11.7 Hz, 2H), 1.91-1.70 (1H), 1.58 (s, 1H); LCMS (M + 1): 663.2 |

TABLE NO 1-continued

| The following compounds were prepared analogue to the procedure described in schemes 1-17 or Examples 1 to 8. | | |
|---|---|---|
| Compd. No. | Compound Name | Analytical data |
| 113 | (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(methyl)(methylimino)-l6-sulfanone | $^1$H-NMR (400 MHz, DMSO-d$_6$) δ 8.25-8.30 (m, 1H), 8.14-8.17 (m, 1H), 8.07 (s, 1H), 7.86 (t, J = 7.9 Hz, 1H), 6.88-7.30 (m, 3H), 6.27 (t, J = 12.4 Hz, 1H), 5.30-5.45 (m, 2H), 4.25-4.37 (m, 1H), 3.97 (d, J = 13.1 Hz, 1H), 3.61-3.77 (m, 2H), 3.38-3.52 (m, 2H), 3.34 (s, 1H), 3.25 (d, J = 11.6 Hz, 2H), 2.80-2.86 (m, 1H), 2.52 (d, J = 4.3 Hz, 3H), 1.98-2.27 (m, 2H), 1.76-1.90 (m, 1H), 1.56-1.61 (m, 1H); LCMS (M + 1): 681.1 |
| 114 | (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)(ethylimino)(methyl)-l6-sulfanone | $^1$H-NMR (400 MHz, DMSO-d$_6$) δ 8.31 (t, J = 8.1 Hz, 1H), 8.13-8.16 (m, 1H), 8.06 (s, 1H), 7.82-7.87 (m, 1H), 7.59 (s, 1H), 6.29 (t, J = 11.8 Hz, 1H), 5.60 (d, J = 17.4 Hz, 1H),5.49 (d, J = 17.1 Hz, 1H), 4.33 (d, J = 12.2 Hz, 1H), 3.95 (d, J = 13.8 Hz, 1H), 3.60-3.79 (m, 2H), 3.35-3.42 (m, 2H), 3.26 (d, J = 11.3 Hz, 1H), 2.73-2.95 (m, 3H), 2.07-2.17 (m, 2H), 1.76-1.84 (m, 1H), 1.54 (q, J = 12.3 Hz, 1H), 1.21-1.32 (m, 2H), 1.08 (td, J = 14.3, 7.1 Hz, 3H); LCMS (M + 1): 730.9 |
| 115 | (ethylimino)(methyl)(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)-l6-sulfanone | $^1$H-NMR (400 MHz, DMSO-d$_6$) δ 8.31 (t, J = 8.7 Hz, 1H), 8.15 (t, J = 6.8 Hz, 1H), 8.06 (d, J = 2.4 Hz, 1H), 7.83-7.87 (m, 1H), 6.49 (s, 1H), 6.29 (t, J = 12.1 Hz, 1H), 5.27 (dd, J = 37.2, 16.9 Hz, 2H), 4.37 (d, J = 13.2 Hz, 1H), 3.97 (d, J = 13.0 Hz, 1H), 3.64-3.79 (m, 1H), 3.38-3.42 (m, 1H), 3.34 (d, J = 2.0 Hz, 2H), 3.25 (d, J = 10.8 Hz, 1H), 2.66-2.95 (m, 3H), 2.19 (d, J = 5.1 Hz, 3H), 2.11 (t, J = 12.0 Hz, 2H), 1.76-1.85 (m, 1H), 1.57 (d, J = 11.5 Hz, 1H), 1.21-1.25 (m, 2H), 1.08 (td, J = 14.1, 7.0 Hz, 3H); LCMS (M + 1): 676.95 |
| 116 | (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(ethylimino)(methyl)-l6-sulfanone | $^1$H-NMR (400 MHz, DMSO-d$_6$) δ 8.31 (t, J = 7.8 Hz, 1H), 8.13-8.16 (m, 1H), 8.06 (d, J = 2.4 Hz, 1H), 7.82-7.87 (m, 1H), 6.88-7.30 (m, 3H), 6.29 (t, J = 12.2 Hz, 1H), 5.30-5.45 (m, 2H), 4.34 (d, J = 13.1 Hz, 1H), 3.89-3.98 (m, 1H), 3.60-3.79 (m, 2H), 3.34-3.42 (m, 2H), 3.20-3.26 (m, 1H), 2.72-2.95 (m, 3H), 2.11 (t, J = 13.6 Hz, 2H), 1.76-1.85 (m, 1H), 1.57 (q, J = 11.7 Hz, 1H), 1.17-1.29 (m, 2H), 1.03-1.15 (m, 3H); LCMS (M + 1): 694.9 |
| 117 | (2-(3-(2-(1-(2-((3-methoxypyridin-2-yl)oxy)acetyl)piperidin-4-yl)thiazol-4-yl)-4,5-dihydroisoxazol-5-yl)-3-(trifluoromethyl)phenyl)(methyl)(methylimino)-l6-sulfanone | $^1$H-NMR (400 MHz, DMSO-d$_6$) δ 8.25-8.30 (m, 1H), 8.15 (d, J = 7.9 Hz, 1H), 8.06 (s, 1H), 7.86 (t, J = 7.8 Hz, 1H), 7.61 (d, J = 4.9 Hz, 1H), 7.28 (d, J = 7.6 Hz, 1H), 6.91 (dd, J = 7.6, 5.2 Hz, 1H), 5.07 (s, 2H), 4.34 (d, J = 12.8 Hz, 1H), 3.93 (d, J = 11.0 Hz, 1H), 3.79 (s, 3H), 3.60-3.72 (m, 2H), 3.34-3.40 (m, 5H), 3.16-3.25 (m, 1H), 2.74-2.80 (m, 1H), 2.52 (s, 3H), 2.09 (d, J = 12.8 Hz, 2H), 1.85 (d, J = 12.8 Hz, 1H), 1.51-1.58 (m, 1H); LCMS (M + 1): 638.1 |
| 118 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(iso-propyl)(methyl)-l6-sulfanone | $^1$H-NMR (400 MHz, DMSO-d$_6$) δ 7.96 (d, J = 2.9 Hz, 1H), 7.12-7.20 (m, 2H), 6.94-7.01 (m, 1H), 6.49 (s, 1H), 6.25-6.35 (m, 1H), 5.33 (d, J = 17.1 Hz, 1H), 5.23 (d, J = 17.1 Hz, 1H), 4.37 (d, J = 13.4 Hz, 1H), 3.97 (d, J = 13.1 Hz, 1H), 3.55-3.70 (m, 2H), 3.34-3.47 (m, 2H), 3.25 (d, J = 13.8 Hz, 1H), 2.92-2.99 (m, 3H), 2.84 (t, J = 12.5 Hz, 1H), 2.20 (s, 3H), 2.10 (t, J = 13.1 Hz, 2H), 1.74-1.84 (m, 1H), 1.51-1.60 (m, 1H), 1.22-1.28 (m, 5H), 1.03 (d, J = 5.8 Hz, 1H); LCMS (M + 1): 657.25 |
| 119 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(iso-propyl)(methyl)-l6-sulfanone | $^1$H-NMR (400 MHz, DMSO-d$_6$) δ 7.96-7.97 (m, 1H), 7.59 (s, 1H), 7.13-7.20 (m, 2H), 6.95-7.01 (m, 1H), 6.25-6.35 (m, 1H), 5.61 (d, J = 17.1 Hz, 1H), 5.50 (d, J = 17.1 Hz, 1H), 4.33 (d, J = 12.8 Hz, 1H), 3.95 (d, J = 13.1 Hz, 1H), 3.55-3.70 (m, 2H), 3.34-3.46 (m, 2H), 3.26 (d, J = 14.7 Hz, 1H), 2.94 (d, J = 11.5 Hz, 3H), 2.86 (t, J = 12.7 Hz, 1H), 2.10 (t, J = 13.4 Hz, 2H), 1.73-1.82 (m, 1H), 1.49-1.58 (m, 1H), 1.22-1.28 (m, 5H), 1.03 (d, J = 5.5 Hz, 1H); LCMS (M + 1): 711.8 |
| 120 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(iso-propyl)(methyl)-l6-sulfanone | $^1$H-NMR (400 MHz, DMSO-d$_6$) δ 7.96 (d, J = 2.8 Hz, 1H), 7.12-7.20 (m, 3H), 6.94-7.04 (m, 2H), 6.89 (d, J = 5.2 Hz, 1H), 6.25-6.35 (m, 1H), 5.43 (d, J = 17.1 Hz, 1H), 5.34 (d, J = 17.1 Hz, 1H), 4.34 (d, J = 12.8 Hz, 1H), 3.96 (d, J = 12.8 Hz, 1H), 3.57-3.70 (m, 2H), 3.34-3.47 (m, 2H), 3.25 (d, J = 12.8 Hz, 1H), 2.92-2.99 (m, 3H), 2.84 (t, J = 12.5 Hz, 1H), 2.06-2.13 (m, 2H), 1.74-1.83 (m, 1H), 1.54-1.61 (m, 1H), 1.22-1.28 (m, 5H), 1.03 (d, J = 6.7 Hz, 1H); LCMS (M + 1): 674.9 |
| 121 | ((2-(3-(2-(1-(2-(3,5-bis(difluoromethyl)-1H-pyrazol-1- | $^1$H-NMR (400 MHz, DMSO-d$_6$) δ 7.96 (d, J = 2.6 Hz, 1H), 6.88-7.30 (m, 5H), 6.71 (dd, J = 18.6, 10.1 Hz, 1H), 6.14 (td, J = 12.7, 9.5 Hz, 1H), 5.43 (d, J = 17.1 Hz, 1H), 5.34 (d, J = 17.1 Hz, 1H), |

TABLE NO 1-continued

The following compounds were prepared analogue to the procedure described in schemes 1-17 or Examples 1 to 8.

| Compd. No. | Compound Name | Analytical data |
|---|---|---|
| | yl)acetyl)piperidin-4-yl)thiazol-4-yl)-4,5-dihydroisoxazol-5-yl)-3-fluorophenyl)imino)(iso-propyl)(methyl)-l6-sulfanone | 4.34 (d, J = 13.4 Hz, 1H), 3.96 (d, J = 13.8 Hz, 1H), 3.65-3.73 (m, 1H), 3.35-3.55 (m, 3H), 3.25 (d, J = 11.6 Hz, 1H), 3.00 (d, J = 2.8 Hz, 3H), 2.84 (t, J = 11.9 Hz, 1H), 2.06-2.13 (m, 3H), 1.74-1.83 (m, 1H), 1.51-1.61 (m, 1H), 1.23-1.33 (m, 5H), 1.17 (d, J = 6.7 Hz, 1H); LCMS (M + 1): 659.15 |
| 122 | ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(iso-propyl)(methyl)-l6-sulfanone | $^1$H-NMR (400 MHz, DMSO-$d_6$) δ 8.39 (d, J = 3.7 Hz, 1H), 8.09-8.11 (m, 1H), 7.96 (d, J = 2.8 Hz, 1H), 7.14-7.21 (m, 2H), 6.99 (d, J = 8.3 Hz, 1H), 6.71 (dd, J = 18.5, 9.9 Hz, 1H), 6.14 (td, J = 12.8, 9.6 Hz, 1H), 5.26 (s, 2H), 4.32 (d, J = 13.4 Hz, 1H), 3.91 (d, J = 13.4 Hz, 1H), 3.65-3.73 (m, 1H), 3.35-3.56 (m, 3H), 3.24 (t, J = 12.5 Hz, 1H), 2.99 (d, J = 2.4 Hz, 3H), 2.79 (t, J = 12.4 Hz, 1H), 2.03-2.10 (m, 2H), 1.83 (t, J = 10.4 Hz, 1H), 1.54 (d, J = 12.1 Hz, 1H), 1.22-1.32 (m, 5H), 1.16 (d, J = 6.7 Hz, 1H); LCMS (M + 1): 653.9 |
| 123 | ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(iso-propyl)(methyl)-l6-sulfanone | $^1$H-NMR (400 MHz, DMSO-$d_6$) δ 7.96 (d, J = 2.4 Hz, 1H), 7.14-7.21 (m, 1H), 6.99 (d, J = 8.3 Hz, 1H), 6.71 (dd, J = 18.5, 10.2 Hz, 1H), 6.49 (s, 1H), 6.14 (td, J = 12.5, 9.5 Hz, 1H), 5.33 (d, J = 16.8 Hz, 1H), 5.23 (d, J = 17.1 Hz, 1H), 4.37 (d, J = 13.4 Hz, 1H), 3.97 (d, J = 14.1 Hz, 1H), 3.65-3.73 (m, 1H), 3.35-3.55 (m, 3H), 3.25 (d, J = 12.2 Hz, 1H), 3.00 (d, J = 2.4 Hz, 3H), 2.83 (t, J = 12.2 Hz, 1H), 2.20 (s, 3H), 2.06-2.13 (m, 2H), 1.76-1.85 (m, 1H), 1.56 (qd, J = 12.2, 3.8 Hz, 1H), 1.22-1.32 (m, 5H), 1.17 (d, J = 6.7 Hz, 1H); LCMS (M + 1): 640.9 |
| 124 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(iso-propyl)(methyl)-l6-sulfanone | $^1$H-NMR (400 MHz, DMSO-$d_6$) δ 7.96 (d, J = 2.4 Hz, 1H), 7.59 (s, 1H), 7.18 (ddd, J = 14.9, 8.2, 5.0 Hz, 1H), 6.99 (d, J = 8.3 Hz, 1H), 6.71 (dd, J = 18.6, 10.4 Hz, 1H), 6.14 (td, J = 12.8, 9.7 Hz, 1H), 5.61 (d, J = 17.1 Hz, 1H), 5.50 (d, J = 17.1 Hz, 1H), 4.33 (d, J = 13.8 Hz, 1H), 3.95 (d, J = 13.4 Hz, 1H), 3.65-3.73 (m, 1H), 3.35-3.56 (m, 3H), 3.26 (d, J = 12.5 Hz, 1H), 3.00 (d, J = 2.4 Hz, 3H), 2.86 (t, J = 11.8 Hz, 1H), 2.07-2.13 (m, 2H), 1.80 (dd, J = 12.1, 8.7 Hz, 1H), 1.48-1.58 (m, 1H), 1.22-1.32 (m, 6H), 1.15-1.19 (m, 2H); LCMS (M + 1): 695.35 |
| 125 | ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(meth-yl)(propyl)-l6-sulfanone | $^1$H-NMR (400 MHz, DMSO-$d_6$) δ 7.97 (d, J = 2.6 Hz, 1H), 7.15-7.22 (m, 1H), 6.96 (q, J = 3.9 Hz, 1H), 6.73 (q, J = 9.2 Hz, 1H), 6.49 (s, 1H), 6.06-6.16 (m, 1H), 5.33 (d, J = 17.1 Hz, 1H), 5.23 (d, J = 17.1 Hz, 1H), 4.37 (d, J = 14.1 Hz, 1H), 3.97 (d, J = 14.4 Hz, 1H), 3.47-3.70 (m, 2H), 3.38 (t, J = 11.8 Hz, 1H), 3.09-3.26 (m, 3H), 3.04-3.07 (m, 3H), 2.83 (t, J = 11.5 Hz, 1H), 2.20 (s, 3H), 2.10 (t, J = 12.1 Hz, 2H), 1.51-1.84 (m, 4H), 0.89 (t, J = 7.5 Hz, 2H), 0.76 (t, J = 7.3 Hz, 1H); LCMS (M + 1): 641.3 |
| 126 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(meth-yl)(propyl)-l6-sulfanone | $^1$H-NMR (400 MHz, DMSO-$d_6$) δ 7.98 (d, J = 2.8 Hz, 1H), 7.59 (s, 1H), 7.18 (dq, J = 15.2, 4.0 Hz, 1H), 6.96 (q, J = 4.0 Hz, 1H), 6.73 (dd, J = 18.6, 8.6 Hz, 1H), 6.06-6.16 (m, 1H), 5.61 (d, J = 17.1 Hz, 1H), 5.49 (d, J = 17.1 Hz, 1H), 4.33 (d, J = 12.8 Hz, 1H), 3.95 (d, J = 12.8 Hz, 1H), 3.48-3.70 (m, 2H), 3.39 (t, J = 11.8 Hz, 1H), 3.04-3.27 (m, 6H), 2.85 (t, J = 11.3 Hz, 1H), 2.06-2.13 (m, 2H), 1.48-1.83 (m, 4H), 0.87-0.95 (m, 2H), 0.76 (t, J = 7.3 Hz, 1H); LCMS (M + 1): 695.3 |
| 127 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(meth-yl)(propyl)-l6-sulfanone | $^1$H-NMR (400 MHz, DMSO-$d_6$) δ 7.97 (d, J = 2.8 Hz, 1H), 7.15-7.22 (m, 2H), 7.03 (d, J = 6.4 Hz, 1H), 6.96 (q, J = 3.9 Hz, 1H), 6.89 (d, J = 4.6 Hz, 1H), 6.73 (dd, J = 18.3, 8.6 Hz, 1H), 6.07-6.16 (m, 1H), 5.43 (d, J = 17.4 Hz, 1H), 5.34 (d, J = 16.8 Hz, 1H), 4.35 (d, J = 13.4 Hz, 1H), 3.96 (d, J = 14.7 Hz, 1H), 3.47-3.70 (m, 2H), 3.36-3.41 (m, 1H), 3.17-3.28 (m, 3H), 3.04 (d, J = 4.0 Hz, 3H), 2.83 (t, J = 11.6 Hz, 1H), 2.06-2.13 (m, 2H), 1.51-1.84 (m, 4H), 0.89 (t, J = 7.3 Hz, 2H), 0.76 (t, J = 7.5 Hz, 1H); LCMS (M + 1): 658.95 |
| 128 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(meth-yl)(propyl)-l6-sulfanone | $^1$H-NMR (400 MHz, DMSO-$d_6$) δ 7.98 (d, J = 4.3 Hz, 1H), 7.10-7.20 (m, 2H), 6.99 (ddd, J = 10.9, 7.8, 1.2 Hz, 1H), 6.49 (s, 1H), 6.22-6.32 (m, 1H), 5.30-5.35 (m, 1H), 5.23 (d, J = 17.1 Hz, 1H), 4.37 (d, J = 12.8 Hz, 1H), 3.97 (d, J = 13.1 Hz, 1H), 3.58-3.71 (m, 2H), 3.38 (td, J = 11.5, 3.1 Hz, 1H), 3.10-3.26 (m, 2H), 2.96-3.03 (m, 4H), 2.83 (t, J = 11.6 Hz, 1H), 2.20 (s, 3H), 2.07-2.13 (m, 2H), 1.46-1.84 (m, 4H), 0.84 (t, J = 7.5 Hz, 2H), 0.67 (t, J = 7.5 Hz, 1H); LCMS (M + 1): 657.05 |
| 129 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(meth-yl)(propyl)-l6-sulfanone | $^1$H-NMR (400 MHz, DMSO-$d_6$) δ 7.98 (d, J = 4.9 Hz, 1H), 7.59 (s, 1H), 7.10-7.20 (m, 2H), 6.99 (ddd, J = 11.0, 7.8, 1.4 Hz, 1H), 6.21-6.32 (m, 1H), 5.61 (d, J = 17.4 Hz, 1H), 5.49 (d, J = 17.1 Hz, 1H), 4.33 (d, J = 11.3 Hz, 1H), 3.95 (d, J = 13.4 Hz, 1H), 3.58-3.71 (m, 2H), 3.36-3.41 (m, 1H), 3.09-3.28 (m, 3H), 2.95-3.03 (m, 4H), 2.83-2.88 (m, 1H), 2.10 (t, J = 12.5 Hz, 2H), 1.46-1.83 (m, 4H), 0.84 (t, J = 7.5 Hz, 1H), 0.66 (t, J = 7.5 Hz, 1H); LCMS (M + 1): 710.95 |

TABLE NO 1-continued

The following compounds were prepared analogue to the procedure described in schemes 1-17 or Examples 1 to 8.

| Compd. No. | Compound Name | Analytical data |
|---|---|---|
| 130 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(methyl)(propyl)-l6-sulfanone | $^1$H-NMR (400 MHz, DMSO-$d_6$) δ 7.98 (d, J = 4.3 Hz, 1H), 7.10-7.20 (m, 3H), 6.97-7.04 (m, 2H), 6.89 (d, J = 4.9 Hz, 1H), 6.22-6.32 (m, 1H), 5.43 (d, J = 17.4 Hz, 1H), 5.34 (d, J = 17.1 Hz, 1H), 4.35 (d, J = 12.2 Hz, 1H), 3.96 (d, J = 13.1 Hz, 1H), 3.58-3.71 (m, 2H), 3.35-3.42 (m, 1H), 3.10-3.26 (m, 2H), 2.96-3.03 (m, 4H), 2.83 (t, J = 11.5 Hz, 1H), 2.09 (t, J = 12.8 Hz, 2H), 1.74-1.83 (m, 1H), 1.46-1.71 (m, 3H), 0.84 (t, J = 7.5 Hz, 1H), 0.67 (t, J = 7.5 Hz, 1H); LCMS (M + 1): 674.95 |
| 131 | ((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(methyl)(propyl)-l6-sulfanone | $^1$H-NMR (400 MHz, DMSO-$d_6$) δ 8.55 (d, J = 1.8 Hz, 1H), 8.38 (d, J = 2.4 Hz, 1H), 7.97 (d, J = 4.6 Hz, 1H), 7.10-7.20 (m, 2H), 6.99 (ddd, J = 11.0, 7.8, 1.4 Hz, 1H), 6.22-6.32 (m, 1H), 5.37 (s, 2H), 4.30 (d, J = 12.5 Hz, 1H), 3.88 (d, J = 13.4 Hz, 1H), 3.58-3.71 (m, 2H), 3.34-3.41 (m, 1H), 3.10-3.27 (m, 3H), 2.95-3.03 (m, 4H), 2.77-2.83 (m, 1H), 2.07 (t, J = 13.8 Hz, 2H), 1.80-1.85 (m, 1H), 1.47-1.69 (m, 3H), 0.84 (t, J = 7.3 Hz, 1H), 0.66 (t, J = 7.3 Hz, 1H); LCMS (M + 1): 670.95 |
| 132 | ((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(methyl)(propyl)-l6-sulfanone | $^1$H-NMR (400 MHz, DMSO-$d_6$) δ 8.39 (d, J = 4.9 Hz, 1H), 8.10 (dd, J = 7.6, 1.2 Hz, 1H), 7.97 (d, J = 4.6 Hz, 1H), 7.10-7.20 (m, 3H), 6.99 (ddd, J = 11.0, 7.8, 1.4 Hz, 1H), 6.22-6.32 (m, 1H), 5.26 (s, 2H), 4.32 (d, J = 12.2 Hz, 1H), 3.91 (d, J = 12.5 Hz, 1H), 3.58-3.71 (m, 2H), 3.35-3.40 (m, 1H), 3.09-3.27 (m, 3H), 2.95-3.03 (m, 4H), 2.79 (t, J = 11.9 Hz, 1H), 2.03-2.10 (m, 2H), 1.81 (d, J = 12.5 Hz, 1H), 1.45-1.69 (m, 3H), 0.84 (t, J = 7.3 Hz, 1H), 0.66 (t, J = 7.3 Hz, 1H); LCMS (M + 1): 669.95 |
| 133 | ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(methyl)(propyl)-l6-sulfanone | $^1$H-NMR (400 MHz, DMSO-$d_6$) δ 7.97 (d, J = 4.6 Hz, 1H), 7.61 (d, J = 4.9 Hz, 1H), 7.28 (dd, J = 7.8, 1.4 Hz, 1H), 7.10-7.20 (m, 2H), 6.99 (ddd, J = 11.0, 7.8, 1.3 Hz, 1H), 6.91 (dd, J = 7.6, 4.9 Hz, 1H), 6.21-6.32 (m, 1H), 5.07 (s, 2H), 4.34 (d, J = 11.6 Hz, 1H), 3.91-3.97 (m, 1H), 3.79 (s, 3H), 3.58-3.71 (m, 2H), 3.35-3.38 (m, 2H), 3.11-3.27 (m, 3H), 2.95-3.03 (m, 3H), 2.75-2.81 (m, 1H), 2.08 (d, J = 13.1 Hz, 2H), 1.80 (d, J = 18.0 Hz, 1H), 1.50-1.69 (m, 3H), 0.84 (t, J = 7.5 Hz, 1H), 0.66 (t, J = 7.5 Hz, 1H); LCMS (M + 1): 632.05 |
| 134 | ((3-fluoro-2-(3-(2-(1-(2-((2-methoxypyridin-3-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, DMSO-$d_6$) δ 7.96 (s, 1H), 7.65-7.69 (m, 1H), 7.17-7.22 (m, 2H), 6.94 (d, J = 7.9 Hz, 1H), 6.85-6.90 (m, 1H), 6.75 (dd, J = 9.8, 8.3 Hz, 1H), 6.13 (dd, J = 12.5, 9.2 Hz, 1H), 4.79-4.93 (m, 2H), 4.35-4.43 (m, 1H), 3.85-3.92 (m, 4H), 3.65-3.72 (m, 1H), 3.47 (dd, J = 16.8, 9.2 Hz, 1H), 3.36 (qd, J = 7.7, 3.9 Hz, 1H), 3.18-3.24 (m, 1H), 3.11-3.14 (m, 6H), 2.77-2.83 (m, 1H), 2.06-2.09 (m, 2H), 1.76-1.82 (m, 1H), 1.51-1.57 (m, 1H); LCMS (M + 1): 588 |
| 135 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diethyl-l6-sulfanone | $^1$H-NMR (400 MHz, DMSO-$d_6$) δ 7.97 (s, 1H), 7.12-7.17 (m, 2H), 6.94-6.99 (m, 1H), 6.49 (s, 1H), 6.29 (t, J = 11.2 Hz, 1H), 5.33 (d, J = 16.8 Hz, 1H), 5.23 (d, J = 17.1 Hz, 1H), 4.37 (d, J = 12.8 Hz, 1H), 3.97 (d, J = 14.1 Hz, 1H), 3.64 (d, J = 11.3 Hz, 2H), 3.36-3.41 (m, 1H), 3.11-3.27 (m, 4H), 3.02 (td, J = 14.4, 7.3 Hz, 1H), 2.84 (t, J = 11.6 Hz, 1H), 2.20 (s, 3H), 2.10 (t, J = 11.8 Hz, 2H), 1.81 (t, J = 12.1 Hz, 1H), 1.50-1.61 (m, 1H), 1.16 (t, J = 7.5 Hz, 3H), 0.98 (t, J = 7.3 Hz, 3H); LCMS (M + 1): 656.85 |
| 136 | ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diethyl-l6-sulfanone | $^1$H-NMR (400 MHz, DMSO-$d_6$) δ 7.96 (s, 1H), 7.62 (dd, J = 4.9, 1.5 Hz, 1H), 7.28 (dd, J = 7.8, 1.4 Hz, 1H), 7.12-7.17 (m, 2H), 6.95-6.99 (m, 1H), 6.91 (dd, J = 7.9, 4.9 Hz, 1H), 6.29 (t, J = 11.2 Hz, 1H), 5.07 (d, J = 1.7 Hz, 2H), 4.34 (d, J = 13.1 Hz, 1H), 3.93 (d, J = 11.6 Hz, 1H), 3.79 (s, 3H), 3.61-3.65 (m, 2H), 3.37 (tt, J = 11.5, 3.7 Hz, 1H), 3.11-3.29 (m, 4H), 3.01 (td, J = 14.4, 7.2 Hz, 1H), 2.79 (t, J = 12.2 Hz, 1H), 2.03-2.09 (m, 2H), 1.76-1.85 (m, 1H), 1.48-1.54 (m, 1H), 1.15 (t, J = 7.5 Hz, 3H), 0.97 (t, J = 7.3 Hz, 3H); LCMS (M + 1): 631.9 |
| 137 | ((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diethyl-l6-sulfanone | $^1$H-NMR (400 MHz, DMSO-$d_6$) δ 8.55 (d, J = 2.4 Hz, 1H), 8.38 (d, J = 2.4 Hz, 1H), 7.96 (s, 1H), 7.12-7.17 (m, 2H), 6.95-6.99 (m, 1H), 6.29 (t, J = 11.2 Hz, 1H), 5.37 (s, 2H), 4.31 (d, J = 14.1 Hz, 1H), 3.86-3.90 (m, 1H), 3.61-3.65 (m, 2H), 3.35-3.41 (m, 1H), 3.11-3.27 (m, 4H), 3.02 (td, J = 14.2, 7.1Hz, 1H), 2.80 (t, J = 11.9 Hz, 1H), 2.03-2.10 (m, 2H), 1.77-1.86 (m, 1H), 1.54 (q, J = 11.0 Hz, 1H), 1.16 (t, J = 7.5 Hz, 3H), 0.97 (t, J = 7.3 Hz, 3H); LCMS (M + 1): 670.9 |
| 138 | diethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)-l6-sulfanone | $^1$H-NMR (400 MHz, DMSO-$d_6$) δ 7.97 (s, 1H), 7.16 (q, J = 7.6 Hz, 1H), 6.97 (d, J = 8.3 Hz, 1H), 6.70 (dd, J = 9.9, 8.7 Hz, 1H), 6.49 (s, 1H), 6.14 (dd, J = 12.5, 8.9 Hz, 1H), 5.28 (dd, J = 39.7, 17.1 Hz, 2H), 4.37 (d, J = 13.1 Hz, 1H), 3.97 (d, J = 13.4 Hz, 1H), 3.68 (dd, J = 16.8, 12.5 Hz, 1H), 3.53 (dd, J = 16.7, 9.0 Hz, 1H), 3.39 (qd, J = 7.6, 3.8 Hz, 1H), 3.07-3.29 (m, 5H), 2.83 (t, J = 11.8 Hz, 1H), 2.20 (s, 3H), 2.06-2.13 (m, 2H), 1.80 (dd, J = 20.9, 11.8 Hz, 1H), 1.51-1.61 (m, 1H), 1.19 (q, J = 7.7 Hz, 3H), 1.07 (t, J = 7.3 Hz, 3H); LCMS (M + 1): 640.9 |

TABLE NO 1-continued

The following compounds were prepared analogue to the procedure described in schemes 1-17 or Examples 1 to 8.

| Compd. No. | Compound Name | Analytical data |
|---|---|---|
| 139 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diethyl-l6-sulfanone | $^1$H-NMR (400 MHz, DMSO-$d_6$) δ 7.97 (s, 1H), 7.59 (s, 1H), 7.16 (td, J = 8.1, 6.8 Hz, 1H), 6.98 (d, J = 7.9 Hz, 1H), 6.70 (dd, J = 10.1, 8.9 Hz, 1H), 6.14 (dd, J = 12.2, 9.2 Hz, 1H), 5.61 (d, J = 17.1 Hz, 1H), 5.49 (d, J = 17.1 Hz, 1H), 4.33 (d, J = 12.5 Hz, 1H), 3.95 (d, J = 14.1 Hz, 1H), 3.68 (dd, J = 16.8, 12.5 Hz, 1H), 3.54 (dd, J = 17.0, 9.0 Hz, 1H), 3.39 (qd, J = 7.6, 3.8 Hz, 1H), 3.07-3.29 (m, 5H), 2.86 (t, J = 11.5 Hz, 1H), 2.10 (t, J = 12.5 Hz, 2H), 1.79 (dd, J = 23.2, 11.0 Hz, 1H), 1.53 (qd, J = 12.2, 3.8 Hz, 1H), 1.17-1.22 (m, 3H), 1.07 (t, J = 7.3 Hz, 3H); LCMS (M + 1): 694.9 |
| 140 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diethyl-l6-sulfanone | $^1$H-NMR (400 MHz, DMSO-$d_6$) δ 7.97 (s, 1H), 6.88-7.30 (m, 5H), 6.70 (dd, J = 10.1, 8.9 Hz, 1H), 6.14 (dd, J = 12.4, 9.0 Hz, 1H), 5.39 (dd, J = 36.7, 17.1 Hz, 2H), 4.35 (d, J = 13.8 Hz, 1H), 3.96 (d, J = 13.4 Hz, 1H), 3.68 (dd, J = 16.8, 12.5 Hz, 1H), 3.53 (dd, J = 16.8, 9.2 Hz, 1H), 3.38 (qd, J = 7.6, 3.8 Hz, 1H), 3.07-3.29 (m, 5H), 2.81-2.86 (m, 1H), 2.06-2.13 (m, 2H), 1.74-1.84 (m, 1H), 1.51-1.61 (m, 1H), 1.17-1.22 (m, 3H), 1.07 (t, J = 7.3 Hz, 3H); LCMS (M + 1): 659.2 |
| 141 | diethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)-l6-sulfanone | $^1$H-NMR (400 MHz, DMSO-$d_6$) δ 7.96 (s, 1H), 7.62 (dd, J = 4.9, 1.5 Hz, 1H), 7.28 (dd, J = 7.9, 1.5 Hz, 1H), 7.16 (td, J = 8.2, 6.8 Hz, 1H), 6.98 (d, J = 7.9 Hz, 1H), 6.91 (dd, J = 7.8, 5.0 Hz, 1H), 6.70 (dd, J = 9.6, 8.4 Hz, 1H), 6.14 (dd, J = 12.2, 9.2 Hz, 1H), 5.07 (s, 2H), 4.34 (d, J = 12.8 Hz, 1H), 3.89-3.95 (m, 1H), 3.79 (s, 3H), 3.68 (dd, J = 17.0, 12.7 Hz, 1H), 3.54 (dd, J = 16.8, 9.2 Hz, 1H), 3.38 (qd, J = 7.7, 3.7 Hz, 1H), 3.06-3.29 (m, 5H), 2.78 (t, J = 12.7 Hz, 1H), 2.03-2.09 (m, 2H), 1.79-1.82 (m, 1H), 1.53 (d, J = 9.2 Hz, 1H), 1.18 (t, J = 7.3 Hz, 3H), 1.07 (t, J = 7.5 Hz, 3H); LCMS (M + 1): 615.9 |
| 142 | diethyl((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)-l6-sulfanone | $^1$H-NMR (400 MHz, DMSO-$d_6$) δ 8.39 (d, J = 4.6 Hz, 1H), 8.10 (d, J = 7.6 Hz, 1H), 7.96 (s, 1H), 7.13-7.19 (m, 2H), 6.98 (d, J = 7.9 Hz, 1H), 6.68-6.72 (m, 1H), 6.14 (dd, J = 12.2, 9.2 Hz, 1H), 5.26 (s, 2H), 4.32 (d, J = 13.1 Hz, 1H), 3.91 (d, J = 13.4 Hz, 1H), 3.68 (dd, J = 16.8, 12.5 Hz, 1H), 3.54 (dd, J = 16.7, 9.0 Hz, 1H), 3.37 (qd, J = 7.6, 4.0 Hz, 1H), 3.06-3.29 (m, 5H), 2.76-2.82 (m, 1H), 2.06 (t, J = 12.8 Hz, 2H), 1.76-1.85 (m, 1H), 1.55 (t, J = 11.0 Hz, 1H), 1.16-1.23 (m, 3H), 1.07 (t, J = 7.3 Hz, 3H); LCMS (M + 1): 654.15 |
| 143 | diethyl((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)-l6-sulfanone | $^1$H-NMR (400 MHz, DMSO-$d_6$) δ 8.55 (d, J = 2.4 Hz, 1H), 8.38 (d, J = 2.4 Hz, 1H), 7.96 (s, 1H), 7.16 (td, J = 8.1, 6.8 Hz, 1H), 6.98 (d, J = 7.9 Hz, 1H), 6.70 (dd, J = 9.6, 8.4 Hz, 1H), 6.14 (dd, J = 12.4, 9.0 Hz, 1H), 5.37 (s, 2H), 4.30 (d, J = 13.1 Hz, 1H), 3.88 (d, J = 13.4 Hz, 1H), 3.68 (dd, J = 17.0, 12.4 Hz, 1H), 3.53 (dd, J = 16.8, 9.2 Hz, 1H), 3.35-3.40 (m, 1H), 3.07-3.29 (m, 5H), 2.80 (t, J = 11.5 Hz, 1H), 2.03-2.10 (m, 2H), 1.77-1.85 (m, 1H), 1.50-1.59 (m, 1H), 1.16-1.22 (m, 3H), 1.07 (t, J = 7.3 Hz, 3H); LCMS (M + 1): 654.85 |
| 144 | (3-(difluoromethyl)-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(methyl)(methylimino)-l6-sulfanone | $^1$H-NMR (400 MHz, DMSO-$d_6$) δ 8.39 (d, J = 3.7 Hz, 1H), 8.05-8.20 (m, 4H), 7.81 (td, J = 7.8, 2.3 Hz, 1H), 7.01-7.29 (m, 2H), 6.60 (t, J = 12.1 Hz, 1H), 5.26 (s, 2H), 4.33 (d, J = 12.2 Hz, 1H), 3.92 (dd, J = 17.3, 11.5 Hz, 2H), 3.34-3.51 (m, 4H), 3.21-3.27 (m, 2H), 2.76-2.82 (m, 1H), 2.52-2.58 (m, 3H), 2.08 (t, J = 11.8 Hz, 2H), 1.76-1.87 (m, 1H), 1.55 (q, J = 11.8 Hz, 1H); LCMS (M + 1): 658.1 |
| 145 | 1-(2-(4-(4-(5-(2-(difluoromethyl)-6-(N,S-dimethylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.29-7.70 (6H), 7.43-6.98 (1H), 6.89-6.52 (1H), 6.48-6.29 (1H), 5.05-4.81 (2H), 4.53-4.29 (1H), 4.19-3.57 (2H), 3.63-3.39 (1H), 3.37-3.33 (~4H), 3.21-3.03 (1H), 3.00-2.77 (1H), 2.63-2.59 (3H), 2.27-2.00 (2H), 1.96-1.71 (1H), 1.72-1.46 (1H); LCMS (M + 1): 658.85 |
| 146 | 3-chloro-1-(2-(4-(4-(5-(2-(difluoromethyl)-6-(N,S-dimethylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one | $^1$H-NMR (400 MHz, DMSO-$d_6$) δ 8.36 (s, 1H), 8.19 (d. J = 7.9 Hz, 1H), 8.12-8.16 (m, 2H), 8.06 (d, J = 7.6 Hz, 1H), 7.81 (td, J = 7.9, 2.3 Hz, 1H), 7.15 (t, J = 54.6 Hz, 1H), 5.01 (dd, J = 19.7, 16.0 Hz, 2H), 4.36 (d, J = 12.8 Hz, 1H), 3.88-4.00 (m, 2H), 3.38-3.51 (m, 3H), 3.33 (s, 2H), 3.25 (dd, J = 8.9, 4.9 Hz, 1H), 2.85 (t, J = 11.9 Hz, 1H), 2.56 (s, 2H), 2.52 (s, 2H), 2.13 (q, J = 12.3 Hz, 2H), 1.76-1.87 (m, 1H), 1.56-1.60 (m, 1H); LCMS (M + 1): 691.9 |
| 147 | (3-(difluoromethyl)-2-(3-(2-(1-(2-(3,5-dimethyl-1H-pyrazol-1- | $^1$H-NMR (400 MHz, DMSO-$d_6$) δ 8.30-7.97 (3H), 7.90-7.71 (1H), 7.40-6.94 (1H), 6.88-6.40 (1H), 6.02-5.35 (1H), 5.12-4.73 (2H), 4.52-4.28 (1H), 4.18-3.63 (2H), 3.57-3.36 (3H), 3.36-3.18 (6H), |

TABLE NO 1-continued

| Compd. No. | Compound Name | Analytical data |
|---|---|---|
| | The following compounds were prepared analogue to the procedure described in schemes 1-17 or Examples 1 to 8. | |
| | yl)acetyl)piperidin-4-yl)thiazol-4-yl)-4,5-dihydroisoxazol-5-yl)phenyl)(methyl)(methyl-imino)-l6-sulfanone | 2.89-2.73 (1H), 2.63-2.53 (3H), 2.17-2.08 (3H), 2.08-2.04 (2H), 1.86-1.68 (1H), 1.65-1.38 (1H); LCMS (M + 1): 590.85 |
| 148 | (3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methyl-imino)-l6-sulfanone | $^1$H-NMR (400 MHz, DMSO-d$_6$) δ 8.11-8.20 (m, 2H), 8.06 (d, J = 8.1 Hz, 1H), 7.81 (td, J = 7.8, 2.4 Hz, 1H), 7.15 (t, J = 54.9 Hz, 1H), 6.60 (t, J = 12.2 Hz, 1H), 6.49 (s, 1H), 5.28 (dd, J = 37.8, 17.0 Hz, 2H), 4.35-4.39 (m, 1H), 3.88-4.12 (m, 2H), 3.33-3.51 (m, 5H), 3.22-3.26 (m, 1H), 2.83 (t, J = 11.7 Hz, 1H), 2.57 (d, J = 4.4 Hz, 2H), 2.53 (d, J = 7.3 Hz, 1H), 2.19 (d, J = 6.4 Hz, 3H), 2.11 (t, J = 12.2 Hz, 2H), 1.83 (t, J = 12.1 Hz, 1H), 1.59 (t, J = 12.0 Hz, 1H); LCMS (M + 1): 644.85 |
| 149 | (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(difluoromethyl)phe-nyl)(methyl)(methylimino)-l6-sulfanone | $^1$H-NMR (400 MHz, DMSO-d$_6$) δ 8.36-7.49 (5H), 7.38-6.98 (1H), 6.87-6.49 (1H), 5.70-5.40 (2H), 4.53-4.26 (1H), 4.17-3.87 (2H), 3.73-3.13 (6H), 2.95-2.73 (1H), 2.51-2.46 (3H), 2.23-2.01 (2H), 1.96-1.71 (1H), 1.67-1.36 (1H); LCMS (M + 1): 698.85 |
| 150 | (Z)-N-((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-d$_6$) δ 8.29-7.50 (5H), 7.37-7.21 (1H), 6.98-6.81 (1H), 6.39-6.03 (1H), 5.28-4.86 (3H), 4.63-3.85 (4H), 3.84-3.43 (4H), 3.26-2.99 (3H), 2.88-2.67 (1H), 2.21-1.93 (2H), 1.94-1.68 (1H), 1.65-1.42 (1H); LCMS (M + 1): 598.8 |
| 151 | (E)-N-((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)-l4-sulfaneylidene)cyanamide | $^1$H-NMR (400 MHz, DMSO-d$_6$) δ 8.29-7.50 (5H), 7.37-7.21 (1H), 6.98-6.81 (1H), 6.39-6.03 (1H), 5.28-4.86 (3H), 4.63-3.85 (4H), 3.84-3.43 (4H), 3.26-2.99 (3H), 2.88-2.67 (1H), 2.21-1.93 (2H), 1.94-1.68 (1H), 1.65-1.42 (1H); LCMS (M + 1): 598.8 |
| 152 | (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(difluoromethyl)phe-nyl)(methyl)(methylimino)-l6-sulfanone | $^1$H-NMR (400 MHz, DMSO-d$_6$) δ 8.11-8.20 (m, 2H), 8.06 (d, J = 7.9 Hz, 1H), 7.81 (td, J = 7.8, 2.3 Hz, 1H), 6.88-7.30 (m, 4H), 6.60 (t, J = 12.1 Hz, 1H), 5.39 (q, J = 17.1 Hz, 2H), 4.35 (d, J = 12.8 Hz, 1H), 3.89-4.12 (m, 2H), 3.34-3.51 (m, 5H), 3.25 (d, J = 11.9 Hz, 1H), 2.82 (q, J = 12.0 Hz, 1H), 2.52-2.58 (m, 3H), 2.11 (t, J = 13.9 Hz, 2H), 1.76-1.86 (m, 1H), 1.53-1.62 (m, 1H); LCMS (M + 1): 663.15 |
| 153 | 1-(2-(4-(4-(5-(2-chloro-6-((diethyl(oxo)-l6-sulfaneylidene)amino)phe-nyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-d$_6$) δ 7.91-7.97 (m, 3H), 7.12-7.17 (m, 2H), 6.94-6.99 (m, 1H), 6.38 (t, J = 6.9 Hz, 1H), 6.29 (t, J = 11.2 Hz, 1H), 4.95 (s, 2H), 4.37 (d, J = 13.4 Hz, 1H), 4.01 (d, J = 13.8 Hz, 1H), 3.61-3.70 (m, 2H), 3.37-3.46 (m, 1H), 3.11-3.29 (m, 4H), 3.02 (td, J = 14.3, 7.1 Hz, 1H), 2.81-2.87 (m, 1H), 2.06-2.15 (m, 2H), 1.79 (dd, J = 23.8, 12.5 Hz, 1H), 1.56 (qd, J = 12.2, 3.8 Hz, 1H), 1.16 (t, J = 7.3 Hz, 3H), 0.98 (dd, J = 7.3, 6.4 Hz, 3H); LCMS (M + 1): 669.85 |
| 154 | (3-(difluoromethyl)-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)(methyl-imino)-l6-sulfanone | $^1$H-NMR (400 MHz, DMSO-d$_6$) δ 8.05-8.20 (m, 3H), 7.81 (td, J = 7.9, 2.3 Hz, 1H), 7.61 (dd, J = 5.0, 1.4 Hz, 1H), 7.01-7.29 (m, 2H), 6.91 (dd, J = 7.8, 5.0 Hz, 1H), 6.60 (t, J = 12.1 Hz, 1H), 5.07 (s, 2H), 4.34 (d, J = 12.4 Hz, 1H), 3.89-4.12 (m, 2H), 3.81 (d, J = 15.6 Hz, 3H), 3.34-3.51 (m, 4H), 3.16-3.26 (m, 2H), 2.75-2.81 (m, 1H), 2.52-2.56 (m, 3H), 2.06 (dd, J = 24.6, 13.9 Hz, 2H), 1.70-1.87 (m, 1H), 1.52-1.61 (m, 1H); LCMS (M + 1): 619.9 |
| 155 | (3-(difluoromethyl)-2-(3-(2-(1-(2-((5-(trifluoromethyl)pyridin-2-yl)oxy)acetyl)piperidin-4-yl)thiazol-4-yl)-4,5-dihydroisoxazol-5-yl)phenyl)(methyl)(methyl-imino)-l6-sulfanone | $^1$H-NMR (400 MHz, DMSO-d$_6$) δ 8.52 (s, 1H), 8.06-8.20 (m, 4H), 7.81 (td, J = 7.9, 2.2 Hz, 1H), 7.01-7.29 (m, 2H), 6.61 (t, J = 12.1 Hz, 1H), 5.21 (s, 2H), 4.33 (d, J = 12.5 Hz, 1H), 4.00 (ddd, J = 64.7, 17.5, 11.7 Hz, 2H), 3.34-3.51 (m, 5H), 3.16-3.27 (m, 3H), 2.77-2.82 (m, 1H), 2.52-2.56 (m, 3H), 2.05-2.13 (m, 2H), 1.76-1.84 (m, 1H), 1.55 (q, J = 11.9 Hz, 1H); LCMS (M + 1): 657.8 |
| 156 | (3-chloro-2-(3-(2-(1-(2-((3-methoxypyridin-2-yl)oxy)acetyl)piperidin-4-yl)thiazol-4-yl)-4,5- | $^1$H-NMR (400 MHz, DMSO-d$_6$) δ 7.98-8.08 (m, 2H), 7.85 (d, J = 7.8 Hz, 1H), 7.61-7.72 (m, 2H), 7.28 (d, J = 7.6 Hz, 1H), 6.79-6.92 (m, 2H), 5.07 (s, 2H), 4.35 (d, J = 12.5 Hz, 1H), 3.92-4.03 (m, 2H), 3.77 (d, J = 10.8 Hz, 3H), 3.57-3.73 (m, 1H), 3.41 (d, J = 33.3 Hz, |

TABLE NO 1-continued

The following compounds were prepared analogue to the procedure described in schemes 1-17 or Examples 1 to 8.

| Compd. No. | Compound Name | Analytical data |
|---|---|---|
| | dihydroisoxazol-5-yl)phenyl)(methyl)(methylimino)-l6-sulfanone | 2H), 3.26 (d, J = 26.9 Hz, 3H), 2.76 (d, J = 17.1 Hz, 1H), 2.52-2.58 (m, 3H), 2.03 (d, J = 38.9 Hz, 2H), 1.81 (d, J = 12.0 Hz, 1H), 1.56 (d, J = 11.7 Hz, 1H); LCMS (M + 1): 603.8 |
| 157 | (3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(ethylimino)(methyl)-l6-sulfanone | $^1$H-NMR (400 MHz, DMSO-$d_6$) δ 7.97-8.32 (m, 2H), 7.43-7.83 (m, 3H), 7.22-7.26 (m, 1H), 6.81-6.98 (m, 2H), 5.04 (s, 2H), 4.32 (d, J = 12.5 Hz, 1H), 3.89-4.06 (m, 1H), 3.49-3.80 (m, 5H), 3.24-3.46 (m, 5H), 2.98-3.20 (m, 1H), 1.95-2.08 (m, 2H), 1.51 (d, J = 11.3 Hz, 1H), 1.15-1.30 (m, 1H), 0.95-1.13 (m, 5H); LCMS (M + 1): 617.85 |
| 158 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)diethyl-l6-sulfanone | $^1$H-NMR (400 MHz, DMSO-$d_6$) δ 7.97 (s, 1H), 6.89-7.30 (m, 6H), 6.29 (t, J = 11.1 Hz, 1H), 5.44 (d, J = 16.5 Hz, 1H), 5.34 (d, J = 16.9 Hz, 1H), 4.35 (d, J = 14.2 Hz, 1H), 3.96 (d, J = 14.9 Hz, 1H), 3.64 (d, J = 11.5 Hz, 2H), 3.38-3.42 (m, 1H), 3.20 (tt, J = 21.8, 7.2 Hz, 4H), 2.99-3.06 (m, 1H), 2.81-2.87 (m, 1H), 2.09 (t, J = 14.1 Hz, 2H), 1.79 (d, J = 12.0 Hz, 1H), 1.54-1.58 (m, 1H), 1.16 (t, J = 7.5 Hz, 3H), 0.98 (t, J = 7.3 Hz, 3H); LCMS (M + 1): 675 |
| 160 | ((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diethyl-l6-sulfanone | $^1$H-NMR (400 MHz, DMSO-$d_6$) δ 8.39 (d, J = 4.0 Hz, 1H), 8.10 (d, J = 7.8 Hz, 1H), 7.96 (s, 1H), 7.12-7.17 (m, 3H), 6.94-6.99 (m, 1H), 6.29 (t, J = 11.2 Hz, 1H), 5.26 (s, 2H), 4.32 (d, J = 13.4 Hz, 1H), 3.91 (d, J = 13.1 Hz, 1H), 3.62-3.69 (m, 2H), 3.38 (qd, J = 7.7, 3.7 Hz, 1H), 3.11-3.27 (m, 4H), 3.01 (td, J = 14.4, 7.1 Hz, 1H), 2.79 (t, J = 12.1 Hz, 1H), 2.03-2.09 (m, 2H), 1.83 (dd, J = 12.4, 9.3 Hz, 1H), 1.53-1.58 (m, 1H), 1.16 (t, J = 7.5 Hz, 3H), 0.95-1.02 (m, 3H); LCMS (M + 1): 671.75 |
| 161 | 5-chloro-1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.26 (d, J = 2.9 Hz, 1H), 8.05-8.10 (m, 1H), 7.97 (s, 1H), 7.12-7.17 (m, 2H), 6.94-6.99 (m, 1H), 6.29 (t, J = 11.1 Hz, 1H), 4.93 (dd, J = 19.3, 15.9 Hz, 2H), 4.36 (d, J = 13.4 Hz, 1H), 3.98 (d, J = 13.9 Hz, 1H), 3.61-3.65 (m, 2H), 3.37-3.44 (m, 1H), 3.22-3.29 (m, 2H), 3.11-3.20 (m, 2H), 3.02 (dt, J = 21.8, 7.4 Hz, 1H), 2.85 (t, J = 11.4 Hz, 1H), 2.07-2.15 (m, 2H), 1.74-1.83 (m, 1H), 1.54-1.61 (m, 1H), 1.16 (t, J = 7.5 Hz, 3H), 0.96-1.00 (m, 3H); LCMS (M + 1): 705.85 |
| 162 | 1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-6-methyl-3-(trifluoromethyl)pyridin-2(1H)-one | $^1$H-NMR (400 MHz, DMSO-$d_6$) δ 7.97 (s, 1H), 7.83 (d, J = 7.3 Hz, 1H), 7.12-7.17 (m, 2H), 6.94-6.99 (m, 1H), 6.27-6.32 (m, 2H), 5.04 (dd, J = 22.8, 17.0 Hz, 2H), 4.37 (d, J = 12.8 Hz, 1H), 4.05 (d, J = 13.8 Hz, 1H), 3.64 (d, J = 11.3 Hz, 2H), 3.41 (tt, J = 11.4, 3.7 Hz, 1H), 3.34 (d, J = 12.5 Hz, 1H), 3.10-3.27 (m, 3H), 3.03 (td, J = 14.3, 7.0 Hz, 1H), 2.86 (t, J = 11.5 Hz, 1H), 2.32 (s, 3H), 2.13 (dd, J = 30.0, 12.2 Hz, 2H), 1.74-1.83 (m, 1H), 1.56 (dd, J = 21.9, 11.5 Hz, 1H), 1.16 (t, J = 7.3 Hz, 3H), 0.99 (t, J = 7.3 Hz, 3H); LCMS (M + 1): 684.15 |
| 163 | 1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one | $^1$H-NMR (400 MHz, DMSO-$d_6$) δ 8.28 (s, 1H), 7.97 (s, 1H), 7.68 (dd, J = 9.5, 2.7 Hz, 1H), 7.12-7.17 (m, 2H), 6.95-6.99 (m, 1H), 6.54 (d, J = 9.5 Hz, 1H), 6.29 (t, J = 11.2 Hz, 1H), 4.92 (s, 2H), 4.36 (d, J = 13.7 Hz, 1H), 4.00 (d, J = 14.7 Hz, 1H), 3.64 (d, J = 11.7 Hz, 2H), 3.37-3.43 (m, 1H), 3.22-3.29 (m, 2H), 3.13-3.20 (m, 2H), 3.00-3.07 (m, 1H), 2.81-2.87 (m, 1H), 2.06-2.15 (m, 2H), 1.80 (dd, J = 12.5, 4.2 Hz, 1H), 1.56 (d, J = 12.5 Hz, 1H), 1.16 (t, J = 7.5 Hz, 3H), 0.98 (t, J = 7.2 Hz, 3H); LCMS (M + 1): 671.75 |
| 164 | 2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile | $^1$H-NMR (400 MHz, DMSO-$d_6$) δ 8.32 (dq, J = 8.0, 1.5 Hz, 1H), 8.20-8.22 (m, 1H), 8.03-8.09 (m, 1H), 7.80 (t, J = 7.8 Hz, 1H), 6.74-7.30 (m, 4H), 5.39 (dd, J = 32.1, 17.1 Hz, 2H), 4.86 (d, J = 1.2 Hz, 1H), 4.34 (d, J = 12.5 Hz, 1H), 3.95-4.04 (m, 2H), 3.48-3.57 (m, 2H), 3.39 (qd, J = 7.6, 3.7 Hz, 2H), 3.26 (d, J = 7.6 Hz, 3H), 2.83 (t, J = 11.9 Hz, 1H), 2.08-2.15 (m, 2H), 1.76-1.86 (m, 1H), 1.56-1.61 (m, 1H); LCMS (M + 1): 624 |
| 165 | (3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(imino)(methyl)-l6-sulfanone | $^1$H-NMR (400 MHz, DMSO-$d_6$) δ 8.01-8.08 (m, 2H), 7.81 (ddd, J = 8.2, 3.3, 1.1 Hz, 1H), 7.61-7.67 (m, 2H), 7.28 (dd, J = 7.8, 1.4 Hz, 1H), 6.89-6.97 (m, 2H), 5.07 (s, 2H), 4.88 (s, 1H), 4.34 (d, J = 12.8 Hz, 1H), 3.73-3.96 (m, 5H), 3.57-3.67 (m, 1H), 3.34-3.40 (m, 1H), 3.22-3.27 (m, 4H), 2.78 (t, J = 11.8 Hz, 1H), 2.00-2.11 (m, 2H), 1.76-1.83 (m, 1H), 1.53 (d, J = 11.9 Hz, 1H); LCMS (M + 1): 589.85 |
| 166 | (3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(methyl)-l6-sulfanone | $^1$H-NMR (400 MHz, DMSO-$d_6$) δ 8.04-8.08 (m, 2H), 7.93 (dd, J = 8.1, 1.0 Hz, 1H), 7.73 (t, J = 8.1 Hz, 1H), 6.50 (t, J = 11.6 Hz, 1H), 5.78 (s, 1H), 5.75 (s, 1H), 4.74-5.03 (m, 5H), 4.37 (d, J = 13.2 Hz, 1H), 3.98 (dd, J = 17.1, 12.2 Hz, 2H), 3.52-3.63 (m, 4H), 3.37 (qd, J = 7.6, 3.9 Hz, 1H), 3.20-3.26 (m, 2H), 3.08 (qd, J = 7.3, 4.8 Hz, 1H), 2.80 (t, J = 12.3 Hz, 1H), 1.98 (d, J = 7.6 Hz, 2H), 1.71-1.78 (m, 1H), 1.56 (t, J = 12.2 Hz, 1H); LCMS (M + 1): 561.10 |

TABLE NO 1-continued

The following compounds were prepared analogue to the procedure described in schemes 1-17 or Examples 1 to 8.

| Compd. No. | Compound Name | Analytical data |
|---|---|---|
| 168 | (3-chloro-2-(3-(2-(1-(2-((5-(trifluoromethyl)pyridin-2-yl)oxy)acetyl)piperidin-4-yl)thiazol-4-yl)-4,5-dihydroisoxazol-5-yl)phenyl)(imino)(methyl)-l6-sulfanone | $^1$H-NMR (400 MHz, DMSO-$d_6$) δ 8.52 (s, 1H), 8.01-8.09 (m, 3H), 7.81 (ddd, J = 8.0, 3.3, 1.1 Hz, 1H), 7.62 (td, J = 8.0, 1.7 Hz, 1H), 7.09 (d, J = 8.9 Hz, 1H), 6.94 (td, J = 11.9, 5.2 Hz, 1H), 5.22 (d, J = 14.4 Hz, 2H), 4.83 (dd, J = 37.7, 1.1 Hz, 1H), 4.33 (d, J = 12.8 Hz, 1H), 3.79-3.99 (m, 2H), 3.60 (dd, J = 17.3, 11.8 Hz, 1H), 3.38 (tt, J = 11.5, 3.8 Hz, 2H), 3.21-3.27 (m, 4H), 2.76-2.84 (m, 1H), 2.01-2.13 (m, 2H), 1.76-1.81 (m, 1H), 1.55 (dd, J = 23.7, 12.4 Hz, 1H); LCMS (M + 1): 627.95 |
| 169 | 1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one | $^1$H-NMR (400 MHz, DMSO-$d_6$) δ 8.02-8.08 (m, 2H), 7.81 (ddd, J = 8.0, 3.4, 1.1 Hz, 1H), 7.60-7.74 (m, 2H), 6.94 (td, J = 11.9, 5.5 Hz, 1H), 6.50-6.56 (m, 1H), 4.88-4.97 (m, 2H), 4.36 (d, J = 13.1 Hz, 1H), 3.95-4.05 (m, 1H), 3.79-3.90 (m, 1H), 3.57-3.73 (m, 2H), 3.37-3.49 (m, 3H), 2.79-2.86 (m, 2H), 2.12 (dd, J = 23.1, 12.7 Hz, 2H), 1.76-1.85 (m, 1H), 1.53-1.62 (m, 1H); LCMS (M + 1): 628 |
| 170 | 1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.05-8.08 (m, 2H), 7.93 (dd, J = 12.6, 7.0 Hz, 2H), 7.80-7.83 (m, 1H), 7.62 (td, J = 8.0, 1.9 Hz, 1H), 6.94 (td, J = 11.9, 6.0 Hz, 1H), 6.38 (t, J = 6.8 Hz, 1H), 4.94-4.97 (m, 2H), 4.89 (d, J = 5.6 Hz, 1H), 4.35-4.38 (m, 1H), 4.01 (d, J = 14.4 Hz, 1H), 3.79-3.90 (m, 1H), 3.57-3.67 (m, 1H), 3.38-3.43 (m, 1H), 3.22-3.25 (m, 3H), 3.08 (d, J = 6.4 Hz, 2H), 2.08-2.17 (m, 2H), 1.80 (d, J = 13.4 Hz, 1H), 1.55-1.59 (m, 1H); LCMS(M + 1): 628.05 |
| 171 | (2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)(imino)(methyl)-l6-sulfanone | $^1$H-NMR (400 MHz, DMSO-$d_6$) δ 8.07 (dd, J = 8.1, 1.2 Hz, 1H), 8.03 (d, J = 10.0 Hz, 1H), 7.81 (ddd, J = 8.1, 3.4, 1.2 Hz, 1H), 7.59-7.65 (m, 2H), 6.93 (td, J = 11.9, 5.5 Hz, 1H), 5.60 (d, J = 17.1 Hz, 1H), 5.50 (d, J = 17.6 Hz, 1H), 4.88 (s, 1H), 4.33 (d, J = 13.4 Hz, 1H), 3.90-3.97 (m, 1H), 3.79-3.87 (m, 1H), 3.60 (dd, J = 17.2, 11.9 Hz, 1H), 3.36-3.42 (m, 1H), 3.22-3.27 (m, 4H), 2.85 (t, J = 11.4 Hz, 1H), 2.08-2.14 (m, 2H), 1.78-1.84 (m, 1H), 1.49-1.56 (m, 1H); LCMS (M + 1): 669.05 |
| 172 | (3-chloro-2-(3-(2-(1-(2-(3-methyl-1H-pyrazol-1-yl)acetyl)piperidin-4-yl)thiazol-4-yl)-4,5-dihydroisoxazol-5-yl)phenyl)(imino)(methyl)-l6-sulfanone | $^1$H-NMR (400 MHz, DMSO-$d_6$) δ 7.92-7.97 (m, 1H), 7.69-7.74 (m, 1H), 7.34-7.40 (m, 2H), 7.18 (t, J = 6.0 Hz, 2H), 6.51 (t, J = 11.6 Hz, 1H), 5.05 (dd, J = 25.1, 16.2 Hz, 2H), 4.86-4.98 (m, 1H), 4.37 (d, J = 13.4 Hz, 1H), 3.85-4.01 (m, 2H), 3.62 (d, J = 8.3 Hz, 2H), 3.54 (dd, J = 17.1, 11.3 Hz, 1H), 3.38 (tt, J = 11.3,3.8 Hz, 1H), 2.77-2.83 (m, 1H), 2.07-2.15 (m, 2H), 1.98-2.02 (m, 3H), 1.96 (s, 2H), 1.70-1.76 (m, 1H), 1.54 (t, J = 11.9 Hz, 1H); LCMS (M + 1): 547 |
| 173 | (3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(methyl)-l6-sulfanone | $^1$H-NMR (400 MHz, DMSO-$d_6$) δ 8.34-8.39 (m, 1H), 8.01-8.11 (m, 3H), 7.81 (ddd, J = 8.0, 3.4, 1.2 Hz, 1H), 7.62 (td, J = 8.0, 1.8 Hz, 1H), 7.16 (dd, J = 7.1, 5.1 Hz, 1H), 6.94 (td, J = 11.9, 5.1 Hz, 1H), 5.23 (d, J = 26.7 Hz, 2H), 4.88 (s, 1H), 4.32 (d, J = 13.2 Hz, 1H), 3.79-3.96 (m, 2H), 3.57-3.69 (m, 1H), 3.34-3.41 (m, 1H), 3.20-3.28 (m, 4H), 2.79 (t, J = 12.6 Hz, 1H), 2.04-2.11 (m, 2H), 1.83-1.89 (m, 1H), 1.55 (d, J = 12.5 Hz, 1H); LCMS (M + 1): 627.85 |
| 174 | 1-(2-(4-(4-(5-(2-chloro-6-(N,S-dimethylsulfonimidoyl)phenyl)-4,5-dihydroisoxazol-3-yl)thiazol-2-yl)piperidin-1-yl)-2-oxoethyl)-6-methyl-3-(trifluoromethyl)pyridin-2(1H)-one | $^1$H-NMR (400 MHz, DMSO-$d_6$) δ 8.03-8.08 (m, 1H), 7.99 (dd, J = 7.9, 1.3 Hz, 1H), 7.82-7.86 (m, 2H), 7.64-7.70 (m, 1H), 6.79-6.94 (m, 1H), 6.30 (d, J = 7.3 Hz, 1H), 5.06 (d, J = 17.1 Hz, 2H), 4.37 (d, J = 13.0 Hz, 1H), 4.05 (d, J = 13.0 Hz, 1H), 3.58-3.80 (m, 1H), 3.27-3.43 (m, 7H), 3.08 (q, J = 7.3 Hz, 1H), 2.79-2.88 (m, 1H), 2.54-2.58 (m, 2H), 2.34 (d, J = 19.1 Hz, 3H), 2.18 (d, J = 12.5 Hz, 1H), 2.11 (d, J = 12.0 Hz, 1H), 1.76-1.84 (m, 1H), 1.52-1.61 (m, 1H); LCMS (M + 1): 656.05 |
| 175 | ((3-fluoro-2-(3-(4-(1-(2-(5-methyl-3-(trifluoromethyl)-1H-pyrazol-1-yl)acetyl)piperidin-4-yl)thiazol-2-yl)-4,5-dihydroisoxazol-5-yl)phenyl)imino)dimethyl-l6-sulfanone | $^1$H-NMR (400 MHz, CHLOROFORM-D) δ 7.18 (td, J = 8.1, 6.4 Hz, 1H), 7.09 (d, J = 7.8 Hz, 1H), 6.96 (s, 1H), 6.71-6.76 (m, 1H), 6.33 (s, 1H), 6.24 (dd, J = 12.5, 9.5 Hz, 1H), 5.02-5.06 (m, 1H), 4.95 (dd, J = 15.9, 2.9 Hz, 1H), 4.64 (d, J = 13.4 Hz, 1H), 4.04 (d, J = 12.7 Hz, 1H), 3.87 (dd, J = 17.1, 9.5 Hz, 1H), 3.68 (dd, J = 17.1, 12.7 Hz, 1H), 3.24-3.30 (m, 1H), 3.07 (s, 3H), 2.96 (s, 3H), 2.78-2.85 (m, 1H), 2.31 (s , 3H), 2.04-2.19 (m, 2H), 1.65-1.72 (m, 2H), 1.24-1.33 (m, 2H), 0.88 (t, J = 7.1 Hz, 2H); LCMS (M + 1): 613.1 |
| 176 | ((2-(3-(4-(1-(2-(3,5-bis(difluoromethyl)-1H-pyrazol-1-yl)acetyl)piperidin-4-yl)thiazol-2-yl)-4,5-dihydroisoxazol-5-yl)-3-fluorophenyl)imino)dimethyl-l6-sulfanone | $^1$H-NMR (400 MHz, CHLOROFORM-D) δ 7.15-7.21 (m, 1H), 6.89-7.10 (m, 3H), 6.53-6.80 (m, 3H), 6.24 (dd, J = 12.6, 9.4 Hz, 1H), 5.14-5.20 (m, 2H), 4.64 (d, J = 13.9 Hz, 1H), 3.83-3.92 (m, 2H), 3.68 (dd, J = 17.1, 12.5 Hz, 1H), 3.26-3.34 (m, 1H), 3.09 (s, 3H), 2.97 (s, 3H), 2.81-2.87 (m, 1H), 2.15-2.24 (m, 2H), 1.72 (t, J = 12.6 Hz, 2H), 1.25-1.33 (m, 2H), 0.88 (t, J = 7.1 Hz, 2H); LCMS (M + 1): 631.1 |
| 177 | ((3-fluoro-2-(3-(2-(1-(2-((3-methoxypyridin-2-yl)oxy)acetyl)piperidin-4-yl)thiazol-4-yl)-4,5- | $^1$H-NMR (400 MHz, DMSO-$d_6$) δ 7.96 (d, J = 4.6 Hz, 1H), 7.61 (dd, J = 5.0, 1.4 Hz, 1H), 7.28 (dd, J = 7.9, 1.5 Hz, 1H), 7.20 (td, J = 8.1, 6.8 Hz, 1H), 6.94 (d, J = 8.3 Hz, 1H), 6.91 (dd, J = 7.8, 5.0 Hz, 1H), 6.72-6.77 (m, 1H), 6.13 (dd, J = 12.2, 9.2 Hz, 1H), 5.07 (s, |

TABLE NO 1-continued

The following compounds were prepared analogue to the procedure described in schemes 1-17 or Examples 1 to 8.

| Compd. No. | Compound Name | Analytical data |
|---|---|---|
| | dihydroisoxazol-5-yl)phenyl)imino)dimethyl-l6-sulfanone | 2H), 4.32-4.50 (m, 3H), 3.91-3.97 (m, 1H), 3.79 (s, 3H), 3.69 (dd, J = 17.3, 12.7 Hz, 1H), 3.48 (dd, J = 17.0, 9.0 Hz, 1H), 3.37 (qd, J = 7.6, 4.0 Hz, 1H), 3.20-3.28 (m, 1H), 3.11 (d, J = 5.5 Hz, 4H), 2.78 (t, J = 11.6 Hz, 1H), 2.03-2.45 (m, 2H), 1.79-1.84 (m, 1H), 1.48-1.56 (m, 1H); LCMS (M + 1): 588 |
| 178 | ((2-(3-(4-(1-(2-(3,5-bis(trifluoromethyl)-1H-pyrazol-1-yl)acetyl)piperidin-4-yl)thiazol-2-yl)-4,5-dihydroisoxazol-5-yl)-3-fluorophenyl)imino)dimethyl-l6-sulfanone | $^1$H-NMR (400 MHz, DMSO-$d_6$) δ 7.58 (s, 1H), 7.52 (s, 1H), 7.21 (dd, J = 15.0, 8.2 Hz, 1H), 6.95 (d, J = 7.8 Hz, 1H), 6.73-6.78 (m, 1H), 6.25 (dd, J = 12.5, 9.3 Hz, 1H), 5.57 (d, J = 17.1 Hz, 1H), 5.48 (d, J = 17.1 Hz, 1H), 4.34 (d, J = 13.2 Hz, 1H), 3.93 (d, J = 13.4 Hz, 1H), 3.77 (dd, J = 16.9, 12.5 Hz, 1H), 3.53 (dd, J = 17.1, 9.3 Hz, 1H), 3.21-3.27 (m, 1H), 3.08 (s, 6H), 2.77-2.85 (m, 1H), 2.02 (t, J = 14.2 Hz, 2H), 1.63-1.73 (m, 1H), 1.50 (qd, J = 12.4, 3.8 Hz, 1H), 1.18-1.29 (m, 2H), 0.85 (t, J = 7.1 Hz, 1H); LCMS (M + 1): 667.05 |
| 179 | ((3-fluoro-2-(3-(4-(1-(2-((3-methoxypyridin-2-yl)oxy)acetyl)piperidin-4-yl)thiazol-2-yl)-4,5-dihydroisoxazol-5-yl)phenyl)imino)dimethyl-l6-sulfanone | $^1$H-NMR (400 MHz, DMSO-$d_6$) δ 7.60 (dd, J = 5.0, 1.6 Hz, 1H), 7.51 (s, 1H), 7.26-7.28 (m, 1H), 7.21 (dd, J = 15.0, 8.2 Hz, 1H), 6.95 (d, J = 7.8 Hz, 1H), 6.89 (dd, J = 7.1, 5.4 Hz, 1H), 6.73-6.78 (m, 1H), 6.25 (dd, J = 12.5, 9.3 Hz, 1H), 5.06 (s, 2H), 4.35 (d, J = 13.9 Hz, 1H), 3.91 (d, J = 13.9 Hz, 1H), 3.74-3.81 (m, 4H), 3.54 (dd, J = 17.1,9.0 Hz, 1H), 3.20 (d, J = 12.5 Hz, 1H), 3.03-3.12 (m, 7H), 2.72 (s, 1H), 2.00 (d, J = 13.9 Hz, 2H), 1.72 (s, 1H), 1.51 (s, 1H), 1.26 (s, 1H); LCMS (M + 1): 588.1 |
| 180 | 1-(2-(4-(2-(5-(2-((dimethyl(oxo)-l6-sulfaneylidene)amino)-6-fluorophenyl)-4,5-dihydroisoxazol-3-yl)thiazol-4-yl)piperidin-1-yl)-2-oxoethyl)-3-(trifluoromethyl)pyridin-2(1H)-one | $^1$H-NMR (400 MHz, DMSO-$d_6$) δ 7.94 (d. J = 7.1 Hz, 1H), 7.90-7.91 (m, 1H), 7.52 (d, J = 0.7 Hz, 1H), 7.21 (td, J = 8.2, 6.8 Hz, 1H), 6.95 (d, J = 7.8 Hz, 1H), 6.75 (dd, J = 10.3, 8.8 Hz, 1H), 6.37 (t, J = 6.8 Hz, 1H), 6.25 (dd, J = 12.5, 9.3 Hz, 1H), 4.93 (d, J = 2.0 Hz, 2H), 4.38 (d, J = 13.2 Hz, 1H), 3.97-4.03 (m, 1H), 3.74-3.82 (m, 1H), 3.54 (dd, J = 17.1, 9.0 Hz, 1H), 3.21-3.27 (m, 1H), 3.08 (s, 6H), 2.76-2.82 (m, 1H), 1.98-2.08 (m, 2H), 1.69 (d, J = 12.5 Hz, 1H), 1.51-1.54 (m, 1H), 1.15-1.18 (m, 1H); LCMS (M + 1): 626.05 |
| 181 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(ethyl)(isopropyl)-l6-sulfanone | $^1$H-NMR (400 MHz, DMSO-$d_6$) δ 7.97 (d, J = 2.0 Hz, 1H), 7.59 (s, 1H), 7.11-7.17 (m, 1H), 7.01 (d, J = 7.8 Hz, 1H), 6.64-6.70 (m, 1H), 6.11-6.16 (m, 1H), 5.61 (d, J = 17.4 Hz, 1H), 5.49 (d, J = 17.1 Hz, 1H), 4.33 (d, J = 13.9 Hz, 1H), 3.95 (d, J = 14.2 Hz, 1H), 3.65-3.72 (m, 1H), 3.47-3.58 (m, 2H), 3.36-3.42 (m, 2H), 3.33 (s, 1H), 3.28 (s, 1H), 3.20 (td, J = 14.4, 7.2 Hz, 1H), 3.07 (dd, J = 14.1, 7.5 Hz, 1H), 2.86 (t, J = 11.7 Hz, 1H), 2.06-2.13 (m, 2H), 1.78 (d, J = 10.5 Hz, 1H), 1.53 (dd, J = 11.9, 4.0 Hz, 1H), 1.28 (dd, J = 8.1, 6.8 Hz, 3H), 1.05-1.22 (m, 6H); LCMS (M + 1): 709.2 |
| 182 | ethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)-l6-sulfanone | $^1$H-NMR (400 MHz, DMSO-$d_6$) δ 7.91 (d, J = 1.2 Hz, 1H), 7.10-7.16 (m, 1H), 7.04 (d, J = 8.3 Hz, 1H), 6.62-6.68 (m, 1H), 6.44 (s, 1H), 6.13-6.19 (m, 1H), 5.21 (s, 2H), 3.95-4.37 (m, 2H), 3.10-3.71 (m, 9H), 3.00-3.03 (m, 1H), 2.06-2.14 (m, 2H), 1.59-1.78 (m, 2H), 1.19-1.33 (m, 9H), 1.12 (q, J = 7.4 Hz, 2H); LCMS (M + 1): 655.2 |
| 183 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(ethyl)(isopropyl)-l6-sulfanone | $^1$H-NMR (400 MHz, DMSO-$d_6$) δ 7.97 (d, J = 2.2 Hz, 1H), 7.11-7.17 (m, 2H), 7.02 (t, J = 6.7 Hz, 2H), 6.89 (d, J = 4.6 Hz, 1H), 6.64-6.70 (m, 1H), 6.14 (t, J = 10.3 Hz, 1H), 5.44 (d, J = 17.1 Hz, 1H), 5.34 (d, J = 17.1 Hz, 1H), 4.35 (d, J = 13.2 Hz, 1H), 3.96 (d, J = 13.4 Hz, 1H), 3.65-3.73 (m, 1H), 3.47-3.58 (m, 2H), 3.35-3.42 (m, 2H), 3.16-3.28 (m, 2H), 3.05-3.12 (m, 1H), 2.84 (t, J = 12.0 Hz, 1H), 2.06-2.13 (m, 2H), 1.75-1.84 (m, 1H), 1.54-1.61 (m, 1H), 1.28 (dd, J = 8.1, 6.8 Hz, 3H), 1.05-1.22 (m,6H); LCMS (M + 1): 673.2 |
| 184 | ethyl((3-fluoro-2-(3-(2-(1-(2-1(3-(trifluoromethyl)pyridin-2-yl)oxy)acetyl)piperidin-4-yl)thiazol-4-yl)-4,5-dihydroisoxazol-5-yl)phenyl)imino)(isopropyl)-l6-sulfanone | $^1$H-NMR (400 MHz, DMSO-$d_6$) δ 8.39 (d, J = 3.7 Hz, 1H), 8.09-8.11 (m, 1H), 7.96 (d, J = 2.2 Hz, 1H), 7.11-7.17 (m, 2H), 7.01 (d, J = 7.6 Hz, 1H), 6.64-6.70 (m, 1H), 6.14 (t, J = 10.0 Hz, 1H), 5.26 (s, 2H), 4.32 (d, J = 12.2 Hz, 1H), 3.91 (d, J = 13.2 Hz, 1H), 3.65-3.73 (m, 1H), 3.47-3.58 (m, 2H), 3.33-3.41 (m, 2H), 3.16-3.28 (m, 2H), 3.07 (q, J = 7.1 Hz, 1H), 2.79 (t, J = 12.6 Hz, 1H), 2.08 (d, J = 13.2 Hz, 2H), 1.81 (q, J = 12.5 Hz, 1H), 1.50-1.58 (m, 1H), 1.28 (dd, J = 8.3, 6.8 Hz, 3H), 1.05-1.22 (m, 62H); LCMS (M + 1): 668.2 |
| 185 | 1-(2-(4-(4-(5-(2-((ethyl(isopropyl)(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 7.91-7.97 (m, 3H), 7.14 (ddd, J = 14.9, 8.3, 3.7 Hz, 1H), 7.01 (d, J = 7.8 Hz, 1H), 6.64-6.70 (m, 1H), 6.38 (t, J = 7.0 Hz, 1H), 6.14 (t, J = 10.3 Hz, 1H), 4.94 (s, 2H), 4.37 (d, J = 13.2 Hz, 1H), 4.01 (d, J = 14.4 Hz, 1H), 3.66-3.73 (m, 1H), 3.47-3.58 (m, 2H), 3.32-3.44 (m, 2H), 3.25-3.28 (m, 1H), 3.20 (ddd, J = 14.2, 7.4, 3.4 Hz, 1H), 3.08 (q, J = 7.2 Hz, 1H), 2.81-2.87 (m, 1H), 2.06-2.16 (m, 2H), 1.73-1.81 (m, 1H), 1.56 (dd, J = 12.2, 3.9 Hz, 1H), 1.28 (dd, J = 7.8, 7.1 Hz, 3H), 1.05-1.22 (m, 6H); LCMS (M + 1): 668.2 |

TABLE NO 1-continued

The following compounds were prepared analogue to the procedure described in schemes 1-17 or Examples 1 to 8.

| Compd. No. | Compound Name | Analytical data |
|---|---|---|
| 186 | ethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(isopropyl)-l6-sulfanone | $^1$H-NMR (400 MHz, DMSO-$d_6$) δ 7.96 (d, J = 2.2 Hz, 1H), 7.62 (dd, J = 4.9, 1.5 Hz, 1H), 7.28 (dd, J = 7.8, 1.5 Hz, 1H), 7.14 (dq, J = 14.9, 4.0 Hz, 1H), 7.01 (d, J = 7.6 Hz, 1H), 6.90 (dd, J = 7.7, 5.0 Hz, 1H), 6.64-6.70 (m, 1H), 6.11-6.16 (m, 1H), 5.07 (d, J = 1.7 Hz, 2H), 4.33 (s, 1H), 4.00-3.84 (1H), 3.79 (s, 3H), 3.65-3.73 (m, 1H), 3.48-3.58 (m, 2H), 3.33-3.40 (m, 2H), 3.18-3.28 (m, 3H), 3.07 (q, J = 7.1 Hz, 1H), 2.75-2.82 (m, 1H), 2.03-2.09 (m, 2H), 1.77-1.85 (m, 1H), 1.48-1.56 (m, 1H), 1.28 (dd, J = 8.3, 6.8 Hz, 3H), 1.05-1.22 (m, 6H); LCMS (M + 1): 630.2 |
| 187 | (3-(difluoromethyl)-2-(3-(2-(1-(2-((3-methoxypyridin-2-yl)oxy)acetyl)piperidin-4-yl)thiazol-4-yl)-4,5-dihydroisoxazol-5-yl)phenyl)(imino)(iso-propyl)-l6-sulfanone | $^1$H-NMR (400 MHz, DMSO-$d_6$) δ 8.22 (t, J = 7.8 Hz, 1H), 8.05-8.11 (m, 2H), 7.79 (t, J = 7.9 Hz, 1H), 7.59-7.62 (m, 1H), 7.00-7.29 (m, 2H), 6.91 (dd, J = 7.8, 4.9 Hz, 1H), 6.76-6.86 (m, 1H), 5.07 (s, 2H), 4.88 (s, 1H), 4.34 (d, J = 13.0 Hz, 1H), 3.92-4.07 (m, 2H), 3.75-3.82 (m, 3H), 3.36-3.45 (m, 3H), 3.20-3.27 (m, 1H), 2.75-2.81 (m, 1H), 1.98-2.10 (m, 2H), 1.76-1.87 (m, 1H), 1.49-1.57 (m, 1H), 1.24 (dd, J = 18.1, 6.6 Hz, 4H), 1.10-1.15 (m, 2H); LCMS (M + 1): 634.15 |
| 188 | (3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(iso-propyl)-l6-sulfanone | $^1$H-NMR (400 MHz, DMSO-$d_6$) δ 8.22 (t, J = 7.6 Hz, 1H), 8.05-8.12 (m, 2H), 7.79 (t, J = 7.9 Hz, 1H), 7.14 (td, J = 54.8, 8.0 Hz, 1H), 6.76-6.86 (m, 1H), 6.49 (s, 1H), 5.32 (d, J = 17.4 Hz, 1H), 5.23 (d, J = 17.1 Hz, 1H), 4.37 (d, J = 13.0 Hz, 1H), 3.95-4.07 (m, 2H), 3.36-3.45 (m, 3H), 3.23-3.29 (m, 2H), 3.05-3.12 (m, 1H), 2.83 (t, J = 11.6 Hz, 1H), 2.08-2.23 (m, 3H), 1.76-1.91 (m, 1H), 1.58 (t, J = 11.9 Hz, 1H), 1.26-1.37 (m, 2H), 1.22 (d, J = 6.6 Hz, 1H), 1.16 (t, J = 7.2 Hz, 2H), 1.11 (d, J = 6.6 Hz, 2H); LCMS (M + 1): 659.15 |
| 189 | (3-(difluoromethyl)-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(iso-propyl)-l6-sulfanone | $^1$H-NMR (400 MHz, DMSO-$d_6$) δ 8.22 (t, J = 7.6 Hz, 1H), 8.05-8.12 (m, 2H), 7.79 (t, J = 7.9 Hz, 1H), 7.14 (td, J = 54.8, 8.0 Hz, 1H), 6.76-6.86 (m, 1H), 6.49 (s, 1H), 5.32 (d, J = 17.4 Hz, 1H), 5.23 (d, J = 17.1 Hz, 1H), 4.37 (d, J = 13.0 Hz, 1H), 3.95-4.07 (m, 2H), 3.36-3.45 (m, 3H), 3.23-3.29 (m, 2H), 3.05-3.12 (m, 1H), 2.83 (t, J = 11.6 Hz, 1H), 2.08-2.23 (m, 3H), 1.76-1.91 (m, 1H), 1.58 (t, J = 11.9 Hz, 1H), 1.26-1.37 (m, 2H), 1.22 (d, J = 6.6 Hz, 1H), 1.16 (t, J = 7.2 Hz, 2H), 1.11 (d, J = 6.6 Hz, 2H); LCMS (M + 1): 672.1 |
| 190 | (2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(difluoromethyl)phe-nyl)(imino)(isopropyl)-l6-sulfanone | $^1$H-NMR (400 MHz, DMSO-$d_6$) δ 8.24 (t, J = 7.7 Hz, 1H), 8.12-8.16 (m, 1H), 8.05-8.09 (m, 1H), 7.81 (t, J = 7.9 Hz, 1H), 6.78-7.32 (m, 5H), 5.45 (d, J = 16.9 Hz, 1H), 5.37 (d, J = 17.1 Hz, 1H), 4.90 (s, 1H), 4.37 (d, J = 12.7 Hz, 1H), 3.97-4.09 (m, 2H), 3.38-3.47 (m, 3H), 3.25-3.30 (m, 1H), 2.82-2.88 (m, 1H), 2.09-2.21 (m, 2H), 1.78-1.93 (m, 1H), 1.59 (q, J = 12.1 Hz, 1H), 1.31 (dd, J = 19.6, 6.8 Hz, 2H), 1.22-1.25 (m, 2H), 1.19 (d, J = 6.4 Hz, 1H), 1.10-1.14 (m, 2H); LCMS (M + 1): 677.15 |
| 191 | (3-(difluoromethyl)-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)(imino)(iso-propyl)-l6-sulfanone | $^1$H-NMR (400 MHz, DMSO-$d_6$) δ 8.55 (d, J = 2.0 Hz, 1H), 8.38 (d, J = 2.4 Hz, 1H), 8.22 (t, J = 7.8 Hz, 1H), 8.09-8.13 (m, 1H), 8.06 (d, J = 8.3 Hz, 1H), 7.79 (t, J = 7.9 Hz, 1H), 7.00-7.27 (m, 1H), 6.80-6.86 (m, 1H), 5.37 (s, 2H), 4.88 (s, 1H), 4.31 (d, J = 12.5 Hz, 1H), 3.99-4.07 (m, 1H), 3.88 (d, J = 14.2 Hz, 1H), 3.36-3.45 (m, 3H), 3.20-3.28 (m, 1H), 2.76-2.83 (m, 1H), 2.01-2.12 (m, 2H), 1.77-1.86 (m, 1H), 1.50-1.59 (m, 1H), 1.20-1.28 (m, 3H), 1.15-1.18 (m, 1H), 1.08-1.12 (m, 2H); LCMS (M + 1): 673.15 |
| 192 | (2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)-3-(difluoromethyl)phe-nyl)(imino)(isopropyl)-l6-sulfanone | $^1$H-NMR (400 MHz, DMSO-$d_6$) δ 8.22 (t, J = 7.6 Hz, 1H), 8.09-8.12 (m, 1H), 8.06 (d, J = 7.8 Hz, 1H), 7.79 (t, J = 7.8 Hz, 1H), 7.00-7.27 (m, 1H), 6.79-6.86 (m, 1H), 6.36 (s, 1H), 5.39 (d, J = 17.1 Hz, 1H), 5.29 (d, J = 16.9 Hz, 1H), 4.88 (s, 1H), 4.38 (d, J = 12.7 Hz, 2H), 3.99-4.06 (m, 2H), 3.37-3.45 (m, 3H), 2.81-2.88 (m, 1H), 2.11 (t, J = 13.7 Hz, 2H), 1.76-1.83 (m, 2H), 1.57 (d, J = 16.4 Hz, 1H), 1.24 (dd, J = 17.9, 6.8 Hz, 3H), 1.09-1.18 (m, 3H), 0.92 (dd, J = 8.3, 2.2 Hz, 2H), 0.68 (t, J = 2.3 Hz, 2H); LCMS (M + 1): 685 |
| 193 | (2-(3-(2-(1-(2-(4-chloro-1H-pyrazol-1-yl)acetyl)piperidin-4-yl)thiazol-4-yl)-4,5-dihydroisoxazol-5-yl)-3-(difluoromethyl)phe-nyl)(imino)(isopropyl)-l6-sulfanone | $^1$H-NMR (400 MHz, DMSO-$d_6$) δ 8.22 (t, J = 7.9 Hz, 1H), 8.05-8.13 (m, 2H), 7.87 (s, 1H), 7.79 (t, J = 7.8 Hz, 1H), 7.51 (d, J = 0.5 Hz, 1H), 7.14 (td, J = 54.9, 8.3 Hz, 1H), 6.75-6.86 (m, 1H), 5.16 (dd, J = 27.6, 16.6 Hz, 2H), 4.88 (s, 1H), 4.37 (d, J = 13.2 Hz, 2H), 3.94-4.06 (m, 2H), 3.34-3.45 (m, 3H), 2.81 (t, J = 12.2 Hz, 1H), 2.08 (dd, J = 31.9, 20.2 Hz, 2H), 1.79 (d, J = 12.2 Hz, 1H), 1.57 (t, J = 10.4 Hz, 1H), 1.21-1.39 (m, 4H), 1.11 (d, J = 6.8 Hz, 2H); LCMS (M + 1): 611 |
| 194 | (2-(3-(2-(1-(2-(2H-indazol-2-yl)acetyl)piperidin-4-yl)thiazol-4-yl)-4,5-dihydroisoxazol-5-yl)-3-(difluoromethyl)phe- | $^1$H-NMR (400 MHz, DMSO-$d_6$) δ 8.32 (d, J = 20.5 Hz, 1H), 8.22 (t, J = 7.6 Hz, 1H), 8.10-8.12 (m, 1H), 8.06 (d, J = 8.1 Hz, 1H), 7.79 (t, J = 7.9 Hz, 1H), 7.65-7.71 (m, 2H), 7.56 (dd, J = 8.7, 0.9 Hz, 1H), 7.00-7.30 (m, 2H), 6.76-6.87 (m, 1H), 5.51 (dd, J = 23.1, 16.0 Hz, 2H), 4.89 (s, 1H), 4.21-4.50 (m, 2H), 3.98-4.14 (m, 2H), 3.38-3.45 |

TABLE NO 1-continued

The following compounds were prepared analogue to the procedure described in schemes 1-17 or Examples 1 to 8.

| Compd. No. | Compound Name | Analytical data |
|---|---|---|
| | nyl)(imino)(isopropyl)-l6-sulfanone | (m, 3H), 3.27 (d, J = 9.8 Hz, 1H), 2.84 (t, J = 12.6 Hz, 1H), 1.79-1.85 (m, 1H), 1.57-1.63 (m, 2H), 1.22-1.28 (m, 4H), 1.11 (d, J = 6.6 Hz, 2H); LCMS (M + 1): 628.2 |
| 195 | ((3-fluoro-2-(3-(4-(1-(2-((3-(trifluoromethyl)pyrazin-2-yl)oxy)acetyl)piperidin-4-yl)thiazol-2-yl)-4,5-dihydroisoxazol-5-yl)phenyl)imino)dimethyl-l6-sulfanone | $^{1}$H-NMR (400 MHz, DMSO-$d_6$) δ 8.53 (d, J = 2.4 Hz, 1H), 8.38 (d, J = 2.8 Hz, 1H), 7.51 (s, 1H), 7.21 (td, J = 8.1, 6.8 Hz, 1H), 6.95 (d, J = 7.6 Hz, 1H), 6.73-6.78 (m, 1H), 6.25 (dd, J = 12.2, 9.2 Hz, 1H), 5.36 (s, 2H), 4.31 (d, J = 12.5 Hz, 1H), 3.74-3.87 (m, 2H), 3.54 (dd, J = 17.1, 9.2 Hz, 1H), 3.17-3.23 (m, 1H), 3.03-3.13 (m, 7H), 2.71-2.77 (m, 1H), 1.95-2.06 (m, 2H), 1.69-1.76 (m, 1H), 1.48-1.54 (m, 1H), 1.09-1.18 (m, 1H); LCMS (M + 1): 627 |
| 196 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(iso-propyl)(propyl)-l6-sulfanone | $^{1}$H-NMR (400 MHz, DMSO-$d_6$) δ 7.97 (d, J = 7.0 Hz, 1H), 7.59 (s, 1H), 7.10-7.17 (m, 1H), 7.02 (dd, J = 7.5, 5.0 Hz, 1H), 6.64-6.70 (m, 1H), 6.08-6.16 (m, 1H), 5.61 (d, J = 17.1 Hz, 1H), 5.49 (d, J = 17.1 Hz, 1H), 4.33 (d, J = 11.9 Hz, 1H), 3.95 (d, J = 13.1 Hz, 1H), 3.47-3.72 (m, 3H), 3.35-3.42 (m, 2H), 3.08-3.27 (m, 2H), 2.92-2.99 (m, 1H), 2.86 (t, J = 12.4 Hz, 1H), 2.10 (t, J = 13.0 Hz, 2H), 1.79 (t, J = 11.8 Hz, 1H), 1.49-1.72 (m, 3H), 1.28 (dd, J = 6.7, 5.2 Hz, 3H), 0.74-1.23 (m, 6H); LCMS (M + 1): 723.15 |
| 197 | ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(iso-propyl)(propyl)-l6-sulfanone | $^{1}$H-NMR (400 MHz, DMSO-$d_6$) δ 7.97 (d, J = 6.6 Hz, 1H), 7.14 (ddd, J = 15.0, 8.2, 3.5 Hz, 1H), 7.02 (dd, J = 7.6, 5.1 Hz, 1H), 6.64-6.70 (m, 1H), 6.49 (s, 1H), 6.08-6.16 (m, 1H), 5.33 (d, J = 17.1 Hz, 1H), 5.23 (d, J = 17.1 Hz, 1H), 4.37 (d, J = 12.5 Hz, 1H), 3.97 (d, J = 12.7 Hz, 1H), 3.47-3.72 (m, 3H), 3.35-3.42 (m, 2H), 3.09-3.26 (m, 2H), 2.92-3.00 (m, 1H), 2.83 (t, J = 12.2 Hz, 1H), 2.20 (s, 3H), 2.04-2.12 (m, 2H), 1.78-1.83 (m, 1H), 1.48-1.70 (m, 3H), 0.74-1.29 (m, 10 H); LCMS (M + 1): 669.1 |
| 198 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(iso-propyl)(propyl)-l6-sulfanone | $^{1}$H-NMR (400 MHz, DMSO-$d_6$) δ 7.97 (d, J = 6.7 Hz, 1H). 7.11-7.17 (m, 2H), 7.02 (dd, J = 8.1, 5.7 Hz, 2H), 6.89 (d, J = 4.9 Hz, 1H), 6.64-6.70 (m, 1H), 6.08-6.16 (m, 1H), 5.44 (d, J = 16.8 Hz, 1H), 5.34 (d, J = 16.8 Hz, 1H), 4.35 (d, J = 12.8 Hz, 1H), 3.96 (d, J = 14.1 Hz, 1H), 3.47-3.72 (m, 2H), 3.36-3.42 (m, 2H), 3.09-3.27 (m, 3H), 2.92-3.00 (m, 1H), 2.83 (t, J = 11.6 Hz, 1H), 2.06-2.13 (m, 2H), 1.79 (d, J = 8.9 Hz, 1H), 1.54-1.68 (m, 3H), 1.28 (dd, J = 6.9, 5.3 Hz, 3H), 0.74-1.23 (m, 6H); LCMS (M + 1): 687.15 |
| 199 | ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(iso-propyl)(propyl)-l6-sulfanone | $^{1}$H-NMR (400 MHz, DMSO-$d_6$) δ 7.97 (d, J = 6.7 Hz, 1H), 7.14 (ddd, J = 15.0, 8.3, 3.4 Hz, 1H), 7.02 (dd, J = 7.9, 5.2 Hz, 1H), 6.64-6.70 (m, 1H), 6.08-6.16 (m, 1H), 5.76 (d, J = 13.1 Hz, 1H), 5.02 (d, J = 16.8 Hz, 1H), 4.92 (d, J = 17.1 Hz, 1H), 4.37 (d, J = 11.9 Hz, 1H), 4.01 (d, J = 13.4 Hz, 1H), 3.61-3.71 (m, 1H), 3.47-3.58 (m, 1H), 3.33-3.42 (m, 2H), 3.09-3.27 (m, 3H), 2.80 (t, J = 12.2 Hz, 1H), 2.05-2.09 (m, 8H), 1.47-1.75 (m, 4H), 1.28 (dd, J = 6.7, 5.2 Hz, 3H), 0.74-1.23 (m, 6H); LCMS (M + 1): 615.2 |
| 200 | ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(iso-propyl)(propyl)-l6-sulfanone | $^{1}$H-NMR (400 MHz, DMSO-$d_6$) δ 8.39 (d, J = 4.0 Hz, 1H), 8.10 (d, J = 6.4 Hz, 1H), 7.96 (d, J = 6.4 Hz, 1H), 7.11-7.17 (m, 2H), 7.02 (dd, J = 7.5, 5.0 Hz, 1H), 6.64-6.70 (m, 1H), 6.08-6.16 (m, 1H), 5.26 (s, 2H), 4.33 (d, J = 15.3 Hz, 1H), 3.91 (d, J = 12.8 Hz, 1H), 3.48-3.72 (m, 3H), 3.35-3.42 (m, 2H), 3.08-3.27 (m, 3H), 2.76-2.82 (m, 1H), 2.08 (d, J = 12.8 Hz, 2H), 1.81 (d, J = 16.5 Hz, 1H), 1.49-1.68 (m, 3H), 1.28 (dd, J = 6.7, 5.2 Hz, 3H), 0.73-1.23 (m, 6H); LCMS (M + 1): 682.15 |
| 201 | ((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(iso-propyl)(propyl)-l6-sulfanone | $^{1}$H-NMR (400 MHz, DMSO-$d_6$) δ 8.55 (d, J = 2.4 Hz, 1H), 8.38 (d, J = 2.8 Hz, 1H), 7.97 (d, J = 6.7 Hz, 1H), 7.11-7.17 (m, 1H), 7.02 (dd, J = 7.6, 4.9 Hz, 1H), 6.64-6.70 (m, 1H), 6.08-6.16 (m, 1H), 5.37 (s, 2H), 4.30 (d, J = 12.2 Hz, 1H), 3.88 (d, J = 13.4 Hz, 1H), 3.47-3.72 (m, 3H), 3.34-3.41 (m, 2H), 3.09-3.27 (m, 3H), 2.80 (t, J = 12.5 Hz, 1H), 2.03-2.10 (m, 2H), 1.82 (dd, J = 12.5, 8.9 Hz, 1H), 1.47-1.72 (m, 3H), 1.28 (dd, J = 6.9, 5.3 Hz, 3H), 0.74-1.23 (m, 6H); LCMS (M + 1): 683.1 |
| 202 | 1-(2-(4-(4-(5-(2-fluoro-6-((isopropyl(oxo)(propyl)-l6-sulfaneylidene)amino)phe-nyl)-4,5-dihydroisoxazol-3-yl)thiazol-2-yl)piperidin-1-yl)-2-oxoethyl)-3-(trifluoromethyl)pyridin-2(1H)-one | $^{1}$H-NMR (400 MHz, DMSO-$d_6$) δ 7.91-7.98 (m, 3H), 7.10-7.17 (m, 1H), 7.02 (dd, J = 7.6, 4.9 Hz, 1H), 6.64-6.70 (m, 1H), 6.38 (t, J = 6.9 Hz, 1H), 6.08-6.16 (m, 1H), 4.94 (s, 2H), 4.37 (d, J = 11.6 Hz, 1H), 4.01 (d, J = 12.8 Hz, 1H), 3.47-3.72 (m, 3H), 3.35-3.43 (m, 2H), 3.09-3.26 (m, 2H), 2.92-3.00 (m, 1H), 2.84 (t, J = 12.4 Hz, 1H), 2.06-2.15 (m, 2H), 1.73-1.83 (m, 1H), 1.48-1.72 (m, 3H), 1.26-1.33 (m, 3H), o.74-1.23 (m, 6H); LCMS (M + 1): 682.15 |
| 203 | 1-(4-(4-(5-(2-fluoro-6-((1-oxido-1l6-thietan-1- | $^{1}$H-NMR (400 MHz, DMSO-$d_6$) δ 8.55 (d, J = 2.1 Hz, 1H), 8.38 (d, J = 2.4 Hz, 1H), 7.99 (d, J = 11.3 Hz, 1H), 7.22 (td, J = 8.3, 6.7 Hz, |

TABLE NO 1-continued

The following compounds were prepared analogue to the procedure described in schemes 1-17 or Examples 1 to 8.

| Compd. No. | Compound Name | Analytical data |
|---|---|---|
| | ylidene)amino)phenyl)-4,5-dihydroisoxazol-3-yl)thiazol-2-yl)piperidin-1-yl)-2-((3-(trifluoromethyl)pyrazin-2-yl)oxy)ethan-1-one | 1H), 6.75-6.83 (m, 2H), 6.15 (dd, J = 12.2, 8.9 Hz, 1H), 5.38 (d, J = 11.0 Hz, 2H), 4.16-4.31 (m, 3H), 3.96-4.03 (m, 2H), 3.87 (d, J = 13.4 Hz, 1H), 3.71 (dd, J = 16.8, 12.2 Hz, 1H), 3.46-3.56 (m, 1H), 3.38 (qd, J = 7.6, 3.7 Hz, 1H), 3.21-3.27 (m, 1H), 2.77-2.83 (m, 1H), 2.03-2.27 (m, 4H), 1.79-1.90 (m, 1H), 1.53-1.58 (m, 1H); LCMS (M + 1): 639 |
| 204 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diiso-propyl-l6-sulfanone | $^{1}$H-NMR (400 MHz, DMSO-$d_6$) δ 7.96 (s, 1H), 7.59 (s, 1H), 7.06-7.12 (m, 2H), 6.60-6.66 (m, 1H), 6.16 (dd, J = 12.2, 9.8 Hz, 1H), 5.61 (d, J = 17.1 Hz, 1H), 5.49 (d, J = 17.1 Hz, 1H), 4.33 (d, J = 13.4 Hz, 1H), 3.95 (d, J = 13.4 Hz, 1H), 3.70 (dd, J = 16.5, 13.1 Hz, 1H), 3.44-3.62 (m, 3H), 2.86 (t, J = 11.6 Hz, 1H), 2.53 (s, 1H), 2.10 (t, J = 13.6 Hz, 2H), 1.78 (dd, J = 21.1, 11.9 Hz, 1H), 1.53 (qd, J = 12.2, 3.8 Hz, 1H), 1.22-1.28 (m, 10H), 1.14 (d, J = 6.7 Hz, 3H); LCMS (M + 1): 723 |
| 205 | ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diiso-propyl-l6-sulfanone | $^{1}$H-NMR (400 MHz, DMSO-$d_6$) δ 7.96 (s, 1H), 7.06-7.12 (m, 2H), 6.60-6.66 (m, 1H), 6.49 (s, 1H), 6.17 (dd, J = 12.2, 9.8 Hz, 1H), 5.33 (d, J = 16.8 Hz, 1H), 5.23 (d, J = 17.1 Hz, 1H), 4.36 (d, J = 13.1 Hz, 1H), 3.97 (d, J = 13.8 Hz, 1H), 3.67-3.74 (m, 1H), 3.45-3.62 (m, 3H), 3.38 (tt, J = 11.4, 3.7 Hz, 1H), 3.24-3.28 (m, 1H), 2.81-2.87 (m, 1H), 2.19 (d, J = 6.1 Hz, 3H), 2.06-2.13 (m, 2H), 1.74-1.83 (m, 1H), 1.55 (qd, J = 12.2, 3.8 Hz, 1H), 1.22-1.28 (m, 9H), 1.14 (d, J = 6.7 Hz, 3H); LCMS (M + 1): 669 |
| 206 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diiso-propyl-l6-sulfanone | $^{1}$H-NMR (400 MHz, DMSO-$d_6$) δ 7.96 (d, J = 6.1 Hz, 1H), 6.88-7.30 (m, 5H), 6.60-6.66 (m, 1H), 6.17 (dd, J = 12.2, 9.5 Hz, 1H), 5.43 (d, J = 17.1 Hz, 1H), 5.34 (d, J = 17.1 Hz, 1H), 4.34 (d, J = 13.4 Hz, 1H), 3.96 (d, J = 13.4 Hz, 1H), 3.67-3.74 (m, 1H), 3.45-3.62 (m, 3H), 3.38 (tt, J = 11.6, 3.8 Hz, 1H), 3.23-3.28 (m, 1H), 2.81-2.87 (m, 1H), 2.06-2.13 (m, 2H), 1.75-1.84 (m, 1H), 1.56 (qd, J = 12.2, 3.8 Hz, 1H), 1.22-1.29 (m, 9H), 1.10-1.15 (m, 3H); LCMS (M + 1): 687 |
| 207 | ((2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)-3-fluorophenyl)imino)diiso-propyl-l6-sulfanone | $^{1}$H-NMR (400 MHz, DMSO-$d_6$) δ 7.96 (s, 1H), 7.06-7.11 (m, 2H), 6.60-6.65 (m, 1H), 6.36 (s, 1H), 6.16 (dd, J = 12.2, 9.8 Hz, 1H), 5.39 (d, J = 16.8 Hz, 1H), 5.28 (d, J = 16.8 Hz, 1H), 4.37 (d, J = 13.4 Hz, 1H), 4.01 (d, J = 14.1 Hz, 1H), 3.66-3.74 (m, 1H), 3.45-3.62 (m, 3H), 3.36-3.42 (m, 2H), 3.25-3.28 (m, 1H), 2.84 (t, J = 11.3 Hz, 1H), 2.07-2.12 (m, 2H), 1.73-1.83 (m, 2H), 1.55-1.61 (m, 1H), 1.22-1.28 (m, 10H), 1.14 (d, J = 6.7 Hz, 3H), 0.87-0.93 (m, 2H), 0.66-0.71 (m, 2H); LCMS (M + 1): 695 |
| 208 | ((3-fluoro-2-(3-(2-(1-(2-((3-methoxypyrazin-2-yl)oxy)acetyl)piperidin-4-yl)thiazol-4-yl)-4,5-dihydroisoxazol-5-yl)phenyl)imino)diiso-propy1-l6-sulfanone | $^{1}$H-NMR (400 MHz, DMSO-$d_6$) δ 7.96 (s, 1H), 7.70-7.72 (m, 1H), 7.65 (d, J = 3.1 Hz, 1H), 7.06-7.12 (m, 2H), 6.60-6.66 (m, 1H), 6.17 (dd, J = 12.2, 9.8 Hz, 1H), 5.15 (dd, J = 15.7, 14.5 Hz, 2H), 4.32 (d, J = 12.5 Hz, 1H), 3.90 (s, 3H), 3.67-3.74 (m, 1H), 3.45-3.62 (m, 3H), 3.38 (qd, J = 7.6, 3.9 Hz, 1H), 3.20-3.27 (m, 1H), 2.79 (t, J = 11.5 Hz, 1H), 2.07 (t, J = 14.2 Hz, 2H), 1.74-1.84 (m, 1H), 1.54 (t, J = 11.2 Hz, 1H), 1.22-1.28 (m, 10H), 1.14 (d, J = 6.7 Hz, 3H); LCMS (M + 1): 645 |
| 209 | ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diiso-propy1-l6-sulfanone | $^{1}$H-NMR (400 MHz, DMSO-$d_6$) δ 8.39 (dd, J = 4.9, 1.2 Hz, 1H), 8.10 (dd, J = 7.5, 1.1 Hz, 1H), 7.95 (d, J = 4.0 Hz, 1H), 7.16 (dd, J = 7.0, 5.2 Hz, 1H), 7.06-7.12 (m, 2H), 6.60-6.65 (m, 1H), 6.17 (dd, J = 12.2, 9.5 Hz, 1H) 5.26 (s, 2H), 4.32 (d, J = 13.4 Hz, 1H), 3.90 (d, J = 11.6 Hz, 1H), 3.70 (dd, J = 17.0, 12.7 Hz, 1H), 3.44-3.62 (m, 3H), 3.37 (tt, J = 11.4, 3.8 Hz, 1H), 3.24 (t, J = 11.9 Hz, 1H), 2.79 (t, J = 11.9 Hz, 1H), 2.03-2.09 (m, 2H), 1.81 (d, J = 10.4 Hz, 1H), 1.54 (d, J = 12.2 Hz, 1H), 1.22-1.28 (m, 9H), 1.10-1.14 (m, 3H); LCMS (M + 1): 682 |
| 210 | 1-(2-(4-(4-(5-(2-((diisopropyl(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one | $^{1}$H-NMR (400 MHz, DMSO-$d_6$) δ 7.90-7.97 (m, 3H), 7.06-7.13 (m, 2H), 6.60-6.66 (m, 1H), 6.38 (t, J = 7.0 Hz, 1H), 6.17 (dd, J = 12.2, 9.5 Hz, 1H), 4.91-4.98 (m, 2H), 4.36 (d, J = 13.4 Hz, 1H), 4.01 (d, J = 14.1 Hz, 1H), 3.67-3.74 (m, 1H), 3.46-3.64 (m, 3H), 3.40 (tt, J = 11.5, 3.8 Hz, 1H), 3.26 (t, J = 11.3 Hz, 1H), 2.81-2.87 (m, 1H), 2.11 (dd, J = 24.0, 13.6 Hz, 2H), 1.79 (qd, J = 12.2, 3.4 Hz, 1H), 1.56 (qd, J = 12.2, 3.8 Hz, 1H), 1.22-1.31 (m, 9H), 1.10-1.19 (m, 3H); LCMS (M + 1): 682 |
| 211 | ((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diiso-propyl-l6-sulfanone | $^{1}$H-NMR (400 MHz, DMSO-$d_6$) δ 7.96 (s, 1H), 7.61 (dd, J = 4.9, 1.5 Hz, 1H), 7.28 (dd, J = 7.8, 1.4 Hz, 1H), 7.06-7.12 (m, 2H), 6.90 (dd, J = 7.8, 5.0 Hz, 1H), 6.60-6.66 (m, 1H), 6.16 (dd, J = 12.1, 9.6 Hz, 1H), 5.07 (d, J = 1.5 Hz, 2H), 4.34 (d, J = 13.4 Hz, 1H), 3.93 (d, J = 12.5 Hz, 1H), 3.79 (s, 3H), 3.70 (dd, J = 16.4, 13.0 Hz, 1H), 3.44-3.62 (m, 3H), 3.38 (qd, J = 7.6, 3.7 Hz, 1H), 3.22 (d, J = 12.5 Hz, 1H), 2.75-2.81 (m, 1H), 2.03-2.09 (m, 2H), 1.79-1.85 (m, 1H), 1.51-1.56 (m, 1H), 1.22-1.30 (m, 9H), 1.14 (d, J = 6.7 Hz, 3H); LCMS (M + 1): 644 |

TABLE NO 1-continued

| The following compounds were prepared analogue to the procedure described in schemes 1-17 or Examples 1 to 8. | | |
|---|---|---|
| Compd. No. | Compound Name | Analytical data |
| 212 | ((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diiso-propyl-l6-sulfanone | $^1$H-NMR (400 MHz, DMSO-$d_6$) δ 8.55-8.55 (m, 1H), 8.38 (d, J = 2.4 Hz, 1H), 7.96 (s, 1H), 7.06-7.12 (m, 2H), 6.60-6.66 (m, 1H), 6.17 (dd, J = 12.1, 9.6 Hz, 1H), 5.37 (s, 2H), 4.30 (d, J = 13.1 Hz, 1H), 3.88 (d, J = 13.8 Hz, 1H), 3.70 (dd, J = 16.7, 13.3 Hz, 1H), 3.45-3.62 (m, 3H), 3.39 (td, J = 7.7, 4.0 Hz, 1H), 3.24 (t, J = 11.2 Hz, 1H), 2.80 (t, J = 11.6 Hz, 1H), 2.03-2.11 (m, 2H), 1.77-1.85 (m, 1H), 1.53-1.59 (m, 1H), 1.22-1.32 (m, 9H), 1.14 (d, J = 6.7 Hz, 3H); LCMS (M + 1): 683 |
| 213 | ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)diiso-propyl-l6-sulfanone | $^1$H-NMR (400 MHz, DMSO-$d_6$) δ 7.95 (d, J = 3.4 Hz, 1H), 7.06-7.11 (m, 2H), 6.60-6.66 (m, 1H), 6.16 (dd, J = 12.1, 9.6 Hz, 1H), 5.78 (s, 1H), 5.01 (d, J = 16.8 Hz, 1H), 4.90-4.96 (m, 1H), 4.36 (d, J = 12.8 Hz, 1H), 4.02 (q, J = 7.1 Hz, 1H), 3.66-3.74 (m, 1H), 3.44-3.62 (m, 3H), 3.37 (qd, J = 7.7, 3.8 Hz, 1H), 3.20-3.27 (m, 1H), 2.80 (t, J = 11.5 Hz, 1H), 2.07 (d, J = 16.8 Hz, 8H), 1.66-1.76 (m, 1H), 1.47-1.58 (m, 1H), 1.22-1.30 (m, 9H), 1.15 (t, J = 7.0 Hz, 3H); LCMS (M + 1): 615 |
| 214 | ((2-(3-(2-(1-(2-((3-chloropyrazin-2-yl)oxy)acetyl)piperidin-4-yl)thiazol-4-yl)-4,5-dihydroisoxazol-5-yl)-3-fluorophenyl)imino)dimeth-yl-l6-sulfanone | $^1$H-NMR (400 MHz, dimethylsulfoxide-d6) δ 8.20 (dd, J = 8.2, 5.5 Hz, 1H), 8.05-8.07 (m, 1H), 7.96 (s, 1H), 7.20 (td, J = 8.2, 6.8 Hz, 1H), 6.95 (d, J = 7.6 Hz, 1H), 6.75 (ddd, J = 10.8, 8.3, 1.0 Hz, 1H), 6.13 (dd, J = 12.3, 9.2 Hz, 1H), 5.25-5.32 (m, 2H), 4.31 (d, J = 13.0 Hz, 1H), 3.88 (d, J = 13.2 Hz, 1H), 3.65-3.73 (m, 1H), 3.48 (dd, J = 17.0, 9.2 Hz, 1H), 3.37 (tt, J = 11.3, 3.7 Hz, 1H), 3.21-3.27 (m, 1H), 3.11 (d, J = 5.9 Hz, 6H), 2.77-2.83 (m, 1H), 2.08 (t, J = 15.0 Hz, 2H), 1.77-1.85 (m, 1H), 1.50-1.59 (m, 1H); LCMS(M + 1): 593.05 |
| 215 | ((3-fluoro-2-(3-(2-(1-(2-((3-(methylthio)pyrazin-2-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, CHLOROFORM-D) δ 8.01 (d, J = 3.1 Hz, 1H), 7.71 (d, J = 3.1 Hz, 1H), 7.47 (s, 1H), 7.16 (td, J = 8.1, 6.4 Hz, 1H), 7.08 (d, J = 7.9 Hz, 1H), 6.71-6.76 (m, 1H), 6.18 (dd, J = 12.5, 9.2 Hz, 1H), 5.09 (d, J = 8.3 Hz, 2H), 4.63 (d, J = 12.8 Hz, 1H), 3.96 (d, J = 13.8 Hz, 1H), 3.80 (dd, J = 16.5, 9.2 Hz, 1H), 3.58 (dd, J = 16.5, 12.5 Hz, 1H), 3.25-3.38 (m, 2H), 3.05-3.11 (m, 3H), 2.94 (s, 3H), 2.81-2.90 (m, 1H), 2.53 (s, 3H), 2.16-2.36 (m, 2H), 1.82-1.92 (m, 2H); LCMS (M + 1): 605.1 |
| 216 | ((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(iso-propyl)(phenyl)-l6-sulfanone | $^1$H-NMR (400 MHz, DMSO-$d_6$) δ 8.54 (s, 1H), 8.37 (s, 1H), 8.02 (d, J = 7.3 Hz, 1H), 7.86-7.88 (m, 2H), 7.68 (t, J = 7.3 Hz, 1H), 7.62 (t, J = 7.5 Hz, 2H), 6.95-7.00 (m, 1H), 6.71 (d, J = 7.9 Hz, 1H), 6.59-6.64 (m, 1H), 6.20 (dd, J = 11.8, 9.9 Hz, 1H), 5.36 (t, J = 14.7 Hz, 2H), 4.30 (d, J = 13.1 Hz, 1H), 3.72-3.89 (m, 3H), 3.21-3.27 (m, 1H), 2.77-2.84 (m, 1H), 2.71 (d, J = 6.1 Hz, 2H), 2.07 (t, J = 13.8 Hz, 2H), 1.81 (q, J = 11.9 Hz, 1H), 1.50-1.59 (m, 1H), 1.00 (d, J = 6.7 Hz, 3H), 0.93 (d, J = 7.0 Hz, 3H); LCMS (M + 1): 717 |
| 217 | ((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(iso-propyl)(phenyl)-l6-sulfanone | $^1$H-NMR (400 MHz, DMSO-$d_6$) δ 8.00-8.03 (m, 1H), 7.86-7.88 (m, 2H), 7.66-7.70 (m, 1H), 7.59-7.64 (m, 3H), 7.27 (dd, J = 7.8, 1.4 Hz, 1H), 6.98 (td, J = 8.2, 6.8 Hz, 1H), 6.89-6.91 (m, 1H), 6.71 (d, J = 7.9 Hz, 1H), 6.59-6.63 (m, 1H), 6.20 (dd, J = 11.9, 9.8 Hz, 1H), 5.06 (dd, J = 20.0, 14.5 Hz, 2H), 4.33 (d, J = 12.5 Hz, 1H), 3.93 (d, J = 14.4 Hz, 1H), 3.72-3.85 (m, 5H), 3.35-3.42 (m, 2H), 3.23 (t, J = 13.0 Hz, 1H), 2.78 (t, J = 11.8 Hz, 1H), 1.98-2.06 (m, 2H), 1.81 (d, J = 11.6 Hz, 1H), 1.51 (dd, J = 12.1, 9.0 Hz, 1H), 1.00 (d, J = 6.7 Hz, 3H), 0.92 (d, J = 7.0 Hz, 3H); LCMS (M + 1): 678 |
| 218 | 3-chloro-1-(2-(4-(4-(5-(2-fluoro-6-((isopropyl(oxo)(phenyl)-l6-sulfaneyl-idene)amino)phenyl)-4,5-dihydroisoxazol-3-yl)thiazol-2-yl)piperidin-1-yl)-2-oxoethyl)-5-(trifluoromethyl)pyridin-2(1H)-one | $^1$H-NMR (400 MHz, DMSO-$d_6$) δ 8.35 (d, J = 1.2 Hz, 1H), 8.15 (d, J = 2.4 Hz, 1H), 8.02 (d, J = 7.0 Hz, 1H), 7.86 (dd, J = 7.0, 1.5 Hz, 2H), 7.66-7.71 (m, 1H), 7.60-7.64 (m, 2H), 6.98 (td, J = 8.2, 6.9 Hz, 1H), 6.71 (d, J = 7.9 Hz, 1H), 6.61 (ddd, J = 10.4, 8.3, 0.9 Hz, 1H), 6.20 (dd, J = 11.8, 9.9 Hz, 1H), 4.98 (d, J = 12.8 Hz, 2H), 4.35 (d, J = 13.1 Hz, 1H), 3.97 (d, J = 13.8 Hz, 1H), 3.72-3.85 (m, 2H), 3.35-3.46 (m, 2H), 3.26-3.29 (m, 1H), 2.82-2.88 (m, 1H), 2.06-2.15 (m, 2H), 1.75-1.84 (m, 1H), 1.51-1.64 (m, 1H), 1.01 (q, J = 6.8 Hz, 3H), 0.93 (t, J = 7.2 Hz, 3H); LCMS (M + 1): 750 |
| 219 | ((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(iso-propyl)(phenyl)-l6-sulfanone | $^1$H-NMR (400 MHz, DMSO-$d_6$) δ 8.01 (s, 1H), 7.80-7.86 (m, 2H), 7.72 (t, J = 7.3 Hz, 1H), 7.62-7.65 (m, 2H), 6.99 (td, J = 8.1, 6.7 Hz, 1H), 6.62 (dd, J = 10.7, 8.3 Hz, 2H), 6.38 (dd, J = 12.1, 9.6 Hz, 1H), 5.76 (d, J = 12.8 Hz, 1H), 5.01 (d, J = 16.8 Hz, 1H), 4.92 (d, J = 16.8 Hz, 1H), 4.36 (d, J = 12.8 Hz, 1H), 4.00 (t, J = 6.7 Hz, 1H), 3.76-3.84 (m, 1H), 3.60 (dd, J = 17.1, 9.5 Hz, 1H), 3.45-3.53 (m, 1H), 3.35-3.41 (m, 1H), 3.23 (t, J = 12.5 Hz, 1H), 2.80 (t, J = 11.6 Hz, 1H), 2.01-2.09 (m, 8H), 1.72 (q, J = 12.0 Hz, 1H), 1.48-1.57 (m, 1H), 1.22-1.26 (m, 3H), 1.12 (dd, J = 12.1, 6.9 Hz, 3H); LCMS (M + 1): 649.15 |
| 220 | 1-(2-(4-(4-(5-(2-fluoro-6-((isopropyl(oxo)(phenyl)-l6-sulfaneyl-idene)amino)phenyl)- | $^1$H-NMR (400 MHz, DMSO-$d_6$) δ 8.29 (s, 1H), 8.02 (s, 1H), 7.80-7.83 (m, 2H), 7.60-7.73 (m, 4H), 6.99 (td, J = 8.3, 6.7 Hz, 1H), 6.62 (dd, J = 10.9, 8.4 Hz, 2H), 6.54 (d, J = 9.8 Hz, 1H), 6.38 (dd, J = 12.1, 9.6 Hz, 1H), 4.92 (dd, J = 19.6, 15.6 Hz, 2H), 4.36 (d, J = 13.1 |

TABLE NO 1-continued

The following compounds were prepared analogue to the procedure described in schemes 1-17 or Examples 1 to 8.

| Compd. No. | Compound Name | Analytical data |
|---|---|---|
| | 4,5-dihydroisoxazol-3-yl)thiazol-2-yl)piperidin-1-yl)-2-oxoethyl)-5-(trifluoromethyl)pyridin-2(1H)-one | Hz, 1H), 4.00 (d, J = 13.4 Hz, 1H), 3.77-3.85 (m, 1H), 3.60 (dd, J = 17.1, 9.5 Hz, 1H), 3.46-3.54 (m, 1H), 3.41 (tt, J = 11.5, 3.7 Hz, 1H), 3.26 (d, J = 11.6 Hz, 1H), 2.81-2.88 (m, 1H),2.11 (dd, J = 24.0, 12.7 Hz, 2H), 1.77-1.85 (m, 1H), 1.57 (qd, J = 12.2, 3.9 Hz, 1H), 1.21-1.27 (m, 3H), 1.03-1.12 (m, 3H); LCMS (M + 1): 716.1 |
| 221 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(iso-propyl)(phenyl)-l6-sulfanone | $^1$H-NMR (400 MHz, DMSO-$d_6$) δ 8.03 (d, J = 7.0 Hz, 1H), 7.83-7.88 (m, 2H), 7.67-7.70 (m, 1H), 7.58-7.65 (m, 2H), 6.88-7.29 (m, 4H), 6.71 (d, J = 8.3 Hz, 1H), 6.61 (dd, J = 9.9, 8.7 Hz, 1H), 6.20 (dd, J = 11.6, 10.1 Hz, 1H), 5.43 (d, J = 17.1 Hz, 1H),5.33 (d, J = 17.1 Hz, 1H), 4.34 (d, J = 12.8 Hz, 1H), 3.96 (d, J = 13.8 Hz, 1H), 3.72-3.85 (m, 2H), 3.35-3.46 (m, 2H), 3.18-3.28 (m, 1H), 2.81-2.89 (m, 1H), 2.06-2.13 (m, 2H), 1.75-1.84 (m, 1H), 1.50-1.61 (m, 1H), 1.00 (d, J = 6.7 Hz, 3H), 0.94 (d, J = 7.0 Hz, 3H); LCMS (M + 1): 721.1 |
| 222 | 1-(2-(4-(4-(5-(2-fluoro-6-((isopropyl(oxo)(phenyl)-l6-sulfaneyl-idene)amino)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 8.02 (s, 1H), 7.95 (d, J = 7.3 Hz, 1H), 7.91-7.92 (m, 1H), 7.78-7.83 (m, 2H), 7.69-7.73 (m, 1H), 7.60-7.65 (m, 2H), 6.99 (td, J = 8.2, 6.7 Hz, 1H), 6.60-6.70 (m, 2H), 6.36-6.41 (m, 2H), 4.90-4.99 (m, 2H), 4.36 (d, J = 13.0 Hz, 1H), 4.01 (d, J = 13.2 Hz, 1H), 3.77-3.85 (m, 1H), 3.60 (dd, J = 17.0, 9.4 Hz, 1H), 3.48-3.54 (m, 1H), 3.41 (tt, J = 11.5, 3.8 Hz, 1H), 3.27 (d, J = 12.7 Hz, 1H), 2.81-2.87 (m, 1H), 2.07-2.16 (m, 2H), 1.78-1.85 (m, 1H), 1.56 (qd, J = 12.3, 4.0 Hz, 1H), 1.21-1.27 (m, 3H), 1.10-1.14 (m, 3H); LCMS (M + 1): 716 |
| 223 | ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(iso-propyl)(phenyl)-l6-sulfanone | $^1$H-NMR (400 MHz, DMSO-$d_6$) δ 8.38 (d, J = 4.3 Hz, 1H), 8.09 (dd, J = 7.6, 1.2 Hz, 1H), 8.01 (d, J = 3.7 Hz, 1H), 7.86-7.88 (m, 2H), 7.68 (t, J = 7.3 Hz, 1H), 7.56-7.63 (m, 2H), 7.14 (d, J = 5.8 Hz, 1H), 6.98 (td, J = 8.2, 6.8 Hz, 1H), 6.71 (d, J = 8.3 Hz, 1H), 6.59-6.65 (m, 1H), 6.20 (dd, J = 11.6, 10.1 Hz, 1H), 5.25 (s, 2H), 4.32 (d, J = 12.8 Hz, 1H), 3.90 (d, J = 13.8 Hz, 1H), 3.72-3.85 (m, 2H), 3.36-3.42 (m, 2H), 3.19-3.23 (m, 1H), 2.79 (t, J = 12.1 Hz, 1H), 2.05 (d, J = 11.6 Hz, 2H), 1.74-1.86 (m, 1H), 1.52-1.58 (m, 1H), 1.00 (d, J = 6.7 Hz, 3H), 0.93 (d, J = 6.7 Hz, 3H); LCMS (M + 1): 716 |
| 224 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)diiso-propyl-l6-sulfanone | $^1$H-NMR (400 MHz, DMSO-$d_6$) δ 7.96 (s, 1H), 7.59 (s, 1H), 7.28 (dd, J = 8.3, 1.0 Hz, 1H), 7.08 (t, J = 8.1 Hz, 1H), 6.89 (dd, J = 7.9, 1.1 Hz, 1H), 6.30-6.36 (m, 1H), 5.60 (d, J = 17.4 Hz, 1H), 5.49 (d, J = 17.1 Hz, 1H), 4.33 (d, J = 13.4 Hz, 1H), 3.95 (d, J = 13.2 Hz, 1H), 3.54-3.70 (m, 3H), 3.35-3.43 (m, 2H), 3.26 (d, J = 11.7 Hz, 1H), 2.83-2.89 (m, 1H), 2.06-2.13 (m, 2H), 1.78 (q, J = 12.9 Hz, 1H), 1.53 (dd, J = 12.1, 3.5 Hz, 1H), 1.19-1.32 (m, 9H), 1.02 (dd, J = 6.7, 1.6 Hz, 3H); LCMS (M + 1): 739.05 |
| 225 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diiso-propy1-l6-sulfanone | $^1$H-NMR (400 MHz, DMSO-$d_6$) δ 7.96 (s, 1H), 7.28 (dd, J = 8.2, 1.1 Hz, 1H), 7.08 (t, J = 8.1 Hz, 1H), 6.89 (dd, J = 7.9, 1.1 Hz, 1H), 6.49 (s, 1H), 6.30-6.36 (m, 1H), 5.33 (d, J = 17.1 Hz, 1H), 5.22 (d, J = 16.9 Hz, 1H), 4.36 (d, J = 13.9 Hz, 1H), 3.97 (d, J = 13.7 Hz, 1H), 3.54-3.70 (m, 3H), 3.35-3.44 (m, 2H), 3.25 (d, J = 11.2 Hz, 1H), 2.84 (t, J = 11.2 Hz, 1H), 2.20 (d, J = 0.5 Hz, 3H), 2.06-2.12 (m, 2H), 1.74-1.81 (m, 1H), 1.55 (dd, J = 12.1, 3.5 Hz, 1H), 1.19-1.27 (m, 9H), 1.03 (d, J = 6.6 Hz, 3H); LCMS (M + 1): 685.05 |
| 226 | ((3-chloro-2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)phenyl)imino)diiso-propy1-l6-sulfanone | $^1$H-NMR (400 MHz, DMSO-$d_6$) δ 7.96 (s, 1H), 7.28 (dd, J = 8.2, 1.1 Hz, 1H), 7.08 (t, J = 8.1 Hz, 1H), 6.89 (dd, J = 8.1, 1.2 Hz, 1H), 6.33 (t, J = 11.9 Hz, 2H), 5.39 (d, J = 16.6 Hz, 1H), 5.28 (d, J = 16.9 Hz, 1H), 4.37 (d, J = 13.7 Hz, 1H), 4.01 (d, J = 13.2 Hz, 1H), 3.54-3.69 (m, 3H), 3.36-3.43 (m, 2H), 3.26 (d, J = 12.7 Hz, 1H), 2.81-2.88 (m, 1H), 2.09 (t, J = 10.9 Hz, 2H), 1.76-1.83 (m, 2H), 1.51-1.61 (m, 1H), 1.19-1.27 (m, 9H), 1.03 (d, J = 6.6 Hz, 3H), 0.87-0.93 (m, 2H), 0.68 (dd, J = 7.3, 4.4 Hz, 2H); LCMS (M + 1): 711.1 |
| 227 | ((2-(3-(2-(1-(2-(3,5-bis(difluoroniethyl)-1H-pyrazol-1-yl)acetyl)piperidin-4-yl)thiazol-4-yl)-4,5-dihydroisoxazol-5-yl)-3-chlorophenyl)imino)diiso-propyl-l6-sulfanone | $^1$H-NMR (400 MHz, DMSO-$d_6$) δ 7.96 (d, J = 6.4 Hz, 1H), 6.88-7.30 (m, 6H), 6.30-6.36 (m, 1H), 5.43 (d, J = 16.9 Hz, 1H), 5.34 (d, J = 17.1 Hz, 1H), 4.34 (d, J = 13.2 Hz, 1H), 3.96 (d, J = 13.9 Hz, 1H), 3.54-3.70 (m, 3H), 3.35-3.44 (m, 2H), 3.25 (d, J = 11.5 Hz, 1H), 2.81-2.88 (m, 1H), 2.06-2.12 (m, 2H), 1.73-1.83 (m, 1H), 1.51-1.60 (m, 1H), 1.26 (dd, J = 6.7, 2.3 Hz, 6H), 1.20 (d, J = 6.6 Hz, 3H), 1.03 (d, J = 6.8 Hz, 3H); LCMS (M + 1): 703.05 |
| 228 | ((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)diiso-propyl-l6-sulfanone | $^1$H-NMR (400 MHz, DMSO-$d_6$) δ 7.96 (s, 1H), 7.28 (dd, J = 8.2, 1.1 Hz, 1H), 7.08 (t, J = 8.1 Hz, 1H), 6.89 (dd, J = 7.8, 1.2 Hz, 1H), 6.30-6.36 (m, 1H), 5.78 (s, 1H), 5.01 (d, J = 16.9 Hz, 1H), 4.92 (d, J = 16.6 Hz, 1H), 4.36 (d, J = 13.4 Hz, 1H), 4.00 (d, J = 12.7 Hz, 1H), 3.54-3.69 (m, 3H), 3.34-3.43 (m, 2H), 3.23 (t, J = 11.6 Hz, 1H), 2.78-2.88 (m, 1H), 2.05-2.09 (m, 8H), 1.66-1.75 (m, 1H), 1.48-1.56 (m, 1H), 1.26 (dd, J = 6.8, 2.0 Hz, 6H), 1.20 (d, J = 6.6 Hz, 3H), 1.02 (d, J = 6.6 Hz, 3H); LCMS (M + 1): 631.15 |

TABLE NO 1-continued

The following compounds were prepared analogue to the procedure described in schemes 1-17 or Examples 1 to 8.

| Compd. No. | Compound Name | Analytical data |
|---|---|---|
| 229 | ((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diiso-propyl-l6-sulfanone | $^1$H-NMR (400 MHz, DMSO-$d_6$) δ 8.39 (d, J = 3.9 Hz. 1H), 8.10 (d, J = 6.4 Hz, 1H), 7.96 (s, 1H), 7.28 (dd, J = 8.2, 1.1 Hz, 1H), 7.16 (dd, J = 7.3, 5.4 Hz, 1H), 7.08 (t, J = 8.2 Hz, 1H), 6.89 (dd, J = 7.9, 1.1 Hz, 1H), 6.30-6.36 (m, 1H), 5.26 (s, 2H), 4.32 (d, J = 13.4 Hz, 1H), 3.91 (d, J = 13.7 Hz, 1H), 3.54-3.70 (m, 3H), 3.39 (td, J = 13.4, 7.1 Hz, 2H), 3.20-3.24 (m, 1H), 2.76-2.83 (m, 1H), 2.02-2.09 (m, 2H), 1.77-1.85 (m, 1H), 1.50-1.58 (m, 1H), 1.25 (dd, J = 6.7, 2.6 Hz, 6H), 1.20 (d, J = 6.6 Hz, 3H), 1.02 (d, J = 6.6 Hz, 3H); LCMS (M + 1): 698.05 |
| 230 | ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diiso-propyl-l6-sulfanone | $^1$H-NMR (400 MHz, DMSO-$d_6$) δ 7.96 (s, 1H), 7.61 (dd, J = 4.9, 1.5 Hz, 1H), 7.28 (dd, J = 8.1, 1.2 Hz, 2H), 7.08 (t, J = 8.1 Hz, 1H), 6.88-6.92 (m, 2H), 6.30-6.36 (m, 1H), 5.07 (d, J = 2.4 Hz, 2H), 4.33 (d, J = 12.5 Hz, 1H), 3.93 (d, J = 14.7 Hz, 1H), 3.79 (s, 3H), 3.54-3.70 (m, 3H), 3.34-3.43 (m, 2H), 3.22 (d, J = 12.7 Hz, 1H), 2.79 (t, J = 11.5 Hz, 1H), 2.03-2.09 (m, 2H), 1.76-1.85 (m, 1H), 1.53 (dd, J = 22.6, 10.4 Hz, 1H), 1.25 (dd, J = 6.8, 2.4 Hz, 6H), 1.20 (d, J = 6.8 Hz, 3H), 1.02 (d, J = 6.8 Hz, 3H); LCMS(M + 1): 660.1 |
| 231 | 1-(2-(4-(4-(5-(2-chloro-6-((diisopropyl(oxo)-l6-sulfaneyl-idene)amino)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 7.91-7.97 (m, 3H), 7.28 (dd, J = 8.2, 1.1 Hz, 1H), 7.08 (t, J = 8.1 Hz, 1H), 6.89 (dd, J = 7.9, 1.1 Hz, 1H), 6.30-6.40 (m, 2H), 4.94 (s, 2H), 4.36 (d, J = 13.4 Hz, 1H), 4.01 (d, J = 13.4 Hz, 1H), 3.54-3.70 (m, 3H), 3.37-3.43 (m, 2H), 3.26 (s, 1H), 2.82-2.88 (m, 1H), 2.06-2.15 (m, 2H), 1.74-1.82 (m, 1H), 1.51-1.60 (m, 1H), 1.26 (dd, J = 6.8, 2.2 Hz, 6H), 1.20 (d, J = 6.6 Hz, 3H), 1.03 (d, J = 6.8 Hz, 3H); LCMS (M + 1): 698.05 |
| 232 | ((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diiso-propyl-l6-sulfanone | $^1$H-NMR (400 MHz, DMSO-$d_6$) δ 8.55 (d, J = 2.0 Hz, 1H), 8.38 (d, J = 2.4 Hz, 1H), 7.96 (s, 1H), 7.28 (dd, J = 8.2, 1.1 Hz, 1H), 7.08 (t, J = 8.1 Hz, 1H), 6.89 (dd, J = 7.9, 1.1 Hz, 1H), 6.30-6.36 (m, 1H), 5.37 (s, 2H), 4.30 (d, J = 15.4 Hz, 1H), 3.88 (d, J = 12.0 Hz, 1H), 3.54-3.70 (m, 3H), 3.35-3.43 (m, 2H), 3.23 (d, J = 12.0 Hz, 1H), 2.81 (t, J = 11.7 Hz, 1H), 2.06 (t, J = 13.8 Hz, 2H), 1.77-1.85 (m, 1H), 1.50-1.59 (m, 1H), 1.26 (dd, J = 6.8, 2.2 Hz, 6H), 1.20 (d, J = 6.6 Hz, 3H), 1.03 (d, J = 6.8 Hz, 3H); LCMS (M + 1): 699.05 |
| 233 | ((2-(3-(2-(1-(2-(2H-indazol-2-yl)acetyl)piperidin-4-yl)thiazol-4-yl)-4,5-dihydroisoxazol-5-yl)-3-chlorophenyl)imino)diiso-propyl-l6-sulfanone | $^1$H-NMR (400 MHz, DMSO-$d_6$) δ 8.29 (d, J = 1.0 Hz, 1H), 7.97 (s, 1H), 7.70 (dt, J = 8.4, 1.0 Hz, 1H), 7.56 (dd, J = 8.8, 1.0 Hz, 1H), 7.28 (dd, J = 8.3, 1.2 Hz, 1H), 7.19-7.23 (m, 1H), 7.08 (t, J = 8.2 Hz, 1H), 7.01 (ddd, J = 8.4, 6.7, 0.9 Hz, 1H), 6.90 (dd, J = 7.9, 1.1 Hz, 1H), 6.31-6.36 (m, 1H), 5.50 (dd, J = 27.4, 16.1 Hz, 2H), 4.38 (d, J = 13.2 Hz, 1H), 4.08 (d, J = 12.5 Hz, 1H), 3.54-3.70 (m, 3H), 3.37-3.44 (m, 2H) 3.27 (s, 1H), 2.85 (t, J = 11.5 Hz, 1H), 2.10 (t, J = 12.1 Hz, 2H), 1.73-1.81 (m, 1H), 1.57 (dd, J = 26.2, 14.2 Hz, 1H), 1.26 (dd, J = 6.8, 2.2 Hz, 6H), 1.20 (d, J = 6.8 Hz, 3H), 1.03 (d, J = 5.9 Hz, 3H); LCMS (M + 1): 653.1 |
| 234 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(iso-propyl)(phenyl)-l6-sulfanone | $^1$H-NMR (400 MHz, DMSO-$d_6$) δ 8.02 (s, 1H), 7.86-7.88 (m, 2H), 7.66-7.71 (m, 1H), 7.58-7.63 (m, 3H), 6.98 (td, J = 8.3, 6.7 Hz, 1H), 6.71 (d, J = 8.3 Hz, 1H), 6.61 (ddd, J = 10.3, 8.3, 1.0 Hz, 1H), 6.20 (dd, J = 11.8, 9.9 Hz, 1H), 5.60 (d, J = 17.4 Hz, 1H), 5.48 (d, J = 17.1 Hz, 1H), 4.32 (d, J = 12.5 Hz, 1H), 3.93-4.03 (m, 1H), 3.72-3.85 (m, 2H), 3.35-3.46 (m, 2H), 3.24-3.27 (m, 1H), 2.86 (t, J = 11.5 Hz, 1H), 2.07-2.13 (m, 2H), 1.73-1.83 (m, 1H), 1.48-1.58 (m, 1H), 1.00 (d, J = 6.7 Hz, 3H), 0.89-0.94 (m, 3H); LCMS (M + 1): 757.25 |
| 235 | ((3-fluoro-2-(3-(2-(1-(2-((3-(methylsulfonyl)pyrazin-2-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, CHLOROFORM-D) δ 8.30-8.35 (m, 2H), 7.50 (d, J = 17.1 Hz, 1H), 7.16 (td, J = 8.2, 6.5 Hz, 1H), 7.08 (d, J = 7.6 Hz, 1H), 6.71-6.76 (m, 1H), 6.18 (dd, J = 12.5, 9.2 Hz, 1H), 5.33 (s, 2H), 4.55 (d, J = 13.1 Hz, 1H), 3.91 (d, J = 13.1 Hz, 1H), 3.80 (dd, J = 16.5, 9.2 Hz, 1H), 3.58 (dd, J = 16.5, 12.5 Hz, 1H), 3.39-3.44 (m, 3H), 3.23-3.38 (m, 2H), 3.05-3.12 (m, 3H), 2.96 (d, J = 15.3 Hz, 3H), 2.84-2.90 (m, 1H), 2.28 (d, J = 11.9 Hz, 1H), 2.17 (d, J = 12.8 Hz, 1H), 1.90-2.00 (m, 1H), 1.74-1.84 (m, 1H); FCMS (M + 1): 637 |
| 236 | ((3-fluoro-2-(3-(2-(1-(2-((6-(trifluoromethyl)pyridazin-3-yl)thio)acetyl)piperidin-4-yl)thiazol-4-yl)-4,5-dihydroisoxazol-5-yl)phenyl)imino)dimethyl-l6-sulfanone | $^1$H-NMR (400 MHz, CHFOROFORM-D) δ 7.52-7.60 (m, 2H), 7.48 (d, J = 4.6 Hz, 1H), 7.16 (td, J = 8.2, 6.5 Hz, 1H), 7.08 (d, J = 7.6 Hz, 1H), 6.70-6.75 (m, 1H), 6.17 (dd, J = 12.5, 9.2 Hz, 1H), 4.68 (d, J = 13.8 Hz, 1H), 4.47-4.51 (m, 1H), 4.39-4.43 (m, 1H), 4.18 (d, J = 13.8 Hz, 1H), 3.80 (dd, J = 16.5, 9.2 Hz, 1H), 3.58 (dd, J = 16.5, 12.5 Hz, 1H), 3.32-3.42 (m, 2H), 3.04-3.10 (m, 3H), 2.85-2.93 (m, 4H), 2.27 (d, J = 12.5 Hz, 1H), 2.18 (d, J = 12.2 Hz, 1H), 1.89-2.00 (m, 1H), 1.79 (ddd, J = 24.8, 11.9, 4.0 Hz, 1H); LCMS (M + 1): 643 |
| 237 | ((2-(3-(2-(1-(2-(3,5-bis(trifluoromethyl)-1H-pyrazol-1-yl)acetyl)piperidin-4-yl)thiazol-4-yl)-4,5- | $^1$H-NMR (400 MHz, DMSO-$d_6$) δ 7.96 (dd, J = 7.2, 2.6 Hz, 1H), 7.59 (s, 1H), 7.10-7.19 (m, 2H), 6.94 (td, J = 7.9, 1.3 Hz, 1H), 6.30 (dd, J = 11.3, 10.4 Hz, 1H), 5.61 (d, J = 17.4 Hz, 1H), 5.47-5.51 (m, 1H), 4.33 (d, J = 12.8 Hz, 1H), 3.95 (d, J = 13.4 Hz, 1H), 3.64 (dd, J = 11.3, 4.3 Hz, 2H), 3.33-3.43 (m, 2H), 3.23-3.28 (m, 1H), 3.10- |

TABLE NO 1-continued

The following compounds were prepared analogue to the procedure described in schemes 1-17 or Examples 1 to 8.

| Compd. No. | Compound Name | Analytical data |
|---|---|---|
| | dihydroisoxazol-5-yl)-3-chlorophenyl)imino)(ethyl)(isopropyl)-l6-sulfanone | 3.18 (m, 1H), 2.86 (t, J = 12.4 Hz, 1H), 2.10 (t, J = 12.4 Hz, 2H), 1.74-1.83 (m, 1H), 1.53 (td, J = 12.0, 8.7 Hz, 1H), 1.21-1.30 (m, 4H), 1.14-1.20 (m, 3H), 1.01 (d, J = 6.7 Hz, 2H), 0.95 (t, J = 7.3 Hz, 1H); LCMS (M + 1): 725.25. |
| 238 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(ethyl)(isopropyl)-l6-sulfanone | $^1$H-NMR (400 MHz, DMSO-$d_6$) δ 7.96 (q, J = 3.1 Hz, 1H), 6.88-7.30 (m, 6H), 6.30 (t, J = 11.2 Hz, 1H), 5.44 (d, J = 16.8 Hz, 1H), 5.34 (d, J = 16.8 Hz, 1H), 4.35 (d, J = 13.1 Hz, 1H), 3.96 (d, J = 14.1 Hz, 1H), 3.64 (dd, J = 11.6, 4.3 Hz, 2H), 3.46-3.53 (m, 1H), 3.33-3.43 (m, 2H), 3.23-3.27 (m, 1H), 3.15 (tdd, J = 14.4, 7.2, 2.6 Hz, 1H), 2.84 (t, J = 12.4 Hz, 1H), 2.06-2.13 (m, 2H), 1.79 (dd, J = 20.9, 11.5 Hz, 1H), 1.56 (dd, J = 21.2, 11.2 Hz, 1H), 1.14-1.27 (m, 7H), 1.01 (d, J = 6.7 Hz, 1H), 0.96 (t, J = 7.3 Hz, 1H); LCMS (M + 1): 689.1 |
| 239 | ((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d. J = 2.4 Hz, 1H), 7.10-7.19 (m, 2H), 6.94 (td, J = 7.9, 1.5 Hz, 1H), 6.49 (s, 1H), 6.30 (t, J = 11.3 Hz, 1H), 5.33 (d, J = 17.1 Hz, 1H), 5.22 (d, J = 16.8 Hz, 1H), 4.37 (d, J = 13.1 Hz, 1H), 3.97 (d, J = 13.4 Hz, 1H), 3.64 (dd, J = 11.3, 4.3 Hz, 2H), 3.32-3.41 (m, 2H), 3.25 (d, J = 12.5 Hz, 1H), 3.16 (td, J = 14.7, 7.3 Hz, 1H), 2.84 (t, J = 12.4 Hz, 1H), 2.18 (t, J = 6.3 Hz, 3H), 2.08 (q, J = 11.8 Hz, 2H), 1.79 (q, J = 11.6 Hz, 1H), 1.51-1.60 (m, 1H), 0.94-1.27 (m, 10H); LCMS (M + 1): 671.1 |
| 240 | ((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d. J = 2.4 Hz, 1H), 7.09-7.19 (m, 2H), 6.94 (td, J = 7.9, 1.3 Hz, 1H), 6.30 (t, J = 11.0 Hz, 1H), 5.78 (s, 1H), 5.01 (d, J = 16.8 Hz, 1H), 4.92 (d, J = 16.8 Hz, 1H), 4.37 (d, J = 12.5 Hz, 1H), 4.01 (d, J = 13.8 Hz, 1H), 3.64 (dd, J = 11.5, 4.1 Hz, 2H), 3.45-3.52 (m, 1H), 3.31-3.40 (m, 2H), 3.11-3.27 (m, 2H), 2.80 (t, J = 12.4 Hz, 1H), 2.02-2.09 (m, 8H), 1.66-1.75 (m, 1H), 1.53 (dd, J = 21.2, 11.5 Hz, 1H), 1.26 (dd, J = 6.7, 1.5 Hz, 3H), 0.93-1.20 (m, 6H); LCMS (M + 1): 618 |
| 241 | ((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 8.55 (d, J = 2.4 Hz, 1H), 8.38 (d, J = 2.8 Hz, 1H), 7.96 (d, J = 2.8 Hz, 1H), 7.10-7.19 (m, 2H), 6.94 (td, J = 8.0, 1.4 Hz, 1H), 6.31 (t, J = 11.2 Hz, 1H), 5.35 (d, J = 14.4 Hz, 2H), 4.31 (d, J = 13.4 Hz, 1H), 3.88 (d, J = 13.4 Hz, 1H), 3.64 (dd, J = 11.6, 4.3 Hz, 2H), 3.46-3.53 (m, 1H), 3.33-3.42 (m, 2H), 3.10-3.27 (m, 2H), 2.91-3.00 (m, 1H), 2.81 (t, J = 12.4 Hz, 1H), 2.03-2.10 (m, 2H), 1.81 (dd, J = 21.2, 11.2 Hz, 1H), 1.53-1.59 (m, 1H), 1.26 (dd, J = 6.9, 2.0 Hz, 3H), 0.93-1.19 (m, 6H); LCMS (M + 1): 671.1 |
| 242 | ((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 8.39 (dd, J = 5.0, 1.1 Hz, 1H), 8.10 (dd, J = 7.6, 1.2 Hz, 1H), 7.96 (d, J = 2.8 Hz, 1H), 7.10-7.19 (m, 3H), 6.94 (td, J = 8.0, 1.2 Hz, 1H), 6.30 (t, J = 11.2 Hz, 1H), 5.24 (d, J = 15.0 Hz, 2H), 4.32 (d, J = 12.5 Hz, 1H), 3.91 (d, J = 13.1 Hz, 1H), 3.62-3.70 (m, 2H), 3.45-3.52 (m, 1H), 3.32-3.41 (m, 2H), 3.10-3.28 (m, 2H), 2.80 (t, J = 12.2 Hz, 1H), 2.03-2.09 (m, 2H), 1.82 (t, J = 11.0 Hz, 1H), 1.53-1.58 (m, 1H), 1.26 (dd, J = 7.0, 2.1 Hz, 3H), 0.93-1.19 (m, 6H); LCMS (M + 1): 684.15 |
| 243 | ((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d, J = 2.8 Hz. 1H), 7.62 (dd, J = 4.9, 1.5 Hz, 1H), 7.28 (dd, J = 7.9, 1.5 Hz, 1H), 7.10-7.19 (m, 2H), 6.89-6.96 (m, 2H), 6.30 (dd, J = 11.3, 10.7 Hz, 1H), 5.04-5.07 (m, 2H), 4.34 (d, J = 12.2 Hz, 1H), 3.92-3.97 (m, 1H), 3.79 (s, 3H), 3.60-3.66 (m, 2H), 3.46-3.52 (m, 1H), 3.32-3.41 (m, 2H), 3.10-3.28 (m, 2H), 2.79 (t, J = 12.2 Hz, 1H), 2.03-2.09 (m, 2H), 1.79-1.85 (m, 1H), 1.53 (d, J = 11.3 Hz, 1H), 1.26 (dd, J = 7.0, 2.1 Hz, 3H), 0.93-1.19 (m, 6H); LCMS (M + 1): 646.15 |
| 244 | ((2-(3-(4-(1-(2-(3,5-bis(trifluoromethyl)-1H-pyrazol-1-yl)acetyl)piperidin-4-yl)thiazol-2-yl)-4,5-dihydroisoxazol-5-yl)-3-fluorophenyl)imino)diethyl-l6-sulfanone | $^1$H-NMR (400 MHz, DMSO-$d_6$) δ 7.58 (s, 1H), 7.52 (s, 1H), 7.18 (td, J = 8.3, 6.9 Hz, 1H), 6.99 (d, J = 7.8 Hz, 1H), 6.71 (dd, J = 9.7, 8.4 Hz, 1H), 6.25 (dd, J = 12.3, 9.2 Hz, 1H), 5.57 (d, J = 17.4 Hz, 1H), 5.47 (d, J = 17.4 Hz, 1H), 4.34 (d, J = 11.7 Hz, 1H), 3.93 (d, J = 14.4 Hz, 1H), 3.75 (dd, J = 17.0, 12.8 Hz, 1H), 3.61 (q, J = 8.7 Hz, 1H), 3.15-3.29 (m, 4H), 3.05-3.13 (m, 2H), 2.77-2.83 (m, 1H), 2.01 (t, J = 15.3 Hz, 2H), 1.64-1.71 (m, 1H), 1.50 (t, J = 12.1 Hz, 1H), 1.17 (t, J = 7.3 Hz, 3H), 1.08 (t, J = 7.5 Hz, 3H); LCMS (M + 1): 695.05 |
| 245 | ((2-(3-(4-(1-(2-(3,5-bis(difluoromethyl)-1H-pyrazol-1-yl)acetyl)piperidin-4-yl)thiazol-2-yl)-4,5-dihydroisoxazol-5-yl)-3-fluorophenyl)imino)diethyl-l6-sulfanone | $^1$H-NMR (400 MHz, DMSO-$d_6$) δ 7.51 (s, 1H), 6.88-7.29 (m, 5H), 6.71 (dd, J = 9.5, 8.3 Hz, 1H), 6.25 (dd, J = 12.6, 9.2 Hz, 1H), 5.41 (d, J = 17.1 Hz, 1H), 5.33 (d, J = 17.1 Hz, 1H), 4.36 (d, J = 12.5 Hz, 1H), 3.94 (d, J = 13.7 Hz, 1H), 3.76 (dd, J = 17.2, 12.8 Hz, 1H), 3.61 (dd, J = 17.0, 9.2 Hz, 1H), 3.05-3.29 (m, 6H), 2.78 (dd, J = 12.6, 10.6 Hz, 1H), 1.97-2.04 (m, 2H), 1.65-1.72 (m, 1H), 1.48-1.55 (m, 1H), 1.17 (t, J = 7.3 Hz, 3H), 1.08 (t, J = 7.5 Hz, 3H); LCMS (M + 1): 659.1 |

TABLE NO 1-continued

The following compounds were prepared analogue to the procedure described in schemes 1-17 or Examples 1 to 8.

| Compd. No. | Compound Name | Analytical data |
|---|---|---|
| 246 | diethyl((3-fluoro-2-(3-(4-(1-(2-(5-methyl-3-(trifluoromethyl)-1H-pyrazol-1-yl)acetyl)piperidin-4-yl)thiazol-2-yl)-4,5-dihydroisoxazol-5-yl)phenyl)imino)-l6-sulfanone | $^1$H-NMR (400 MHz, DMSO-d$_6$) δ 7.51 (s, 1H), 7.15-7.21 (m, 1H), 6.99 (d, J = 8.1 Hz, 1H), 6.69-6.73 (m, 1H), 6.48 (s, 1H), 6.25 (dd, J = 12.7, 9.3 Hz, 1H), 5.30 (d, J = 16.9 Hz, 1H), 5.21 (d, J = 17.9 Hz, 1H), 4.38 (d, J = 12.2 Hz, 1H), 3.95 (d, J = 10.8 Hz, 1H), 3.76 (dd, J = 17.0, 12.3 Hz, 1H), 3.61 (dd, J = 17.0, 9.2 Hz, 1H), 3.05-3.27 (m, 6H), 2.75-2.81 (m, 1H), 2.19 (s, 3H), 1.97-2.04 (m, 2H), 1.64-1.76 (m, 1H), 1.46-1.57 (m, 1H), 1.17 (t, J = 7.3 Hz, 3H), 1.08 (t, J = 7.3 Hz, 3H); LCMS (M + 1): 641.1 |
| 247 | diethyl((3-fluoro-2-(3-(4-(1-(2-((3-methoxypyridin-2-yl)oxy)acetyl)piperidin-4-yl)thiazol-2-yl)-4,5-dihydroisoxazol-5-yl)phenyl)imino)-l6-sulfanone | $^1$H-NMR (400 MHz, DMSO-d$_6$) δ 7.60 (dd, J = 5.1, 1.5 Hz, 1H), 7.51 (s, 1H), 7.27 (dd, J = 7.8, 1.5 Hz, 1H), 7.15-7.21 (m, 1H), 6.99 (d, J = 8.1 Hz, 1H), 6.87-6.91 (m, 1H), 6.71 (dd, J = 9.5, 8.3 Hz, 1H), 6.25 (dd, J = 12.6, 9.2 Hz, 1H), 5.06 (s, 2H), 4.36 (d, J = 13.4 Hz, 1H), 3.91 (d, J = 12.2 Hz, 1H), 3.72-3.80 (m, 4H), 3.61 (dd, J = 17.1, 9.0 Hz, 1H), 3.02-3.28 (m, 6H), 2.70-2.75 (m, 1H), 1.94-2.00 (m, 2H), 1.67-1.73 (m, 1H), 1.46-1.52 (m, 1H), 1.17 (t, J = 7.3 Hz, 3H), 1.07 (t, J = 7.3 Hz, 3H); LCMS (M + 1): 616.1 |
| 248 | diethyl((3-fluoro-2-(3-(4-(1-(2-((3-(trifluoromethyl)pyridin-2-yl)oxy)acetyl)piperidin-4-yl)thiazol-2-yl)-4,5-dihydroisoxazol-5-yl)phenyl)imino)-l6-sulfanone | $^1$H-NMR (400 MHz, DMSO-d$_6$) δ 8.37 (d, J = 3.9 Hz, 1H), 8.10 (d, J = 7.6 Hz, 1H), 7.51 (s, 1H), 7.13-7.21 (m, 2H), 6.99 (d, J = 8.1 Hz, 1H), 6.69-6.73 (m, 1H), 6.25 (dd, J = 12.6, 9.2 Hz, 1H), 5.25 (d, J = 3.4 Hz, 2H), 4.33 (d, J = 12.2 Hz, 1H), 3.89 (d, J = 13.0 Hz, 1H), 3.76 (dd, J = 16.9, 12.7 Hz, 1H), 3.61 (dd, J = 17.0, 9.2 Hz, 1H), 3.03-3.26 (m, 6H), 2.70-2.76 (m, 1H), 1.95 (d, J = 13.0 Hz, 2H), 1.71 (s, 1H), 1.51 (s, 1H), 1.17 (t, J = 7.3 Hz, 4H), 1.07 (t, J = 7.5 Hz, 3H); LCMS (M + 1): 654.1 |
| 249 | diethyl((3-fluoro-2-(3-(4-(1-(2-((3-(trifluoromethyl)pyrazin-2-yl)oxy)acetyl)piperidin-4-yl)thiazol-2-yl)-4,5-dihydroisoxazol-5-yl)phenyl)imino)-l6-sulfanone | $^1$H-NMR (400 MHz, DMSO-d$_6$) δ 8.53 (d, J = 2.0 Hz, 1H), 8.38 (d, J = 2.4 Hz, 1H), 7.51 (s, 1H), 7.15-7.21 (m, 1H), 6.99 (d, J = 7.8 Hz, 1H), 6.71 (dd, J = 9.5, 8.3 Hz, 1H), 6.25 (dd, J = 12.5, 9.0 Hz, 1H), 5.35 (s, 2H), 4.31 (d, J = 11.7 Hz, 1H), 3.86 (d, J = 15.9 Hz, 1H), 3.76 (dd, J = 17.1, 12.5 Hz, 1H), 3.61 (dd, J = 17.0, 9.2 Hz, 1H), 3.04-3.27 (m, 6H), 2.71-2.77 (m, 1H), 1.94-2.02 (m, 2H), 1.71 (d, J = 11.7 Hz, 1H), 1.50 (s, 1H), 1.17 (t, J = 7.5 Hz, 3H), 1.08 (t, J = 7.5 Hz, 3H); LCMS (M + 1): 655.05 |
| 250 | 1-(2-(4-(2-(5-(2-((diethyl(oxo)-l6-sulfaneylidene)amino)-6-fluorophenyl)-4,5-dihydroisoxazol-3-yl)thiazol-4-yl)piperidin-1-yl)-2-oxoethyl)-3-(trifluoromethyl)pyridin-2(1H)-one | $^1$H-NMR (400 MHz, DMSO-d$_6$) δ 7.94 (d, J = 7.3 Hz, 1H), 7.90-7.91 (m, 1H), 7.52 (s, 1H), 7.18 (td, J = 8.2, 6.8 Hz, 1H), 6.99 (d, J = 7.8 Hz, 1H), 6.71 (dd, J = 9.5, 8.3 Hz, 1H), 6.37 (t, J = 7.0 Hz, 1H), 6.25 (dd, J = 12.5, 9.0 Hz, 1H), 4.93 (dd, J = 19.1, 16.6 Hz, 2H), 4.32-4.39 (m, 1H), 3.99 (d, J = 12.5 Hz, 1H), 3.76 (dd, J = 16.8, 12.6 Hz, 1H), 3.61 (dd, J = 16.9, 9.0 Hz, 1H), 3.06-3.29 (m, 6H), 2.76-2.81 (m, 1H), 2.02 (q, J = 13.1 Hz, 2H), 1.65-1.74 (m, 1H), 1.48-1.55 (m, 1H), 1.17 (t, J = 7.3 Hz, 3H), 1.03-1.10 (m, 3H); LCMS (M + 1): 654.1 |
| 251 | ((3-fluoro-2-(3-(2-(1-(2-((6-methoxypyrimidin-4-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, CHLOROFORM-D) δ 8.42 (s, 1H), 7.47 (s, 1H), 7.16 (td, J = 8.1, 6.3 Hz, 1H), 7.08 (d, J = 7.9 Hz, 1H), 6.71-6.76 (m, 1H), 6.24 (s, 1H), 6.18 (dd, J = 12.2, 9.2 Hz, 1H), 5.09 (d, J = 1.8 Hz, 2H), 4.64 (d, J = 14.1 Hz, 1H), 3.92 (t, J = 14.1 Hz, 4H), 3.80 (q, J = 8.6 Hz, 1H), 3.58 (dd, J = 16.5, 12.2 Hz, 1H), 3.25-3.38 (m, 2H), 3.09 (d, J = 9.8 Hz, 3H), 2.92 (d, J = 13.4 Hz, 3H), 2.85 (t, J = 12.2 Hz, 1H), 2.16-2.25 (m, 2H), 1.89 (d, J = 11.6 Hz, 2H); LCMS (M + 1): 589.1 |
| 252 | ((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diiso-butyl-l6-sulfanone | $^1$H-NMR (400 MHz, DMSO-d$_6$) δ 7.98 (d, J = 7.3 Hz, 1H), 7.59 (s, 1H), 7.16 (td, J = 8.2, 6.8 Hz, 1H), 7.01 (d, J = 7.8 Hz, 1H), 6.67-6.72 (m, 1H), 6.09 (dd, J = 12.0, 9.8 Hz, 1H), 5.60 (d, J = 17.1 Hz, 1H), 5.49 (d, J = 17.1 Hz, 1H), 4.34 (d, J = 12.7 Hz, 1H), 3.96 (d, J = 13.7 Hz, 1H), 3.54-3.68 (m, 2H), 3.36-3.43 (m, 1H), 3.24-3.27 (m, 1H), 3.07-3.19 (m, 3H), 2.90-2.97 (m, 1H), 2.82-2.88 (m, 1H), 2.06-2.22 (m, 4H), 1.79 (t, J = 12.3 Hz, 1H), 1.47-1.57 (m, 1H), 0.88-0.99 (m, 9H), 0.77 (d, J = 6.6 Hz, 3H); LCMS (M + 1): 751.1 |
| 253 | ((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diiso-butyl-l6-sulfanone | $^1$H-NMR (400 MHz, DMSO-d$_6$) δ 8.00 (d, J = 7.8 Hz, 1H), 7.18 (td, J = 8.2, 6.8 Hz, 1H), 7.03 (d, J = 7.6 Hz, 1H), 6.71 (dd, J = 9.5, 8.3 Hz, 1H), 6.51 (s, 1H), 6.11 (dd, J = 12.1, 9.9 Hz, 1H), 5.35 (d, J = 17.1 Hz, 1H), 5.24 (d, J = 16.9 Hz, 1H), 4.39 (d, J = 13.4 Hz, 1H), 3.99 (d, J = 14.2 Hz, 1H), 3.56-3.70 (m, 2H), 3.40 (qd, J = 7.6, 3.7 Hz, 1H), 3.27 (d, J = 11.7 Hz, 1H), 3.09-3.21 (m, 3H), 2.93-2.99 (m, 1H), 2.82-2.88 (m, 1H), 2.08-2.22 (m, 7H), 1.82 (t, J = 12.6 Hz, 1H), 1.55-1.66 (m, 1H), 0.94-0.98 (m, 9H), 0.77-0.81 (m, 3H); LCMS (M + 1): 697.1 |
| 254 | ((2-(3-(2-(1-(2-(3,5-dimethyl-1H-pyrazol-1-yl)acetyl)piperidin-4-yl)thiazol-4-yl)-4,5- | $^1$H-NMR (400 MHz, DMSO-d$_6$) δ 7.98 (s, 1H), 7.13-7.19 (m, 1H), 7.01 (d, J = 7.6 Hz, 1H), 6.67-6.72 (m, 1H), 6.09 (dd, J = 12.0, 9.8 Hz, 1H), 5.78 (s, 1H), 5.01 (d, J = 16.9 Hz, 1H), 4.92 (d, J = 16.6 Hz, 1H), 4.37 (d, J = 13.2 Hz, 1H), 4.01 (d, J = 13.9 Hz, 1H), 3.53- |

TABLE NO 1-continued

The following compounds were prepared analogue to the procedure described in schemes 1-17 or Examples 1 to 8.

| Compd. No. | Compound Name | Analytical data |
|---|---|---|
| | dihydroisoxazol-5-yl)-3-fluorophenyl)imino)diiso-butyl-l6-sulfanone | 3.68 (m, 2H), 3.35-3.41 (m, 1H), 3.07-3.26 (m, 4H), 2.91-2.97 (m, 1H), 2.76-2.82 (m, 1H), 2.16 (td, J = 13.1, 6.6 Hz, 2H), 2.07 (d, J = 16.9 Hz, 8H), 1.71 (d, J = 12.7 Hz, 1H), 1.50-1.53 (m, 1H), 0.92-0.96 (m, 9H), 0.77 (d, J = 6.6 Hz, 3H); LCMS (M + 1): 643.1 |
| 255 | ((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diiso-butyl-l6-sulfanone | $^1$H-NMR (400 MHz, DMSO-$d_6$) δ 7.98 (d, J = 6.4 Hz, 1H), 6.88-7.30 (m, 6H), 6.67-6.72 (m, 1H), 6.09 (dd, J = 12.0, 9.8 Hz, 1H), 5.44 (d, J = 17.4 Hz, 1H), 5.34 (d, J = 17.1 Hz, 1H), 4.35 (d, J = 13.0 Hz, 1H), 3.97 (d, J = 13.4 Hz, 1H), 3.54-3.68 (m, 2H), 3.38-3.42 (m, 1H), 3.08-3.19 (m, 3H), 2.92-2.97 (m, 1H), 2.83 (t, J = 11.6 Hz, 1H), 2.05-2.21 (m, 4H), 1.78 (d, J = 12.0 Hz, 1H), 1.53-1.56 (m, 1H), 0.91-0.99 (m, 9H), 0.76-0.79 (m, 3H); LCMS (M + 1): 715.05 |
| 256 | ((2-(3-(2-(1-(2-(4-chloro-1H-pyrazol-1-yl)acetyl)piperidin-4-yl)thiazol-4-yl)-4,5-dihydroisoxazol-5-yl)-3-fluorophenyl)imino)diiso-butyl-l6-sulfanone | $^1$H-NMR (400 MHz, DMSO-$d_6$) δ 7.98 (s, 1H), 7.87 (d, J = 0.7 Hz, 1H), 7.51 (d, J = 0.7 Hz, 1H), 7.16 (td, J = 8.1, 6.8 Hz, 1H), 7.00 (d, J = 7.6 Hz, 1H), 6.69 (dd, J = 9.5, 8.3 Hz, 1H), 6.09 (dd, J = 12.0, 9.8 Hz, 1H), 5.15 (dd, J = 30.8, 16.4 Hz, 2H), 4.37 (d, J = 13.2 Hz, 1H), 3.96 (d, J = 13.4 Hz, 1H), 3.53-3.68 (m, 2H), 3.34-3.41 (m, 1H), 3.08-3.26 (m, 4H), 2.94 (dd, J = 14.1, 6.2 Hz, 1H), 2.80 (t, J = 11.4 Hz, 1H), 2.06-2.21 (m, 4H), 1.74 (d, J = 11.2 Hz, 1H), 1.52-1.58 (m, 1H), 0.92-0.96 (m, 10H), 0.75-0.78 (m, 3H); LCMS (M + 1): 649.05 |
| 257 | ((3-fluoro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)diiso-butyl-l6-sulfanone | $^1$H-NMR (400 MHz, DMSO-$d_6$) δ 7.97 (d, J = 7.8 Hz, 1H), 7.39 (s, 1H), 7.13-7.20 (m, 2H), 7.01 (d, J = 7.8 Hz, 1H), 6.69 (dd, J = 9.5, 8.3 Hz, 1H), 6.09 (dd, J = 12.2, 9.8 Hz, 1H), 5.05 (dd, J = 30.6, 16.1 Hz, 2H), 4.37 (d, J = 13.4 Hz, 1H), 3.99 (d, J = 13.9 Hz, 1H), 3.53-3.68 (m, 2H), 3.34-3.41 (m, 1H), 3.07-3.24 (m, 4H), 2.91-2.97 (m, 1H), 2.76-2.81 (m, 1H), 2.16 (qd, J = 13.1, 6.6 Hz, 2H), 2.05 (d, J = 12.5 Hz, 2H), 2.00 (s, 3H), 1.70 (t, J = 11.6 Hz, 1H), 1.50-1.58 (m, 1H), 0.92-0.98 (m, 9H), 0.77 (t, J = 6.7 Hz, 3H); LCMS (M + 1): 629.1 |
| 258 | ((2-(3-(2-(1-(2-(2H-indazol-2-yl)acetyl)piperidin-4-yl)thiazol-4-yl)-4,5-dihydroisoxazol-5-yl)-3-fluorophenyl)imino)diiso-butyl-l6-sulfanone | $^1$H-NMR (400 MHz, DMSO-$d_6$) δ 8.29 (d, J = 1.0 Hz, 1H), 7.99 (s, 1H), 7.70 (dt, J = 8.4, 1.0 Hz, 1H), 7.56 (dd, J = 8.7, 0.9 Hz, 1H), 7.14-7.23 (m, 2H), 6.99-7.03 (m, 2H), 6.67-6.72 (m, 1H), 6.10 (dd, J = 12.0, 9.8 Hz, 1H), 5.50 (dd, J = 27.1, 15.9 Hz, 2H), 4.39 (d, J = 13.2 Hz, 1H), 4.08 (d, J = 13.2 Hz, 1H), 3.54-3.68 (m, 2H), 3.38-3.43 (m, 1H), 3.26 (s, 1H), 3.08-3.19 (m, 3H), 2.94 (dd, J = 13.9, 6.1 Hz, 1H), 2.81-2.88 (m, 1H), 2.06-2.23 (m, 4H), 1.73-1.83 (m, 1H), 1.51-1.64 (m, 1H), 0.88-0.99 (m, 9H), 0.78 (d, J = 6.6 Hz, 3H); LCMS (M + 1): 665.1 |
| 259 | ((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diiso-butyl-l6-sulfanone | $^1$H-NMR (400 MHz, DMSO-$d_6$) δ 8.38-8.39 (m, 1H), 8.10 (dd, J = 7.6, 1.0 Hz, 1H), 7.97 (d, J = 7.8 Hz, 1H), 7.14-7.19 (m, 2H), 7.01 (d, J = 7.6 Hz, 1H), 6.67-6.72 (m, 1H), 6.09 (dd, J = 12.2, 9.8 Hz, 1H), 5.26 (s, 2H), 4.33 (d, J = 13.0 Hz, 1H), 3.91 (d, J = 13.4 Hz, 1H), 3.54-3.68 (m, 2H), 3.34-3.41 (m, 1H), 3.21-3.27 (m, 1H), 3.07-3.19 (m, 3H), 2.91-2.97 (m, 1H), 2.79 (t, J = 12.0 Hz, 1H), 2.12-2.22 (m, 2H), 2.02-2.11 (m, 2H), 1.79-1.86 (m, 1H), 1.48-1.57 (m, 1H), 0.92-0.99 (m, 9H), 0.77 (d, J = 6.8 Hz, 3H); LCMS (M + 1): 710.1 |
| 260 | ((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diisobutyl-l6-sulfanone | $^1$H-NMR (400 MHz, DMSO-$d_6$) δ 7.97 (d, J = 7.8 Hz, 1H), 7.39 (s, 1H), 7.13-7.20 (m, 2H), 7.01 (d, J = 7.8 Hz, 1H), 6.69 (dd, J = 9.5, 8.3 Hz, 1H), 6.09 (dd, J = 12.2, 9.8 Hz, 1H), 5.05 (dd, J = 30.6, 16.1 Hz, 2H), 4.37 (d, J = 13.4 Hz, 1H), 3.99 (d, J = 13.9 Hz, 1H), 3.53-3.68 (m, 2H), 3.34-3.41 (m, 1H), 3.07-3.24 (m, 4H), 2.91-2.97 (m, 1H), 2.76-2.81 (m, 1H), 2.16 (qd, J = 13.1, 6.6 Hz, 2H), 2.05 (d, J = 12.5 Hz, 2H), 2.00 (s, 3H), 1.70 (t, J = 11.6 Hz, 1H), 1.50-1.58 (m, 1H), 0.92-0.98 (m, 9H), 0.77 (t, J = 6.7 Hz, 3H); LCMS (M + 1): 672.1 |
| 261 | ((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diiso-butyl-l6-sulfanone | $^1$H-NMR (400 MHz, DMSO-$d_6$) δ 8.54-8.55 (m, 1H), 8.38 (d, J = 2.7 Hz, 1H), 7.97 (d, J = 7.8 Hz, 1H), 7.13-7.19 (m, 1H), 7.01 (d, J = 7.8 Hz, 1H), 6.67-6.72 (m, 1H), 6.09 (dd, J = 12.1, 9.7 Hz, 1H), 5.37 (s, 2H), 4.31 (d, J = 13.2 Hz, 1H), 3.88 (d, J = 13.4 Hz, 1H), 3.54-3.68 (m, 2H), 3.38 (qd, J = 7.7, 3.6 Hz, 1H), 3.24 (t, J = 12.1 Hz, 1H), 3.08-3.19 (m, 3H), 2.94 (dd, J = 13.9, 6.4 Hz, 1H), 2.80 (t, J = 11.7 Hz, 1H), 2.13-2.22 (m, 2H), 2.06 (t, J = 13.9 Hz, 2H), 1.79-1.85 (m, 1H), 1.50-1.64 (m, 1H), 0.88-0.99 (m, 9H), 0.77 (t, J = 6.8 Hz, 3H); LCMS (M + 1): 711.1 |
| 262 | ((3-fluoro-2-(3-(2-(1-(2-((2-(trifluoromethyl)pyridin-3-yl)oxy)acetyl)piperidin-4-yl)thiazol-4-yl)-4,5-dihydroisoxazol-5-yl)phenyl)imino)dimethyl-l6-sulfanone | $^1$H-NMR (400 MHz, CHLOROFORM-D) δ 8.31 (d, J = 4.6 Hz, 1H), 7.56 (d, J = 8.6 Hz, 1H), 7.45-7.49 (m, 2H), 7.16 (td, J = 8.1, 6.4 Hz, 1H), 7.08 (d, J = 7.8 Hz, 1H), 6.70-6.75 (m, 1H), 6.17 (dd, J = 12.5, 9.0 Hz, 1H), 4.86 (dd, J = 17.4, 13.4 Hz, 2H), 4.59 (d, J = 13.4 Hz, 1H), 4.18 (d, J = 13.7 Hz, 1H), 3.78 (dd, J = 16.5, 9.2 Hz, 1H), 3.56 (dd, J = 16.6, 12.5 Hz, 1H), 3.25-3.35 (m, 2H), 3.08 (d, J = 11.0 Hz, 3H), 2.83-2.93 (m, 4H), 2.18 (d, J = 13.7 Hz, 2H), 1.71-1.82 (m, 2H); LCMS (M + 1): 626 |

TABLE NO 1-continued

The following compounds were prepared analogue to the procedure described in schemes 1-17 or Examples 1 to 8.

| Compd. No. | Compound Name | Analytical data |
|---|---|---|
| 263 | ((2-(3-(2-(1-(2-(1H-pyrazol-1-yl)acetyl)piperidin-4-yl)thiazol-4-yl)-4,5-dihydroisoxazol-5-yl)-3-chlorophenyl)imino)(ethyl)(isopropyl)-l6-sulfanone | $^1$H-NMR (400 MHz, DMSO-$d_6$) δ 7.96 (d, J = 2.7 Hz, 1H), 7.64-7.65 (m, 1H), 7.41 (t, J = 0.9 Hz, 1H), 7.10-7.19 (m, 2H), 6.94 (td, J = 8.0, 1.3 Hz, 1H), 6.30 (t, J = 11.4 Hz, 1H), 6.24 (t, J = 2.0 Hz, 1H), 5.09-5.21 (m, 2H), 4.38 (d, J = 13.2 Hz, 1H), 4.00 (d, J = 13.9 Hz, 1H), 3.64 (dd, J = 11.5, 4.2 Hz, 2H), 3.33-3.41 (m, 2H), 3.11-3.29 (m, 3H), 2.81 (t, J = 12.1 Hz, 1H), 2.02-2.08 (m, 2H), 1.65-1.74 (m, 1H), 1.55 (t, J = 11.7 Hz, 1H), 1.21-1.35 (m, 3H), 1.13-1.20 (m, 3H), 1.00 (d, J = 6.6 Hz, 2H), 0.95 (t, J = 7.3 Hz, 1H); LCMS (M + 1): 589.05 |
| 264 | ((3-chloro-2-(3-(2-(1-(2-(3-(trifluoromethyl)-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d, J = 2.9 Hz, 1H), 7.88 (q, J = 1.1 Hz, 1H), 7.10-7.19 (m, 2H), 6.94 (td, J = 7.9, 1.4 Hz, 1H), 6.71 (dd, J = 2.4, 0.5 Hz, 1H), 6.30 (t, J = 11.2 Hz, 1H), 5.33 (dd, J = 32.2, 16.5 Hz, 2H), 4.38 (d, J = 13.0 Hz, 1H), 3.95 (d, J = 13.9 Hz, 1H), 3.64 (dd, J = 11.5, 4.2 Hz, 2H), 3.46-3.53 (m, 1H), 3.33-3.42 (m, 1H), 3.11-3.29 (m, 2H), 2.96 (dt, J = 21.3, 7.3 Hz, 1H), 2.83 (t, J = 12.5 Hz, 1H), 2.10 (d, J = 9.5 Hz, 2H), 1.72-1.82 (m, 1H), 1.51-1.60 (m, 1H), 1.22-1.35 (m, 3H), 1.13-1.21 (m, 3H), 1.00-1.06 (m, 2H), 0.95 (t, J = 7.3 Hz, 1H); LCMS (M + 1): 657 |
| 265 | ((3-chloro-2-(3-(2-(1-(2-((6-methyl-3-(trifluoromethyl)pyridin-2-yl)oxy)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.94-7.97 (m, 2H), 7.10-7.19 (m, 2H), 6.85-7.03 (m, 2H), 6.30 (t, J = 11.2 Hz, 1H), 5.06-5.27 (m, 2H), 4.35 (d, J = 12.5 Hz, 1H), 3.94 (d, J = 13.0 Hz, 1H), 3.64 (dd, J = 11.2, 4.4 Hz, 2H), 3.46-3.53 (m, 1H), 3.37-3.43 (m, 1H), 3.10-3.29 (m, 3H), 2.93-3.00 (m, 1H), 2.77-2.84 (m, 1H), 2.40 (d, J = 9.0 Hz, 2H), 2.06 (d, J = 16.6 Hz, 2H), 1.81 (d, J = 12.5 Hz, 1H), 1.59 (d, J = 37.2 Hz, 1H), 1.21-1.35 (m, 3H), 1.13-1.19 (m, 3H), 1.00 (d, J = 6.6 Hz, 2H), 0.95 (t, J = 7.2 Hz, 1H); LCMS (M + 1): 698 |
| 266 | ((3-chloro-2-(3-(2-(1-(2-(4-chloro-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d, J = 2.9 Hz, 1H), 7.87 (d, J = 0.7 Hz, 1H), 7.51 (d, J = 0.7 Hz, 1H), 7.10-7.19 (m, 2H), 6.94 (td, J = 7.9, 1.4 Hz, 1H), 6.30 (t, J = 11.2 Hz, 1H), 5.16 (dd, J = 30.1, 16.6 Hz, 2H), 4.37 (d, J = 13.4 Hz, 1H), 3.96 (d, J = 13.4 Hz, 1H), 3.64 (dd, J = 11.5, 4.2 Hz, 2H), 3.46-3.52 (m, 1H), 3.33-3.41 (m, 1H), 3.11-3.29 (m, 2H), 2.96 (q, J = 7.0 Hz, 1H), 2.78-2.85 (m, 1H), 2.07 (s, 2H), 1.70-1.79 (m, 1H), 1.50-1.59 (m, 1H), 1.13-1.29 (m, 6H), 1.00 (d, J = 5.6 Hz, 2H), 0.95 (t, J = 7.3 Hz, 1H); LCMS (M + 1): 623 |
| 267 | ((3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d, J = 2.9 Hz, 1H), 7.39 (s, 1H), 7.10-7.20 (m, 3H), 6.94 (td, J = 7.9, 1.4 Hz, 1H), 6.30 (t, J = 11.2 Hz, 1H), 5.05 (dd, J = 30.1, 16.4 Hz, 2H), 4.37 (d, J = 11.5 Hz, 1H), 3.99 (d, J = 14.2 Hz, 1H), 3.64 (dd, J = 11.5, 4.2 Hz, 2H), 3.34-3.39 (m, 1H), 3.13-3.24 (m, 2H), 2.95 (q, J = 7.0 Hz, 1H), 2.80 (t, J = 12.3 Hz, 1H), 2.06 (d, J = 12.5 Hz, 2H), 2.00 (s, 3H), 1.67-1.70 (m, 1H), 1.53 (d, J = 12.0 Hz, 1H), 1.26 (dd, J = 6.7, 1.8 Hz, 3H), 1.13-1.19 (m, 3H), 1.00 (d, J = 6.6 Hz, 2H), 0.95 (t, J = 7.3 Hz, 2H); LCMS (M + 1): 603.05 |
| 268 | 1-(2-(4-(4-(5-(2-chloro-6-((ethyl(isopropyl)(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one | $^1$H-NMR (400 MHz, DMSO-$d_6$) δ 7.91-7.97 (m, 3H), 7.10-7.19 (m, 2H), 6.94 (td, J = 7.9, 1.3 Hz, 1H), 6.38 (t, J = 7.0 Hz, 1H), 6.30 (t, J = 11.1 Hz, 1H), 4.93 (d, J = 15.2 Hz, 2H), 4.37 (d, J = 14.2 Hz, 1H), 4.01 (d, J = 13.4 Hz, 1H), 3.64 (dd, J = 11.5, 4.2 Hz, 2H), 3.38-3.44 (m, 1H), 3.35 (s, 1H), 3.28 (d, J = 11.5 Hz, 1H), 3.16 (td, J = 14.3, 7.2 Hz, 1H), 2.85 (t, J = 12.2 Hz, 1H), 2.06-2.15 (m, 2H), 1.77-1.84 (m, 1H), 1.51-1.60 (m, 1H), 1.25-1.33 (m, 3H), 1.13-1.20 (m, 3H), 1.01 (d, J = 6.4 Hz, 2H), 0.95 (t, J = 7.2 Hz, 1H); LCMS (M + 1): 684 |
| 269 | ((3-chloro-2-(3-(2-(1-(2-(4-chloro-3,5-dimethyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone | $^1$H-NMR (400 MHz, DMSO-$d_6$) δ 7.96 (d. J = 2.7 Hz, 1H), 7.10-7.19 (m, 2H), 6.94 (td, J = 7.9, 1.3 Hz, 1H), 6.30 (t, J = 11.4 Hz, 1H), 5.12 (d, J = 16.9 Hz, 1H), 5.03 (d, J = 17.1 Hz, 1H), 4.35 (d, J = 13.7 Hz, 1H), 3.97 (d, J = 14.4 Hz, 1H), 3.64 (dd, J = 11.6, 4.0 Hz, 2H), 3.49 (t, J = 6.8 Hz, 2H), 3.36-3.40 (m, 1H), 3.13-3.24 (m, 3H), 2.81 (t, J = 12.5 Hz, 1H), 2.08 (d, J = 9.3 Hz, 9H), 1.76 (d, J = 11.7 Hz, 1H), 1.54 (d, J = 11.7 Hz, 1H), 1.26 (dd, J = 7.0, 1.8 Hz, 3H), 1.13-1.20 (m, 3H), 1.01 (d, J = 6.6 Hz, 2H), 0.95 (t, J = 7.3 Hz, 1H); LCMS (M + 1): 651 |

* Compound names generated using Chemdraw Professional 19.1

As described herein, the compounds of general formula (I) show fungicidal activities which are exerted with respect to numerous phytopathogenic fungi which attack on important agricultural crops. The compounds of the present invention were assessed for their activity as described in the following tests:

BIOLOGY EXAMPLES

*Phytophthora infestans* (Late Blight of Potato & Tomato):

IN VITRO TEST: The compounds were dissolved in 0.3% dimethyl sulfoxide and then added to Rye Agar medium just prior to dispensing it into petri dishes. 5 mL medium with the compound in the desired test concentration was dispensed into 60 mm sterile petri-plates. After solidification, each plate was seeded with a 5 mm size mycelial disc taken from the periphery of an actively growing virulent culture plate. Plates were incubated in growth chambers at 18° C. temperature and 95% relative humidity for seven days and the radial growth was measured and compared to the one of the untreated control.

| Compounds | 1 | 2 | 3 | 4 | 5 | 6 | 7 | 8 |
|---|---|---|---|---|---|---|---|---|
| 11 | 13 | 14 | 16 | 17 | 18 | 19 | 20 | 21 |
| 22 | 23 | 24 | 27 | 28 | 30 | 31 | 32 | 33 |
| 34 | 35 | 36 | 37 | 38 | 39 | 40 | 41 | 42 |
| 43 | 44 | 45 | 46 | 47 | 48 | 49 | 50 | 51 |
| 55 | 56 | 57 | 58 | 61 | 62 | 63 | 64 | 65 |
| 66 | 67 | 68 | 69 | 70 | 71 | 72 | 73 | 74 |
| 75 | 76 | 77 | 78 | 79 | 80 | 82 | 83 | 84 |
| 85 | 86 | 87 | 88 | 89 | 90 | 91 | 92 | 93 |
| 94 | 95 | 96 | 97 | 98 | 99 | 100 | 101 | 102 |
| 103 | 104 | 105 | 106 | 107 | 108 | 109 | 110 | 111 |
| 112 | 113 | 114 | 115 | 116 | 117 | 118 | 119 | 120 |
| 121 | 122 | 123 | 124 | 125 | 126 | 127 | 128 | 129 |
| 130 | 131 | 132 | 133 | 135 | 136 | 137 | 138 | 139 |
| 141 | 142 | 143 | 144 | 146 | 147 | 148 | 149 | 150 |
| 151 | 152 | 153 | 154 | 155 | 156 | 157 | 158 | 160 |
| 161 | 162 | 164 | 165 | 166 | 169 | 171 | 173 | 174 |
| 175 | 176 | 177 | 178 | 179 | 181 | 182 | 183 | 184 |
| 186 | 187 | 188 | 189 | 190 | 191 | 196 | 197 | 198 |
| 199 | 201 | 202 | 203 | 204 | 205 | 206 | 207 | 208 |
| 209 | 211 | 212 | 213 | 214 | 215 | 216 | 217 | 218 |
| 219 | 220 | 221 | 222 | 226 | 227 | 228 | 229 | 230 |
| 232 | 233 | 234 | 235 | 239 | 240 | 241 | 242 | 243 |
| 244 | 245 | | | | | | | |

at 30 ppm gave equal to or more than 70% control in these tests when compared to the untreated check which showed extensive disease development.

GREENHOUSE

Example A: *Phytophthora infestans* Test in Tomato

The compounds were dissolved in 2% dimethyl sulfoxide/acetone and then mixed with water containing emulsifier to a calibrated spray volume of 50 mL. The test solutions were poured into spray bottles for further applications.

To test the preventive activity of compounds, healthy young tomato plants, raised in the greenhouse were sprayed with the active compound preparation at the stated application rates inside the spray cabinets using hollow cone nozzles. One day after treatment, the plants were inoculated with a sporangial suspension (cold sterile water) containing $0.24\times10^6$ *Phytophthora infestans* inoculum. After inoculation, the plants were kept in darkness at 15° C. during 24 h, and then moved to a greenhouse chamber with 18° C. temperature and 95-100% relative humidity for disease expression.

A visual assessment of the performance of the compound was carried out by rating the disease severity (0-100% scale) on treated plants 3, 7, 10 and 15 days after application. Efficacy (% control) of the compound was calculated by comparing the disease rating in the treatment with the one of the untreated control. The compounds were also assessed for their plant compatibility by recording symptoms like necrosis, chlorosis and stunting.

| Componds | 3 | 4 | 5 | 6 | 7 | 14 | 19 |
|---|---|---|---|---|---|---|---|
| 20 | 21 | 26 | 31 | 32 | 33 | 40 | 41 |
| 42 | 45 | 49 | 50 | 51 | 55 | 57 | 61 |
| 65 | 66 | 67 | 68 | 69 | 70 | 71 | 72 |

-continued

| | | | | | | | |
|---|---|---|---|---|---|---|---|
| 73 | 75 | 82 | 83 | 84 | 85 | 86 | 99 |
| 100 | 102 | 104 | 105 | 108 | 109 | 110 | 111 |
| 112 | 113 | 114 | 115 | 116 | 117 | 118 | 119 |
| 120 | 121 | 122 | 123 | 124 | 125 | 126 | 127 |
| 128 | 129 | 130 | 131 | 132 | 133 | 135 | 136 |
| 137 | 138 | 139 | 140 | 141 | 142 | 143 | 144 |
| 147 | 148 | 149 | 150 | 151 | 152 | 154 | 155 |
| 156 | 157 | 158 | 160 | 172 | | | |

at 50 ppm gave equal to or more than 70% control in these tests when compared to the untreated check which showed extensive disease development.

Example B: *Plasmopara viticola* Test in Grape

The compound were dissolved in 2% DMSO/Acetone and then mixed with water containing emulsifier to a calibrated spray volume of 50 mL. The spray solutions were poured into spray bottles for further applications.

To test the preventive activity of compounds, 5 week old healthy grape seedlings, cv. Thompson seedless, raised in the greenhouse, were sprayed with the active compound preparation at the stated application rates inside spray cabinets using hallow cone nozzles. One day after treatment, the plants were inoculated with an inoculum suspension (sterile water) containing $6\times10^4$ *Plasmopara viticola* inoculum. The inoculated plants were then kept in a greenhouse chamber at 18-21° C. temperature and 95-100% relative humidity for disease expression.

A visual assessment of the performance of the compound was carried out by rating the disease severity (0-100% scale) on treated plants 3, 7 and 10 days after application. Efficacy (% control) of the compound was calculated by comparing the disease rating in the treatment with the one of the untreated control. The compounds were also assessed for their plant compatibility by recording symptoms like necrosis, chlorosis & stunting. Compounds 3 4 5 6 7 175 177 at 50 ppm gave equal to or more than 70% control in these tests when compared to the untreated check which showed extensive disease development.

Having described the invention with reference to certain preferred embodiments, other embodiments will become apparent to one skilled in the art from consideration of the specification. It will be apparent to those skilled in the art that many modifications, both to materials and methods, may be practiced without departing from the scope of the invention.

The invention claimed is:

1. A compound of formula (I),

Formula (I)

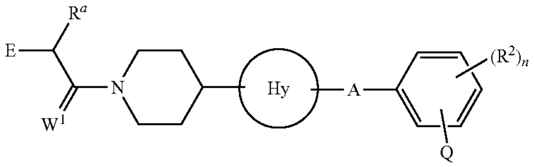

wherein,

E is selected from the group consisting of E-1 to E-3 and may be optionally substituted with one or more $R^1$;

E-1

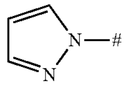

E-2

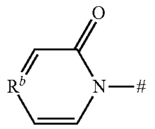

E-3

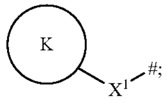

wherein, # indicates the point of attachment;

Hy is selected from the group consisting of Hy-1 and Hy-2;

Hy-1

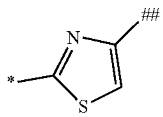

Hy-2

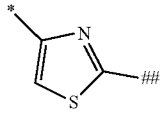

* indicates the point of attachment to piperidine;

indicates the point of attachment to A;

K represents a 5- or 6-membered heteroaryl ring containing one to three nitrogen heteroatoms;

$R^b$ is selected from atoms selected from C or N;

$R^a$ is selected from the group consisting of hydrogen and $C_1$-$C_4$ alkyl;

$R^1$ is selected from the group consisting of hydrogen, halogen, cyano, hydroxy, $C_1$-$C_6$ alkyl, $C_1$-$C_6$ alkoxy, $C_1$-$C_6$ alkylthio, $C_1$-$C_6$ alkylsulfonyl, $C_1$-$C_6$ alkylsulfinyl, $C_2$-$C_6$ alkenyl, $C_2$-$C_6$ alkynyl, $C_1$-$C_6$ haloalkyl, $C_1$-$C_6$ haloalkoxy, $C_2$-$C_6$ haloalkenyl, $C_2$-$C_6$ haloalkynyl and $C_3$-$C_6$ cycloalkyl; or two $R^1$ together with the atom to which they are attached or together with further atoms selected from the group consisting of C, N, O, S and optionally including 1 to 3 ring members selected from the group consisting of C(═O), C(═S), S(O)m and $Si(R')_2$ may form a five to six membered ring, which for its part may be substituted by one or more groups selected from the group consisting of halogen, cyano, $C_1$-$C_4$ alkyl, $C_1$-$C_3$ haloalkyl, $C_1$-$C_4$ alkoxy, $C_1$-$C_4$ alkylthio;

$X^1$ is selected from the group consisting of —O—, —$S(O)_{0-2}$—, —$NR^3$;

wherein, $R^3$ is selected from the group consisting of cyano, hydroxy, $C_1$-$C_6$ alkyl, $C_1$-$C_6$ alkoxy, and $C_3$-$C_6$ cycloalkyl, wherein $C_1$-$C_6$ alkyl, $C_1$-$C_6$ alkoxy, and $C_3$-$C_6$ cycloalkyl may optionally be substituted with one or more halogen;

$W^1$ is O or S;

A is $A^1$ $A^1$

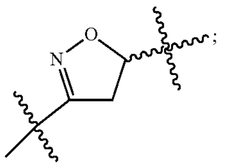

$R^2$ is selected from the group consisting of halogen, cyano, hydroxy, $C_1$-$C_6$ alkyl, $C_1$-$C_6$ alkoxy, $C_1$-$C_6$ alkylthio, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_3$-$C_6$ halocycloalkyl, $C_1$-$C_6$ alkylsulfinyl, and $C_1$-$C_6$ alkylsulfonyl;

n is an integer selected from 0 to 3;

Q is selected from, —$S(═O)_{0-1}(R^5)(═NR^4)$ or —N═S$(═O)_{0-1}(R^6)(R^7)$;

$R^4$ is selected from the group consisting of hydrogen, cyano, hydroxy, $C_1$-$C_4$ alkyl and $C_3$-$C_6$ cycloalkyl, $C_3$-$C_6$ cycloalkyl-$C_1$-$C_4$ alkyl, $C_1$-$C_4$ alkyl carbonyl and $C_1$-$C_4$ haloalkyl carbonyl;

$R^5$ and $R^6$ are independently selected from the group consisting of $C_1$-$C_4$ alkyl, $C_2$-$C_6$ alkenyl, $C_3$-$C_6$ cycloalkyl, $C_3$-$C_6$ cycloalkyl-$C_1$-$C_4$ alkyl, $C_1$-$C_4$ haloalkyl and $C_3$-$C_6$ halocycloalkyl;

$R^7$ is selected from the group consisting of $C_1$-$C_4$ alkyl, $C_2$-$C_6$ alkenyl, $C_3$-$C_6$ cycloalkyl, $C_3$-$C_6$ cycloalkyl-$C_1$-$C_4$ alkyl, $C_1$-$C_4$ haloalkyl, $C_3$-$C_6$ halocycloalkyl and phenyl; or $R^4$ or $R^5$ with the C atom contiguous to the C atom substituted with Q may form a 4- to 6-membered non-aromatic heterocyclic ring, which optionally contains one to three heteroatoms selected from N, O or $S(O)_{0-2}$, and wherein the C atoms of the heterocyclic ring may be optionally replaced by C(═O) or C(═S); or $R^6$ and $R^7$ together with the S atom to which they are attached may form a 4-to 6-membered non-aromatic heterocyclic ring, which optionally contains one to three heteroatoms selected from N, O or $S(O)_{0-2}$, and wherein the C atoms of the heterocyclic ring may be optionally replaced by C(═O) or C(═S); or $R^5$ or $R^6$ or $R^7$ with the $R^2$ may form a 4- to 6-membered non-aromatic heterocyclic ring which optionally contains one to three heteroatoms selected from N, O or $S(O)_{0-2}$, and wherein the C atoms of the heterocyclic ring may be optionally replaced by C(═O) or C(═S); or $R^6$ or $R^7$ with the C atom contiguous to the C atom substituted with Q may form a 4- to 6-membered non-aromatic heterocyclic ring which optionally contains one to three heteroatoms selected from N, O or $S(O)_{0-2}$, and wherein the C atoms of the heterocyclic ring may be optionally replaced by C(═O) or C(═S); wherein, said heterocyclic rings may be optionally substituted with the group consisting of halogen, cyano, $C_1$-$C_4$ alkyl, $C_3$-$C_6$ cycloalkyl, $C_1$-$C_4$ haloalkyl and $C_3$-$C_6$ halocycloalkyl;

or an agronomically acceptable salt, an N-oxide, or a stereoisomer thereof.

2. The compound of claim 1, wherein

W represents O.

3. The compound of claim 1, wherein,

K is selected from the group consisting of $K^1$ to $K^{14}$:

$K^1$

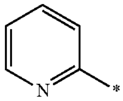

$K^2$

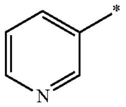

$K^3$

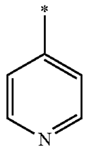

$K^4$

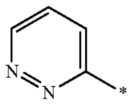

$K^5$

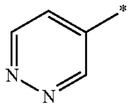

$K^6$

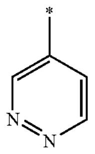

$K^7$

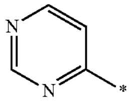

$K^8$

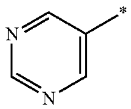

$K^9$

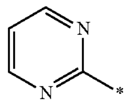

$K^{10}$

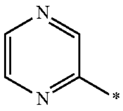

$K^{11}$

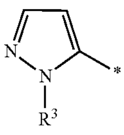

-continued $K^{12}$

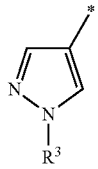

$K^{13}$

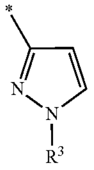

and $K^{14}$

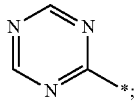

and * indicates a point of attachment.

4. The compound of claim 1, wherein said compound of formula (1) is selected from the group consisting of:

5-chloro-1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2 (1H)-one;

3-chloro-1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-5-(trifluoromethyl)pyridin-2 (1H)-one;

(2-(3-(2-(1-(2-(3,5-bis(difluoromethyl)-1H-pyrazol-1-yl) acetyl)piperidin-4-yl)thiazol-4-yl)-4,5-dihydroisoxazol-5-yl)-3-chlorophenyl)(imino)(methyl)-l6-sulfanone;

(3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(methyl)-l6-sulfanone;

(3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone;

((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)dimethyl-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)dimethyl-l6-sulfanone;

((3-fluoro-2-(3-(2-(1-(2-(4-methyl-1H-pyrazol-1-yl) acetyl)piperidin-4-yl)thiazol-4-yl)-4,5-dihydroisoxazol-5-yl)phenyl)imino)dimethyl-l6-sulfanone;

((2-(3-(2-(1-(2-(4-chloro-1H-pyrazol-1-yl)acetyl)piperidin-4-yl)thiazol-4-yl)-4,5-dihydroisoxazol-5-yl)-3-fluorophenyl)imino)dimethyl-l6-sulfanone;

((2-(3-(2-(1-(2-(2H-indazol-2-yl)acetyl)piperidin-4-yl) thiazol-4-yl)-4,5-dihydroisoxazol-5-yl)-3-fluorophenyl)imino)dimethyl-l6-sulfanone;

3-chloro-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-5-(trifluoromethyl)pyridin-2(1H)-one;

1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one;

((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)dimethyl-l6-sulfanone;

((3-fluoro-2-(3-(2-(1-(2-((6-methyl-3-(trifluoromethyl)pyridin-2-yl)oxy)acetyl)piperidin-4-yl)thiazol-4-yl)-4,5-dihydroisoxazol-5-yl)phenyl)imino)dimethyl-l6-sulfanone;

5-bromo-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-6-oxo-1,6-dihydropyridine-3-carbonitrile;

((3-(3-(2-(1-(2-(3,5-bis(difluoromethyl)-1H-pyrazol-1-yl)acetyl)piperidin-4-yl)thiazol-4-yl)-4,5-dihydroisoxazol-5-yl)phenyl)imino)dimethyl-l6-sulfanone;

dimethyl((3-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)-l6-sulfanone;

((3-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)dimethyl-l6-sulfanone;

1-(4-(4-((5S)-5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-((5R)-5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-(5-(6-fluoro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

2-(3,5-dimethyl-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one;

2-(5-methyl-3-(trifluoromethyl)-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-(5-(3-((1-oxidotetrahydro-1l6-thiophen-1-ylidene)amino)phenyl)-4,5-dihydroisoxazol-3-yl)thiazol-2-yl)piperidin-1-yl)ethan-1-one;

((2-(3-(2-(1-(2-(1H-pyrazol-1-yl)acetyl)piperidin-4-yl)thiazol-4-yl)-4,5-dihydroisoxazol-5-yl)-3-fluorophenyl)imino)dimethyl-l6-sulfanone;

2-(3,5-bis(difluoromethyl)-1H-pyrazol-1-yl)-1-(4-(4-(5-(2-fluoro-6-((1-oxidotetrahydro-1l6-thiophen-1-ylidene)amino)phenyl)-4,5-dihydroisoxazol-3-yl)thiazol-2-yl)piperidin-1-yl)ethan-1-one;

1-(4-(4-(5-(2-fluoro-6-((1-oxidotetrahydro-1l6-thiophen-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one;

3-bromo-5-chloro-1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)pyridin-2(1H)-one;

1-(2-(4-(4-(5-(2-((dimethyl(oxo)-l6-sulfaneylidene)amino)-6-fluorophenyl)-4,5-dihydroisoxazol-3-yl)thiazol-2-yl)piperidin-1-yl)-2-oxoethyl)-5-(trifluoromethyl)pyridin-2(1H)-one;

(3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)(imino)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)dimethyl-l6-sulfanone;

2-(3,5-bis(difluoromethyl)-1H-pyrazol-1-yl)-1-(4-(4-((5S)-5-(6-fluoro-2-methyl-2-oxido-3H-2l4-benzo[c]isothiazol-7-yl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-((5R)-5-(6-fluoro-2-methyl-2-oxido-3H-2l4-benzo[c]isothiazol-7-yl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-((5S)-5-(2-methyl-2-oxido-3H-2l4-benzo[c]isothiazol-7-yl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-((5R)-5-(2-methyl-2-oxido-3H-2l4-benzo[c]isothiazol-7-yl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-(5-(2-methyl-2-oxido-3H-2l4-benzo[c]isothiazol-7-yl)-4,5-dihydroisoxazol-3-yl)thiazol-2-yl)piperidin-1-yl)ethan-1-one;

N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)(methyl)(oxo)-l6-sulfaneylidene)cyanamide;

(Z)-N-((3-fluoro-2-(3-(2-(1-(2-(3-methyl-1H-pyrazol-1-yl)acetyl)piperidin-4-yl)thiazol-4-yl)-4,5-dihydroisoxazol-5-yl)phenyl)(methyl)-l4-sulfaneylidene)cyanamide;

N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(oxo)-l6-sulfaneylidene)cyanamide;

(E)-N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide;

(Z)-N-((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-l4-sulfaneylidene)cyanamide;

(E)-N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)(methyl)-l4-sulfaneylidene)cyanamide;

(3-chloro-2-((R)-3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(isopropyl)-l6-sulfanone;

(3-chloro-2-((S)-3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(isopropyl)-l6-sulfanone;

(3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(isopropyl)-l6-sulfanone;

1-(4-(4-((5S)-5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-((5R)-5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-(5-(2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-(5-methyl-3-(trifluoromethyl)-1H-pyrazol-1-yl)ethan-1-one;

1-(2-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one;

1-(2-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one;

1-(2-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-3-(trifluoromethyl)pyridin-2(1H)-one;

2-(3,5-bis(difluoromethyl)-1H-pyrazol-1-yl)-1-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one;

2-(3,5-bis(difluoromethyl)-1H-pyrazol-1-yl)-1-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)ethan-1-one;

1-(2-(4-(4-((5S)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one;

1-(2-(4-(4-((5R)-5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one;

1-(2-(4-(4-(5-(5-chloro-2-methyl-2-oxido-3H-2l4-benzo[c]isothiazol-7-yl)-4,5-dihydroisoxazol-3-yl)thiazol-2-yl)piperidin-1-yl)-2-oxoethyl)-6-methyl-3-(trifluoromethyl)pyridin-2(1H)-one;

(2-((R)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(imino)(isopropyl)-l6-sulfanone;

(3-chloro-2-(3-(2-(1-(2-(4-chloro-1H-pyrazol-1-yl)acetyl)piperidin-4-yl)thiazol-4-yl)-4,5-dihydroisoxazol-5-yl)phenyl)(imino)(isopropyl)-l6-sulfanone;

(3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)(imino)(isopropyl)-l6-sulfanone;

1-(2-(4-(4-(5-(2-chloro-6-(propan-2-ylsulfonimidoyl)phenyl)-4,5-dihydroisoxazol-3-yl)thiazol-2-yl)piperidin-1-yl)-2-oxoethyl)-3-(trifluoromethyl)pyrazin-2(1H)-one;

(3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(isopropyl)-l6-sulfanone;

rac-N-((Z)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-14-sulfaneylidene)cyanamide;

rac-N-((E)-(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)-14-sulfaneylidene)cyanamide;

(2-((S)-3-(2-(1-(2-(3,5-bis(difluoromethyl)-1H-pyrazol-1-yl)acetyl)piperidin-4-yl)thiazol-4-yl)-4,5-dihydroisoxazol-5-y)-3-chlorophenyl)(imino)(isopropyl)-l6-sulfanone;

N-((E)-((6R)-6-((SR)-3-(2-(1-(2-(3,5-bis(difluoromethyl)-1H-pyrazol-1-yl)acetyl)piperidin-4-yl)thiazol-4-yl)-4,5-dihydroisoxazol-5-yl)-5-chlorocyclohexa-2,4-dien-1-yl)(methyl)-14-sulfaneylidene)cyanamide;

(2-((5R)-3-(2-(1-(2-(3,5-bis(difluoromethyl)-1H-pyrazol-1-yl)propanoyl)piperidin-4-yl)thiazol-4-yl)-4,5-dihydroisoxazol-5-yl)-3-chlorophenyl)(methyl)(methylimino)-l6-sulfanone;

(2-((5S)-3-(2-(1-(2-(3,5-bis(difluoromethyl)-1H-pyrazol-1-yl)propanoyl)piperidin-4-yl)thiazol-4-yl)-4,5-dihydroisoxazol-5-yl)-3-chlorophenyl)(methyl)(methylimino)-l6-sulfanone;

(3-chloro-2-((R)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone;

(3-chloro-2-((S)-3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)dimethyl-l6-sulfanone;

(3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(ethylimino)(methyl)-l6-sulfanone;

(Z)-N-((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(isopropyl)-14-sulfaneylidene)cyanamide;

imino(methyl)(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)-l6-sulfanone;

(2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(imino)(methyl)-l6-sulfanone;

(2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)(imino)(methyl)-l6-sulfanone;

(Z)-N-((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)(isopropyl)-14-sulfaneylidene)cyanamide;

1-(4-(4-(5-(2-chloro-6-((1-oxido-1l6-thietan-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-y)-3-chlorophenyl)imino)dimethyl-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)dimethyl-l6-sulfanone;

((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)dimethyl-l6-sulfanone;

dimethyl((2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)imino)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)imino)dimethyl-l6-sulfanone;

1-(2-(4-(4-(5-(2-chloro-6-((dimethyl(oxo)-l6-sulfaneylidene)amino)phenyl)-4,5-dihydroisoxazol-3-yl)thiazol-2-yl)piperidin-1-yl)-2-oxoethyl)-6-methyl-3-(trifluoromethyl)pyridin-2(1H)-one;

((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)dimethyl-l6-sulfanone;

ethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone;

((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(ethyl)(methyl)-l6-sulfanone;

ethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(methyl)-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(ethyl)(methyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazo-5-yl)-3-chlorophenyl)imino)(ethyl)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(ethyl)(methyl)-l6-sulfanone;

((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)(ethyl)(methyl)-l6-sulfanone;

((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(ethyl)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)imino)dimethyl-l6-sulfanone;

((2-(3-(2-(1-(2-((3-methoxypyridin-2-yl)oxy)acetyl)piperidin-4-yl)thiazol-4-yl)-4,5-dihydroisoxazol-5-yl)-3-(trifluoromethyl)phenyl)imino)dimethyl-l6-sulfanone;

(3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(methyl)-l6-sulfanone;

(2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(difluoromethyl)phenyl)(imino)(methyl)-l6-sulfanone;

1-(2-(4-(4-(5-(2-(difluoromethyl)-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one;

2-(3-(2-(1-(2-((3-methoxypyridin-2-yl)oxy)acetyl)piperidin-4-yl)thiazol-4-yl)-4,5-dihydroisoxazol-5-yl)-3-(S-methylsulfonimidoyl)benzonitrile;

2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile;

2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile;

1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-(5-methyl-3-(trifluoromethyl)-1H-pyrazol-1-yl)ethan-1-one;

2-(3,5-bis(difluoromethyl)-1H-pyrazol-1-yl)-1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)ethan-1-one;

1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-((3-(trifluoromethyl)pyridin-2-yl)oxy)ethan-1-one;

1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)-2-((3-methoxypyridin-2-yl)oxy)ethan-1-one;

2-(3,5-bis(trifluoromethyl)-1H-pyrazol-1-yl)-1-(4-(4-(5-(2-chloro-6-((1-oxidotetrahydro-1l6-thiophen-1-ylidene)amino)phenyl)-4,5-dihydroisoxazol-3-yl)thiazol-2-yl)piperidin-1-yl)ethan-1-one;

methyl(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)(methylimino)-l6-sulfanone;

(2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(methyl)(methylimino)-l6-sulfanone;

(2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(trifluoromethyl)phenyl)(ethylimino)(methyl)-l6-sulfanone;

(ethylimino)(methyl)(2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)-3-(trifluoromethyl)phenyl)-l6-sulfanone;

(2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(trifluoromethyl)phenyl)(ethylimino)(methyl)-l6-sulfanone;

(2-(3-(2-(1-(2-((3-methoxypyridin-2-yl)oxy)acetyl)piperidin-4-yl)thiazol-4-yl)-4,5-dihydroisoxazol-5-yl)-3-(trifluoromethyl)phenyl)(methyl)(methylimino)-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)(methyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(isopropyl)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(isopropyl)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(isopropyl)(methyl)-l6-sulfanone;

((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)(methyl)-l6-sulfanone;

((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)(methyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(isopropyl)(methyl)-l6-sulfanone;

((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)(propyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(methyl)(propyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(methyl)(propyl)-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(methyl)(propyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(methyl)(propyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(methyl)(propyl)-l6-sulfanone;

((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(methyl)(propyl)-l6-sulfanone;

((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(methyl)(propyl)-l6-sulfanone;

((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(methyl)(propyl)-l6-sulfanone;

((3-fluoro-2-(3-(2-(1-(2-((2-methoxypyridin-3-yl)oxy)acetyl)piperidin-4-yl)thiazol-4-yl)-4,5-dihydroisoxazol-5-yl)phenyl)imino)dimethyl-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diethyl-l6-sulfanone;

((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diethyl-l6-sulfanone;

((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diethyl-l6-sulfanone;

diethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diethyl-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diethyl-l6-sulfanone;

diethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)-l6-sulfanone;

diethyl((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)-l6-sulfanone;

diethyl((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)-l6-sulfanone;

(3-(difluoromethyl)-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(methyl)(methylimino)-l6-sulfanone;

1-(2-(4-(4-(5-(2-(difluoromethyl)-6-(N,S-dimethylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one;

3-chloro-1-(2-(4-(4-(5-(2-(difluoromethyl)-6-(N,S-dimethylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one;

(3-(difluoromethyl)-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)(methyl)(methylimino)-l6-sulfanone;

(3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(methyl)(methylimino)-l6-sulfanone;

(2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-(difluoromethyl)phenyl)(methyl)(methylimino)-l6-sulfanone;

(Z)-N-((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)-14-sulfaneylidene)cyanamide;

(E)-N-((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)-14-sulfaneylidene)cyanamide;

(2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(difluoromethyl)phenyl)(methyl)(methylimino)-l6-sulfanone;

1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one;

(3-(difluoromethyl)-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)(methylimino)-l6-sulfanone;

(3-(difluoromethyl)-2-(3-(2-(1-(2-((5-(trifluoromethyl)pyridin-2-yl)oxy)acetyl)piperidin-4-yl)thiazol-4-yl)-4,5-dihydroisoxazol-5-yl)phenyl)(methyl)(methylimino)-l6-sulfanone;

(3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(methyl)(methylimino)-l6-sulfanone;

(3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(ethylimino)(methyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)diethyl-l6-sulfanone;

((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diethyl-l6-sulfanone;

5-chloro-1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one;

1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-6-methyl-3-(trifluoromethyl)pyridin-2(1H)-one;

1-(2-(4-(4-(5-(2-chloro-6-((diethyl(oxo)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one;

2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(S-methylsulfonimidoyl)benzonitrile;

(3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)(imino)(methyl)-l6-sulfanone;

(3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)(imino)(methyl)-l6-sulfanone;

(3-chloro-2-(3-(2-(1-(2-((5-(trifluoromethyl)pyridin-2-yl)oxy)acetyl)piperidin-4-yl)thiazol-4-yl)-4,5-dihydroisoxazol-5-yl)phenyl)(imino)(methyl)-l6-sulfanone;

1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-5-(trifluoromethyl)pyridin-2(1H)-one;

1-(2-(4-(4-(5-(2-chloro-6-(S-methylsulfonimidoyl)phenyl)-4,5-dihydroisoxazol-3-yl)thiazol-2-yl)piperidin-1-yl)-2-oxoethyl)-3-(trifluoromethyl)pyridin-2(1H)-one;

(2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)(imino)(methyl)-l6-sulfanone;

(3-chloro-2-(3-(2-(1-(2-(3-methyl-1H-pyrazol-1-yl)acetyl)piperidin-4-yl)thiazol-4-yl)-4,5-dihydroisoxazol-5-yl)phenyl)(imino)(methyl)-l6-sulfanone;

(3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(methyl)-l6-sulfanone;

1-(2-(4-(4-(5-(2-chloro-6-(N,S-dimethylsulfonimidoyl)phenyl)-4,5-dihydroisoxazol-3-yl)thiazol-2-yl)piperidin-1-yl)-2-oxoethyl)-6-methyl-3-(trifluoromethyl)pyridin-2(1H)-one;

((3-fluoro-2-(3-(4-(1-(2-(5-methyl-3-(trifluoromethyl)-1H-pyrazol-1-yl)acetyl)piperidin-4-yl)thiazol-2-yl)-4,5-dihydroisoxazol-5-yl)phenyl)imino)dimethyl-l6-sulfanone;

((2-(3-(4-(1-(2-(3,5-bis(difluoromethyl)-1H-pyrazol-1-yl)acetyl)piperidin-4-yl)thiazol-2-yl)-4,5-dihydroisoxazol-5-yl)-3-fluorophenyl)imino)dimethyl-l6-sulfanone;

((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)dimethyl-l6-sulfanone;

((2-(3-(4-(1-(2-(3,5-bis(trifluoromethyl)-1H-pyrazol-1-yl)acetyl)piperidin-4-yl)thiazol-2-yl)-4,5-dihydroisoxazol-5-yl)-3-fluorophenyl)imino)dimethyl-l6-sulfanone;

((3-fluoro-2-(3-(4-(1-(2-((3-methoxypyridin-2-yl)oxy)acetyl)piperidin-4-yl)thiazol-2-yl)-4,5-dihydroisoxazol-5-yl)phenyl)imino)dimethyl-l6-sulfanone;

1-(2-(4-(2-(5-(2-((dimethyl(oxo)-l6-sulfaneylidene)amino)-6-fluorophenyl)-4,5-dihydroisoxazol-3-yl)thiazol-4-yl)piperidin-1-yl)-2-oxoethyl)-3-(trifluoromethyl)pyridin-2(1H)-one;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(ethyl)(isopropyl)-l6-sulfanone;

ethyl((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(ethyl)(isopropyl)-l6-sulfanone;

ethyl((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)-l6-sulfanone;

1-(2-(4-(4-(5-(2-((ethyl(isopropyl)(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one;

ethyl((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(isopropyl)-l6-sulfanone;

(3-(difluoromethyl)-2-(3-(2-(1-(2-((3-methoxypyridin-2-yl)oxy)acetyl)piperidin-4-yl)thiazol-4-yl)-4,5-dihydroisoxazol-5-yl)phenyl)(imino)(isopropyl)-l6-sulfanone;

(3-(difluoromethyl)-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)(imino)(isopropyl)-l6-sulfanone;

(3-(difluoromethyl)-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)(imino)(isopropyl)-l6-sulfanone;

(2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-(difluoromethyl)phenyl)(imino)(isopropyl)-l6-sulfanone;

(3-(difluoromethyl)-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)(imino)(isopropyl)-l6-sulfanone;

(2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)-3-(difluoromethyl)phenyl)(imino)(isopropyl)-l6-sulfanone;

(2-(3-(2-(1-(2-(4-chloro-1H-pyrazol-1-yl)acetyl)piperidin-4-yl)thiazol-4-yl)-4,5-dihydroisoxazol-5-yl)-3-(difluoromethyl)phenyl)(imino)(isopropyl)-l6-sulfanone;

(2-(3-(2-(1-(2-(2H-indazol-2-yl)acetyl)piperidin-4-yl)thiazol-4-yl)-4,5-dihydroisoxazol-5-yl)-3-(difluoromethyl)phenyl)(imino)(isopropyl)-l6-sulfanone;

((3-fluoro-2-(3-(4-(1-(2-((3-(trifluoromethyl)pyrazin-2-yl)oxy)acetyl)piperidin-4-yl)thiazol-2-yl)-4,5-dihydroisoxazol-5-yl)phenyl)imino)dimethyl-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(isopropyl)(propyl)-l6-sulfanone;

((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(isopropyl)(propyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(isopropyl)(propyl)-l6-sulfanone;

((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(isopropyl)(propyl)-l6-sulfanone;

((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)(propyl)-l6-sulfanone;

((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(isopropyl)(propyl)-l6-sulfanone;

1-(2-(4-(4-(5-(2-fluoro-6-((isopropyl(oxo)(propyl)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one;

1-(4-(4-(5-(2-fluoro-6-((1-oxido-1l6-thietan-1-ylidene)amino)phenyl)-4,5-dihydroisoxazol-3-yl)thiazol-2-yl)piperidin-1-yl)-2-((3-(trifluoromethyl)pyrazin-2-yl)oxy)ethan-1-one;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diisopropyl-l6-sulfanone;

((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diisopropyl-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diisopropyl-l6-sulfanone;

((2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)-3-fluorophenyl)imino)diisopropyl-l6-sulfanone;

((3-fluoro-2-(3-(2-(1-(2-((3-methoxypyrazin-2-yl)oxy)acetyl)piperidin-4-yl)thiazol-4-yl)-4,5-dihydroisoxazol-5-yl)phenyl)imino)diisopropyl-l6-sulfanone;

((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diisopropyl-l6-sulfanone;

1-(2-(4-(4-(5-(2-((diisopropyl(oxo)-l6-sulfaneylidene)amino)-6-fluorophenyl)-4,5-dihydroisoxazol-3-yl)thiazol-2-yl)piperidin-1-yl)-2-oxoethyl)-3-(trifluoromethyl)pyridin-2(1H)-one;

((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diisopropyl-l6-sulfanone;

((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diisopropyl-l6-sulfanone;

((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)diisopropyl-l6-sulfanone;

((2-(3-(2-(1-(2-((3-chloropyrazin-2-yl)oxy)acetyl)piperidin-4-yl)thiazol-4-yl)-4,5-dihydroisoxazol-5-yl)-3-fluorophenyl)imino)dimethyl-l6-sulfanone;

((3-fluoro-2-(3-(2-(1-(2-((3-(methylthio)pyrazin-2-yl)oxy)acetyl)piperidin-4-yl)thiazol-4-yl)-4,5-dihydroisoxazol-5-yl)phenyl)imino)dimethyl-l6-sulfanone;

((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(isopropyl)(phenyl)-l6-sulfanone;

((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(isopropyl)(phenyl)-l6-sulfanone;

3-chloro-1-(2-(4-(4-(5-(2-fluoro-6-((isopropyl(oxo)(phenyl)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one;

((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)(isopropyl)(phenyl)-l6-sulfanone;

1-(2-(4-(4-(5-(2-fluoro-6-((isopropyl(oxo)(phenyl)-l6-sulfaneylidene)amino)phenyl)-4,5-dihydroisoxazol-3-yl)thiazol-2-yl)piperidin-1-yl)-2-oxoethyl)-5-(trifluoromethyl)pyridin-2(1H)-one;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)(isopropyl)(phenyl)-l6-sulfanone;

1-(2-(4-(4-(5-(2-fluoro-6-((isopropyl(oxo)(phenyl)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one;

((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(isopropyl)(phenyl)-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)diisopropyl-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diisopropyl-l6-sulfanone;

((3-chloro-2-(3-(2-(1-(2-(5-cyclopropyl-3-(trifluoromethyl)-1H-pyrazol-1-yl)acetyl)piperidin-4-yl)thiazol-4-yl)-4,5-dihydroisoxazol-5-yl)phenyl)imino)diisopropyl-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)diisopropyl-l6-sulfanone;

((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)diisopropyl-l6-sulfanone;

((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diisopropyl-l6-sulfanone;

((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diisopropyl-l6-sulfanone;

1-(2-(4-(4-(5-(2-chloro-6-((diisopropyl(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one;

((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diisopropyl-l6-sulfanone;

((2-(3-(2-(1-(2-(2H-indazol-2-yl)acetyl)piperidin-4-yl)thiazol-4-yl)-4,5-dihydroisoxazol-5-yl)-3-chlorophenyl)imino)diisopropyl-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)(isopropyl)(phenyl)-l6-sulfanone;

((3-fluoro-2-(3-(2-(1-(2-((3-(methylsulfonyl)pyrazin-2-yl)oxy)acetyl)piperidin-4-yl)thiazol-4-yl)-4,5-dihydroisoxazol-5-yl)phenyl)imino)dimethyl-l6-sulfanone;

((3-fluoro-2-(3-(2-(1-(2-((6-(trifluoromethyl)pyridazin-3-yl)thio)acetyl)piperidin-4-yl)thiazol-4-yl)-4,5-dihydroisoxazol-5-yl)phenyl)imino)dimethyl-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-chlorophenyl)imino)(ethyl)(isopropyl)-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-chlorophenyl)imino)(ethyl)(isopropyl)-l6-sulfanone;

((3-chloro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-(3,5-dimethyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-((3-methoxypyridin-2-yl)oxy)acetyl)piperidin-4-yl)thiazol-4-yl)-4,5-dihydroisoxazol-5-yl)phenyl)imino)(ethyl)(isopropyl)-l6-sulfanone;

((2-(3-(4-(1-(2-(3,5-bis(trifluoromethyl)-1H-pyrazol-1-yl)acetyl)piperidin-4-yl)thiazol-2-yl)-4,5-dihydroisoxazol-5-yl)-3-fluorophenyl)imino)diethyl-l6-sulfanone;

((2-(3-(4-(1-(2-(3,5-bis(difluoromethyl)-1H-pyrazol-1-yl)acetyl)piperidin-4-yl)thiazol-2-yl)-4,5-dihydroisoxazol-5-yl)-3-fluorophenyl)imino)diethyl-l6-sulfanone;

diethyl((3-fluoro-2-(3-(4-(1-(2-(5-methyl-3-(trifluoromethyl)-1H-pyrazol-1-yl)acetyl)piperidin-4-yl)thiazol-2-yl)-4,5-dihydroisoxazol-5-yl)phenyl)imino)-l6-sulfanone;

diethyl((3-fluoro-2-(3-(4-(1-(2-((3-methoxypyridin-2-yl)oxy)acetyl)piperidin-4-yl)thiazol-2-yl)-4,5-dihydroisoxazol-5-yl)phenyl)imino)-l6-sulfanone;

diethyl((3-fluoro-2-(3-(4-(1-(2-((3-(trifluoromethyl)pyridin-2-yl)oxy)acetyl)piperidin-4-yl)thiazol-2-yl)-4,5-dihydroisoxazol-5-yl)phenyl)imino)-l6-sulfanone;

diethyl((3-fluoro-2-(3-(4-(1-(2-((3-(trifluoromethyl)pyrazin-2-yl)oxy)acetyl)piperidin-4-yl)thiazol-2-yl)-4,5-dihydroisoxazol-5-yl)phenyl)imino)-l6-sulfanone;

1-(2-(4-(2-(5-(2-((diethyl(oxo)-l6-sulfaneylidene)amino)-6-fluorophenyl)-4,5-dihydroisoxazol-3-yl)thiazol-4-yl)piperidin-1-yl)-2-oxoethyl)-3-(trifluoromethyl)pyridin-2(1H)-one;

((3-fluoro-2-(3-(2-(1-(2-((6-methoxypyrimidin-4-yl)oxy)acetyl)piperidin-4-yl)thiazol-4-yl)-4,5-dihydroisoxazol-5-yl)phenyl)imino)dimethyl-l6-sulfanone;

((2-(3-(2-(1-(2-(3,5-bis(trifluoromethyl)-1H-pyrazol-1-yl)acetyl)piperidin-4-yl)thiazol-4-yl)-4,5-dihydroisoxazol-5-yl)-3-fluorophenyl)imino)diisobutyl-l6-sulfanone;

((3-fluoro-2-(3-(2-(1-(2-(5-methyl-3-(trifluoromethyl)-1H-pyrazol-1-yl)acetyl)piperidin-4-yl)thiazol-4-yl)-4,5-dihydroisoxazol-5-yl)phenyl)imino)diisobutyl-l6-sulfanone;

((2-(3-(2-(1-(2-(3,5-dimethyl-1H-pyrazol-1-yl)acetyl)piperidin-4-yl)thiazol-4-yl)-4,5-dihydroisoxazol-5-yl)-3-fluorophenyl)imino)diisobutyl-l6-sulfanone;

((2-(3-(2-(1-(2-(3,5-bis(difluoromethyl)-1H-pyrazol-1-yl)acetyl)piperidin-4-yl)thiazol-4-yl)-4,5-dihydroisoxazol-5-yl)-3-fluorophenyl)imino)diisobutyl-l6-sulfanone;

((2-(3-(2-(1-(2-(4-chloro-1H-pyrazol-1-yl)acetyl)piperidin-4-yl)thiazol-4-yl)-4,5-dihydroisoxazol-5-yl)-3-fluorophenyl)imino)diisobutyl-l6-sulfanone;

((3-fluoro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)diisobutyl-l6-sulfanone;

((2-(3-(2-(1-(2-(2H-indazol-2-yl)acetyl)piperidin-4-yl)thiazol-4-yl)-4,5-dihydroisoxazol-5-yl)-3-fluorophenyl)imino)diisobutyl-l6-sulfanone;

((3-fluoro-2-(3-(2-(1-(2-((3-(trifluoromethyl)pyridin-2-yl)oxy)acetyl)piperidin-4-yl)thiazol-4-yl)-4,5-dihydroisoxazol-5-yl)phenyl)imino)diisobutyl-l6-sulfanone;

((3-fluoro-2-(3-(2-(1-(2-((3-methoxypyridin-2-yl)oxy)acetyl)piperidin-4-yl)thiazol-4-yl)-4,5-dihydroisoxazol-5-yl)phenyl)imino)diisobutyl-l6-sulfanone;

((3-fluoro-2-(3-(2-(1-(2-((3-(trifluoromethyl)pyrazin-2-yl)oxy)acetyl)piperidin-4-yl)thiazol-4-yl)-4,5-dihydroisoxazol-5-yl)phenyl)imino)diisobutyl-l6-sulfanone;

((3-fluoro-2-(3-(2-(1-(2-((2-(trifluoromethyl)pyridin-3-yl)oxy)acetyl)piperidin-4-yl)thiazol-4-yl)-4,5-dihydroisoxazol-5-yl)phenyl)imino)dimethyl-l6-sulfanone;

((2-(3-(2-(1-(2-(1H-pyrazol-1-yl)acetyl)piperidin-4-yl)thiazol-4-yl)-4,5-dihydroisoxazol-5-yl)-3-chlorophenyl)imino)(ethyl)(isopropyl)-l6-sulfanone;

((3-chloro-2-(3-(2-(1-(2-(3-(trifluoromethyl)-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-((6-methyl-3-(trifluoromethyl)pyridin-2-yl)oxy)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-(4-chloro-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone;

((3-chloro-2-(3-(2-(1-(2-(4-methyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone;

1-(2-(4-(4-(5-(2-chloro-6-((ethyl(isopropyl)(oxo)-l6-sulfaneylidene)amino)phenyl)-4,5-dihydroisoxazol-3-yl)thiazol-2-yl)piperidin-1-yl)-2-oxoethyl)-3-(trifluoromethyl)pyridin-2(1H)-one and ((3-chloro-2-(3-(2-(1-(2-(4-chloro-3,5-dimethyl-1H-pyrazol-1-yl)acetyl)piperidin-4-yl)thiazol-4-yl)-4,5-dihydroisoxazol-5-yl)phenyl)imino)(ethyl)(isopropyl)-l6-sulfanone.

5. A process for preparing in the compound of claim 1, wherein said process comprising steps of:

a) converting a compound of formula (IX) to a compound of formula (VIII) according to the reaction scheme as depicted below:

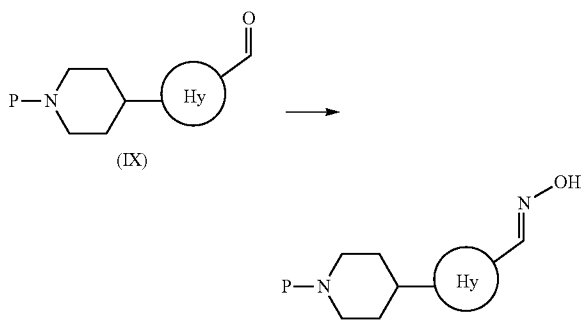

(IX)

(VIII)

b) reacting compound of formula (VIII) with a compound of formula (VII) to obtain a compound of formula (VI) according to the reaction scheme as depicted below:

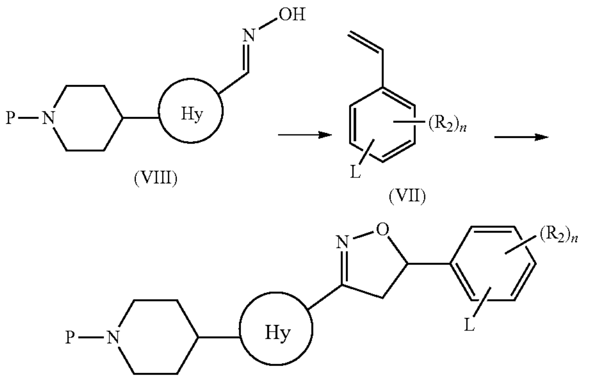

(VIII) (VII)

(VI)

c) converting compound of formula (VI) to compound of formula (IV) according to the reaction scheme as depicted below:

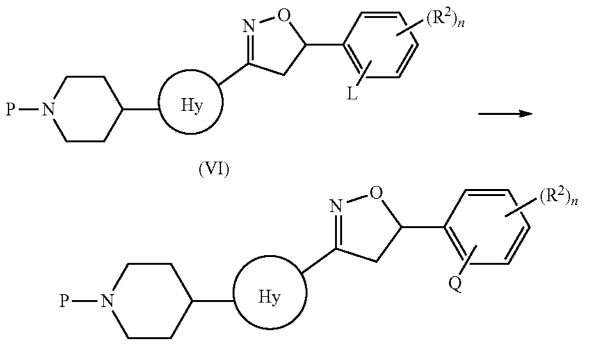

(VI)

(IV)

d) converting compound of formula (IV) to compound of formula (III) according to the reaction scheme as depicted below:

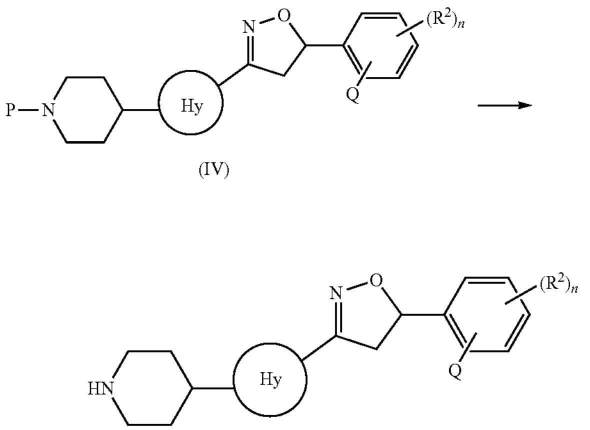

(IV)

(III)

e) reacting compound of formula (III) with compound of formula (II) to obtain a compound of formula (I) according to the reaction scheme as depicted below:

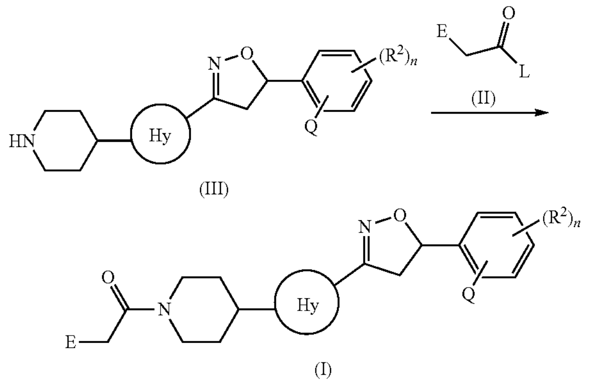

(III) (II) (I)

wherein in the above reaction schemes, P is protecting group, and L is leaving group.

6. A composition for controlling or preventing phytopathogenic micro-organisms comprising a biologically effective amount of the compound of claim 1 and at least one additional component selected from the group consisting of surfactants and auxiliaries.

7. The composition as claimed in claim 6, wherein said composition additionally comprises at least one additional biological active compound selected from the group consisting of fungicides, insecticides, nematicides, acaricides, biopesticides, herbicides, plant growth regulators, antibiotics, fertilizers and nutrients.

8. The composition as claimed in claim 6, wherein said biologically effective amount of the compound ranges from 0.1% to 99% by weight with respect to the total weight of the composition.

9. A combination comprising a biologically effective amount of the compound of claim 1 and at least one additional biological active compatible compound selected from fungicides, insecticides, nematicides, acaricides, biopesticides, herbicides, plant growth regulators, antibiotics, fertilizers and nutrients.

10. A method for controlling or preventing phytopathogenic fungi, stramenopiles, and bacteria in agricultural crops and/or horticultural crops, the method comprising:

applying the compound of claim 1 to the agricultural crops and/or horticultural crops.

11. A method for controlling or preventing phytopathogenic fungi, stramenopiles, bacteria, insects, nematodes, tremadotes and mites in agricultural crops and/or horticultural crops, the method comprising:

applying the composition of claim 7 to the agricultural crops and/or horticultural crops.

12. A method for controlling or preventing phytopathogenic fungi, stramenopiles, bacteria, insects, nematodes, trematodes and mites in agricultural crops and/or horticultural crops, the method comprising:

applying the combination of claim 9 to the agricultural crops and/or horticultural crops.

13. A method for controlling or preventing oomycetes in agricultural crops and/or horticultural crops, the method comprising:

applying the compound of claim 1 to the agricultural crops and/or horticultural crops.

14. The method of claim 10, wherein the agricultural crops are selected from cereals, corn, rice, soybean and other leguminous plants, fruits and fruit trees, grapes, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and other vegetables and ornamentals.

15. A method of controlling or preventing infestation of useful plants by phytopathogenic micro-organisms in agricultural crops and/or horticultural crops, the method comprising:

applying the compound of claim 1 to the plants, to parts thereof or the locus thereof.

16. A method of controlling or preventing infestation of useful plants by phytopathogenic micro-organisms in agricultural crops and/or horticultural crops, the method comprising:

applying the compound of claim 1 to seeds.

* * * * *